United States Patent [19]

Leonard et al.

[11] Patent Number: 4,604,388
[45] Date of Patent: Aug. 5, 1986

[54] FUSED AROMATIC OXAZEPINONES, THIAZEPINONES, DIAZEPINONES AND SULFUR ANALOGS THEREOF IN A METHOD OF COUNTERACTING HISTAMINE

[75] Inventors: Charles A. Leonard; Bernard V. Franko, both of Richmond; Albert D. Cale, Jr., Mechanicsville, all of Va.

[73] Assignee: A. H. Robins Company, Incorporated, Richmond, Va.

[21] Appl. No.: 753,325

[22] Filed: Jul. 9, 1985

Related U.S. Application Data

[63] Continuation-in-part of Ser. No. 652,007, Sep. 19, 1984, abandoned, which is a continuation-in-part of Ser. No. 527,558, Aug. 29, 1983, abandoned, which is a continuation-in-part of Ser. No. 431,998, Sep. 30, 1982, abandoned.

[51] Int. Cl.$^4$ ............................................. A61U 31/55
[52] U.S. Cl. ..................................................... 514/211
[58] Field of Search ..................... 260/239.3 B, 239.37; 514/211

[56] References Cited

U.S. PATENT DOCUMENTS 3,738,999  6/1973  Krapcho et al. ................. 260/239 B
3,794,639  2/1974  Kpapcho et al. ............... 260/239 B

*Primary Examiner*—Stanley J. Friedman

[57] ABSTRACT

A method of counteracting the effects of histamine with aromatic azepinones and diazepinones and thiones thereof having the formula

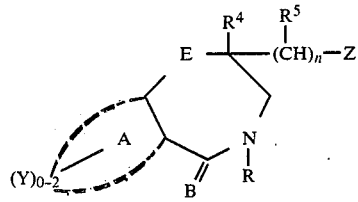

wherein:
A is benzene, naphthalene, quinoline or pyridine;
B is oxygen or sulfur:
E is oxygen, sulfur or loweralkyl substituted nitrogen;
n is 1, 2 or 3;
Z is an amino or a heterocyclic nitrogen containing radical;
R is hydrogen, loweralkyl, cycloalkyl or phenyl-loweralkyl;
and compositions therefor are disclosed.

258 Claims, No Drawings

FUSED AROMATIC OXAZEPINONES, THIAZEPINONES, DIAZEPINONES AND SULFUR ANALOGS THEREOF IN A METHOD OF COUNTERACTING HISTAMINE

REFERENCE TO PARENT APPLICATIONS

This application is a continuation-in-part of U.S. patent application Ser. No. 652,007 filed Sept. 19, 1984, which is a continuation-in-part of U.S. application Ser. No. 527,558 filed Aug. 29, 1983, which is a continuation-in-part of U.S. application Ser. No. 431,998 filed Sept. 30, 1982, all are now abandoned.

BACKGROUND OF THE INVENTION

1. Field of Invention

The present invention relates to a novel method of counteracting the effects of histamine in a living animal body by administration of certain aromatic oxazepinones, thiazepinones and diazepinones and sulfur analogs thereof and is particularly concerned with aromatic 1,4-oxazepinones, thiazepinones, diazepinones and thiones of all, which have the aromatic component fused into the oxazepine, thiazepine or diazepine component, each component thereby having two commonly shared carbon atoms and the oxazepine, thiazepine or diazepine ring having an oxo (or thioxo) function on the carbon atom adjacent to one of the shared carbon atoms and a short chain aminoalkyl, alkylaminoalkyl or heterocyclicaminoalkyl radical attached to the carbon atom two positions away from the other shared carbon atom.

2. Information Disclosure Statement

3-Aryl-1,4-benzoxazepin-5(4H)-ones substituted in the 2-position by a phenyl radical and substituted on the oxazepine nitrogen by an amino alkyl radical have been disclosed by Schenker, K. in Swiss Patent No. 505.850 (C.A. 75, 98600s). The compounds were reported to have analgetic and antiphlogistic activities.

The aromatic 2,3-dihydro-1,4-oxazepin-5(4H)-ones and their thiazepin and thione analogs substituted by a short chain aminoalkyl radical of the present invention have not previously been disclosed and are the novel subject of an application, U.S. Ser. No. 431,500 filed on Sept. 30, 1982, and consecutive continuation-in-part applications, U.S. Ser. No. 527,559 filed on Aug. 29, 1983, and another thereof filed on even date herewith.

OBJECTS AND SUMMARY OF THE INVENTION

The oxazepine, thiazepine and diazepine derivatives which exhibit antihistaminic activity and are useful in the method of the present invention have the formula:

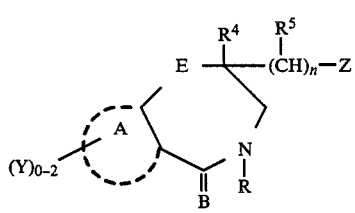

Formula I wherein;

A represents an aromatic ring having two of its carbon atoms held mutually with the oxazepine, thiazepine or diazepine moiety selected from the group consisting of benzene, naphthalene, a quinoline, or a pyridine in any of its four positions, any of the rings optionally substituted by one or two Y radicals selected from the group consisting of halo, loweralkyl, loweralkoxy, diloweralkylamino, nitro, or trifluoromethyl;

E is selected from oxygen, sulfur or loweralkyl-substituted nitrogen;

B is selected from oxygen or sulfur;

R is selected from the group consisting of hydrogen, loweralkyl, cycloalkyl or phenyl-loweralkyl, of which phenyl may be optionally substituted by one or two radicals selected from halo, lower alkyl, loweralkoxy, nitro or trifluoromethyl;

n is 1, 2 or 3;

$R^4$ and $R^5$ are selected from hydrogen or loweralkyl (1–5 C);

Z is selected from the group consisting of $-NR^1R^2$, 1H-pyrazol-1-yl, 1H-imidazol-1-yl, 1H-imidazol-2-yl, or 4,5-dihydro-1H-imidazol-2-yl;

$R^1$ and $R^2$ are selected from the group consisting of hydrogen, loweralkyl, cycloalkyl and phenyl-loweralkyl, of which phenyl may be optionally substituted by 1 or 2 radicals selected from halo, loweralkyl, loweralkoxy, nitro, trifluoromethyl or cyano, or $R^1$ and $R^2$ taken together with the adjacent nitrogen atom may form a heterocyclic residue selected from the group consisting of 1-azetidinyl, 1-pyrrolidinyl, 2,5-dimethylpyrrolidin-1-yl, 2-methylpyrrolidin-1-yl, 1-piperidinyl, 4-substituted piperidin-1-yl, 4-[bis(4-fluorophenyl)methyl]-piperidin-1-yl, 4-morpholinyl, 1-piperazinyl, 4-substituted piperazin-1-yl, 1,2,3,6-tetrahydropyridin-1-yl, 1H-pyrrol-1-yl or 2,5-dihydro-1H-pyrrol-1-yl, the optical isomers thereof, and the pharmaceutically acceptable salts thereof with the proviso that when R=H, Z is never a primary or secondary amine, and a further proviso that when n=3, Z is not pyrazolyl, or imidazolyl.

The oxazepine, thiazepine and diazepine precursors leading to compounds of Formula I have the formula:

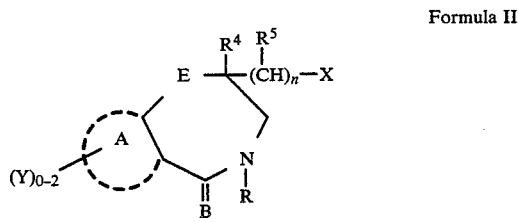

Formula II wherein A, B, E, R, $R^4$, $R^5$ and Y are as defined under Formula I above, except R is not hydrogen, n is 1 or 2, and X is chlorine, bromine, cyano, or 1-phthalimido, the optical isomers thereof, and the acid addition salts thereof.

Other chemical intermediates in the preparation of compounds of Formula II are novel and have the formula:

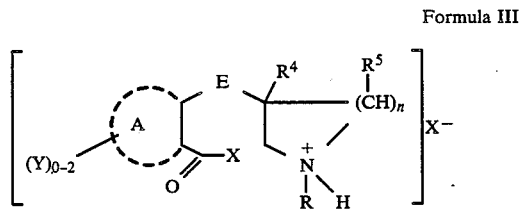

Formula III wherein A, E, R, $R^4$, $R^5$, n and Y are as defined under Formula II above and X is chlorine or bromine.

Other chemical intermediates leading to compounds of Formula III have the formula:

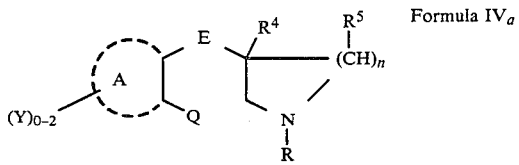

Formula IV$_a$ wherein A, E, R, $R^4$, $R^5$, n and Y are as defined under Formula II, and Q is selected from

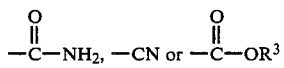

where $R^3$ is H, alkali metal ion or an esterifying radical. Compounds of Formula IVa are novel except wherein A is phenyl or substituted phenyl and E is oxygen when n is two.

Other chemical intermediates used in alternate procedures for preparing compounds of Formula I and which are not precursors of Formula III type compounds have the formulas V and VI.

Formula V

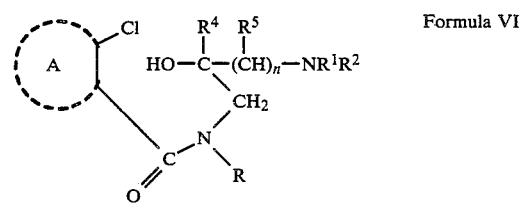

Formula VI wherein A, $R^1$, $R^2$, $R^4$ and $R^5$ have the values assigned under Formula I, and $R^3$ is H or alkali metal ion. Compounds of Formulas V and VI are not part of the present invention but are intended to be the subject of a separate application.

In the further definition of symbols in the formulas hereof and where they appear elsewhere throughout this specification and the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec. butyl, tert. butyl, amyl, isoamyl, hexyl, heptyl and octyl radicals and the like. The term "loweralkoxy" has the formula —O-loweralkyl.

The term "cycloalkyl" as used herein includes primarily cyclic alkyl radicals containing 3-9 carbon atoms inclusive and includes such groups as cyclopropyl, cyclobutyl, cyclopentyl, cyclohexyl, methylcyclohexyl, cycloheptyl and the like.

The terms "halo" or "halogen" when referred to herein include fluorine, chlorine, bromine and iodine unless otherwise stated.

"Pharmaceutically acceptable salts" include acid addition salts, hydrates, alcoholates and quaternary salts of the compounds of Formula I, which are physiologically compatible in warm-blooded animals. The acid addition salts may be formed by either strong or weak acids. Representative of strong acids are hydrochloric, sulfuric and phosphoric acids. Representative of weak acids are fumaric, maleic, succinic, oxalic, citric, tartaric, hexamic, and the like.

Suitable quaternary salts include the loweralkyl halides and loweralkyl sulfates.

By "sulfurizing agent" is meant any agent or mixture of agents which will convert diazepinones, ox- and thiazepinones to diazepine-thiones, ox- and thiazepinethiones, such as 2,4-bis(4-methoxyphenyl)-1,3,2,4-dithiadiphosphetane-2,4-disulfide (Lawesson) reagent or a mixture of phosphorus pentasulfide and alkalimetal sulfide or mixture of phosphorus pentasulfide in a suitable solvent such as acetonitrile, toluene or pyridine. By the use of "sulfurizing agent" the azepinones are thereby "sulfurized" to azepine-thiones.

The compounds of the present invention exhibit antihistaminic activity in guinea pigs. The method of testing is a modification of the procedure of Tozzi et al (Agents and Actions, Vol. 4/4, 264–270, 1974) as follows: Guinea pigs are fasted 18–24 hrs in individual cages. Water is available ad libitum. On the test day, animals in groups of 3 are injected intraperitoneally with 30 mg/kg of the test compound prepared in an appropriate vehicle. Thirty minutes later histamine at a dosage level of 1.2 mg/kg ($=2\times$the $LD_{99}$) is injected into a marginal ear vein. Survival of the guinea pigs for 24 hrs is positive evidence of antihistaminic activity. If the vehicle used for the test compound is other than water, its effect is established by testing an equal amount as a control. The dose protecting 50% of the animals ($PD_{50}$) from death may be established from dose-response curves. The non-sedative nature of the compounds is discussed hereinbelow under "Additional Pharmacology."

The process by which compounds of this invention are made comprises the following steps:

Step (1) Halogenating a compound of the formula

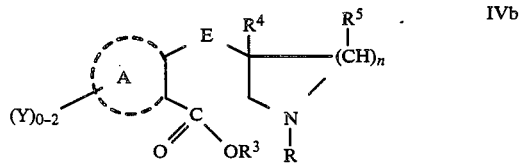

IVb wherein;

A represents an aromatic ring selected from benzene, naphthalene, a quinoline, or a pyridine in any one of its four positions, any of the rings optionally substituted by one or two Y-radicals selected from halo, loweralkyl, loweralkoxy, diloweralkylamino, nitro, or trifluoromethyl;

E is oxygen, sulfur, or loweralkyl substituted nitrogen,

R is selected from the group consisting of loweralkyl, cycloalkyl or phenyl-loweralkyl, of which phenyl may be optionally substituted by one or two radicals selected from halo, loweralkyl, loweralkoxy, nitro or trifluoromethyl;

R³ is hydrogen or an acid neutralizing ion;

R⁴ and R⁵ are hydrogen or loweralkyl (1–5 C); and n is one or two, to give a compound of the formula

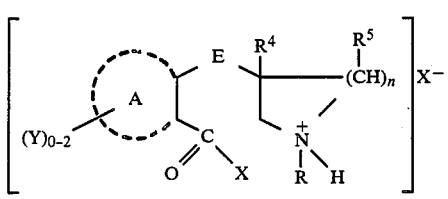

or its free base wherein X is chlorine or bromine and A, E, R, R⁴, R⁵, Y and n are the same as the starting values. Among suitable halogenating agents are (a) thionyl halides
(b) triphenylphosphine and a carbon tetrahalide
(c) phosphorus pentahalides
(d) phosphorus trihalides, and
(e) triphenylphosphine dihalide.

Step (2) Neutralizing, if necessary, and fusing the carboxylic acid halide derivative prepared in step 1 to give an oxazepinone, thiazepinone or diazepinone of the formula

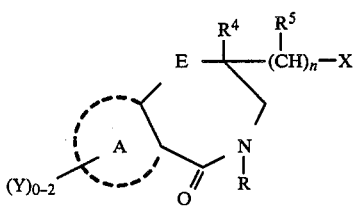

wherein A, E, R, R⁴, R⁵, X, Y and n are as defined above in step 1, and A now has two of its carbon atoms held mutually with the oxazepine, thiazepine, or diazepine moiety;

Step (3) Optionally reacting the compound prepared in step 2 with a sulfurizing agent to obtain an oxazepinethione, thiazepinethione, or diazepinethione of the formula

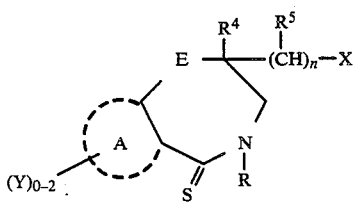

wherein A, E, R, R⁴, R⁵, X, Y and n are as defined above in step 2.

Step (4) When required, reacting a compound prepared in step 2 with an alkali-metal cyanide to obtain a compound of the formula

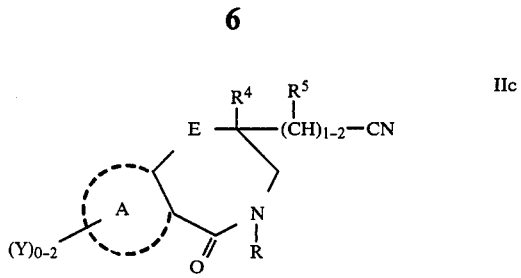

wherein A, E, Y, R, R⁴ and R⁵ are as defined in step 2,

Step (5) Reacting a halogen compound prepared in step 2 or 3 with a compound of the formula

ZH wherein Z is selected from —NR¹R², 1H-pyrazol-1-yl, 1H-imidazol-1-yl, 1H-imidazol-2-yl, or 4,5-dihydro-1H-imidazol-2-yl, and wherein R¹ and R² are selected from hydrogen, loweralkyl, cycloalkyl and phenyl-loweralkyl, of which phenyl may be optionally substituted with 1 or 2 radicals selected from halo, loweralkyl, loweralkoxy, nitro, trifluoromethyl or cyano, or R¹ and R² taken together with the adjacent nitrogen atom may form a heterocyclic residue selected from the group consisting of 1-azetidinyl, 1-pyrrolidinyl, 2,5-dimethylpyrrolidin-1-yl, 2-methyl-pyrrolidin-1-yl, 1-piperidinyl, 4-substituted-piperidine-1-yl, 4-[bis(4-fluorophenyl)methyl]piperidin-1-yl, 4-morpholinyl, 1-piperazinyl, 4-substituted-piperazin-1-yl 1,2,3,6-tetrahydropyridine-1-yl, 2,5-dihydro-1H-pyrrol-1-yl, 1H-pyrrol-1-yl, or 1-phthalimidyl to give the compound of the formula

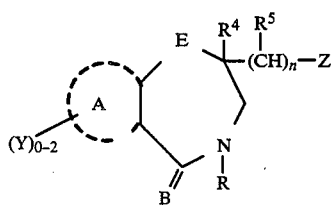

wherein A, E, R, R⁴, R⁵, n and Y are as defined above in step 2, Z is the same as in the ZH compound, and B is an oxygen or sulfur atom, Step (6) Optionally reacting a compound prepared in step 5 wherein B is an oxygen atom with a sulfurizing agent, preferably phosphorus pentasulfide in pyridine to obtain a compound of the formula

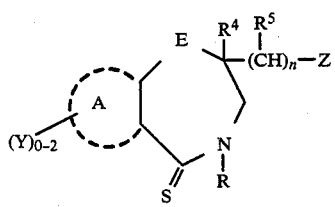

wherein A, E, R, R⁴, R⁵, n, Y and Z are as defined in step 5.

Step (7) Reducing a cyano compound (Formula IIc) prepared in step 4, or reacting a phthalimido compound prepared in step 4 with hydrazine hydrate to give a primary amine of the formula

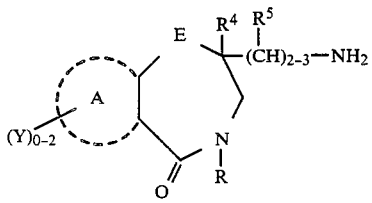

wherein A, E, Y, R, $R^4$ and $R^5$ are defined in steps 2 and 4.

Step (8) When required, reacting a primary amine prepared in steps 5 or 7 of the formula

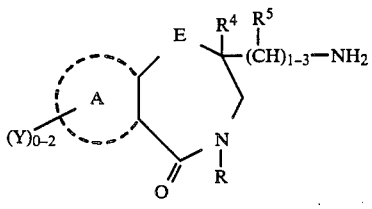

wherein A, E, Y, R, $R^4$ and $R^5$ are as defined in step 2 with one of the following reactants or sets of reactants:
(a) formaldehyde and formic acid to give a tertiary dimethylamine,
(b) a dihalide or alkenedihalide to give a heterocyclic amine,
(c) a dialdehyde and sodium cyanoborohydride to give a heterocyclic amine,
(d) equal molar amounts of aldehyde or ketone, sodium cyanoborohydride with large excess of above primary amine to give a secondary amine,
(e) equal molar amounts of the primary amine and sodium cyanoborohydride with at least two equivalents of aldehyde or ketone,
(f) in sequence: trifluoroacetyl chloride, alkyl or phenyl-alkyl halide, potassium hydride and potassium hydroxide to give a secondary amine,
all products being encompassed by the formula

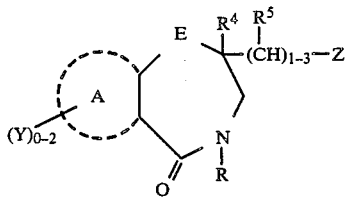

wherein A, E, Y, R, $R^4$ and $R^5$ are as defined in step 2 and Z is $-NR^1R^2$ wherein $R^1$ and $R^2$ are loweralkyl, cycloalkyl and phenyl-loweralkyl with phenyl being optionally substituted by halo, loweralkyl, loweralkoxy, nitro, trifluoromethyl or cyano or $R^1$ and $R^2$ taken together with the adjacent nitrogen may form a heterocyclic residue selected from 1-azetidinyl, 1-pyrrolidinyl, 1-piperidinyl, 4-substituted-piperidin-1-yl, 4-[bis(4-fluorophenyl)methyl]piperidin-1-yl, 4-morpholinyl, 1-piperazinyl, 4-substituted-piperazin-1-yl, 1,2,3,6-tetrahydropyridin-1-yl, 1H-pyrrol-1-yl or 2-methylpyrrolidin-1-yl, and optionally sulfurizing the diazepinone, azepinone or thiazepinone to give the corresponding thione as in step 6.

Step (9) When required, reacting a benzyl or substituted benzyl compound obtained in steps 5, 6, or 8 wherein Z is tertiary amino, or non-reactive heterocycle radical such as pyrazolyl or imidazolyl of the formula

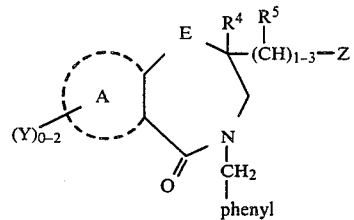

wherein A, E, Y, $R^4$ and $R^5$ are as defined in step 2, and Z is a radical taken from the definition of Z under Formula I, subject to the same provisos given thereunder, with sodium and ammonia to give a compound of the formula

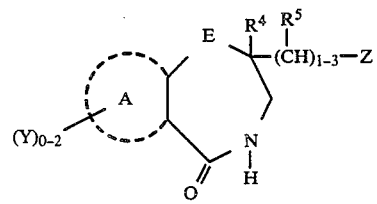

wherein A, E, Y, $R^4$ and $R^5$ are as defined in step 2 n is 1 to 3 and Z is the same as the starting compound in this step, Step (10) Optionally reacting the free base of any compound prepared in steps 5 to 9 with a pharmaceutically acceptable acid or quaternary forming halide or sulfate to form a pharmaceutically acceptable salt thereof and, as explained hereinbelow, optically active compounds are obtained by using optically active starting compounds in step 1.

The compounds of Formula I wherein n is 2 are preferred for their antihistaminic activity. The process which includes steps 1 to 3, 5, 6 and 10 wherein compounds prepared have a methyl or ethyl side chain (n=1 or 2) represents a preferred process corresponding to a succession of steps designated A to F as explained hereinbelow.

The compounds of Formulas Ia, Ib, $I_{c-1}$ to $I_{c-7}$, $I_{c-1a}$, $I_d$, $I_e$, $I_f$ are all encompassed by Formula I and the compounds of Formulas $II_a$, $II_b$, $II_c$, $II_d$ and $II_e$ are all encompassed by Formula II.

Steps 1 to 4 also represent a novel process for preparing compounds of Formula $II_a$, $II_b$, $II_c$, all encompassed by Formula II.

It is therefore an object of the present invention to provide a method of counteracting histamine in warm-blooded animals by administering effective amounts of certain novel aromatic 1,4-oxazepinones, thiazepinones and diazepinones and sulfur analogs thereof as described hereinabove under "Field of Invention" and as defined under Formula I.

Another object is to provide pharmaceutical compositions containing suitable adjuncts for administration in the foregoing method of countering histamine.

Additional objects and advantages of the present invention will be apparent to one skilled in the art and others will become apparent from the following description of the best mode of carrying out the present invention and from the appended claims.

DETAILED DESCRIPTION OF THE INVENTION

The present invention encompasses the use of the novel diazepine, oxazepine and thiazepine derivatives set forth in Formula I in the method of counteracting histamine and in the pharmaceutical compositions described hereinbelow.

Charts I and II illustrate the preparation of all intermediates. R is never hydrogen.

Chart III illustrates reaction sequence for preparing end-products wherein R is other than hydrogen and n is 1 or 2.

Chart IV illustrates preparation of compounds having ethyl and propyl radicals-omega substituted by primary amine (—NH$_2$). R is never hydrogen.

Chart V illustrates methods of converting the omega-NH$_2$-substituted ethyl and propyl compounds to secondary and tertiary amines. This is an alternate method for preparing the ethyl-secondary and tertiary amines. R is never hydrogen.

Chart VI illustrates preparation of compounds wherein R is hydrogen.

Preparations 1–40 and 42–51 illustrate syntheses of compounds of Formulas IVa, IVb or provide certain starting materials therefor. Preparation 41 provides a starting material for an alternate process. See Chart VIII, Formula VI. Intermediates 1–78 (see also Table 1) illustrate preparation of compounds encompassed by Formula II, which are chemical intermediates substituted with haloalkyl, cyanoalkyl, or phthalimidoalkyl radicals. The compounds of Formula II are formed in the reaction mixture usually without isolation.

Charts VII and VIII illustrate the preparation of compounds of Formula I by novel alternate methods illustrated further in Examples 68b, 90 and 107 to 109.

Examples 1–152 (see also Table 2) illustrate preparation of compounds encompassed by Formula I. The scope of the invention is not limited by the preparations, intermediates and example, however.

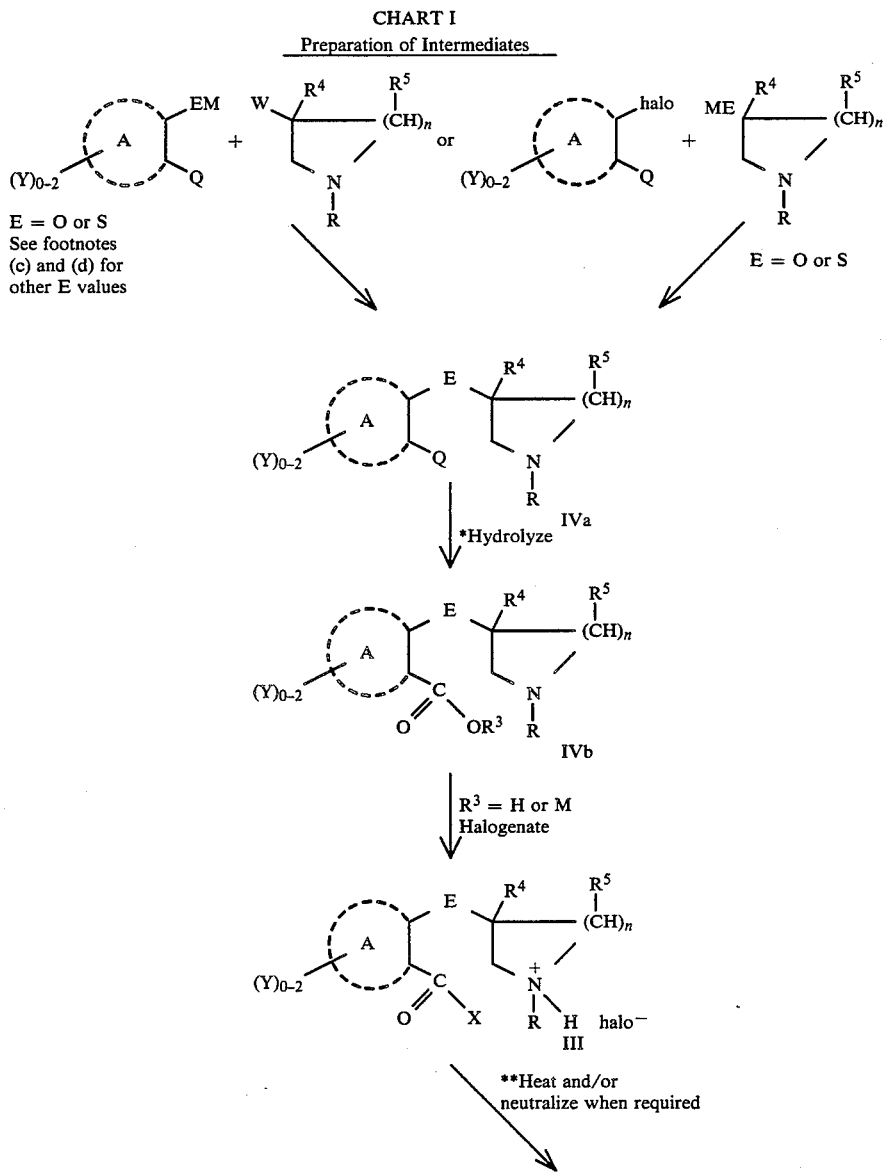

CHART I
Preparation of Intermediates

-continued

CHART I

Preparation of Intermediates

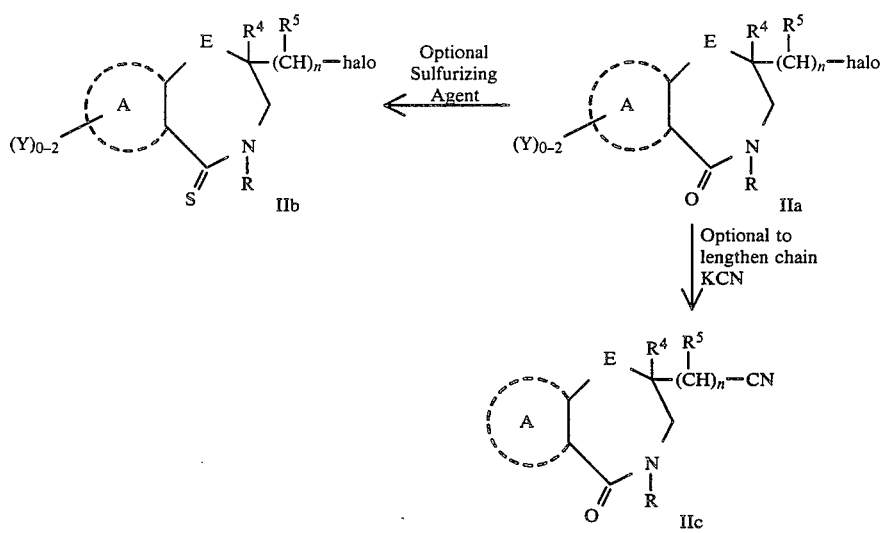

Footnotes (Chart I):

(a) R is never hydrogen.

(b) n = 1 or 2.

X = Halogen (Cl, Br)

W = Aryl sulfonate, alkyl sulfonate or X.

M = Acid neutralizing ion, e.g. alkali-metal

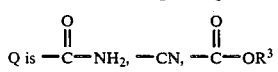

Q is $-\overset{O}{\underset{\|}{C}}-NH_2$, $-CN$, $-\overset{O}{\underset{\|}{C}}-OR^3$ where $R^3$ is H, M or esterifying radical.

*Hydrolyze when Q is other than $-\overset{O}{\underset{\|}{C}}-OH$ or $\overset{O}{\underset{\|}{C}}-OM$.

**Diagram illustrating the suggested formation and cleavage of bonds to effect rearrangement.

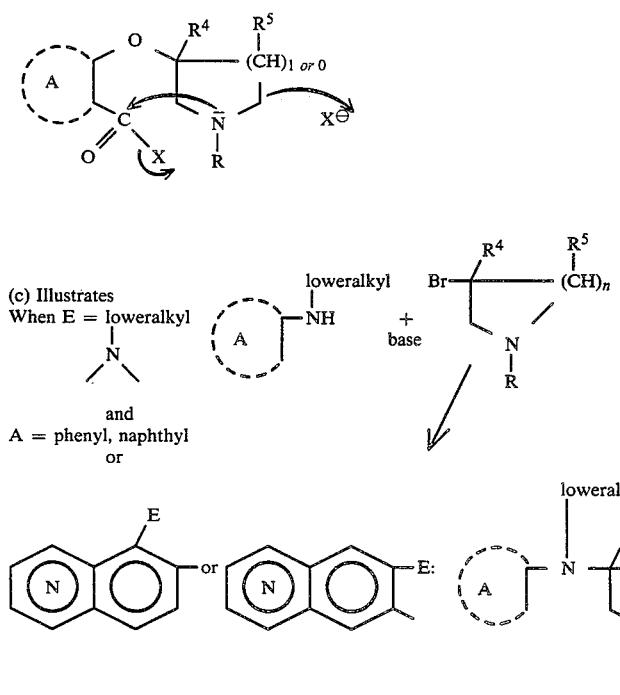

-continued
CHART I
Preparation of Intermediates
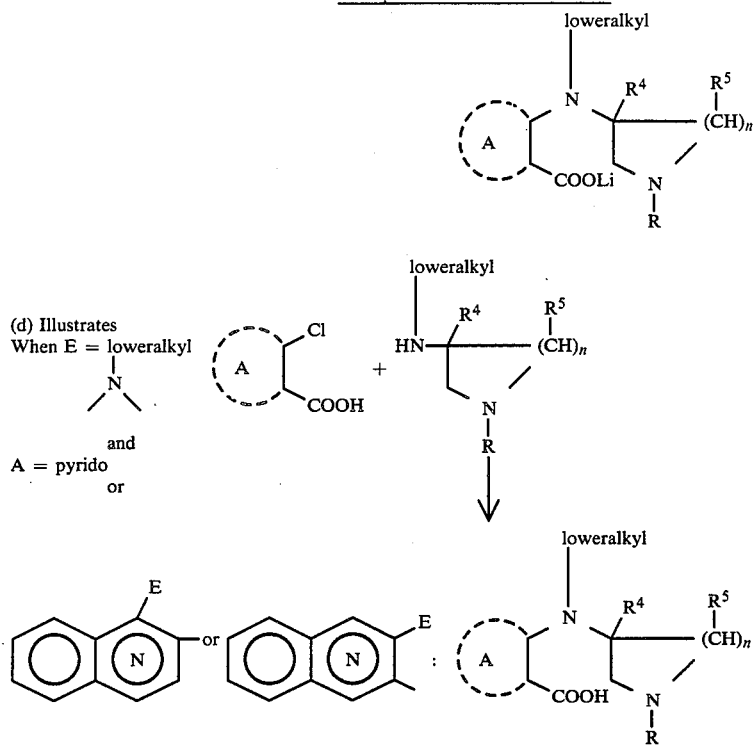
(d) Illustrates
When E = loweralkyl
and
A = pyrido
or
CHART II
Alternate Method of Preparing Pyrido Ring - Halogenated Intermediate[a]
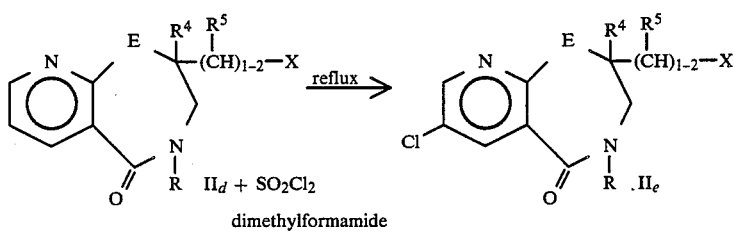
Footnotes:
X = Cl, Br, CN
E and R are as defined in Formula I
[a] n = 1 or 2
CHART III
Preparation of End Products
(n = 1 or 2; R = other than H)
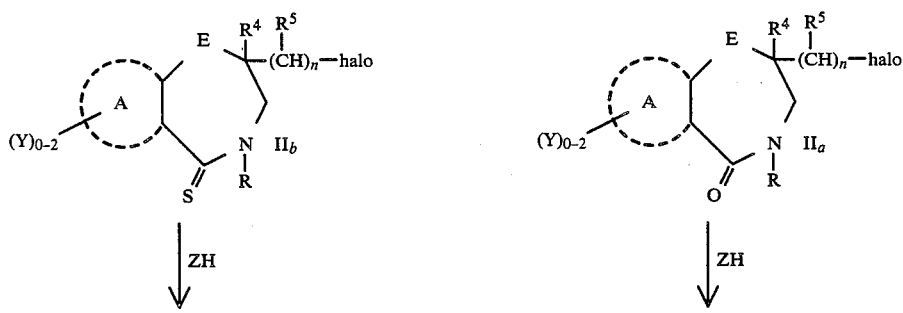

-continued
CHART III
Preparation of End Products
(n = 1 or 2; R = other than H)

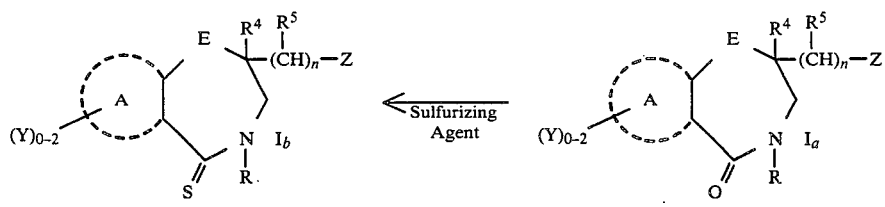

Footnote:
Z is as defined for n = 1 or 2 under Formula I.

CHART IV
Preparation of Primary Ethyl and Propyl Amino Compounds wherein R is other than Hydrogen from Cyano Intermediate

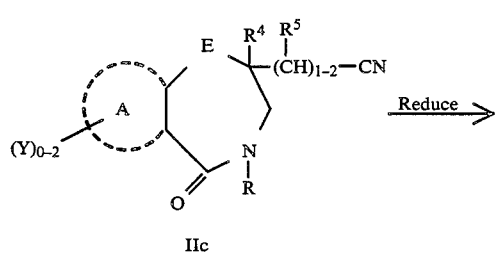

CHART VI
Preparation of Compounds Having Unsubstituted Azepine Nitrogen (R = H)

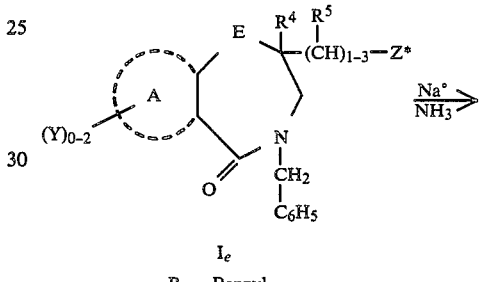

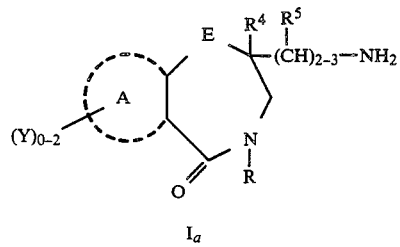

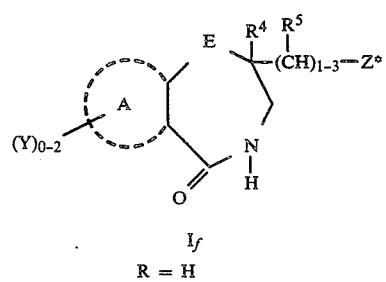

Footnote:
*Z cannot be a primary or secondary amine.

CHART V
Additional Preparations of Secondary and Tertiary Amino-alkyl Compounds wherein R is other than H[a]

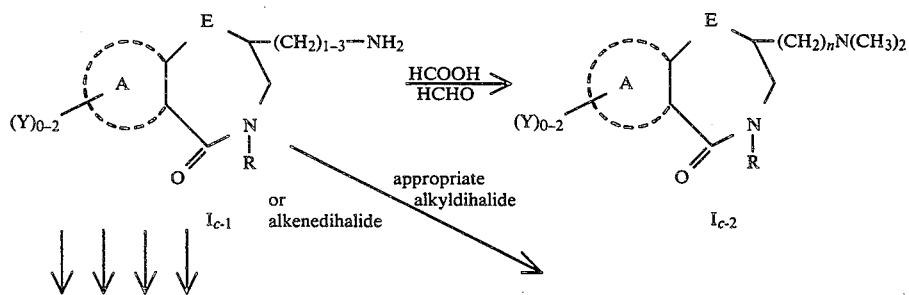

-continued
CHART V

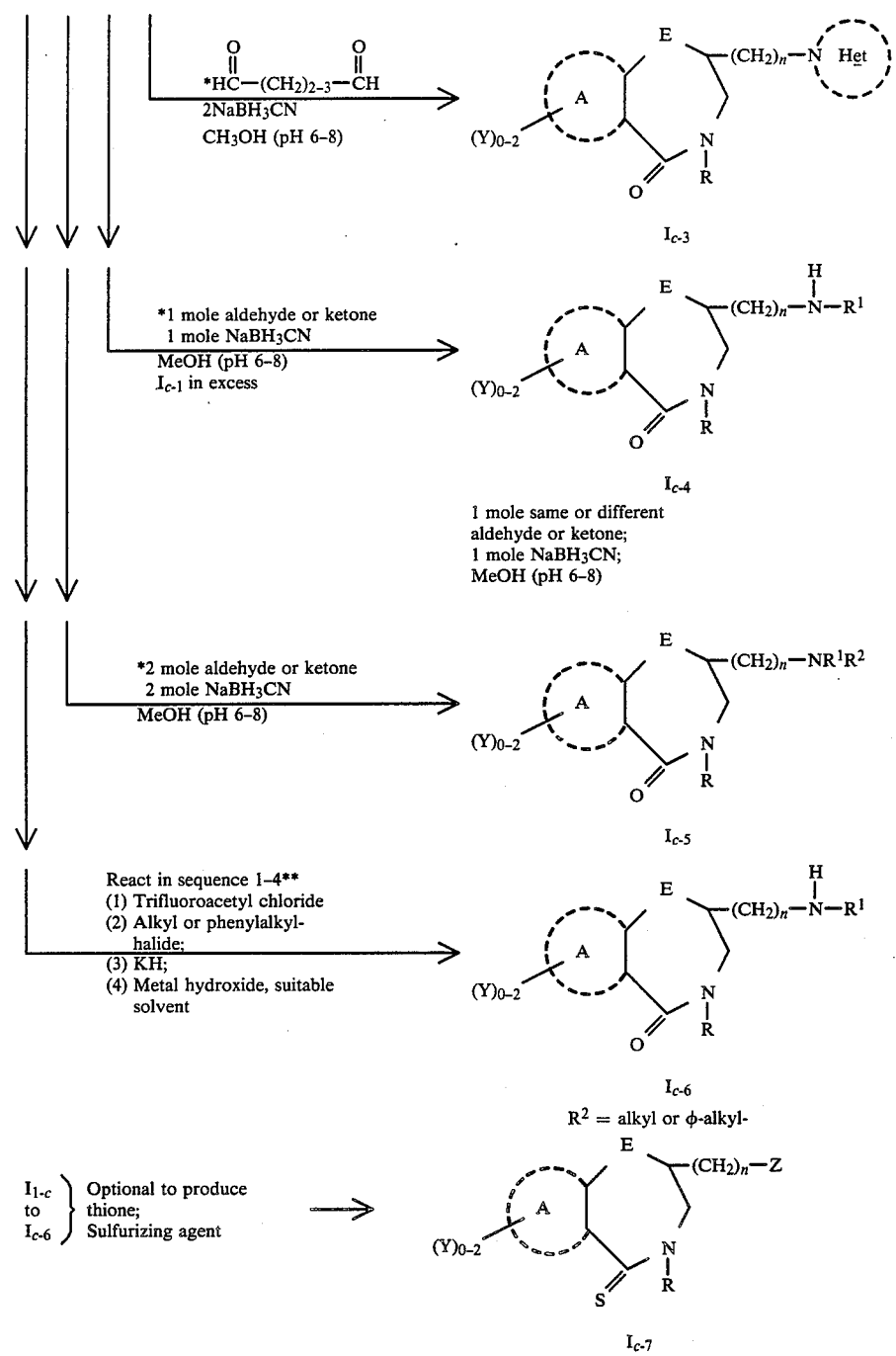

Footnotes:
(a)Illustrated for $R^4$ and $R^5$ = H and is applicable for $R^4$ and/or $R^5$ = loweralkyl (1-5c).
n = 1-3
*Method described by R. F. Borch, et al,. J. Amer. Chem. Soc. 93, 2897 (1971).
Illustration of reaction of a compound of Formula $I_{c-1}$ wherein Z is $NH_2$ with aldehydes and ketones follows:

| | Reactant | Z—Radical Produced |
|---|---|---|
| (1) | 1 mole acetaldehyde<br>1 mole $NaBH_3CN$<br>excess primary amine<br>(Z = $NH_2$) | —$NHC_2H_5$ |
| (2) | 1 mole acetone<br>1 mole $NaBH_3CN$ | —$NHCH(CH_3)_2$ |
| (3) | 1 mole benzaldehyde<br>1 mole $NaBH_3CN$<br>excess primary amine | —$NHCH_2C_6H_5$ |

-continued
CHART V
(Z = NH₂)
(4) 1 mole cyclohexanone         —NHC₆H₁₁
    1 mole NaBH₃CN
(5) 2 mole acetaldehyde          —N(C₂H₅)₂
    2 mole NaBH₃CN
(6) 1 mole acetaldehyde
    1 mole NaBH₃CN
    excess primary amine
    (Z = H)                      } —N(CH₃)C₂H₅
    followed by
    1 mole formaldehyde
    1 mole NaBH₃CN
**J. E. Norlander et al., Tetrahedron Letters 1978 (50) pp 4987–4990.
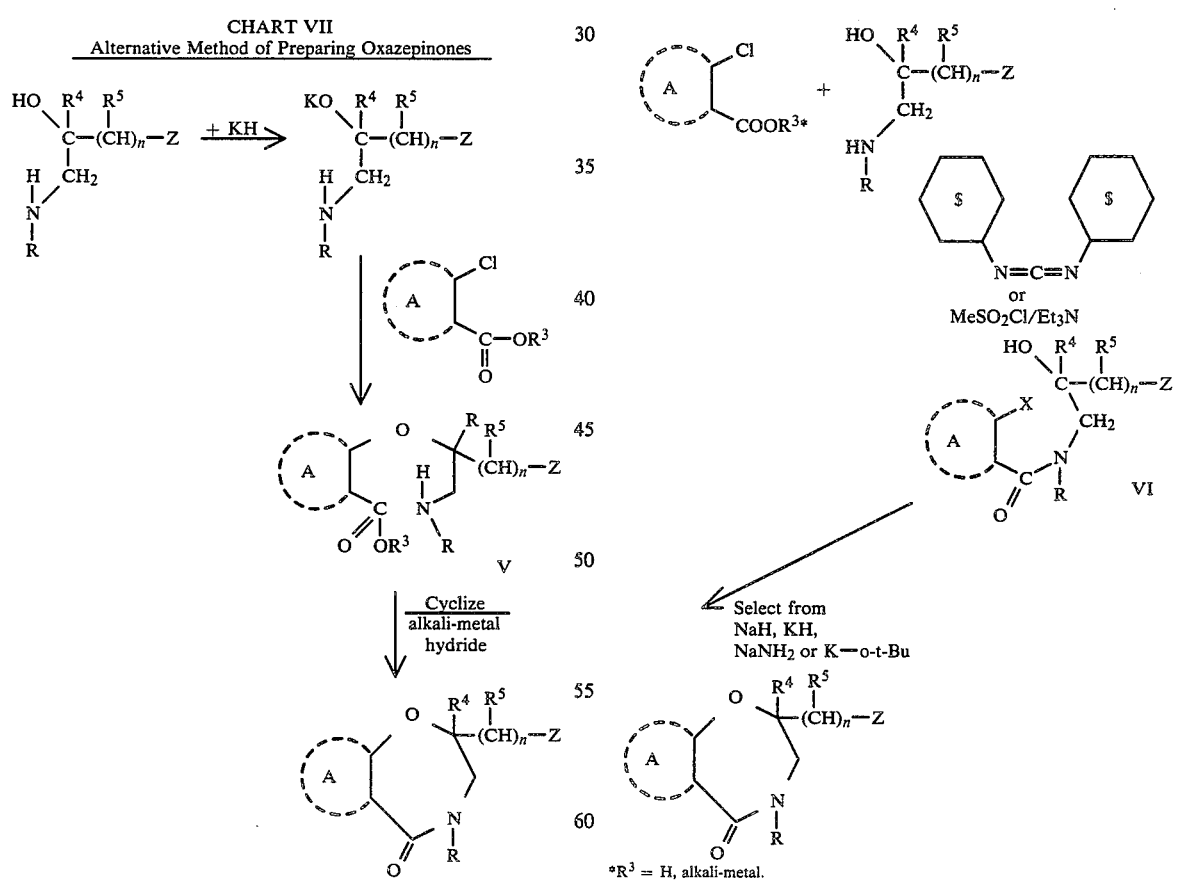

CHART IX
Synthetic Preparation of Enantiomers using Resolved Chemicals

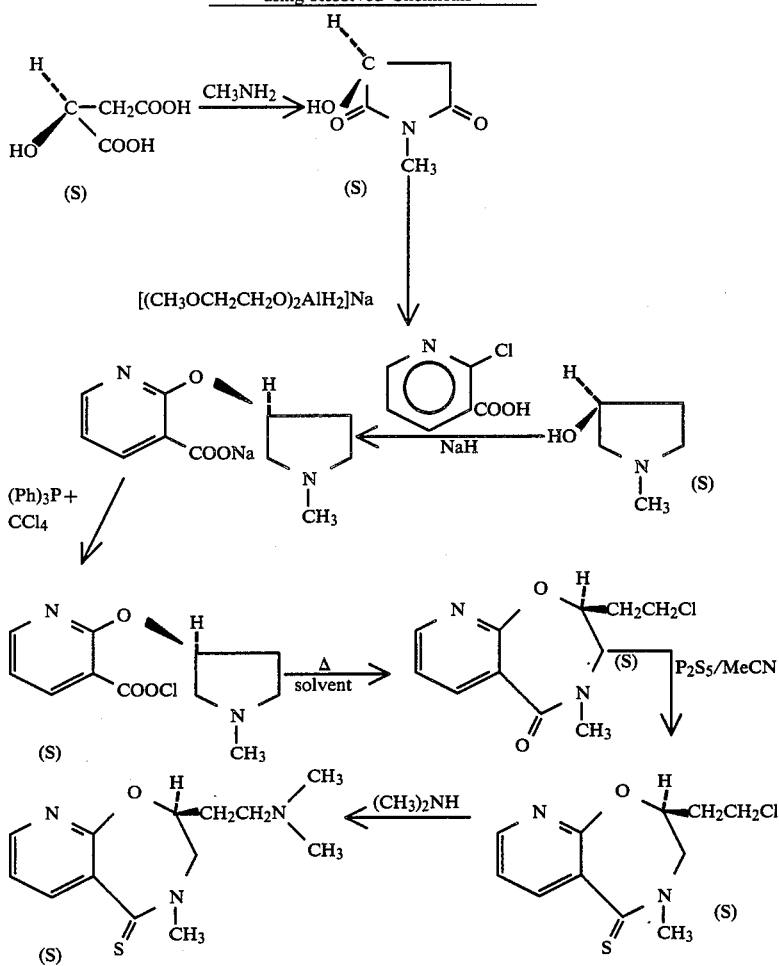

(a) Equations show (S) configuration;(R) configured chemicals lead to the other enantiomers.

Compounds of Formulas I and II have a chiral center in the oxazepine, thiazepine or diazepine moiety at the site of the carbon carrying the side-chain and therefore there is potential for separation of the enantiomers (optical isomers) or for synthesis of the enantiomers using already resolved starting chemicals or chemical intermediates. Such a synthesis for n=2 using resolved chemicals is outlined in Chart IX. Thus, by way of further amplification of possible methods of preparation of enantiomers of Formula I and II, one or more of the following procedures may be involved:

(a) resolving a racemic mixture of a compound of Formula I or II using optically active acids and separating the salts;

(b) preparing optically active compounds of Formula I from optically active compounds of Formula II prepared in (a) preceding, (c) or (d) following;

(c) starting the synthesis with known optically active enantiomers, for example, (S) or (R) malic acids illustrated in Chart IX. The method is suitable only when the E to carbon bond is not broken; and (d) resolving one of the precursors of compounds of Formula II and proceding with the synthesis illustrated in Chart IX.

Preparation of enantiomers of compounds of Formula I and II were demonstrated by combinations of procedures (b), (c), and (d), see Preparations, 42-47, Intermediates 65-67 and Examples 125 and 126.

One of the intermediates, (S)-1-methyl-3-pyrrolidinol, was synthetized with retention of optical purity as shown in Chart IX starting with (S)-malic acid. The (S)-1-methyl-3-pyrrolidinol was shown to be dextrorotatory. As an alternative method of obtaining the resolved isomers of 1-methyl-3-pyrrolidinol, the racemic mixture was treated with (2S,3S)-tartaric acid in methanol. The resulting crystals, after one recrystallization, were converted to the base. This base was the dextrorotatory (S)-1-methyl-3-pyrrolidinol identical to that produced from (S)-malic acid.

The levorotatory (R)-1-methyl-3-pyrrolidinol was made in the same manner using (2R,3R)-tartaric acid.

The synthesis illustrated in Chart IX was carried out on both the R and S isomers using the resolved 1-methyl-3-pyrrolidinols as the starting material.

The lack of racemization at each step was demonstrated with NMR spectra by use of the optically active shift reagent technique. In each intermediate and the final product, it was demonstrated that both optical isomers could be seen in the racemic mixture; however, none of the opposing isomers were detected in any of the resolved compounds.

The enantiomer active agent (Example 126):

(R)-2-[2-(dimethylamino)ethyl]-2,3-dihydro-4-methyl-pyrido[3,2-f]-1,4-oxazepine-5(4H)-thione
is primarily responsible for the activity of the racemic mixture (active agent of the compound of Example 12), at low dosage being considerably more potent than the corresponding (S) isomer (active agent of Example 125).

In reference to the processes and the process steps of the invention summarized above as they apply to the preparation of compounds of Formulas I, II and III, the following further description is applicable.

In step 1, starting compounds of Formula $IV_b$ (See Chart I) bearing a carboxylic acid or an acid neutralizing ion such as an alkali-metal salt thereof on the A ring ortho to the ether linkage as a substantially pure entity or preferably derived in a reaction mixture resulting from hydrolysis of precursors bearing in the same ortho position, carbamoyl, cyano or carboxylic acid ester functions without substantial isolation of the carboxylic acid (or salt) compound from the reaction mixture, are treated with any suitable halogenating agent such as are described above, preferably thionyl chloride or triphenyl phosphine and carbon tetrachloride. The halogenation is conducted in any suitable organic solvent, preferably a refluxing organic solvent or a refluxing halogenating agent such as the preferred thionyl chloride. Temperatures for the cholrination over a wide range may be employed, for example, from room temperature to 100° C. or above; however, temperatures of 50°–80° C. are preferred, which temperatures encompass that of refluxing chloroform or thionyl chloride. When excess halogenating agent such as thionyl chloride has been used as carrier, it is advantageously evaporated. When solvent such as chloroform is used, it may, but not necessarily, be evaporated away. In any event a solution comprising a solvent and compounds of Formula III or a residue comprised of Formula III compounds, all of which are confirmed by infra-red analysis is available for use in the next step.

In step 2, the halogenated compounds of Formula III, prepared in step 1, if not already in a solvent, are solubilized with organic solvent, preferably chloroform and usually neturalized or basified preferably with a tertiary amine such as triethyl amine, and then heated at a temperature and for a time sufficient to effect a fusion of the carbonyl with the basic nitrogen and cleavage of the cyclic amine and formation of the chloro or bromoalkyloxazepinone, thiazepinone or diazepinone compounds of Formula IIa. If the tendency to fuse is sufficiently great, the neutralization of basification may be eliminated. The Formula IIa compounds may be isolated by conventional means, for example, by partitioning between a suitable organic solvent or mixture of solvents and aqueous acid or base followed by drying and evaporating the organic layer and recrystallizing the residue from a suitable solvent.

In step 3, the compounds of Formula IIa may optionally be converted to the oxazepinethione, thiazepinethione or diazepinethione (IIb) by heating together with sulfurizing agent in a suitable organic solvent such as toluene acetonitrile. The thione (IIb) may be isolated by conventional means, preferably by partitioning between an organic solvent and dilute alkali metal base and crystallizing from a suitable solvent such as ethanol.

In step 4, an oxazepinone, thiazepinone or diazepinone (IIa) is reacted with potassium cyanide in a hot protic solvent using a phase transfer catalyst such as tetrabutyl ammonium bromide. The resulting cyano compound is then extracted into a suitable solvent such as ethyl acetate, and the solution dried and evaporated. The residue is then recrystallized from suitable solvent such as a mixture of ethyl acetate and isopropyl ether or ethyl acetate alone. As will be realized, the compounds produced have cyano-methyl and cyano-ethyl side chains (n=1 or 2) which lead to side chain lengthening to amino propyl n=3 or as an alternate starting material for lengthening of a methyl chain to amino ethyl.

In step 5, the oxazepinone, thiazepinone (IIa) or diazepinone obtained in step 2 or the oxazepinethione and thiazepinethione (IIb) or diazepinethione obtained in step 3 are reacted with pyrazole, imidazole or with an amine of the formula $NHR^1R^2$ wherein $R^1$ and $R^2$ have the value given under Formula I above to give compounds of Formulas Ia and Ib, respectively. The latter reaction is preferably conducted in excess amine as in the instance of volatile methylamines. The free bases of products of Formula Ia and Ib are isolated by conventional means by removing volatiles and partitioning between dilute aqueous alkali metal base and a solvent such as chloroform or methylene chloride followed by evaporation. The free base may be converted to a pharmaceutically acceptable salt with an appropriate acid and in the case of a quaternary salt with a loweralkyl halide or sulfate and recrystallized by conventional means. The free bases may be recovered from the acid addition salts, usually in a purer form, by again partitioning the salt between aqueous base and a suitable solvent followed by evaporation. As will be realized and as shown in Chart I, the side chain of the intermediate produced is limited to aminomethyl and aminoethyl (n=2).

In step 6, when it is desirable, a compound prepared in step 5 where B is oxygen is sulfurized, preferably by refluxing in dry pyridine with phosphorus pentasulfide for several hours. The resulting thione is isolated by cooling the solution and partitioning between a suitable solvent such as chloroform and an aqueous base and evaporating the organic phase and isolating by conventional means.

In step 7, a cyano compound (IIc) prepared in step 4 which is a diazepinone, an oxazepinone or a thiazepinone is reduced, preferably with hydrogen using Raney nickel catalyst at about 60° C. The primary aminoethyl or aminopropyl compound (n=2 or 3) produced is isolated by conventional means, preferably as an acid addition salt which may be converted back to the free base by partitioning between a suitable solvent and aqueous base and thereafter drying and evaporating the organic layer.

In step 8 (see Chart V), a primary amine is converted to a secondary or tertiary amine by a choice of reactants. The method provides a route to secondary and tertiary amino compounds of Formula I having n=3 not afforded by step 5 and, in addition, provides an alternate route to secondary and tertiary amino compounds of Formula I wherein n=1 or 2. The preparation of dimethylamino derivatives by reaction of primary amine with formaldehyde and formic acid is a conventional method for preparing tertiary dimethyl amines as is reaction of a dihalide to give a heterocyclic amine such as 1-pyrrolidino, piperidino or 4-morpholino. The alternatives employing sodium cyanoborohydride follow the procedures described by R. F. Borch et al, J. Amer. Chem. Soc. 93, 2897 (1971). The procedure which employs conversion to a trifluoroacetamide is described by J. E. Norlander et al, Tetrahedron Letters, 1978 (50) pp 4987–4990.

In step 9, a 4-benzyloxazepinone, 4-benzyl-thiazepinone or 4-benzyldiazepinone derivative (R=Benzyl) under Formula I excluding primary or secondary amines is converted to the corresponding N-unsubstituted (R=H) oxazepinone, thiazepinone or diazepinone by reaction with sodium and ammonia and may be isolated as illustrated in Example 68.

Step 10 is optional depending on whether the compound of Formula I is already in the form of a pharmaceutically acceptable salt or whether it is desirable to convert to another salt or whether the free base is desired. To obtain the free base from any addition salt of Formula I, the salt is partitioned between a suitable organic solvent such as chloroform and a dilute aqueous base. The organic layer is dried and condensed to give the free base which is then, if desired, reacted with an acid described above to give the desired salt.

As mentioned above, the preferred steps for reaching the preferred compounds having an ethyl side chain in the 2-position include steps 1 to 3, 5, 6 and 10 of the general process for preparing all the compounds of Formula I. Inasmuch as the compounds having a methyl side chain can be made by the same process, compounds wherein n=1 are included in the preferred process. These steps of a preferred process are designated A to F corresponding to the numbered steps of the general process with the limitation that n=1 or 2 and R is other than hydrogen as follows:

| Preferred Process Step Designation | Corresponding General Step Number with Description Pertaining to n = 1 or 2 |
| --- | --- |
| A | 1 |
| B | 2 |
| C | 3 |
| D | 5 |
| E | 6 |
| F | 10 |

Compounds of Formula I wherein E is O or S are preferred because of their potency as antihistamines based on test comparisons made.

PREPARATION 1

2-(1-Benzyl-3-pyrrolidinyloxy)benzamide

To a susepnsion of 4.3 g (0.11 mole) of sodium amide in 60 ml of dry toluene was added to 19.3 g (0.11 mole) of 1-benzyl-3-pyrrolidinol at a rate to maintain a temperature of 35° C. Stirring was continued at room temperature for 3 hours. To the mixture was added at rapid drop 19 g (0.1 mole) of o-toluenesulfonyl chloride with ice bath cooling to maintain a temperature of 20°–30° C. Stirring was continued at room temperature for 2.5 hours and the mixture allowed to stand overnight. The toluene was washed twice with water, dried with sodium sulfate and concentrated.

To a suspension of 5.4 g (0.1 mole) of sodium methoxide in 50 ml of dimethylformamide in another vessel was added 13.6 g (0.1 mole) of salicylamide in 75 ml of dimethylformamide at a rate to maintain a temperature of 50° C. After stirring 15 minutes, the above prepared sulfonate in 25 ml of dimethylformamide was added dropwise and the solution refluxed 5 hours. The material was partitioned between 500 ml of ethyl acetate and 500 ml of water. The ethyl acetate was extracted with dilute hydrochloric acid, the acid basified with dilute sodium hydroxide and extracted with ethyl acetate. The organic layer was dried, concentrated, and the residue crystallized twice from isopropyl ether-ethyl acetate. Yield of product was 12.5 g (42%), m.p. 120.5°–122° C.

Analysis: Calculated for $C_{18}H_{20}N_2O_2$: C, 72.95; H, 6.80; N, 9.46. Found: C, 73.23; H, 6.78; N, 9.56.

PREPARATION 2

2-(1-Methyl-3-pyrrolidinyloxy)benzamide to 85.6 g (2.2 moles) of sodium amide in 1.5 liter of dry toluene was added 202 g (2 moles) of 1-methyl-3-pyrrolidinol so as not to exceed a temperature of 50° C. The mixture was then heated to 70° C. for 4.5 hours. The mixture was cooled and 381 g (2 moles) of o-toluenesulfonylchloride was added at a rapid drop while maintaining a temperature of 20°–30° C. with an ice bath. The mixture was stirred at room temperature for 2.5 hours and washed with water. The toluene solution was dried with sodium sulfate and concentrated. The residue, dissolved in 500 ml of dimethylformamide, was added to a reaction mixture prepared by adding 119 g (2.2 moles) of sodium methoxide and 274 g (2.0 moles) of salicylamide to one liter of dimethylformamide and the mixture was worked up as in preparation 1. Yield of product was 170 g (38%), m.p. 116°–118° C.

Analysis: Calculated for $C_{12}H_{16}N_2O_2$: C, 65.43; H, 7.32; N, 12.72. Found: C, 65.28; H, 7.28 N, 12.77.

PREPARATION 3

2-[3-(1-Benzyl)pyrrolidinyloxy]benzoic acid

To a solution of 20.3 g (0.52 mole) of sodium hydroxide in 600 ml of ethanol and 400 ml of water was added 150 g (0.51 mole) of 2-[3-(1-benzyl)pyrrolidinyloxy]benzamide and the mixture was stirred at reflux for 48 hours. The mixture was concentrated on the rotary evaporator to one-half volume and the residue was extracted with ethyl acetate to remove unreacted amide. The water layer was filtered and the pH of the filtrate adjusted to 6.5 with hydrochloric acid. The filtrate was concentrated on the rotary evaporator. The residue was dissolved in isopropyl alcohol. The resulting mixture was filtered and the filtrate concentrated. The residue 85.7 g was comprised substantially of the title compound.

PREPARATION 4

3-[(1-Methyl-3-pyrrolidinyl)oxy]-2-naphthalenecarboxamide

To a cooled solution of 68 g (0.67 mole) of 1-methyl-3-pyrrolidinol and 74 g (0.73 mole) triethylamine in 700 ml of dry benzene was added dropwise 74 g (0.63 mole) of methanesulfonyl chloride. After stirring at room temperature for 45 min, the mixture was filtered and the filtrate concentrated under reduced pressure and dissolved in 100 ml of dimethylformamide.

To a cooled suspension of 10.8 g (0.45 mole) of sodium hydride in 75 ml of dimethylformamide in another vessel, 84 g (0.45 mole) of 3-hydroxy-2-naphthalenecarboxamide dissolved in 400 ml of dimethylformamide was added dropwise. The above prepared sulfonate solution was added dropwise and the reaction mixture stirred and heated at reflux for 16 hr. The cooled solution was diluted with 1000 ml of water and extracted twice with 500 ml portions of chloroform. The chloroform was washed with water and extracted twice with 500 ml portions of 3N hydrochloric acid. The aqueous extracts were made alkaline with 50% sodium hydroxide and extracted thrice with 500 ml portions of chloroform. After drying over magnesium sulfate, the chloroform was evaporated under reduced pressure affording 27.4 g (22%) of a pale yellow solid. Recrystallized from ethyl acetate, m.p.=128°-130° C.

Analysis: Calculated for $C_{16}H_{18}N_2O_2$: C, 71.09; H, 6.71; N, 10.36. Found: C, 70.88; H, 6.68; N, 10.37.

PREPARATION 5

3-[(1-Methyl-3-pyrrolidinyl)oxy]-2-naphthalenecarboxylic acid oxalate [2:1]

To a solution of 21.6 g (0.54 mole) of sodium hydroxide in 500 ml of water was added 74 g (0.27 mole) of 3-[1-methyl-3-pyrrolinyl)oxy]-2-naphthalenecarboxamide. The solution was heated at reflux for 16 hrs and on cooling, the pH was adjusted to 6.8 with concentrated hydrochloric acid. The resultant solid was separated by filtration and the pH of the filtrate was adjusted to 6.02. The filtrate was concentrated under reduced pressure and the residue boiled in 200 ml of isopropyl alcohol and filtered. The filtrate was again concentrated under reduced pressure to give 69 g (94%) of an amorphous solid. An aliquot was dissolved in isopropanol and treated with oxalic acid. The oxalate salt was recrystallized from ethanol/water, m.p. 209°-212° C.

Analysis: Calculated for $C_{17}H_{18}NO_5$: C, 64.55; H, 5.74; N, 4.43. Found: C, 63.86; H, 5.68; N, 4.37.

PREPARATION 6

Sodium 2-[(1-methyl-3-pyrrolidinyl)oxy]-3-pyridinecarboxylate

To a stirred suspension of 6.4 g (0.13 mole) of 50% sodium hydride (mineral oil) in 50 ml of dimethylsulfoxide was added dropwise 6.4 g (0.063 mole) of 1-methyl-3-pyrrolidinol. During addition, the temperature rose from 25° C. to 31° C. After 10 minutes, a solution of 10 g (0.063 mole) of 2-chloronicotinic acid in 50 ml of dimethylsulfoxide was added dropwise causing the temperature to rise. When the temperature reached 55° C., it was maintained there by the intermittent use of an ice bath until addition was complete. The mixture was then heated to 55°-60° C. for 1.5 hr., cooled and filtered. The filter cake was suspended in 100 ml of ethyl acetate and filtered. The solid was recrystallized from ethyl acetatemethanol. Yield of product was 5 g., dec. 240° C. The NMR analysis showed that the compound contained ⅓ mole of sodium acetate as impurity.

Analysis: Calculated for $C_{11}H_{13}N_2O_3Na\cdot\tfrac{1}{3}C_2H_3O_2Na$: C, 51.62; H, 5.20; N, 10.32. Found: C, 51.81; H, 5.15; N, 10.39.

PREPARATION 7

4-Chloro-2-[(1-methyl-3-pyrrolidinyl)oxy]benzamide

To a solution of 55.5 g (0.55 mole) of triethylamine in 500 ml of dry benzene was added dropwise 50.5 g (0.50 mole) of 1-methyl-3-pyrrolidinol at such a rate as to maintain a temperature of 25°-35° C. To the mixture, maintained at 20°-50° C., was added dropwise, 57 g (0.50 mole) os methanesulfonyl chloride. After stirring for 1 hr at room temperature, the mixture was filtered and the precipitate washed with 250 ml of hot benzene. The filtrate and wash were combined and concentrated under reduced pressure and the residue dissolved in 200 ml dimethylformamide.

To a cooled suspension of 19.6 g (0.41 mole) of sodium hydride in 100 ml of dimethylformamide in another vessel was added dropwise a solution of 70 g (0.41 mole) of 4-chlorosalicylamide in 200 ml dimethylformamide at a rate such as to maintain a temperature of 20° C. To the resulting reaction mixture was added dropwise the above-prepared sulfonate salt and the mixture was heated at reflux for 19 hrs. The reaction mixture was cooled and diluted with one liter of water. The diluted mixture was extracted three times with 300 ml portions of chloroform. The chloroform extracts were combined and extracted with two 500 ml portions of 3N hydrochloric acid. The combined aqueous extract was made alkaline with 50% sodium hydroxide and extracted three times with 500 ml portions of ethyl acetate. The combined ethyl acetate extract was dried over magnesium sulfate and concentrated under reduced pressure to give 46.5 g (45%) beige solid. The solid was recrystallized from ethyl acetate, m.p. 122°-123° C.

Analysis: Calculated for $C_{12}H_{15}N_2ClO_2$: C, 56.58; H, 5.94; N, 10.99. Found: C, 56.48; H, 5.96; N, 10.84.

PREPARATION 8

5-Bromo-2-[(1-methyl-3-pyrrolidinyl)oxy]benzamide

To a cooled solution of 101 g (1.0 mole) 1-methyl-3-pyrrolidinol, 111 g (1.1 mole) triethylamine in 1000 ml of dry benzene was added dropwise 114 g (1.0 mole) of methanesulfonyl chloride. The reaction mixture was stirred at room temperature for 1 hour and filtered. The filtrate was concentrated under reduced pressure and dissolved in 100 ml dimethylformamide.

To a cooled suspension of 30 g (0.63 mole) sodium hydride in 100 ml dimethylformamide in another vessel was added dropwise 5-bromosalicylamide (137 g, 0.63 mole) dissolved in 750 ml of dimethylformamide. The above prepared sulfonate was added dropwise and the reaction mixture heated at reflux for 18 hrs. The cooled solution was diluted with 1000 ml of water and extracted thrice with 500 ml portions of chloroform. The chloroform extracts were washed with water and extracted four times with 500 ml portions of 3N hydrochloric acid. The aqueous layer was made alkaline with 50% sodium hydroxide and extracted with chloroform. The chloroform extracts were washed with water, dried over magnesium sulfate and evaporated under reduced pressure to give 52 g (28%) of a yellow solid. The solid was recrystallized from ethyl acetate/chloroform, m.p. 160°-162° C.

Analysis: Calculated for $C_{12}H_{15}N_2BrO_2$: C, 48.18; H, 5.05; N, 9.36. Found: C, 48.02; H, 5.01; N, 9.22.

PREPARATION 9

5-Chloro-2-[(1-methyl-3-pyrrolidinyl)oxy]benzamide hemihydrate

To a cooled suspension of 2.4 g (0.41 mole) sodium hydride in 50 ml of dimethylformamide was added dropwise 17 g (0.1 mole) of 5-chlorosalicylamide dissolved in 50 ml of dimethylformamide at a rate such that the temperature did not exceed 20° C. After addition of the salicylamide was complete, 16.7 g (0.1 mole) of 3-bromo-1-methylpyrrolidine dissolved in 50 ml of dimethylformamide was added dropwise. The reaction mixture was stirred and heated at reflux for 19 hr. The cooled solution was diluted with 250 ml of water and extracted twice with 250 ml portions of chloroform. The chloroform was extracted thrice with 500 ml portions of 3N hydrochloric acid. The aqueous extracts were made alkaline with 50% sodium hydroxide and extracted with ethyl acetate. Drying over magnesium sulfate and evaporation of the ethyl acetate under reduced pressure gave 6 g (23%) of product as a beige solid. The solid was recrystallized from ethyl acetate, m.p. 126°–128° C.

Analysis: Calculated for $C_{24}H_{32}N_4Cl_2O_5$: C, 54.65; H, 6.11; N, 10.62. Found: C, 54.87; H, 6.12; N, 10.69.

PREPARATION 10

1-[(1-Methyl-3-pyrrolidinyl)oxy]-2-naphthalene carboxamide

A solution of 118 g (0.63 mole) of 1-hydroxy-2-naphthalenecarboxamide in 250 ml of dimethylsulfoxide was added dropwise to a suspension of 27.6 g (0.69 mole) of 50% sodium hydride (mineral oil) in 250 ml of dimethylsulfoxide. The reaction was exothermic and the temperature rose to 60° C.

In another vessel, 79 g (0.69 mole) of methanesulfonylchloride was added dropwise to a solution of 69.7 g (0.69 mole) of 1-methyl-3-pyrrolidinol and 77 g (0.76 mole) of triethylamine in 500 ml of dry benzene while cooling with an ice bath. The mixture was stirred 15 minutes and filtered. The filter cake was washed with 500 ml of benzene and the benzene filtrates were combined and concentrated on the rotary evaporator to about 200 ml. The residue was added dropwise to the above prepared dimethylsulfoxide solution containing the sodium salt of 1-hydroxy-2-naphthalenecarboxamide while stirring at 75° C. The temperature was maintained at 75° C. for 18 hr with external heat. The resulting solution was cooled and an equal volume of water was added. The mixture was extracted with three portions of chloroform. The washes were combined and concentrated. The residue was partitioned between ethyl acetate and dilute hydrochloric acid. The acid layer was made basic with sodium hydroxide and extracted twice with ethyl acetate. The ethyl acetate washes were combined, dried over sodium sulfate and concentrated. The residue was crystallized from ethyl acetate-isooctane. Yield of solid was 55 g (32%). A portion was recrystallized twice from ethyl acetate-isooctane, m.p. 122°–129° C.

Analysis: Calculated for $C_{16}H_{18}N_2O_2$: C, 71.11; H, 6.71; N, 10.36. Found: C, 70.96; H, 6.71; N, 10.31.

PREPARATION 11

5-methoxy-2-[(1-methyl-3-pyrrolidinyl)oxy]benzamide

To a solution of 151 g (1.5 mole) 1-methyl-3-pyrrolidinol and 166 g (1.6 mole) triethylamine in 1500 ml of dry benzene was added dropwise 171 g (1.5 mole) of methanesulfonyl chloride with cooling. The reaction mixture was stirred at room temperature for one hour and filtered. The filtrate was concentrated under reduced pressure to give an orange-colored oil.

In another vessel, to a suspension of 50% sodium hydride/mineral oil (72 g; 1.5 mole) in 150 ml dimethylformamide the sulfonate prepared above and 139 g (0.93 mole) of 5-methoxy salicylamide dissolved in 600 ml dimethylformamide were added dropwise with cooling. The reaction mixture was heated at reflux for 14 hr. After cooling, the reaction was diluted with 1000 ml of water and extracted three times with 700 ml portions of chloroform. The combined chloroform extracts were washed thrice with water and extracted thrice with 500 ml portions of 3N hydrochloric acid. The aqueous layer was made alkaline and extracted with chloroform. The chloroform extracts were washed thrice with water, dried over magnesium sulfate and evaporated under reduced pressure to give a viscous brown oil. Vacuum distillation of this material yielded a viscous orange oil which was dissolved in chloroform, extracted in acid; made alkaline and extracted into chloroform again. Evaporation of the solvent gave a dark brown oil which solidified under reduced pressure. Three recrystallizations from ethyl acetate gave 10 g of white crystals (4%), m.p. 85°–87° C.

Analysis: Calculated for $C_{13}H_{18}N_2O_3$: C, 62.38; H, 7.25; N, 11.19. Found: C, 62.47; H, 7.26; N, 11.20.

PREPARATION 12

3-[(1-Methyl-3-pyrrolidinyl)oxy]-4-pyridinecarbonitrile fumarate [1:2]

A solution of 55 g (0.55 mole) of 1-methyl-3-pyrrolidinol in 55 ml of dry dimethylformamide was added dropwise to a suspension of 22 g (0.58 mole) of 60% sodium hydride/40% mineral oil in 300 ml of dimethylformamide. The mixture was stirred at room temperature for one hour and 73 g (0.53 mole) of 3-chloro-4-cyanopyridine in 200 ml of dimethylformamide was added dropwise with mild cooling to maintain a temperature of 30°–40° C. The solution was stirred 3 hours and an equal volume of water added. The solution was made acidic with dilute hydrochloric acid and extracted with isopropyl ether. The aqueous layer was made basic with sodium hydroxide and extracted 5 times with chloroform. The extracts were combined, dried over sodium sulfate and concentrated. The residue was treated with 50 g of fumaric acid in 400 ml of isopropyl alcohol and 40 ml of water. The resulting crystals (51 g; 21%) were collected. A 2 g sample was recrystallized from methyl isobutyl ketone. Yield of product was 1.5 g, m.p. 172°–174° C.

Analysis: Calculated for $C_{19}H_{21}N_3O_9$: C, 52.42; H, 4.86; N, 9.65. Found: C, 52.40; H, 4.90; N, 9.68.

PREPARATION 13

1-[(1-Methyl-3-pyrrolidinyl)oxy]-2-naphthalenecarbonitrile oxalate

A solution of 29 g (0.11 mole) of 1-[(1-methylpyrrolidinyl)oxy]-2-naphthalenecarboxamide and 38 g (0.32 mole) of thionyl chloride in 150 ml of chloroform was heated to reflux for 6 hr. The solution was poured into ice and made basic with sodium hydroxide. The chloroform layer was separated, dried over sodium sulfate and concentrated. The residue was dissolved in hot isooctane. The solution was treated with charcoal, filtered and concentrated. The residue was dissolved in isopropyl alcohol and oxalic acid was added. The precipitate was recrystallized from isopropyl alcohol-water mixture. Yield of product was 11.5 g (31%), m.p. 176°–184° C.

Analysis: Calculated for $C_{18}H_{18}N_2O_5$: C, 63.15; H, 5.30; N, 8.18. Found: C, 63.00; H, 5.29; N, 8.15.

PREPARATION 14

3,5-Diiodo-methylsalycilate

To one liter of absolute methanol was added 150 g (0.39 mole) of 3,5-diiodosalicylic acid. Hydrogen chloride was bubbled through the reaction mixture under agitation and refluxed for 3 hrs. The reaction mixture turned cloudy and suddenly a large volume of white crystals precipitated. The mixture was filtered to give, after drying, 136 g (83%) of product, m.p. 198°–202° C.

PREPARATION 15

2-Hydroxy-3,5-diiodobenzamide

A stainless steel bomb, cooled with dry ice acetone, was charged with excess liquid ammonia, 3,5-diiodomethylsalicylate and a catalytic amount of sodium hydride. The bomb was sealed and shaken at room temperature for 16 hrs. On cooling again, the contents of the bomb were poured out and excess ammonia allowed to evaporate at room temperature. The product melted 190°–195° C. with decomposition. Mass spec analysis confirmed molecular weight of the title compound.

PREPARATION 16

3,5-Diiodo-2-[(1-methyl-3-pyrrolidinyl)oxy]benzamide

Following the procedure of preparation 1, substituting 2-hydroxy-3,5-diiodobenzamide for salicylamide, the title compound is prepared.

PREPARATION 17

Sodium-2-[(1-methyl-3-azetidinyl)oxy]-3-pyridinecarboxylate

The title compound is prepared by following the procedure of preparation 6 but substituting 1-methyl-3-azetidinol for 1-methyl-3-pyrrolidinol.

PREPARATION 18

4-[(1-Methyl-3-pyrrolidinyl)oxy]-3-pyridine carboxylic acid sodium salt

4-Chloropyridine is reacted with diisopropyl lithium amide and carbon dioxide to give the lithium salt of 3-carboxy-4-chloropyridine which is then reacted with 1-methyl-3-pyrrolidinol as in Preparation 6.

PREPARATION 19

3-[(1-Methyl-3-pyrrolidinyl)oxy]-2-pyridinecarbonitrile fumarate

2-Carboxamido-3-hydroxypyridine is reacted with

to give 2-cyano-3-chloropyridine which is then reacted with 1-methyl-3-pyrrolidinol as in preparation 12 to give the title compound.

PREPARATION 20

1-Methyl-3-pyrrolidinethiol acetate (ester) ethanedioate

To a solution of 101 g (1 mole) of 1-methyl-3-pyrrolidinol and 110 g (1.1 mole) of triethylamine in 700 ml of dry benzene was added dropwise 115 g (1 mole) of methanesulfonyl chloride while stirring and cooling with an ice bath. The resulting mixture was stirred for 0.5 hr. and filtered. The filtrate was concentrated on the rotary evaporator to about 200 ml being careful not to overheat. The residue was dissolved in about 150 ml of ethanol.

In a separate vessel, 25.3 g (1.1 mole) of sodium was dissolved in 800 ml of 200 proof ethanol under nitrogen gas sweep. After dissolution was complete, 83.6 g (1.1 mole) of thiolacetic acid was added slowly and the resulting solution was stirred an additional 10 min. The above prepared ethanolic solution of methanesulfonate was added and the resulting solution was heated to 60° C. for 20 hrs. The mixture was cooled to 25° C. and filtered and the filtrate was concentrated on a rotary evaporator. The residue was dissolved in isopropyl ether and the mixture filtered to remove a small amount of solid. The filtrate was concentrated and the residue distilled to yield 70 g of the free base title ester, b.p. 95–105/15 mm.

A 7 g portion of the free base was treated with 4 g of oxalic acid in isopropyl alcohol and the salt obtained was recrystallized from isopropyl alcohol to give 8.4 g of title product, m.p. 108°–111° C.

PREPARATION 21

1-Methyl-3-pyrrolidinethiol oxalate

A solution of 62 g (0.39 mole) of 1-methyl-3-pyrrolidinethiol acetate (ester) in 200 ml of absolute methanol was treated with a 2 mm sphere of sodium and the resulting solution was distilled at 1 atm. pressure to a pot temperature of 100° C. Vacuum was applied and the pressure was slowly decreased to 100 mm. The residue was distilled to a pot temperature of 130° C., yielding 25 g (56%) of distillate with a boiling point of 95°–100° C./100 mm which was the free base of the title compound. A 4 g sample was treated with oxalic and in isopropyl alcohol to give 5.5 g of oxalate salt, m.p. 80°–82° C.

PREPARATION 22

2-[(1-Methyl-3-pyrrolidinyl)thiol]-3-pyridinecarboxylic acid

To a stirred suspension of 80 g (2 mole) of 60% sodium hydride (in mineral oil) in 800 ml of dry dimethylformamide, all heated to 60° C. and using nitrogen gas flow was added dropwise, a solution of 157.0 g (1 mole) of 2-chloronicotinic acid and 117 g (1 mole) of 1-methyl-3-pyrrolidinethiol in 300 ml of dimethylformamide at a rate which maintained a temperature of 60°–67° C. The mixture was heated to 65° C. for 6 hr and allowed to stand overnight at room temperature and then filtered. The collected solid was suspended in one liter of isopropyl alcohol and hydrogen chloride was bubbled into the suspension until a pH of 6.2 was reached. The mixture was brought to a boil and filtered. The solid was dissolved in 2 liters of water and extracted with isopropyl ether. The pH was adjusted to 6.0 and the solution was concentrated to a volume of 800 ml and placed in a refrigerator. The resulting solid (85 g) collected by filtration, was a mixture consisting of about 85% of the title compound and 15% sodium chloride. A sample portion of this was crystallized once from ethanol and twice from isopropyl alcohol-water. The recrystallized product decomposed at about 225° C.

PREPARATION 23

Sodium 2-[(1-Cyclohexyl-3-azetidinyl)oxy]-3-pyridine carboxylate

A solution of 105 g (0.68 mole) of 1-cyclohexyl-3-azetidinol and 106 g (0.68 mole) of 2-chloronicotinic acid in 400 ml of dry dimethylformamide was added at a rapid drop to 52 g (1.35 mole) of 60% sodium hydride/mineral oil suspended in 400 ml of dry dimethylformamide at 60° C. Mild exothermic reaction was noted. After stirring for 2 hr at 60° C., the mixture was filtered. The filter cake was washed with ethylacetate and dried at 80° C./2 mm to give 174 g (86%) of crude title compound.

PREPARATION 24

2-[N-Methyl, N-(3-(1-ethylpyrrolidinyl)]-benzoic acid lithium salt

A mixture of 1068 g (6 mole) of 3-bromo-1-ethylpyrrolidine, 828 g (6 mole) of potassium carbonate and 1700 ml of N-methylaniline was stirred at reflux for 2 hr, cooled and filtered. The filtrate was extracted with dilute aqueous sodium hydroxide, dried over anhydrous sodium sulfate and distilled. Yield of 1-ethyl-3-(N-methyl, N-phenylamino)pyrrolidine was 452 g (37.5%), b.p. 100–105/0.1 mm.

The above prepared compound, 20.5 g (0.1 mole) and 46.5 g of 15.1% butyllithium and 20 ml of diethyl ether were heated at reflux for 2 hr. The reaction mixture was then poured onto a slurry of dry ice in diethyl ether. The excess carbon dioxide was allowed to evaporate over a period of time and the residue was stirred in diethyl ether and filtered. The filter cake was dried in vacuo to give 15 g of the title product.

PREPARATION 25

2-Chloro-3-quinolinecarboxylic acid

To a solution of 21.3 ml (0.15 mole) of diisopropyl amine in 300 ml of dry tetrahydrofuran under a continuous nitrogen blanket, at −70° C., was added 61.6 ml of 2.7M n-butyllithium in hexane (0.165 mole) while maintaining the temperature at −60° to −70° C. Subsequent to this addition, the temperature was maintained at −65° C. for approximately 20 minutes. A solution of 20 g (0.12 mole) of 2-chloroquinoline in 60 ml of tetrahydrofuran was added dropwise while maintaining the temperature at −60° to −70° C. After holding the temperature at −65° C. for 20 minutes subsequent to this addition, the entire reaction mixture was poured onto a large excess of dry ice. Most of the solvent was evaporated in a stream of air; the residual solvent was removed by rotary evaporation. The residue was taken up in 300 ml water, made basic with dil aq. sodium hydroxide and washed with 3×50 ml of isopropyl ether. The aqueous layer was filtrate and made acidic (4 to 5 pH) with dilute aqueous hydrochloric acid. The precipitate was collected, washed with water, isopropyl alcohol, and isopropyl ether, and dried, giving 15.4 g (62%) of white crystals, m.p. 190°–210° C. (decomp.). A sample was recrystallized from isopropyl alcohol giving an analytical sample, m.p. 190°–210° C. (decomp.).

Analysis: Calculated for $C_{10}H_6NO_2$: C, 57.85; H, 2.91; N, 6.75. Found: C, 57.80; H, 2.96; N, 6.6.

PREPARATION 26

4-Chloro-7-(trifluoromethyl)-3-quinolinecarboxylic acid

To a cooled solution of 15.8 ml (0.11 mole) of diisopropyl amine in 250 ml of tetrahydrofuran under a blanket of dry nitrogen at −70° C. was added 44 ml of 2.7M n-butyllithium in hexane at −60° to −70° C. The solution was stirred for 20 minutes at −70° C. and a solution/suspension of 25 g (0.11 mole) of 3-chloro-7-trifluoromethyl quinoline in 125 ml of tetrahydrofuran was added dropwise while maintaining the temperature between −60° and −70° C. The temperature was held at −70° C. for 20 minutes subsequent to the addition of the quinoline. The solution (deep red) was poured onto a large excess of dry ice and the solvent allowed to evaporate overnight at room temperature. The residual solvent was removed by rotary evaporation (60° C., 30 mm) and the residue taken up in 800 ml of dil sodium hydroxide. An attempted wash with 75 ml of chloroform caused the sodium salt of the product acid to precipitate out. This precipitate was collected and washed with 1 liter of chloroform and suspended in 500 ml of water. The suspension was stirred while acidifying with 6N hydrochloric acid to pH 2. The solid was collected and washed with 500 ml of water. After drying, 16.2 g (53%) of white solid was collected, m.p. 310° C.

Analysis: Calculated for $C_{11}H_5NO_2ClF_3$: C, 47.94; H, 1.83; N, 5.08. Found: C, 47.56; H, 1.79; N, 4.99.

PREPARATION 27

3,5-Dichloro-4-pyridinecarboxylic acid

To a solution of 4.96 ml (0.036 mole) of diisopropylamine in 200 ml of tetrahydrofuran at −65° C. under a nitrogen blanket was added dropwise 14.9 ml of 2.5M n-butyllithium in hexane while maintaining the above temperature. Twenty minutes subsequent to that addition, a solution 5.0 g (0.034 mole) of 3,5-dichloropyridine in 30 ml tetrahydrofuran at −60° to −70° C. was added. The reaction mixture was stirred at −70° C. for ½ hr, poured onto a large excess of dry ice and allowed to evaporate overnight at room temperature. The residue was taken up in 100 ml of dilute aqueous sodium hydroxide, washed with 3×30 ml of methylenechloride and filtered. The filtrate was acidified to ∼pH 2 with dilute hydrochloric acid to precipitate out the product. After cooling, the precipitate was collected and recystallized from ethyl acetate/hexane giving 1.9 g (29%) of white analytically pure crystals, m.p. 231°–35° C. (decomp.).

Analysis: Calculated for $C_6H_3NO_2Cl_2$: C, 37.53; H, 1.57; N, 7.30. Found: C, 37.33; H, 1.56; N, 7.21.

PREPARATION 28

5-Hydroxy-6-isoquinolinecarboxamide

5-Hydroxy-6-isoquinolinecarboxylic acid methyl ester as reported by Dyke, S. F. et al., in Tetrahedron 1973, 29(6), 857–62, is reacted with excess ammonia in a steel bomb for 12–18 hr. The excess ammonia is allowed to evaporate and the residue is crystallized from a suitable solvent mix such as ethyl acetate-toluene to give the title compound.

PREPARATION 29

5-[(1-Methyl-3-pyrrolidinyl)oxy]-6-isoquinolinecarboxamide

Following the procedure of Preparation 10, but substituting 5-hydroxy-6-isoquinolinecarboxamide for 1-hydroxy-2-naphthalenecarboxamide, the title compound is prepared.

PREPARATION 30

7-Hydroxy-6-isoquinolinecarboxamide

7-Hydroxy-5-isopuinolinecarboxylic acid methyl ester as reported by Dyke (see ref. given in Prep. 28) is reacted with excess ammonia in a steel bomb for 12–18 hr. The excess ammonia is allowed to evaporate and the residue is crystallized from a suitable solvent mix such as ethyl acetate-toluene to give the title compound.

PREPARATION 31

7-[(1-Methyl-3-pyrrolidinyl)oxy]-6-isoquinolinecarboxamide

Following the procedure of Preparation 10, but substituting 5-hydroxy-6-isoquinolinecarboxamide for 1-hydroxy-2-naphthalenecarboxamide, the title compound is prepared.

PREPARATION 32

5-Methyl-8-[(1-methyl-3-pyrrolidinyl)oxy]-7-quinolinecarboxamide

Following the procedure of Preparation 10, but substituting 8-hydroxy-5-methyl-7-quinolinecarboxamide [as reported by V-Kappor et al, Indian J. Chem. 4(10), 438–51 (1966); (C. A. 66, 75802p)] for 1-hydroxy-2-naphthalenecarboxamide, the title compound is prepared.

PREPARATION 33

8-Hydroxy-2-methyl-7-quinolinecarboxylic acid methyl ester

8-Hydroxy-2-methyl-7-quinolinecarboxylic acid (as reported by Meek, W. H. et al., in J. Chem. Eng. Data 1969, 14(3), 388–91) is reacted with methanolic boron trifluoride solution for several hours. The resulting mixture is added to an aqueous solution of sodium bicarbonate to give finally a basic solution. The solution is extracted with chloroform. The chloroform extract is dried over anhydrous sodium sulfate and concentrated and the residue is crystallized from a suitable solvent such as isooctane to give the title compound.

PREPARATION 34

8-Hydroxy-2-methyl-7-quinolinecarboxamide

8-Hydroxy-2-methyl-7-quinolinecarboxylic acid methyl ester is reacted with excess ammonia in a steel bomb for 12–18 hr. The excess ammonia is allowed to evaporate and the residue is crystallized from a suitable solvent to give the title compound.

PREPARATION 35

2-Methyl-8-[(1-methyl-3-pyrrolidinyl)oxy]-7-quinolinecarboxamide

Following the procedure of Preparation 10, but substituting 8-hydroxy-2-methyl-7-quinolinecarboxamide for 1-hydroxy-2-naphthalenecarboxamide, the title compound is prepared.

PREPARATION 36

6-Hydroxy-5-quinolinecarboxylic acid methyl ester

6-Hydroxy-5-quinolinecarboxylic acid [as reported by Da Re, P. et al. in Ann. Chem. (Rome) 1970, 60(3), 215–24 (C. A. 73, 25338m)] is reacted with methanolic boron trifluoride solution for several hours. The resulting mixture is added to an aqueous solution of sodium bicarbonate to give finally a basic solution. The solution is extracted with chloroform. The chloroformm extract is dried over anhydrous sodium sulfate and concentrated and the residue is crystallized from a suitable solvent.

PREPARATION 37

6-Hydroxy-5-quinolinecarboxamide

6-Hydroxy-5-quinolinecarboxylic acid methyl ester is reacted with excess ammonia in a steel bomb for 12–18 hr. The excess ammonia is allowed to evaporate and the residue is crystallized from a suitable solvent to give the title compound.

PREPARATION 38

6-[(1-Methyl-3-pyrrolidinyl)oxy]-5-quinolinecarboxamide

Following the procedure of Preparation 10, but substituting 6-hydroxy-5-quinolinecarboxamide for 1-hydroxy-2-naphthalenecarboxamide, the title compound is prepared.

PREPARATION 39

8-Hydroxy-7-quinolinecarboxamide

8-Hydroxy-7-quinolinecarboxylic acid methyl ester [as reported by Eckstein, Z. et al. in Pol. J. Chem. 1979, 53(11), 2373–7 (C. A. 92, 215243s)] is reacted with excess ammonia in a steel bomb for 12–18 hr. The excess ammonia is allowed to evaporate and the residue is crystallized from a suitable solvent to give the title compound.

PREPARATION 40

8-[(1-Methyl-3-pyrrolidinyl)oxy]-7-quinolinecarboxamide

Folling the procedure of Preparation 10, but substituting 8-hydroxy-7-quinolinecarboxamide for 1-hydroxy-2-naphthalenecarboxamide, the title compound is prepared.

PREPARATON 41 (Refer to Chart VIII)

2-Chloro-N-[4-(dimethylamino)-2-hydroxybutyl]-3-pyridinecarboxamide monohydrochloride To a suspension of 11.9 g (0.076 mole) of 2-chloronicotinic in 200 ml of methylene chloride was added 10.2 g (0.076 mole) of 1-hydroxybenzotriazole, 10 g (0.076 mole) of 1-amino-4-(dimethylamino)-2-butanol, and 15.6 g (0.076 mole) of dicyclohexylcarbodiimide. The resulting solution was stirred at room temperature for 6 hr and allowed to stand for 66 hr. The resulting mixture was filtered and the filtrate concentrated on the rotary evaporator. The residue was shaken with a mixture of dilute hudrochloric acid and isopropyl ether. The resulting 3 phase system (1 solid, 2 liquid) was filtered and the solid discarded. The aqueous layer was separated, made basic with sodium hydroxide and extracted 3 times with chloroform. The combined chloroform extracts were combined, dried over anhydrous sodium sulfate and concentrated. The residue was dissolved in isopropyl alcohol and acidified with ethereal hydrogen chloride. The resulting precipitate was dissolved by heating and adding methanol. The crystals obtained on cooling were recrystallized from ethanol to give 9.6 g (41%), m.p. 182°–192° C.

Analysis: Calculated for $C_{12}H_{19}N_3O_2Cl_2$: C, 46.77; H, 6.21; N, 13.63. Found: C, 46.67; H, 6.42; N, 13.91.

PREPARATION 42

(S)-3-Hydroxy-1-methyl-2,5-pyrrolidinedione

To a stirred solution of 134 g (1 mole) of (S)-malic acid in 700 ml of toluene was added 97 ml of 40% aqueous methylamine. The temperature slowly rose to 50° C. After 0.5 hr the stirred mixture was heated to reflux and the water was collected in a Dean-Stark trap for 48 hr. A total of 93 ml of water was collected. The toluene residue was treated with 300 ml of ethanol and concentrated on the rotary evaporator. The residue was distilled. The yield of product obtained was 101 g (78%), b.p. 140°/2 mm; 145°/0.5 mm.

A sample of the above compound was crystallized from ethyl acetate-isopropyl ether, m.p. 87°–89° C.; $[\alpha]_D^{25} = -79.2$ (methanol).

Analysis: Calculated for $C_5H_7NO_3$: C, 46.51; H, 5.46; N, 10.84. Found: C, 46.77; H, 5.55; N, 11.03.

PREPARATION 43

(S)-1-Methyl-3-pyrrolidinol-(2S,3S)-tartrate [1:1]

A solution of 25.3 g (0.2 mole) of (S)-3-hydroxy-1-methyl-2,5-pyrrolidinedione in 150 ml of tetrahydrofuran was added dropwise so as to maintain reflux to a stirred solution of 226 g (0.78 mole) of Red-al (bis(methoxyethoxy)sodium aluminum hydride) in 500 ml of tetrahydrofuran. The refluxing was continued 1 hr after addition was complete. The solution was cooled with an ice bath and 30 ml of water was added dropwise followed by 30 ml of 15% sodium hydroxide which was followed by 90 ml of water. The resulting mixture was heated to reflux for 0.5 hr, cooled to 30° C. and the layers separated. The aqueous layer was extracted 5 times with chloroform. The organic layers were combined, dried over sodium sulfate and concentrated. The residue was distilled. Yield of product was 13 g (64%), b.p. 95°–100° C./90 mm. $[\alpha]_D^{25} = +0.794$ (neat). 1 gram of the liquid was treated with 1.5 g (2S,3S) tartaric acid in methanol. The resulting crystals weighed 2 g, m.p. 129°–131° C. $[\alpha]_D^{25} = -11.5$ (water).

(Analysis: Calculated for $C_9H_{17}NO_7$: C, 43.02; H, 6.82; N, 5.57. Found: C, 42.98; H, 6.87; N, 5.55.

PREPARATION 44

(S)-1-Methyl-3-pyrrolidinol (2S,3S)-tartrate [1:1]

To a solution of 420 g (4.16 mole) of racemic mixture of 1-methyl-3-pyrrolidinol in 1 liter of dry methanol cooled in an ice bath was added 500 g (3.33 mole) of (2S,3S) tartaric acid dissolved in 1 liter of methanol. At 50° C. the solution was seeded with crystals obtained in Preparation 43. The resulting crystals were collected by filtration and and recrystallized three times with methanol to give 235 g (45%) of analytically pure white crystals, m.p. 125°–129° C. $[\alpha]_D^{25} = (-)$ 11.6 (water).

Analysis: Calculated for $C_9H_{17}NO_7$: C, 43.02; H, 6.82; N, 5.57. Found: C, 42.75; H, 6.87; N, 5.46.

PREPARATION 45

(S)-1-Methyl-3-pyrrolidinol

A 235 g sample of (S)-1-methyl-3-pyrrolidinol (2S,3S) tartrate [1:1] was treated with 135 g of potassium hydroxide in 200 ml of water and the solution was continuously extracted with chloroform for 24 hr. The chloroform solution was dried over sodium sulfate, concentrated and distilled. Yield of product was 80 g, b.p. 103°–106/37–40 mm; $[\alpha]D^{25} = +0.817°$ (neat).

Analysis: Calculated for $C_5H_{11}NO$: C, 59.37; H, 10.96; N, 13.85. Found: C, 57.64; H, 10.40; N, 13.47.

PREPARATION 46

(R)-1-Methyl-3-pyrrolidinol (2R,3R)-tartrate [1:1]

To a solution of 420 g (4.16 mole) of 1-methyl-3-pyrrolidinol in 1 liter of dry methanol cooled in an ice bath was added 500 g (3.33 mole) of −(2S,3S) tartaric acid dissolved in 1 liter of methanol. At 50° C. the solution was seeded with (S)-1-methyl-3-pyrrolidinol-(2S,3S)-tartrate [1:1]. The resulting crystals were collected by filtration and the organic layer was concentrated. The residue was partitioned between dilute sodium hydroxide and chloroform and the aqueous layer extracted by continuous extraction with chloroform for 24 hr. The organic layers were combined, dried over sodium sulfate and concentrated. The residue was dissolved in 500 ml of methanol and to this solution was added 150.09 g (1 mole) of (2R,3R) tartaric acid dissolved in 500 ml of methanol. The mixture was filtered and the solid recrystallization two times from methanol to give 75.2 g, (14%) of analytically pure white crystals, m.p. 124°–127° C.; $[\alpha]_D^{25} = (+)$ 11.1(water).

Analysis: Calculated for $C_9H_{17}NO_7$: C, 43.02; H, 6.82; N, 5.57. Found: C, 42.84; H, 6.91; N, 5.63.

PREPARATION 47

(R)-1-Methyl-3-pyrrolidinol

A 200 g sample of (R)-1-methyl-3-pyrrolidinol-(2R,3R) tartrate [1:1] was treated with 135 g of potassium hydroxide and the resulting solution continuously extracted with chloroform for 24 hr. The chloroform extract was dried over anhydrous sodium sulfate, concentrated and distilled. Yield of product was 73 g, b.p. 103–106/35 mm, $[\alpha]_D^{25} = -0.852°$ (neat).

Analysis: Calculated for $C_5H_{11}NO$: C, 59.37; H, 10.96; N, 13.85. Found: C, 57.71; H, 10.78; N, 13.49.

PREPARATION 48

5-Bromo-2-chloro-3-pyridinecarboxylic acid

To 15 g (0.069 mole) of 5-bromo-2-hydroxy nicotinic acid was added 75 ml of thionyl chloride and 3 ml of dimethylformamide. The mixture was heated to reflux for 30 minutes. After cooling, the excess thionyl chloride was removed by rotary evaporation and the residue poured into water (1 liter) with vigorous agitation. The precipitate was collected and the mother liquor condensed to ½ the volume, yielding additional precipitate. The precipitates were combined and crystallized from toluene giving 6 g (37%) of material. The product was recrystallized from toluene, m.p. 174°–177° C.

Analysis: Calculated for $C_6H_3NO_2ClBr$: C, 30.48; H, 1.28; N, 5.92. Found: C, 30.21; H, 1.25; N, 5.89.

PREPARATION 49

5-Bromo-2-hydroxy-3-pyridinecarboxylic acid

To a solution of 10 g (0.07 mole) of 2-hydroxy-nicotinic acid in 16.8 g of 50% sodium hydroxide (0.21 mole) diluted with 25 ml of water was added 200 ml of sodium hypobromite solution prepared by adding 13.6 g (0.17 mole) of bromine to a solution of 20.16 g of 50% sodium hydroxide (0.25 mole) in 125 ml of water at 0° C. diluted to 400 ml. After 24 hrs of stirring at room temperature, another 100 ml portion of the above sodium hypobromite solution was added and the reaction solution was stirred for another 24 hr. The reaction solution was cooled in an ice bath and acidified carefully with 12N hydrochloric acid. Crystallization from isopropyl alcohol gave 9.7 g (63.5%) of product. A sample was further recrystallized from 95% ethanol, m.p. 245° C.

Analysis: Calculated for $C_6H_4NO_3$: C, 33.06; H, 1.85; N, 6.42. Found: C, 32.98; H, 1.83; N, 6.44.

PREPARATION 50

2-(1-Methyl-3-pyrrolidinyloxy)-5-nitrobenzamide

To a cooled suspension of sodium hydride (2.42 g of 60% content 0.06 mole) in 50 ml of dimethylformamide under nitrogen was added dropwise a solution of 10 g (0.055 mole) of 2-chloro-5-nitrobenzamide in 20 ml of dimethylformamide. The suspension was stirred at room temperature for 1 hr and heated to 60° C. at which time 9.9 g (0.055 mole) of N-methyl-3-pyrrolidinylmesylate (freshly prepared) in 10 ml of dimethylformamide was added. The reaction mixture was heated to 135° C. for 24 hr. Since little product was observed, 9.9 g (0.055 mole) additional N-methyl-3-pyrrolidinylmesylate and 1.21 g (60% in oil, 0.03 mole) of sodium hydride was added. Heating was continued for 24 hr. Another 4 equivalents of the above mesylate was added after cooling the reaction mixture to 100° C. The reaction mixture was maintained at 100° C. for 24 hr. The dimethylformamide was removed by rotary evaporation at 60° C., 0.5 mm Hg. The residue was taken up in 400 ml of methylene chloride and washed with 3×200 ml of 1N sodium hydroxide and 2×200 ml water. The organic layer was extracted with 3×200 ml of 1N hydrochloric acid. The aqueous extracts were combined and washed with ~200 ml chloroform. The aqueous layer was made basic with concentrated sodium hydroxide and extracted with 2×300 ml of methylene chloride. The organic extracts were combined, dried over sodium sulfate, filtered, and concentrated by rotary evaporation. The residue was crystallized from toluene to give 1.7 g (12%) of crude crystals. One recrystallization from toluene afforded light beige crystals, m.p. 215°–10° C.

Analysis: Calculated for $C_{12}H_{15}N_3O_4$: C, 54.34; H, 5.70; N, 15.84. Found: C, 54.30; H, 5.73; N, 15.80.

PREPARATION 51

5-Fluoro-2-(1-methyl-3-pyrrolidinyloxy)benzamide

To a suspension of 0.44 g (60% in oil, 0.011 mole) of sodium hydride in 10 ml of dimethylformamide was added 1.55 g (0.01 mole) of 5-fluoro-2-hydroxybenzamide in 10 ml of dimethylformamide under nitrogen atmosphere at room temperature. The reaction mixture was heated to 60° C. and 1.80 g (0.01 mole) of 1-methyl-3-pyrrolidinol methane sulfonate (ester) was added. The reaction mixture was then heated to 100° C. for 18 hr. The dimethylformamide was removed by rotary evaporation at 70° C., 0.5 mm Hg. The residue was taken up in 200 ml of methylene chloride, washed with 2×50 ml of 1N sodium hydroxide and 50 ml of water. The organic phase was extracted with 2×50 ml of 1N hydrochloric acid. The combined aqueous extracts were washed with 50 ml of methylene chloride, made basic with concentrated sodium hydroxide and extracted into 2×50 ml of methylene chloride. The combined organic extracts were dried over sodium sulfate, filtered and concentrated by rotary evaporation. The residual oil was crystallized from hexane to give 1.0 g of off-white crystals, m.p. 90°–93° C.

Analysis: Calculated for $C_{14}H_{15}N_2O_2F$: C, 60.49; H, 6.35; N, 11.76. Found: C, 60.47; H, 6.39; N, 11.75.

INTERMEDIATE 1

2-(2-Chloroethyl)-2,3-dihydro-4-methyl-1,4-benzoxazepin-5(4H)-one

To 54 g (1.35 mole) of sodium hydroxide in 800 ml of water was added 148 g (0.67 mole) of 2-[(1-methyl-3-pyrrolidinyl)oxy]benzamide and the mixture brought to reflux for 18 hr. The pH was adjusted to 7 with hydrochloric acid and the solution filtered and concentrated. The residue was boiled with 400 ml of isopropanol and filtered. The filtrate was concentrated and the residue (which crystallized) was refluxed with 300 ml of thionyl chloride for 0.5 hr. and concentrated in vacuo. The residue was dissolved in 300 ml of chloroform and the solvent boiled off in vacuo. The residue was redissolved in chloroform, 150 ml of triethyl amine added and the mixture refluxed 1 hr. The solution was concentrated in vacuo and the residue partitioned between 400 ml of ethyl acetate, 400 ml of isopropyl ether and 500 ml of dilute hydrochloric acid. The organic layer was washed twice with water and once with dilute sodium hydroxide, dried with sodium sulfate and concentrated. The residue was crystallized from isopropanol-water. Yield of product was 75 g (47%), m.p. 97°–107° C.

Analysis: Calculated for $C_{12}H_{14}NO_2Cl$: C, 60.13; H, 5.89; N, 5.84. Found: C, 60.35; H, 5.91; N, 5.65.

INTERMEDIATE 2

4-Benzyl-2-(2-chloroethyl)-2,3-dihydro-1,4-benzoxazepin-5(4H)-one

To 85.7 g (0.29 mole) of 2-[(1-benzyl-3-pyrrolidinyl)oxy]-benzoic acid was added 150 ml of thionyl chloride. The solution stood for 15 min and was then refluxed 30 min. and concentrated in vacuo. The residue was twice treated with 250 ml of chloroform and concentrated in vacuo. The residue was dissolved in 500 ml of chloroform and 101 g (1 mole) of triethylamine added slowly with stirring. The solution was refluxed 1 hr. and concentrated in vacuo. The residue was partitioned between 50% ethyl acetate-50% isopropyl ether and dilute hydrochloric acid. The organic layer was washed with dilute sodium hydroxide and concentrated. The residue was crystallized 5 times from isopropyl ether-ethyl acetate. Yield of product was 23.8 g (26%), m.p. 145.0°–147° C.

Analysis: Calculated for $C_{18}H_{18}NO_2Cl$: C, 68.46; H, 5.74; N, 4.44. Found: C, 68.47; H, 5.89; N, 4.32.

INTERMEDIATE 3

2-(2-(Chloroethyl)-2,3-dihydro-4-methylnaphth[2,3-f][1,4]oxazepin-5(4H)-one

To a solution of 21.6 g (0.54 mole) sodium hydroxide in 500 ml of water was added 74 g (0.27 mole) of 3-[1-methyl-3-pyrrolidinyl)oxy]-2-naphthalenecarboxamide and the mixture heated at reflux for 16 hr. The pH was adjusted to 6.8 with concentrated hydrochloric acid, the solution was filtered and concentrated. The residue was boiled with 200 ml of isopropyl alcohol and filtered. The filtrate was concentrated under reduced pressure and the residue dissolved in chloroform. Thionyl chloride (59 g, 0.50 mole) was added and the reaction mixture heated at reflux for 4 hr. After cooling (67 g, 0.67 mole) triethylamine was added dropwise. The mixture was washed sequentially; twice with 3N hydrochloric acid, twice with water, twice with 10% sodium hydroxide, twice with water and dried over magnesium sulfate. Evaporation of the chloroform under reduced pressure gave 44 g (58%) of a viscous dark brown oil. The material was purified by high pressure liquid chromatography (50/50 ethyl acetate/hexane) and recrystallized from isopropyl alcohol to yield brown crystals, m.p.=101°–102° C.

Analysis: Calculated for $C_{16}H_{16}NClO_2$: C, 66.32; H, 5.57; N, 4.83. Found: C, 66.19; H, 5.63; N, 4.77.

INTERMEDIATE 4

2-(2-Chloroethyl)-2,3-dihydro-4-methylpyrido[3,2-f][1,4]-oxazepin-5(4H)-one hydrochloride Hydrogen chloride gas was bubbled into a suspension of 150 g (0.61 mole) of sodium 2-[(1-methyl-3-pyrrolidinyl)oxy]-3-pyridinecarboxylate in 1 liter of chloroform until a pH of 6 was reached. To the stirred mixture was added 350 g (1.34 mole) of triphenylphosphine and 350 g (2.3 mole) of carbon tetrachloride and the resulting cloudy solution was stirred at reflux for 1.5 hr. About 100 ml of ethanol was added and the heat removed. The solution was stirred for 1 hour while cooling and 200 ml of isooctane was added. The solution was extracted 4 times with a total of 800 ml of dilute hydrochloric acid. The acid extracts were combined, made basic with sodium hydroxide and extracted with chloroform. The chloroform layer was separated and dried over sodium sulfate and concentrated. The residue was dissolved in a mixture of 500 ml each of isopropyl alcohol and isopropyl ether and acidified with ethereal hydrogen chloride. The resulting crystals weighed 82 g (49%). A portion was recrystallized from isopropyl alcohol, m.p. 149°–153° C.

Analysis: Calculated for $C_{11}H_{14}N_2O_2Cl_2$: C, 47.67; H, 5.09; N, 10.11. Found: C, 47.57; H, 5.18; N, 10.00.

INTERMEDIATE 5

8-Chloro-2-(2-chloroethyl)-2,3-dihydro-4-methyl-1,4-benzoxazepin-5(4H)-one

To a solution of 10.4 g (0.26 mole) of sodium hydroxide in 150 ml of water was added 32 g (0.13 mole) of 4-chloro-2-[(1-methyl-3-pyrrolidinyl)oxy]benzamide and the mixture was heated at reflux for 24 hr. The reaction mixture was adjusted to pH 6 with concentrated hydrochloric acid and filtered and the filtrate concentrated. The residue was boiled with 100 ml of isopropyl alcohol and the mixture filtered. The filtrate was concentrated and heated at reflux with 98 g (0.83 mole) of thionyl chloride for 1 hr. The excess thionyl chloride was evaporated under reduced pressure. The residue was dissolved in 70 ml of chloroform and the solvent evaporated under reduced pressure. The residue was redissolved in 75 ml of chloroform and 40 ml of triethylamine was added gradually. The mixture was heated at reflux for 1 hr. The solvent was evaporated under reduced pressure to give a dark-brown solid. The solid was dissolved in ethyl acetate and the resulting solution washed twice with 200 ml of water and twice with 250 ml of 20% sodium hydroxide. The organic layer was dried over magnesium sulfate and concentrated under reduced pressure to give 21 g (59%) of dark-brown solid. The solid was recrystallized from isopropyl alcohol to give the title compound, m.p. 85°–87° C.

Analysis: Calculated for $C_{12}H_{13}NCl_2O_2$: C, 52.57; H, 4.78; N, 5.11. Found: C, 52.57; H, 4.77; N, 5.04.

INTERMEDIATE 6

7-Bromo-2-(2-chloroethyl)-2,3-dihydro-4-methyl-1,4-benzoxazepine-5(4H)-one

To a solution of 9.6 g (0.24 mole) of sodium hydroxide in 200 ml of water was added 37 g (0.12 mole) of 5-bromo-2-[(1-methyl-3-pyrrolidinyl)oxy]-benzamide and the mixture was heated at reflux for 18 hr. The pH of the mixture was adjusted to 6.7 with concentrated hydrochloric acid solution. The solution was concentrated under reduced pressure and the residue was boiled in 250 ml of isopropyl alcohol for 1 hr. The mixture was filtered and the filtrate was concentrated. The residue was dissolved in chloroform and to the solution was added 28.3 g (0.24 mole) of thionyl chloride. The mixture was heated at reflux for 0.5 hr and cooled to 15° C. with an ice bath. To the mixture was added dropwise 26.6 g (0.26 mole) of triethylamine at such a rate that the temperature did not exceed 25° C. The reaction mixture was stirred at room temperature for 1 hr, then washed consecutively with 3N hydrochloric acid, 15% aqueous sodium hydroxide and water. The chloroform layer was dried over magnesium sulfate and concentrated under reduced pressure to give 23 g (60%) of brown solid. A portion of the solid was recrystallized from ethyl acetate-isopropyl ether, m.p. 92°–94° C.

Analysis: Calculated for $C_{12}H_{13}NBrClO_2$: C, 45.24; H, 4.11 N, 4.40. Found: C, 45.61; H, 4.17; N, 4.42.

INTERMEDIATE 7

7-Chloro-2-(2-chloroethyl)-2,3-dihydro-4-methyl-1,4-benzoxazepin-5(4H)-one

Hydrogen chloride was bubbled through a solution of 113 g (0.44 mole) 5-chloro-2-[(1-methyl-3-pyrrolidinyl)oxy]benzamide dissolved in 500 ml of glacial acetic acid for 15 min while the reaction was cooled with an ice bath. Butylnitrite (142 g, 1.38 mole) was then added in one portion; the reaction was stirred at room temperature for 16 hr and heated at reflux for an additional 6 hr. The acetic acid was evaporated under reduced pressure, tetrachloroethane was added twice to the residue and evaporated.

The residue was dissolved in chloroform, treated with 163 g (1.38 mole) of thionyl chloride and heated at reflux for 22 hr. The reaction mixture was cooled with an ice bath and 152 g (1.5 mole) of triethylamine was added dropwise at such a rate that the temperature was kept at 25°–30° C. The reaction mixture was diluted with 200 ml of chloroform and washed consecutively with 3N hydrochloric acid, water, 10% sodium hydroxide and water. The chloroform was evaporated under reduced pressure to give 40 g of a black, tar-like residue (33%).

An aliquot of this residue was purified on a silica gel column using ethyl acetate as the eluting solvent. Recrystallization from isopropyl alcohol gave beige crystals, m.p. 101°–103° C.

Analysis: Calculated for $C_{12}H_{13}NCl_2O_2$: C, 52.57; H, 4.78; N, 5.11. Found: C, 52.63; H, 4.83; N, 5.05.

INTERMEDIATE 8

2-(2-Chloroethyl)-2,3-dihydro-4-methylnaphth[2,1-f][1,4]oxazepin-5(4H)-one

Hydrogen chloride gas was bubbled into a solution of 8 g (0.03 mole) of 1-[(1-methyl-3-pyrrolidinyl)oxy]-2-naphthalenecarboxamide in 40 ml of acetic acid for about 2 min. The solution was cooled with an ice bath and 6.1 g (0.06 mole) of n-butyl nitrite was added slowly beneath the surface of the liquid at 12°–15° C. (about 10 minutes required). The solution was stirred at 25° C. for 18 hr and heated on the steam bath for 3 hr. The solution was concentrated on the rotary evaporator. The residue was dissolved in 60 ml of 1,1,2,2-tetrachloroethane which was removed on the rotary evaporator at 0.5 mm/steam temperature.

The residue was dissolved in 75 ml of chloroform and treated with 7 g (0.06 mole) of thionyl chloride and brought to reflux for 12 hr. The solution was extracted with water (tested acidic) followed by dilute sodium hydroxide, dried over sodium sulfate and concentrated. The residue was crystallized twice from isopropyl etherethyl acetate. Yield of product was 3.2 g (37%), m.p. 109°–111° C.

Analysis: Calculated for $C_{16}H_{16}NO_2Cl$: C, 66.32; H, 5.57; N, 4.84. Found: C, 66.15; H, 5.56; N, 4.76.

INTERMEDIATE 9

2-(2-Chloroethyl)-2,3-dihydro-7-methoxy-4-methyl-1,4-benzoxazepin-5(4H)-one

To a solution of 19.2 g (0.48 mole) of sodium hydroxide in 500 ml of water was added 60 g (0.24 mole) of 5-methoxy-2-[(1-methyl-3-pyrrolidinyl)oxy]-benzamide and the mixture was heated at reflux for 24 hr. The reaction mixture was cooled and the pH adjusted to 6.8 with concentrated hydrochloric acid. The mixture was concentrated under reduced pressure and the residue was boiled in isopropyl alcohol for 1 hour. The mixture was filtered and the filtrate was concentrated. The residue was dissolved in 500 ml of chloroform and to this solution was added 114 g (0.96 mole) of thionyl chloride. The mixture was heated at reflux for 48 hr, then cooled with an ice/acetone bath. To the mixture was added dropwise 97 g (0.96 mole) of triethylamine at such a rate that the temperature did not exceed 25° C. The reaction solution was washed in sequence with water, 3N hydrochloric acid solution, water, 15% aqueous sodium hydroxide and water and finally dried over magnesium sulfate. The solvent was evaporated under reduced pressure to give a black solid. The solid was purified on a silica gel column using ethyl acetate as the eluting solvent to give on isolation 15 g (23%) of beige colored product, m.p. 98°–100° C.

Analysis: Calculated for $C_{13}H_{16}NClO_3$: C, 57.89; H, 5.98; N, 5.19. Found: C, 57.53; H, 6.00; N, 5.16.

INTERMEDIATE 10

2-(2-Chloroethyl)-2,3-dihydro-4-methyl-1,4-benzoxazepine-5(4H)-thione

A mixture of 18.5 g (0.0834 mole) of phosphorus pentasulfide and 18.5 g potassium sulfide was ground together and added to a solution of 100 g (0.417 mole) of 2-(2-chloroethyl)-2,3-dihydro-4-methyl-1,4-benzoxazepin-5(4H)-one in dry toluene, the mixture refluxed 24 hr. and filtered. The filtrate was concentrated and partitioned between chloroform and dilute sodium hydroxide. The chloroform layer was concentrated and the residue was crystallized several times from ethanol. Yield of product was 55 g (52%), m.p. 105°–108° C.

Analysis: Calculated for $C_{12}H_{14}NSOCl$: C, 56.35; H, 5.52; N, 5.48; S, 12.54. Found: C, 56.55; H, 5.47; N, 5.49; S, 12.55.

INTERMEDIATE 11

2-(2-Chloroethyl)-2,3-dihydro-4-methylpyrido[3,2-f][1,4]-oxazepine-5(4H)-thione

To a solution of 59 g (0.25 mole) of 2-(2-chloroethyl)-2,3-dihydro-4-methylpyrido[3,2-f][1,4]oxazepin-5(4H)one hydrochloride in 1500 ml of chloroform was added 41.5 g (0.19 mole) of phosphorus pentasulfide and the mixture was heated to reflux for 18 hr. The mixture was filtered and the filtrate was extracted with dilute sodium hydroxide. The chloroform layer was concentrated and the residue was dissolved in 250 ml of boiling isopropyl alcohol. On cooling, 28 g (44%) of yellow solid precipitated. A portion was recrystallized from isopropyl alcohol, m.p. 134°–136° C.

Analysis: Calculated for $C_{11}H_{13}N_2ClOS$: C, 51.46; H, 5.10; N, 10.81. Found: C, 51.35; H, 5.21; N, 10.72.

INTERMEDIATE 12

2-(2-Chloroethyl)-2,3-dihydro-4-methylnaphth[2,3-f][1,4]oxazepine-5(4H)-thione

To a solution of 16.6 g (0.06 mole) of 2-(2-chloroethyl)-2,3-dihydro-4-methylnaphth[2,3-f][1,4]oxazepin-5(4H)-one in 150 ml of dry toluene was added a mixture of 8.6 g (0.045 mole) of phosphorus pentasulfide and 8.6 g of potassium sulfide which had been ground together. The reaction mixture was stirred and heated at reflux for 24 hr. The mixture was filtered hot and the filtrate concentrated under reduced pressure. Yellow solid, 6.5 g (35%) was obtained which was recrystallized from ethanol, m.p. 166°–168° C.

Analysis: Calculated for $C_{16}H_{16}NClOS$: C, 62.84; H, 5.27; N, 4.58. Found: C, 62.29; H, 5.48; N, 4.47.

INTERMEDIATE 13

8-Chloro-2-(2-chloroethyl)-2,3-dihydro-4-methyl-1,4-benzoxazepine-5(4H)-thione

To a solution of 43 g (0.16 mole) of 8-chloro-2-(2-chloroethyl)-2,3-dihydro-4-methyl-1,4-benzoxazepin-5(4H)-one in 400 ml of dry toluene was added a mixture of 23 g (0.12 mole) of phosphorus pentasulfide and 23 g of potassium sulfide which had been ground together. The reaction mixture was stirred and heated at reflux for 24 hr. The mixture was filtered hot and the filtrate concentrated under reduced pressure to give 25.5 g (55%) of orange oil which solidified on standing at room temperature. The solid was recrystallized from ethanol, m.p. 105°–106° C.

Analysis: Calculated for $C_{12}H_{13}NCl_2OS$: C, 49.66; H, 4.52; N, 4.83. Found: C, 49.63; H, 4.53; N, 4.75.

INTERMEDIATE 14

7-Bromo-2-(2-chloroethyl)-2,3-dihydro-4-methyl-1,4-benzoxazepine-5(4H)-thione

To a solution of 11.0 g (0.035 mole) of 7-bromo-2-(2-chloroethyl)-2,3-dihydro-4-methyl-1,4-benzoxazepin-5(4H)-one in 150 ml of dry toluene was added a mixture of 13.4 g (0.07 mole) of phosphorus pentasulfide and 13.4 g of potassium sulfide which had been ground together. The reaction mixture was heated at reflux for 5 hr under a nitrogen atmosphere. The mixture was filtered hot and the filtrate concentrated under reduced pressure. The residue was dissolved in chloroform. The chloroform solution was washed twice with dilute aqueous sodium hydroxide, dried over magnesium sulfate and concentrated under reduced pressure to give 8.5 g (72%) of yellow solid. The solid was recrystallized from ethanol, m.p. 118°–120° C.

Analysis: Calculated for $C_{12}H_{13}NBrClOS$: C, 43.07; H, 3.92; N, 4.18. Found: C, 43.08; H, 3.88; N, 4.12.

INTERMEDIATE 15

2-(2-Chloroethyl)-2,3-dihydro-4-methylnaphth[2,1-f][1,4]oxazepine-5(4H)-thione

A mixture of 9.55 g of phosphorus pentasulfide and 9.5 g of potassium sulfide were ground together and added to a solution of 20.2 g (0.07 mole) of 2-(2-chloroethyl)-2,3-dihydro-4-methylnaphth[2,1-f][1,4]oxazepin-5(4H)-one in 200 ml of dry toluene. The mixture was stirred and heated at reflux for 7 hr. The hot reaction mixture was filtered and the product crystallized from the cooled filtrate. Recrystallization from chloroform gave 18 g (84%) of yellow crystals, m.p. 167°–170° C.

Analysis: Calculated for $C_{16}H_{16}NClOS$: C, 62.84; H, 5.27; N, 4.58. Found: C, 62.85; H, 5.20; N, 4.55.

INTERMEDIATE 16

2-(2-Chloroethyl)-2,3-dihydro-4-methylpyrido[4,3-f][1,4]-oxazepin-5(4H)-one hydrochloride A 49 g (0.11 mole) sample of 3-[(1-methyl-3-pyrrolidinyl)oxy]-4-pyridinecarbonitrile fumarate [1:2] was partitioned between chloroform and a saturated solution of potassium carbonate. The aqueous layer was extracted twice with chloroform. All chloroform extracts were combined, dried and concentrated. The residue was dissolved in 125 ml of t-butanol and added to 34 g (0.6 mole) of potassium hydroxide pellets. The mixture was stirred at room temperature for 88 hr. and then diluted with 150 ml of toluene. This mixture was filtered and the filtrate concentrated. The residue was dissolved in chloroform, with cooling, and the pH adjusted to 6.0 with hydrogen chloride gas. The resulting mixture was concentrated and 400 ml of dry toluene was added to the residue. The toluene was removed on the rotary evaporator (steam heat/reduced pressure) to remove any water. The residue was dissolved in 400 ml of chloroform and 63 g of triphenylphosphine was added followed by 70 g of carbon tetrachloride. The solution was stirred at reflux for 2 hr and another 30 g of triphenylphosphine added. After an additional hour reflux, 70 g more carbon tetrachloride and 63 g more of triphenylphosphine were added and reflux was continued for 4 hr. The solution was extracted with dilute sodium hydroxide, then concentrated. The residue was partitioned between toluene and dilute hydrochloric acid. The toluene layer was extracted five times with dilute hydrochloric acid. The acid extracts were combined, basified with sodium hydroxide and extracted with chloroform. The chloroform layer was dried over sodium sulfate and concentrated. The residue was chromatographed on a 7×25 cm column of silica gel with acetone liquid phase. Free base of the title compound isolated after evaporation amounted to 5.8 g (20%). To a portion of the free base dissolved in isopropyl alcohol was added ethereal hydrogen chloride and isopropyl ether. The resulting crystals were collected and dried, m.p. 188°–190° C.

Analysis: Calculated for $C_{11}H_{14}N_2O_2Cl_2$: C, 47.67; H, 5.09; N, 10.11. Found: C, 48.33; H, 5.22; N, 9.73.

INTERMEDIATE 17

2-(2-Chloroethyl)-2,3-dihydro-4-methylpyrido[3,4-f][1,4]oxazepin-5(4H)-one hydrochloride In the procedure of Intermediate 4, equal molar amounts of sodium 4-[(1-methyl-3-pyrrolidinyl)oxy]-3-pyridinecarboxylate was substituted for 2-[(1-methyl-3-pyrrolidinyl)oxy]-3-pyridinecarboxylic acid and the title compound was obtained.

INTERMEDIATE 18

2-(2-Chloroethyl)-2,3-dihydro-4-methylpyrido[2,3-f][1,4]oxazepin-5(4H)-one hydrochloride The procedure of Intermediate 16, 3-[(1-methyl-3-pyrrolidinyl)oxy]-2-pyridinecarbonitrile fumarate is substituted for 3-[(1-methyl-3-pyrrolidinyl)oxy]-4-pyridinecarbonitrile fumarate, the title compound is obtained.

INTERMEDIATE 19

7-Chloro-2-(2-chloroethyl)-2,3-dihydro-4-methyl-1,4-benzoxazepine-5(4H)-thione

To a solution of 20 g (0.07 mole) of 7-chloro-2-(2-chloroethyl)-2,3-dihydro-4-methyl-1,4-benzoxazepin-5(4H)-one in 200 ml of toluene was added a mixture of 9.55 g (0.05 mole) of phosphorus pentasulfide and 9.5 g of potassium sulfide which had been ground together. The reaction mixture was filtered and the filtrate concentrated under reduced pressure to give a yellow solid. Recrystallization from absolute ethanol gave 12.5 g (68%) of the product, m.p. 102°–104° C.

Analysis: Calculated for $C_{12}H_{13}NCl_2OS$: C, 49.66; H, 4.52; N, 4.83. Found: C, 49.62; H, 4.55; N, 4.76.

INTERMEDIATE 20

2-(2-Chloroethyl)-7,9-diiodo-2,3-dihydro-4-methyl-1,4-benzoxazepin-5(4H)-one

When in the procedure of Intermediate 1, 3,5-diido-2-[(1-methyl-3-pyrrolidinyl)oxy]-benzamide is substituted for 2-[(1-methyl-3-pyrrolidinyl)oxy]benzamide, the title compound is prepared.

INTERMEDIATE 21

2-Chloromethyl-2,3-dihydro-4-methylpyrido[3,2-f][1,4]oxazepin-5(4H)-hydrochloride When in the procedure of Intermediate 4, an equal molar amount of sodium 2-[(1-methyl-3-azetidinyl)oxy]-3-pyridinecarboxylate sodium acetate is substituted for sodium 2-[(1-methyl-3-pyrrolidinyl)oxy]-3-pyridinecarboxylate, the title compound is prepared.

INTERMEDIATE 22

2-(2-Chloroethyl)-2,3-dihydro-4-methylpyrido[4,3-f][1,4]oxazepine-5(4H)-thione

A solution of 5 g (0.021 mole) of 2-(2-chloroethyl)-2,3-dihydro-4-methylpyrido[4,3-f][1,4]-oxazepin-5(4H)-one and 5.1 g (0.0126 mole) of 2,4-bis(4-methoxyphenyl)-1,3,2,4-dithiodiphosphetane-2,4-disulfide in 100 ml of dry toluene was stirred at reflux for 2.5 hr. The solution was cooled and extracted three times with sodium bicarbonate solution. The toluene layer was dried over sodium sulfate and concentrated. The residue was chromatographed (high pressure liquid chromatograph) using a silica column and ethyl acetate liquid phase. The fraction containing the product was concentrated by evaporation and the residue was crystallized from ethyl alcohol to give 0.6 g (11%) of the title compound.

INTERMEDIATE 23

2-(2-Chloroethyl)-2,3-dihydro-7-methoxy-4-methyl-1,4-benzoxazepine-5(4H)-thione

To a solution of 10.3 g (0.04 mole) of 2-(2-chloroethyl)-2,3-dihydro-7-methoxy-4-methyl-1,4-benzoxazepin-5(4H)-one in 200 ml of chloroform was added a mixture of 5.7 g (0.03 mole) of phosphorus pentasulfide and 5.7 g of potassium sulfide which had been ground together. The reaction mixture was stirred and heated at reflux under nitrogen atmosphere for 5 hr. The mixture was filtered hot and the filtrate concentrated under reduced pressure. The residue, an orange solid, was recrystallized from ethanol to give 7.4 g (65%) of product, m.p. 98°–100° C.

Analysis: Calculated for $C_{13}H_{16}NClO_2S$: C, 54.64; H, 5.65; N, 4.90. Found: C, 54.57; H, 5.67; N, 4.85.

INTERMEDIATE 24

When in the procedure of Intermediate 2, equal molar amounts of the following are substituted for 2-(1-benzyl-3-pyrrolidinyloxy)benzoic acid:

2-[(1-cyclohexyl-3-pyrrolidinyl)oxy]benzoic acid,
2-[(1-ethyl-3-pyrrolidinyl)oxy]benzoic acid,
2-[(1-isopropyl-3-pyrrolidinyl)oxy]benzoic acid,
2-[[(1-(4-chlorobenzyl)-3-pyrrolidinyl]oxy]benzoic acid,
2-[[1-(4-methylbenzyl)-3-pyrrolidinyl]oxy]benzoic acid,
2-[[1-(3,5-dimethoxybenzyl)-3-pyrrolidinyl]oxy]benzoic acid,
2-[[1-(trifluoromethylbenzyl)-3-pyrrolidinyl]oxy]benzoic acid, and
2-[[1-(4-nitrobenzyl)-3-pyrrolidinyl]oxy]benzoic acid, and there are obtained:

(a) 2-(2-chloroethyl)-4-cyclohexyl-2,3-dihydro-1,4-benzoxazepin-5(4H)-one,
(b) 2-(2-chloroethyl)-2,3-dihydro-4-ethyl-1,4-benzoxazepin-5(4H)-one,
(c) 2-(2-chloroethyl)-2,3-dihydro-4-isopropyl-1,4-benzoxazepin-5(4H)-one,
(d) 2-(2-chloroethyl)-4-(4-chlorobenzyl)-2,3-dihydro-1,4-benzoxazepin-5(4H)-one,
(e) 2-(2-chloroethyl)-2,3-dihydro-4-(4-methylbenzyl)-1,4-benzoxazepin-5(4H)-one,
(f) 2-(2-chloroethyl)-2,3-dihydro-4-(3,5-dimethoxybenzyl)-1,4-benzoxazepin-5(4H)-one,
(g) 2-(2-chloroethyl)-2,3-dihydro-4-(3-trifluoromethylbenzyl)-1,4-benzoxazepin-5(4H)-one,
(h) 2-(2-chloroethyl)-2,3-dihydro-4-(4-nitrobenzyl)-1,4-benzoxazepin-5(4H)-one.

INTERMEDIATE 25

When in the procedure of Intermediate 4, equal molar amounts of the following are substituted for sodium 2-[(1-methyl-3-pyrrolidinyl)oxy]-3-pyridine carboxylate:

2-[(1-cyclohexyl-3-pyrrolidinyl)oxy]-3-pyridine carboxylate,
2-[(1-ethyl-3-pyrrolidinyl)oxy]-3-pyridine carboxylate,
2-[1-isopropyl-3-pyrrolidinyl)oxy]-3-pyridine carboxylate,
2-[[1-(4-chlorobenzyl)-3-pyrrolidinyl]oxy]-3-pyridine carboxylate,
2-[[1-(4-methylbenzyl)-3-pyrrolidinyl]oxy]-3-pyridine carboxylate,
2-[[1-(4-methoxybenzyl)-3-pyrrolidinyl]oxy]-3-pyridine carboxylate,
2-[[1-(3-trifluoromethylbenzyl)-3-pyrrolidinyl]oxy]-3-pyridine carboxylate, and
2-[[1-(4-nitrobenzyl)-3-pyrrolidinyl]oxy]-3-pyridine carboxylate, there are obtained:

(a) 2-(2-chloroethyl)-4-cyclohexyl-2,3-dihydropyrido[3,2-f][1,4]oxazepin-5(4H)-one hydrochloride,
(b) 2-(2-chloroethyl)-2,3-dihydro-4-ethylpyrido[3,2-f][1,4]-oxazepin-5(4H)one hydrochloride,
(c) 2-(2-chloroethyl)-2,3-dihydro-4-isopropyl-pyrido[3,2-f][1,4]-oxazepin-5(4H)-one hydrochloride,
(d) 2-(2-chloroethyl)-4-(4-chlorobenzyl)-2,3-dihydropyrido[3,2-f][1,4]-oxazepin-5(4H)-one hydrochloride,
(e) 2-(2-chloroethyl)-2,3-dihydro-4-(4-methylbenzyl)-pyrido[3,2-f][1,4]-oxazepin-5(4H)-one hydrochloride,
(f) 2-(2-chloroethyl)-2,3-dihydro-4-(4-methoxybenzyl)-pyrido[3,2-f][1,4]-oxazepin-5(4H)-one hydrochloride,
(g) 2-(2-chloroethyl)-2,3-dihydro-4-(3-trifluoromethylbenzyl)pyrido[3,2-f][1,4]-5(4H)-one hydrochloride, and
(h) 2-(2-chloroethyl)-2,3-dihydro-4-(4-nitrobenzyl)-pyrido)[3,2-f][1,4]-oxazepin-5(4H)-one hydrochloride.

INTERMEDIATE 26

2-(2-Chloroethyl)-2,3-dihydro-4-methylpyrido[3,2-f][1,4]-thiazepin-5(4H)-one

A mixture of 80.75 g (0.34 mole) of 2-[(1-methyl-3-pyrrolidinyl)thio]-3-pyridinecarboxylic acid, 500 ml of chloroform, 200 g of carbon tetrachloride and 178 g (0.68 mole) of triphenylphosphine was stirred at reflux for 2.5 hr. The resulting solution was extracted with one 500 ml and three 125 ml portions of 1N hydrochloric acid. The acid extracts were combined and extracted with isopropyl ether. The aqueous layer was basified with sodium hydroxide and extracted three times with chloroform. The combined chloroform extract was dried over sodium sulfate and concentrated. A portion of the residue was chromatographed on the high pressure liquid chromatograph using a silica column and ethyl acetate. The compound obtained was crystallized from isopropyl ether-isopropyl alcohol, m.p. 97°–100° C.

Analysis: Calculated for $C_{11}H_{13}N_2OSCl$: C, 51.46; H, 5.10; N, 10.91. Found: C, 51.63; H, 5.12; N, 10.85.

INTERMEDIATE 27

2-(2-Chloroethyl)-2,3-dihydro-4-methylpyrido[3,2-f][1,4]-thiazepine-5(4H)-thione A mixture of 4.3 g (0.017 mole) of 2-(2-chloroethyl)-2,3-dihydro-4-methylpyrido[3,2-f][1,4]thiazepin-5(4H)-one, 100 ml of toluene and 4.8 g (0.012 mole) of 2,4-bis(4-methoxyphenyl)-1,3,2,4-dithiadiphosphetane-2,4-disulfide was refluxed for 3 hr and then extracted twice with dilute sodium hydroxide. The organic layer was concentrated and the residue chromatographed on the high pressure liquid chromatograph using a silica column and 50% ethyl acetate-50% hexane. The yield of title compound was 2 g, m.p. 160°–162° C.

Analysis: Calculated for $C_{11}H_{13}N_2S_2Cl$: C, 48.43; H, 4.80; N, 10.27. Found: C, 48.46; H, 4.81; N, 10.51.

INTERMEDIATE 28

2-(2-Chloroethyl)-2,3-dihydro-4-methylpyrido[3,4-f][1,4]oxazepin-5(4H)-one

A solution of 78 g (0.5 mole) of 4-chloronicotinic acid and 52 g (0.52 mole) of 1-methylpyrrolidinol in 150 ml of dimethylformamide was added to a suspension of 44 g (1.1 mole) of 60% sodium hydride/mineral oil in 800 ml of dimethylformamide at a rate so as to maintain a temperature of 55°–70° C. (preheated to 55° C.). The resulting mixture was heated to 60° C. for 4 hr and filtered while hot. The filtrate was concentrated on the rotary evaporator (5 mm/steam bath). The residue was dissolved in 600 ml of water and extracted with isopropyl ether. The pH of the aqueous layer was adjusted to 6 with hydrochloric acid and the solution was concentrated on the rotary evaporator (5 mm/steam bath). The residue was suspended in 800 ml of chloroform and 188 g (1.1 mole) of triphenylphosphine added followed by 250 ml of carbon tetrachloride. The mixture was gently heated to 60° C. whereupon the reaction became exothermic and an ice bath was used to maintain a temperature of 60°–65° C. for about 20 minutes. The ice bath was removed and the mixture was heated to reflux for 3.5 hr and cooled. The solution was extracted with 600 ml of water followed by two 200 ml portions of 1N hydrochloric acid. The acid layer was made basic with sodium hydroxide and extracted three times with chloroform. The chloroform was concentrated and the residue was chromatographed by high pressure liquid chromatography using silica gel and eluting with ethyl acetate. Yield of product was 30 g (25%). The mass spectra and NMR are in agreement with the structure of the title compound.

INTERMEDIATE 29

2-(2-Chloroethyl)-2,3-dihydro-4-methylpyrido[3,4-f][1,4]oxazepine-5(4H)-thione monohydrochloride 2-(2-Chloroethyl)-2,3-dihydro-4-methylpyrido[3,4-f][1,4]oxazepin-5(4H)-one, 15 g (0.06 mole), was dissolved in 200 ml of dry toluene and 15 g (0.037 mole) of 2,4-bis(4-methoxyphenyl)-1,3,2,4-dithiaphosphetane-2,4-disulfide was added. The mixture was refluxed for 2.5 hr and the toluene solution decanted. The residue was partitioned between dilute sodium hydroxide and chloroform. The chloroform was dried and concentrated. The residue was chromatographed on a high pressure liquid chromatograph (Waters 500) using a silica column and eluting with ethyl acetate. The fraction containing material of molecular weight 257 was concentrated. The residue in isopropyl alcohol was treated with hydrogen chloride and the resulting crystals were collected. Yield of hydrochloride salt was 0.1 g (0.6%), m.p. 168°–171° C.

Analysis: Calculated for $C_{11}H_{14}N_2OSCl_2$: C, 45.06; H, 4.81; N, 9.55. Found: C, 45.15; H, 4.98; N, 9.26.

INTERMEDIATE 30

2,3,4,5-Tetrahydro-4-methyl-5-oxopyrido[3,2-f][1,4]oxazepine-2-propanenitrile 2-(2-Chloroethyl)-2,3-dihydro-4-methylpyrido[3,2-f][1,4]oxazepin-5(4H)-one hydrochloride, 100 g (0.415 mole) was partitioned between dilute aqueous sodium hydroxide (200 ml) and chloroform (200 ml). The organic layer was saved and the aqueous layer extracted with chloroform (3×50 ml). The organic layer were combined, dried over sodium sulfate and concentrated by rotary evaporation (70° C., water aspirator). The residue, the free base of the starting hydrochloride, 89 g (0.37 mole) was dissolved in 150 ml of toluene and to the solution was added tetrabutyl ammonium bromide, 9 g (0.027 mole). Saturated aqueous potassium cyanide (100 ml) was then added and the mixture stirred mechanically at reflux. After 2 hr, additional tetrabutyl ammonium bromide, 3 g (0.009 mole) and saturated aqueous potassium cyanide (20 ml) were added and the mixture stirred for 0.75 hr at reflux. The contents of the reaction vessel were extracted with ethyl acetate (3×50 ml). (Note: chloroform should be used instead). The organic layer dried over sodium sulfate and concentrated by rotary evaporation (70° C., water aspirator) to ⅓ the original volume. Upon cooling, crystallization ensued. The crystals were filtered and washed with several portions of ethyl acetate and isopropyl ether. Thirty g (35%) of off-white crystals were collected, m.p. 104°–105° C. A sample was recrystallized from ethyl acetate, m.p. 104°–105° C.

Analysis: Calculated for $C_{12}H_{13}N_3O_2$: C, 62.33; H, 5.67; N, 18.17. Found: C, 62.06; H, 5.65 N, 17.97.

INTERMEDIATE 31

2-(2-Chloroethyl)-4-ethyl-2,3-dihydropyrido[3,2-f][1,4]oxazepin-5(4H)-one hydrochloride To a stirred suspension of sodium hydride mineral oil (81.45 g of 60% dispersion 2.036 mole) in dimethylsulfoxide (500 ml) heated to 50° C. was added dropwise a solution of 2-chloronicotinic acid (142 g, 0.905 mole) and N-ethyl-2-pyrrolidinol (99 g, 0.86 mole) in dimethylsulfoxide (500 ml) at a rate to maintain 55°–60° C. (occasional cooling was necessary). After the addition was complete, the mixture was stirred at 50°–60° C. for 1.5 hr and allowed to cool. The solid which precipitated was filtered, washed with ethyl acetate and dried.

The dry sodium salt (172.53 g, 0.62 mole) was suspended in chloroform (1 liter). Hydrogen chloride gas was bubbled through the suspension until the pH meter read 5.76. Triphenylphosphine (365.5 g, 1.395 mole) and $CCl_4$ (365.5 g) were added and the mixture stirred at reflux. After 45 minutes, IR showed 95% reaction. Additional triphenylphosphine (100 g, 0.38 mole) and $CCl_4$ (100 g) were added and the solution stirred at reflux an additional 45 min. IR showed >99% reaction. After cooling, the solution was extracted several times with dilute hydrochloric acid (1.5 liter total). The aqueous layer was then made basic with concentrated sodium hydroxide solution and extracted into chloroform (3×250 ml). The organic layer was dried over sodium sulfate and concentrated by rotary evaporation (70° C., water aspirator). The residuel oil was dissolved in isopropyl alcohol (500 ml) and acidified with hydrogen chloride gas. Upon cooling, an oil was noted and the volume reduced to ⅓ the original volume. Upon cooling, 70 g (0.241 mole, 28%) of pale brown crystals were collected, m.p. 153°–155° C.

Analysis: Calculated for $C_{12}H_{16}N_2O_2Cl_2$: C, 49.50; H, 5.53; N, 9.62. Found: C, 49.64; H, 5.62; N, 9.32.

INTERMEDIATE 32

2-(2-Chloroethyl)-4-ethyl-2,3-dihydropyrido[3,2-f][1,4]oxazepin-5(4H)-thione hydrochloride 2-(2-Chloroethyl)-4-ethyl-2,3-dihydropyrido[3,2-f][1,4]oxazepin-5(4H)-one hydrochloride, approximately 50 g, was partitioned between dilute aqueous sodium hydroxide (50 ml) and chloroform (50 ml). The organic layer was saved and the aqueous layer extracted with additional methylene chloride (2×50 ml). The organic layers were combined, dried over sodium sulfate, filtered and concentrated by rotary evaporation (70° C., water aspirator) yielding 39 g (0.153 mole) of the free base. The free base thus obtained was dissolved in chloroform (1.2 l), and phosphorus pentasulfide (33.9 g, 0.153 mole) was added while stirring. The resulting mixture was heated to reflux for 16 hr. After cooling, the reaction mixture was filtered, washed with dilute aqueous sodium hydroxide (3×300 ml), dried over sodium sulfate and concentrated by rotary evaporation (70° C., water aspirator) to a yellow viscous oil. The oil was taken up in isopropyl alcohol (~200 ml) and made acidic with hydrogen chloride gas. Upon cooling, 20 g (43%) of crystals were collected, m.p. 133°–135° C.

Analysis: Calculated for $C_{12}H_{16}N_2OSCl_2$: C, 46.91; H, 5.25; N, 9.12. Found: C, 47.33; H, 5.38; N, 9.10.

INTERMEDIATE 33

7-Chloro-2-(2-chloroethyl)-2,3-dihydro-4-methyl-pyrido[3,2-f][1,4]oxazepin-5(4H)-one A sample of 2-(2-chloroethyl)-2,3-dihydro-4-methyl-pyrido[3,2-f][1,4]-oxazepin-5-(4H)-one hydrochloride (10 g, 136 mole) was dissolved in dimethylformamide (150 ml) and heated to reflux. Sulfuryl chloride (20 g, 0.148 mole) was then added dropwise over a period of 40-50 minutes. The reaction was allowed to stir at reflux for 30 minutes following the addition of $SO_2CL_2$. After cooling, the contents of the flask were partitioned between water (150 ml) and benzene (150 ml). The benzene layer was saved and the water layer extracted with an additional amount of benzene (2×50 ml). The benzene extracts were combined and washed with dilute aqueous potassium hydroxide (2×50 ml) followed by dilute aqueous hydrochloric acid (2×50 ml). The benzene layer was dried over sodium sulfate and concentrated by rotary evaporation (~70° C., water aspirator) yielding 2.61 g of crude material. The crude material was recrystallized from isopropyl ether giving 1.25 g (12.6%) of off-white crystals, m.p. 78°–79° C.

Analysis: Calculated for $C_{11}H_{12}N_2O_2Cl_2$: C, 48.02; H, 4.40; N, 10.18. Found: C, 48.07; H, 4.53; N, 10.10.

INTERMEDIATE 34

7-Chloro-2-(2-chloroethyl)-2,3-dihydro-4-methyl-pyrido[3,2-f][1,4]oxazepine-5(4H)thione 7-Chloro-2-(2-chloroethyl)-2,3-dihydro-4-methyl-pyrido[3,2-f][1,4]oxazepine-5(4H)-one, 6.0 g (0.022 mole) was suspended in 200 ml of toluene. To this suspension was added 2,4-bis(4-methoxyphenyl)-1,3-dithia-2,4-diposphetane-2,4-dilsulfide. The mixture was heated to reflux with vigorous stirring for 2 hours. Because the reaction was not complete, an additional amount (3.0 g) of 2,4-bis(4-methoxyphenyl)-1,3-dithia-2,4-diphosphe-tane-2,4-disulfide was added and the mixture stirred at reflux for 2 hr and left standing for 56 hr at room temperature. The toluene layer was decanted and washed with 50 ml of dilute aqueous sodium hydroxide and 50 ml of dilute hydrochloric acid. Toluene was removed by rotary evaporation (~80° C., wafter aspirator). The crude oil was recrystallized from isopropyl alcohol giving 3.5 g (54%) of pale yellow crystals, m.p. 125°–127° C.

Analysis: Calculated for $C_{11}H_{12}N_2OSCl_2$: C, 45.37; H, 4.15; N, 9.62. Found: C, 45.40; H, 4.20; N, 9.71.

INTERMEDIATE 35

2-(Chloromethyl)-4-cyclohexyl-2,3-dihydropyrido[3,2-f][1,4]oxazepin-5(4H)-one

A 15 g (0.05 mole) sample of sodium 2-[(1-cyclohexyl-3-azetidinyl)oxy]-3-pyridine carboxylate obtained in Preparation 23 was suspended in 100 ml of chloroform and hydrogen chloride passed in until a pH of 5.8 remained steady. To the stirred mixture was added 18 g of thionyl chloride. The resulting solution was stirred at room temperature for 3 hr. An I.R. spectrum showed a peak at 1770 $cm^1$ which is characteristic of acid chloride. Forty milliliters of triethylamine was added dropwise while cooling to about 25° C. with an ice bath. The chloroform solution was stirred an additional 0.5 hr and was extracted with water, dried over sodium sulfate and concentrated. The residue was chromatographed on a 7×20 cm silica column using ethanol as the eluent. The desired material was the first to be removed from the column. The ethanolic solution was concentrated and the residue crystallized once from ethyl acetate-isopropyl ether and once from isopropyl alcohol. Yield of title compound was 1 g (7%), m.p. 120°–122° C.

Analysis: Calculated for $C_{15}H_{19}N_2O_2Cl$: C, 61.12; H, 6.50; N, 9.50. Found: C, 61.11; H, 6.62; N, 9.32.

INTERMEDIATE 36

2-(2-Chloroethyl)-2,3-dihydro-4-(phenylmethyl)-pyrido[3,2-f][1,4]oxazepin-5(4H)one The title compound was prepared in crude form in the first part of Example 67.

INTERMEDIATE 37

2,3-Dihydro-2-[1,3-dihydro-1,3-dioxo-2H-isoindol-2-yl)ethyl-4-methylpyrido[3,2-f][1,4]oxazepin-5(4H)-one To a solution of 4.92 g (0.02 mole) of 2-(2-chloroethyl)-2,3-dihydro-4-methylpyrido[3,2-f]-1,4-oxazepin-5-(4H)one in 35 ml of dimethylformamide was added 7.55 g (0.041 mole) of potassium phthalimide. The mixture was stirred for 5 hr at 100° C. and left standing at room temperature overnight. Dimethylformamide was removed by rotary evaporation (80° C. vacuum pump). The residue was taken up in 100 ml of chloroform and washed with water (2×30 ml) and 2M potassium hydroxide (2×3 ml). The organic layer was dried over anhydrous sodium sulfate, filtered and concentrated by rotary evaporation (70° C., water aspirator). The 6.26 g of crude product was recrystallized from isopropyl alcohol to give 2.60 g (36%) white crystalline powder, m.p. 146°–47° C.

Analysis: Calculated for $C_{19}H_{17}N_3O_4$: C, 64.95; H, 4.88; N, 11.95. Found: C, 65.18; H, 4.91; N, 12.09.

INTERMEDIATE 38

2-2-(2,3-Dihydro-4-methyl-5(4H)-thioxopyrido[3,2-f][1,4-oxazepin-2-yl)-ethyl]-1H-isoindole-1,3(2H)-dione To a solution of 1.0 g (0.0038 mole) of 2-(2-chloroethyl)-2,3-dihydro-4 methylpyrido[3,2-f]-1,4-oxazepine-5(4H)-thione in 20 ml dimethylformamide was added 1.43 g (0.0078 mole) of potassium phthalimide. The mixture was heated to 100° C. for 6 hr with stirring.

The dimethylformamide was removed by rotary evaporation (70°, vacuum pump) and the residue taken up in chloroform (100 ml). The organic layer was washed with 2N potassium hydroxide (2×30 ml), dried over anhydrous sodium sulfate, filtered, and concentrated by rotary evaporation (~70° C., water aspirator). The crude oil (1.2 g) was recrystallized from isopropyl alcohol giving 0.95 g (68%) of pale white crystals, m.p. 172°–73° C.

Analysis: Calculated for $C_{19}H_{17}N_3O_3S$: C, 62.11; H, 4.66; N, 11.44. Found: C, 61.86; H, 4.70; N, 11.53.

INTERMEDIATE 39

2,3,4,5-Tetrahydro-4-methyl-5-thioxopyrido[3,2-f][1,4]-oxazepine-2-propanenitrile To a solution of 11.0 g (0.04 mole) of 2,3,4,5-tetrahydro-4-methyl-5-oxopyrido[3,2-f][1,4]-oxazepine-2-propanenitrile in 175 ml toluene was added 10.5 g (0.026 mole) of 2,4-bis(4-methoxyphenyl)-1,3-dithia-2,4-diphosphetane-2,4-disulfide. The reaction mixture was heated to reflux for 2 hr with vigorous mechanical stirring. Another 3.0 g (0.007 mole) of 2,4 bis(4-methoxyphenyl)-1,3-dithia-2,4-diphosphetane 2,4-disulfide was added and heating continued for 1 hr additional. The reaction mixture was allowed to cool and stand overnight at room temperature. Toluene was removed by rotary evaporation (90° C., water aspirator) and the residue taken up in 200 ml chloroform. This was washed with 2×50 ml 2M aqueous potassium hydroxide and concentrated by rotary evaporator (90° C., water aspirator). Crystallization ensued upon cooling. Recrystallization from isopropyl alcohol afforded 1.60 g (13.8%) product, m.p. 155°–56° C.

Analysis: Calculated for $C_{12}H_{13}N_3OS$: C, 58.28; H, 5.30; N, 16.99. Found: C, 58.00; H, 5.26; N, 17.13.

INTERMEDIATE 40

2-(2-Chloro-1-methylethyl)-2,3-dihydro-4-methylpyrido[3,2-f][1,4]-oxazepin-5(4H)-one hydrochloride To a suspension of 59.6 g (60%) in oil, 1.49 mole) of sodium hydride in 400 ml of tetrahydrofuran heated to reflux was added a solution of 110 g (0.71 mole) of 2-chloronicotinic acid and 81.3 g (0.71 mole) of 1,4-dimethyl-3-pyrrolidinol in 400 ml of tetrahydrofuran at a rate such that good reflux was maintained (20–35 minutes). Heating at reflux was continued for 2 hr subsequent to the completion of the addition. Because mass spectra showed 30% starting material at this point, 25.0 g (0.63 mole) additional sodium hydride was added and reflux continued for 4 hr. The reaction mixture was left standing overnight.

The mixture was quenched with isopropyl alcohol and filtration attempted. However, when filtration failed, the solvent was stripped off by rotary evaporation.

This crude salt was suspended in 1 liter of chloroform and hydrogen chloride gas was bubbled in until a pH of 6 was reached. To this suspension was added 372 g (1.42 mole) of triphenylphosphine and 372 g carbon tetrachloride and the entire mixture heated at reflux for 1.5 hr. However, reaction was not complete as evidenced by I.R. An additional 100 g (0.38 mole) of triphenyl phosphine and 100 g of carbon tetrachloride was added and reflux continued overnight. After cooling the reaction, 100 g of triethylamine was added.

The reaction mixture was extracted with 4×200 ml of dil aqueous hydrochloric acid. The hydrochloric acid extracts were made basic with conc. sodium hydroxide and extracted into a total of 1 liter of chloroform. The chloroform was removed by rotary evaporation (70° C.; 3 mm) and the residue taken up in 300 ml toluene.

The toluene was extracted with 4×125 ml of dil aqueous hydrochloric acid. The hydrochloric acid extracts were combined and washed with 4×200 ml of methylene chloride. The hydrochloric acid layer was basified with conc. sodium hydroxide and extracted with methylene chloride. The organic extracts were combined, dried over sodium sulfate, filtered and concentrated by rotary evaporation. The residue was taken up in isopropyl alcohol and treated with hydrogen chloride gas. Approximately 34 g (16%) of white crystals were collected. Recrystallization in isopropyl alcohol gave an analytical sample, m.p. 178°–81° C.

Analysis: Calculated for $C_{12}H_{16}N_2O_2Cl_2$: C, 49.50; H, 5.54; N, 9.62. Found: C, 49.46; H, 5.54; N, 9.50.

INTERMEDIATE 41

2-(2-Chloroethyl)-2,3-dihydro-2,4-dimethylpyrido[3,2-f]-1,4-oxazepin-5(4H)-one hydrochloride To a suspension of 60 g (60% in oil, 1.5 mole) of sodium hydride in 400 ml of tetrahydrofuran heated to reflux was added a solution of 110 g (0.70 mole) of 2-chloronicotinic acid and 80 g (0.70 mole) of 1,3-dimethyl-3-pyrrolidinol so as to maintain good reflux. Heating at reflux was continued overnight. The mass spectra showed very little product at this point; therefore, 400 ml of dimethylformamide was added and heating at 77° C. was continued overnight. Approximately 10% of the desired product was then observed by mass spectra. The tetrahydrofuran was evaporated by passing nitrogen gas over the reaction mixture while at the same time being replaced with dimethylformamide. The temperature was concomitantly increased to 100° C. The mixture was stirred overnight at 100° C. After cooling, no salt precipitated out; therefore, dimethylformamide was removed by rotary evaporation (90° C.; 5 mm). Approximately 250 g of crude salt was collected.

Into a suspension of 230 g (~0.88 mole) of this crude salt in 1 liter of chloroform was bubbled hydrogen chloride gas to pH 6. To this suspension was added 463 g (1.77 mole) of triphenyl phosphine and 463 g of carbon tetrachloride. The mixture was then heated to reflux. After 8 minutes a vigorous exotherm ensued which subsided in 30 minutes. Reflux was continued for 2.5 hr. According to infrared analysis, the reaction was near completion. Approximately 40 ml of triethylamine was added to drive the reaction to completion. The mixture was left standing overnight at room temperature.

The reaction mixture was extracted with 700 ml dil. aq. hydrochloric acid. The hydrochloric acid extracts were combined and washed with 4×100 ml of chloroform. The combined aqueous hydrochloric acid extracts were then made basic with conc. sodium hydroxide and extracted with 5×200 ml of methylene chloride. The organic extracts were combined, dried over anhydrous sodium sulfate, filtered and concentrated by rotary evaporation (70° C.; 30 mm). The residue was taken up in 600 ml of toluene and treated with activated charcoal 4 times. The toluene was then removed by rotary evaporation and the residue treated with hydrogen chloride in isopropyl alcohol which afforded 53 g (21%). Recrystallization from isopropyl alcohol afforded an analytically pure sample, m.p. 155°–158° C.).

Analysis: Calculated for $C_{12}H_{16}N_2O_2Cl_2$: C, 49.50; H, 5.54; N, 9.62. Found: C, 49.49; H, 5.61 N, 9.75.

INTERMEDIATE 42

2-(2-Chloroethyl)-2,3-dihydro-2,4-dimethylpyrido[3,2-f]1,4-oxazepine-5(4H)-thione To a suspension of 4.6 g (0.04 mole) of phosphorus pentasulfide in 50 ml of acetonitrile was added, all at once, a solution of 20 g (0.079 mole) of 2-(2-chloroethyl)-2,3-dihydro-2,4-dimethylpyrido[3,2-f]-1,4-oxazepin-5(4H)-one in 50 ml of acetonitrile. The mixture was heated to reflux for 4 hr with stirring, at which time the mass spectra showed no starting material. The reaction was left standing overnight at room temperature.

To the reaction mixture was added 100 ml of toluene followed by stirring for 15 minutes. Some tar-like material collected on the sides of the reaction vessel. The solution was filtered with much difficulty. The filtrate was saved and washed *cautiously* with 3×50 ml of saturated aqueous sodium bicarbonate. The organic phase was dried over anhydrous sodium sulfate, treated with activated charcoal, filtered, dried again over anhydrous sodium sulfate, filtered, and concentrated by rotary evaporation (80° C.; 30 mm). The crude oil (9.2 g) was crystallized from isopropyl alcohol, giving 6.0 g (28%) of yellow crystals, m.p. 119°–121° C.

Analysis: Calculated for $C_{12}H_{15}N_2OSCl$: C, 53.23; H, 5.58; N, 10.35. Found: C, 53.05; H, 5.60; N, 10.34.

INTERMEDIATE 43

2-(2-Chloropropyl)-2,3-dihydro-4-methylpyrido[3,2-f]1,4-oxazepin-5(4H)-one hydrochloride To a suspension of 36.1 g of 60% sodium hydride in oil (0.90 mole) in 300 ml of tetrahydrofuran heated to reflux and under a nitrogen blanket was added a solution of 68.3 g (0.43 mole) of 2-chloronicotinic acid and 50 g (0.43 mole) of 1,2-dimethyl-4-pyrrolidinol in 300 ml of tetrahydrofuran at a rate such that good reflux was maintained (20 min). Subsequent to this addition, heating at reflux was maintained for 2.5 hr at which time the reaction appeared to be complete (by mass spec.). The crude sodium salt was filtered and washed with ethyl acetate affording 135 g of the crude sodium salt.

To a suspension of 115 g (~0.44 mole) of the above sodium salt in 650 ml of chloroform was added hydrogen chloride to reach a pH of 6. To this mixture was added 231.8 g (0.88 mole) of triphenylphosphine and 231.8 g of carbon tetrachloride and the entire reaction mixture heated to reflux for 3 hr. After cooling, the reaction mixture was extracted with 4×250 ml of dihydrochloric acid. The aqueous layer was washed with 4×125 ml of chloroform and made basic with concentrated sodium hydroxide. The aqueous layer was then extracted with 3×250 ml of chloroform. The organic extracts were combined, dried over anhydrous sodium sulfate, filtered and concentrated by rotary evaporation. To the residue was added 800 ml of toluene and the resulting solution decolorized 3 times with activated charcoal. The solvent was removed by rotary evaporation (90° C., 30 mm). The residue was taken up in 300 ml of isopropyl alcohol and the solution was saturated with hydrogen chloride, seeded, and left standing overnight at room temperature. Approximately 30 g (~23%) of salt was collected. An analytical sample was prepared by recrystallizating the salt 3 times from isopropyl alcohol, m.p. 143°–49° C.

Analysis: Calculated for $C_{12}H_{16}N_2O_2Cl_2$: C, 49.50; H, 5.54 N, 9.62. Found: C, 49.85; H, 5.62 N, 9.84.

INTERMEDIATE 44

2-(2-Chloropropyl)-2,3-dihydro-3-methylpyrido[3,2-f]-1,4-oxazepine-5(4H)-thione To a suspension of 4.90 g (0.022 mole) of phosphorus pentasulfide in 30 ml of acetonitrile was added a solution of 10 g (0.039 mole) of 2-(2-chloropropyl)-2,3-dihydro-4-methylpyrido[3,2-f]-1,4-oxazepin-5(4H)-one in 25 ml of acetonitrile. The mixture was heated to reflux, with stirring, for 5.5 hours and left standing at room temperature overnight. To the reaction mixture was added 50 ml of toluene, followed by stirring for a few minutes. The mixture was filtered and the residue washed with 25 ml of toluene/acetonitrile. The filtrate was washed *cautiously* with 3×75 ml of saturated aqueous sodium bicarbonate, dried over anhydrous sodium sulfate, filtered, treated with activated charcoal, filtered and concentrated by rotary evaporation (90° C.; 30 mm). The crude syrup (10.0 g) was crystallized from isopropyl ether/isopropyl alcohol, giving 5 g of yellow crystals, m.p. 95°–97° C. A second crop was collected, bringing the total to 6 g (57%).

Analysis: Calculated for $C_{12}H_{15}N_2OSCl$: C, 53.28; H, 5.58; N, 10.35. Found: C, 53.13; H, 5.58; N, 10.35.

INTERMEDIATE 45

2-(2-Chloro-1-methylethyl)-2,3-dihydro-4-methylpyrido[3,2-f]-1,4-oxazepine-5(4H)-thione hydrochloride To a suspension of 5.35 g (0.024 mole) of phosphorus pentasulfide in 25 ml of acetonitrile was added a solution of 10.9 g (0.043 mole) of 2-(2-chloro-1-methylethyl)-2,3-dihydro-4-methylpyrido[3,2-f]-1,4-oxazepin-5(4H)-one in 25 ml of acetonitrile. The mixture was heated to reflux for 2.75 hr and left standing at room temperature overnight.

To the cooled reaction mixture was added 50 ml of toluene, followed by filtration. The residue was washed with 45 ml of 3/1, V/V toluene/acetonitrile. The filtrate was washed *cautiously* with 3×75 ml of saturated sodium bicarbonate, dried over anhydrous sodium sulfate, filtered, treated with activated charcoal, filtered, and concentrated by rotary evaporation. The residue was treated with hydrogen chloride in isopropyl alcohol/isopropyl ether which yielded one crop of 4.5 g of yellow crystals, m.p. 148°–51° C. [(Note: a second crop of 1.5 g was collected, bringing the total yield to 6.0 g (45.4%)].

Analysis: Calculated for $C_{12}H_{16}N_2OSCl_2$: C, 46.91; H, 5.25; N, 9.12. Found: C, 48.86; H, 5.34; N, 9.06.

INTERMEDIATE 46

2-(2-Chloroethyl)-2,3-dihydro-4-methyl-1,4-oxazepino[6,7-b]-quinolin-5(4H)-one To 21.3 ml (0.15 mole) of diisopropylamine in 300 ml of tetrahydrofuran at −70° C. was added dropwise, at a rate to keep the temperature between −70° and −60° C., 61.1 ml of 2.7M n-butyllithium (0.16 mole). The temperature was maintained at −70° C.±3° C. for 20 minutes. A solution of 2-chloroquinoline in 60 ml of tetrahydrofuran was added dropwise at a rate such that temperature remained between −70° and −60° C. After 20 minutes, the darkened reaction solution was poured onto a large excess of dry ice. The solvent was evaporated with a stream of air.

The residue was taken up in 300 ml of water, made basic with dilute aqueous sodium hydroxide and washed with 3×50 ml of isopropyl ether. The aqueous phase was filtered and treated with dilute hydrochloric acid to ~pH 4-5, at which time a copious precipitate formed. The precipitate was collected and the filtrate reacidified yielding more precipitate. The precipitates were combined and washed with water, isopropyl alcohol, and isopropyl ether. Approximately 15.4 g (61.5%) of off-white crystals were collected.

To a suspension of 4.0 g of 60% sodium hydride in oil (0.10 mole) in 100 ml tetrahydrofuran heated to reflux was added a solution of 5.5 g (0.048 mole) of N-methyl-3-pyrrolidinol and 10 g (0.048 mole) of the above prepared 2-chloro-3-quinolinecarboxylic and in 50 ml of tetrahydrofuran at such rate as to maintain good reflux. Reflux was maintained for 1.5 hr and the reaction mixture cooled. The solvent was removed by rotary evaporation yielding 26 g crude product.

The entire crude product from above was suspended in 150 ml chloroform and hydrogen chloride bubbled in until pH of 5.76 was reached (note: after hydrogen chloride addition ceased, the pH continued to lower to 1.7). To this suspension was added 25.0 g (0.096 mole) of triphenylphosphine and 25 g of carbon tetrachloride. After 45 min, an additional 10 g (0.038 mole) of triphenylphosphine and 10 g of carbon tetrachloride was added. After 30 minutes, the heat was removed and the reaction driven to completion by dropwise addition of 20 ml of triethylamine.

The reaction mixture was extracted with 3×50 ml of 3N hydrochloric acid. The aqueous extracts were combined, washed with 2×50 ml chloroform, made basic with concentrated sodium hydroxide and extracted with 3×50 ml of chloroform. The organic extracts were combined and concentrated by rotary evaporation. The syrupy residue was taken up in 100 ml of toluene and treated with activated charcoal. The toluene was removed by rotary evaporation and the syrupy residue crystallized from isopropyl alcohol, giving 1.5 g (11%) of white crystals, m.p. 133°-134° C.

Analysis: Calculated for $C_{15}H_{15}N_2O_2Cl$: C, 61.97; H, 5.20; N, 9.63. Found: C, 61.73; H, 5.18 N, 9.54.

INTERMEDIATE 47

2-(2-Chloroethyl)-2,3-dihydro-4-methyl-1,4-oxazepino[6,7-b]quinoline-5(4H)-thione To 3.0 g (0.01 mole) of 2-(2-chloroethyl)-2,3-dihydro-4-methyl-1,4-oxazepino[6,7-b]-quinolin-5(4H)-one in 30 ml of acetonitrile was added 1.3 g (0.006 mole) of phosphorus pentasulfide. The mixture was stirred vigorously at reflux for 2 hr. After cooling, the reaction mixture was diluted with 60 ml of toluene and filtered. The residue on the filter paper was washed with 50 ml of additional toluene/acetonitrile, 3/1, V/V. The filtrate was washed with 3×50 ml saturated sodium carbonate (caution: gas evolved), dried over anhydrous sodium sulfate, filtered, treated with activated charcoal, filtered again and concentrated by rotary evaporation (90° C., 30 mm). The residual syrup was crystallized from isopropyl alcohol, yielding 1.6 g (52%) of yellow crystals, m.p. 114°-116° C.

Analysis: Calculated for $C_{15}H_{15}N_2OClS$: C, 58.72; H, 4.93; N, 9.13. Found: C, 38.38; H, 4.92; N, 9.07.

INTERMEDIATE 48

2-(2-Chloroethyl)-2,3-dihydro-4-methyl-9-(trifluoromethyl)-1,4-oxazepino[6,7-c]quininolin-5(4H)-one hydrochloride To a suspension of 3.16 g (60% in oil, 0.08 mole) of sodium hydride in 250 ml of tetrahydrofuran under dry nitrogen atmosphere heated to reflux was added a solution of 10.42 g (0.038 mole) of 4-chloro-7-(trifluoromethyl)-3-quinolinecarboxylic acid and 3.81 g (0.038 mole) of N-methyl-3-pyrrolidinol in 50 ml of tetrahydrofuran at such a rate as to maintain good reflux. Heating at reflux was continued for 3 hr. The solvent was removed by rotary evaporation (80° C., 30 mm), and the crude sodium salt (12 g) was dried overnight.

The entire amount of crude sodium salt was suspended in 250 ml of methylene chloride. Hydrogen chloride was added to a pH of 2. To this suspension was added 19.4 g (0.074 mole) of triphenyl phosphine and 19.4 g of carbon tetrachloride. The extire mixture was heated to reflux for 3 hrs. IR indicated presence of acid chloride; therefore, the reaction was driven to completion by the addition of 15 ml of triethylamine. After cooling, the reaction mixture was extracted with 2×75 ml of 3N hydrochloric acid. The acid washings were combined and washed with 75 ml of methylene chloride. The water layer was made basic (after cooling with ice) and extracted with 3×75 ml methylene chloride. The methylene chloride was removed by rotary evaporation and the residue taken up in 100 ml of toluene. The solution was treated with activated charcoal, filtered, and concentrated by rotary evaporation (90° C., 30 mm). The residue was dissolved in isopropyl alcohol and acidified with ethereal hydrogen chloride. Approximately 1.1 g (7.3%) of white needles were collected, m.p. 172°-174° C.

Analysis: Calculated for $C_{16}H_{15}N_2O_2Cl_2F_3$: C, 48.63; H, 3.83; N, 7.09. Found: C, 48.78; H, 3.84; N, 7.04.

INTERMEDIATE 49

2-(2-Chlorophenyl)-2,3-dihydro-4-methyl-9-(trifluoromethyl-1,4-oxazepino[6,7-c]quinoline-5(4H)-thione To a suspension of 0.85 g (0.004 mole) of phosphorus pentasulfide in 25 ml of acetonitrile was added to a solution of 2.3 g (0.0064 mole) of 2-(2-chloroethyl)-2,3-dihydro-4-methyl-9-(trifluoromethyl)-1,4-oxazepino[6,7-c]quinolin-5(4H)-one and the mixture heated to reflux. TLC in ethyl acetate showed only 50% conversion; therefore, 0.5 g (0.0022 mole) of phosphoruspentasulfide was added. After an additional 2 hr, no change was seen in starting material/product. Heat was removed and the reaction mixture left standing overnight. The mixture was diluted with 75 ml of toluene and washed cautiously (gas evolved) with 3×50 ml of saturated sodium bicarbonate. The solvent was removed by rotary evaporation and the residue combined with a previous run of the same material. The combined products were purified by column chromatography over silica gel eluting with ethyl acetate. The solvent was removed from the fractions containing the product giving 0.9 g of yellow oil. The oil was recrystallized from isopropyl ether giving 0.55 g of yellow crystals, m.p. 135°-37° C.

Analysis: Calculated for $C_{16}H_{14}N_2OSF_3Cl$: C, 51.27; H, 3.77; N, 7.47. Found: C, 51.41; H, 3.83; N, 7.42.

INTERMEDIATE 50

2-Chloromethyl-1,2,3,4-tetrahydro-1-methyl-4-(1-methylethyl)-5H)1,4-benzodiazepin-5-one To a stirring solution of 266 ml (0.64 mole) of 2.4 m butyllithium solution in hexane, was slowly added 117.5 g (0.58 mole) of N-methyl-N-phenyl-1-(1-methylethyl)-3-azetidineamine. The temperature of the mixture rose to 55° C. which was then allowed to reflux for 5.5 hours. When cooled, the solution was poured slowly with vigorous stirring onto a slurry of dry ice in hexane and allowed to stand overnight. The residue was dissolved in chloroform and 117.0 g (1.16 mole) of phosphorous oxychloride was added dropwise while stirring. The solution was reflued for two hours. Upon cooling, the solution was washed, first with a dilute hydrochloric acid solution, then with a dilute sodium hydroxide solution. The hexane layer was dried over anhydrous sodium sulfate, filtered, and concentrated in vacuo. The residue was dissolved in hot isopropyl ether. The crystals obtained on cooling were recrystallized from the same solvent. The white solid weighed 45.0 g (29%). The solid was recrystallized twice more to give an analytical sample, m.p. 90°–92° C.

Analysis: Calculated for $C_{14}H_{19}Cl_1N_2O$: C, 63.03; H, 7.18; N, 10.50. Found: C, 62.59; H, 7.09; N, 10.40.

INTERMEDIATE 51

2-(2-Chloroethyl)-4-ethyl-1-methyl-1,2,3,4-tetrahydro-5H-1,4-benzodiazepin-5-one To 206 g (1 mole) of 1-ethyl-3-methylanilinopyrrolidine was added 660 ml (1.05 moles) of 14.98% butyllithium in hexane and the solution refluxed for 2 hours and poured on solid carbon dioxide. The carbon dioxide hexane mixture was allowed to evaporate overnight, leaving a dry yellow solid. The solid was dissolved in chloroform. To this solution was added dropwise with stirring 1 mole of phosphorous trichloride. The temperature rose to reflux during addition and remained there throughout most of the addition. When the addition was complete, the mixture was stirred one hour and water was added cautiously. The resulting mixture was made basic with sodium hydroxide. The chloroform layer was separated, dried over anhydrous sodium sulfate and concentrated. The residue was crystallized from isopropyl ether to yield 112 g (42%), m.p. 75°–79° C. A 25 g sample was recrystallized from isopropyl ether to give 18 g of product, m.p. 78°–80° C.

Analysis: Calculated for $C_{14}H_{19}N_2O_1Cl$: C, 63.03; H, 7.18; N, 10.50. Found: C, 63.27; H, 7.22; N, 10.55.

INTERMEDIATE 52

6-Chloro-2-(2-chloroethyl)-2,3-dihydro-4-methylpyrido[4,3-f]-1,4-oxazepin-5(4H)-one To a suspension of 2.1 g (60% in oil, 0.052 mole) of sodium hydride in 125 ml of dimethylformamide heated to 60° C. under a nitrogen gas blanket was added a solution of 2.65 g (0.026 mole) of N-methyl-3-pyrrolidinol and 5.0 g (0.026 mole) of 3,5-dichloropyridine-4-carboxylic acid in 40 ml of dimethylformamide dropwise at such a rate as to maintain 60° C. Subsequent to this addition, the mixture was heated to 75° C. for 3 hr. The solvent was then removed by rotary evaporation (60° C., 5 mm). The entire solid residue was suspended in 150 ml methylene chloride and hydrogen chloride added until a pH of 3 was reached. To the resulting mixture was added 15 g (0.057 mole) of triphenylphosphine and 15 g carbon tetrachloride and the entire mixture heated to reflux. After 1 hr, 7.5 g (0.029 mole) of triphenylphosphine and 7.5 g carbon tetrachloride were added, followed by the same increments 1 hr later. The reaction was driven to completion by adding 20 ml of triethylamine. The reaction mixture was washed with 6×50 ml of 3N hydrochloric acid, dried over sodium sulfate, filtered and concentrated by rotary evaporation. To the residue was added ethyl acetate, which caused much tarry material to fall out of solution, leaving the desired product and triphenylphosphine oxide in solution. The mixture was chromatographed by column chromatography using silica gel as the stationary phase and ethyl acetate as eluent. Similar fractions were combined and ethyl acetate removed by rotary evaporation, yielding 0.6 g (7%), of white crystals, m.p. 134°–38° C.

Analysis: Calculated for $C_{11}H_{12}N_2O_2Cl_2$: C, 48.02; H, 4.40 N, 10.18. Found: C, 47.89; H, 4.38; N, 10.12.

INTERMEDIATE 53

2-(2-Chloroethyl)-2,3-dihydro-4-methyl-1,4-oxazepino[7,6-f]isoquinolin-5(4H)-one Following the procedure of Intermediate 8, 5-[(1-methyl-3-pyrrolidinyl)oxy]-6-isoquinolinecarboxamide is converted to the title compound.

INTERMEDIATE 54

2-(2-Chloroethyl)-2,3-dihydro-4-methyl-1,4-oxazepino[7.6-f]isoquinoline-5(4H)-thione Following the procedure of Intermediate 47, 2-(2-chloroethyl)-2,3-dihydro-4-methyl-1,4-oxazepino[7,6-f]isoquinoline-5(4H)-one is sulfurized to give the title compound.

INTERMEDIATE 55

2-(2-Chloroethyl)-2,3-dihydro-4-methyl-1,4-oxazepino[6,7-g]isoquinolin-5(4H)-one Following the procedure of Intermediate 8, 7-[(1-methyl-3-pyrrolidinyl)oxy]-6-isoquinolinecarboxamide is converted to the title compound.

INTERMEDIATE 56

2-(2-Chloroethyl)-2,3-dihydro-4-methyl-1,4-oxazepino[6,7-g]isoquinoline-5(4H)-thione Following the procedure of Intermediate 47, 2-(2-chloroethyl)-2,3-dihydro-4-methyl-1,4-oxazepino[6,7-g]isoquinolin-5(4H)-one is sulfurized to give the title compound.

INTERMEDIATE 57

2-(2-Chloroethyl)-2,3-dihydro-4,7-dimethyl-1,4-oxazepino[6,7-h]quinolin-5(4H)-one Following the procedure of Intermediate 8, 5-methyl-8-[(1-methyl-3-pyrrolidinyl)oxy]-7-quinolinecarboxamide is converted to the title compound.

INTERMEDIATE 58

2-(2-Chloroethyl)-2,3-dihydro-4,7-dimethyl-1,4-oxazepino[6,7-h]quinoline-5(4H)-thione Following the procedure of Intermediate 47, 2-(2-chloroethyl)-2,3-dihydro-4,7-dimethyl-1,4-oxazepino[6,7-h]quinoline-5(4H)-one is sulfurized to give the title compound.

INTERMEDIATE 59

2-(2-Chloroethyl)-2,3-dihydro-4,10-dimethyl-1,4-oxazepino[6,7-h]quinolin-5(4H)-one Following the procedure of Intermediate 8, 2-methyl-8[(1-methyl-3-pyrrolidinyl)oxy]-7-quinolinecarboxamide is converted to the title compound.

INTERMEDIATE 60

2-(2-Chloroethyl)-2,3-dihydro-4,10-dimethyl-1,4-oxazepino[6,7-h]quinoline(5-4H)-thione Following the procedure of Intermediate 47, 2-(2-chloroethyl)-2,3-dihydro-4,10-dimethyl-1,4-oxazepino[6,7-h]quinoline-5(4H)-one is sulfurized to give the title compound.

INTERMEDIATE 61

2-(2-Chloroethyl)-3,4-dihydro-2-methyl[1,4]-oxazepino[6,7-f]quinolin-1(2H)-one

Following the procedure of Intermediate 8, 6-[(1-methyl-3-pyrrolidinyl)-oxy]-5-quinolinecarboxamide is converted to the title compound.

INTERMEDIATE 62

4-(2-Chloroethyl)-3,4-dihydro-2-methyl[1,4]-oxazepino[6,7-f]quinoline-1(2H)-thione Following the procedure of Intermediate 47, 2-(2-chloroethyl)-3,4-dihydro-2-methyl[1,4]-oxazepino[6,7-f]quinolin-1(2H)one is sulfurized to give the title compound.

INTERMEDIATE 63

2-(2-Chloroethyl)-2,3-dihydro-4-methyl-1,4-oxazepino[6,7-h]quinolin-5(4H)-one

Following the procedure of Intermediate 8, 8-[(1-methyl-3-pyrrolidinyl)oxy]-7-quinolinecarboxamide is converted to the title compound.

INTERMEDIATE 64

2-(2-Chloroethyl)-2,3-dihydro-4-methyl-1,4-oxazepino[6,7-h]quinoline-5(4H)-thione Following the procedure of Intermediate 47, 2-(2-chloroethyl)-2,3-dihydro-4-methyl-1,4-oxazepino[6,7-h]quinolin-5(4H)-one is sulfurized to give the title compound.

INTERMEDIATE 65

(S)-2-(2-Chloroethyl)2,3-dihydro-4-methylpyrido[3,2-f][1,4]oxazepin-5(4H)-one hydrochloride [1:1]

A solution of 47.4 g (0.3 mole) of 2-chloronicotinic acid and 30 g (0.3 mole) of -(S)-1-methyl-3-pyrrolidinol in 400 ml of tetrahydrofuran was added over a period of 1 hr to a stirred suspension of 26.4 g (0.66 mole) of 60% sodium hydride)mineral oil in 500 ml of tetrahydrofuran at 50°-60° C. The mixture was stirred at reflux for 2.5 hr and allowed to cool to 25° C. About 400 ml of methylene chloride was added to the slurry followed by the dropwise addition of 34.5 g (0.36 mole) of methane sulfonic acid in 100 ml of methylene chloride. The mixture was stirred 10 min and 157 g (0.6 mole) of triphenylphosphine was added followed in 200 ml of carbon tetrachloride. The mixture was heated to reflux for 1 hr. To the cooled (25° C.) solution was added at a rapid drop, 100 ml of triethylamine. The solution was concentrated on the rotary evaporator and the residue was partitioned between methylene chloride and dilute hydrochloric acid. The methylene chloride was extracted 6 times with dilute hydrochloric acid. The acid extracts were combined, made basic with sodium hydroxide and extracted with chloroform. The extract was dried over sodium sulfate and concentrated. The residue was dissolved in isopropyl alcohol and treated with a solution of hydrogen chloride in isopropyl alcohol. The resulting hydrochloride salt weighed 21 g (25%). One gram of the salt was recrystallized from isopropyl alcohol, m.p. 149°-151° C. $[\alpha]_D^{25} = -38.3$ (water).

Analysis: Calculated for $C_{11}H_{14}N_2O_2Cl_2$: C, 47.67; H, 5.09; N, 10.11. Found: C, 47.66; H, 5.11; N, 10.11.

INTERMEDIATE 66

(S)-2-(2-Chloroethyl)-2,3-dihydro-4-methylpyrido[3,2-f][1,4]oxazepin-5(4H)-one

A 20 g sample of (S)-2-(2-chloroethyl)-2,3-dihydro-4-methylpyrido[3,2-f]-1,4-oxazepin-5(4H)-one hydrochloride [1:1] was partitioned between chloroform and dilute sodium hydroxide. The chloroform was dried over soduum sulfate and concentrated. The residue was crystallized from isopropyl ether. A yield of 16 g was obtained, m.p. 61°-62° C. $[\alpha]_D^{25} = -22.95$ (methanol).

Analysis: Calculated for $C_{11}H_{13}N_2O_2Cl$: C, 54.89; H, 5.44; N, 11.64. Found: C, 54.89; H, 5.47; N, 11.59.

INTERMEDIATE 67

(R)-2-(2-Chloroethyl)-2,3-dihydro-4-methylpyrido[3,2-f]-1,4-oxazepin-5-(4H)-one hydrochloride [1:1]

A solution of 47.4 g (0.3 mole) of 2-chloronicotinic acid and 30 g (0.3 mole) of (R)-1-methyl-3-pyrrolidinol in 400 ml of tetrahydrofuran was added over a period of 1 hr to a stirred suspension of 26.4 g (0.66 mole) of 60% sodium hydride/mineral oil in 500 ml of tetrahydrofuran at 55°-60° C. The mixture was stirred at reflux for 2.5 hr and allowed to cool to 25° C. About 400 ml of methylene chloride was added to the slurry followed by a dropwise addition of 34.5 g (0.36 mole) of methane sulfonic acid in 100 ml of methylene chloride. The mixture was stirred for 10 min and 157 g (0.6 mole) of triphenylphosphine was added followed by 200 ml of carbon tetrachloride. The mixture was heated to reflux for 4 hr. To the cooled (25° C.) solution was added 100 ml of triethylamine at a rapid drop. The solution was concentrated on the rotary evaporator and the residue was partitioned between methylene chloride and dilute hydrochloric acid. The methylene chloride was extracted 6 times with dilute hydrochloric acid. The acid extracts were combined, made basic with sodium hydroxide and extracted with chloroform which was dried and concentrated. The residue was dissolved in isopropyl alcohol and treated with a solution of hydrogen chloride in isopropyl alcohol. The resulting hydrochloride weighed 25 g (30%). One gram was recrystallized from isopropyl alcohol, m.p. 152°-154° C.; $[\alpha]_D^{25} = +36.2$ (water).

Analysis: Calculated for $C_{11}H_{14}N_2O_2Cl_2$: C, 47.67; H, 5.09; N, 10.11. Found: C, 47.65; H, 5.20; N, 9.03.

INTERMEDIATE 68

(R)-2-(2-Chloroethyl)-2,3-dihydro-4-methylpyrido[3,2-f][1,4]oxazepin-5(4H)-one

A 24 g sample of (R)-2-(2-chloroethyl)-2,3-dihydro-4-methylpyrido[3,2-f]-1,4-oxazepin-5-(4H)-one hydrochloride [1:1] was partitioned between chloroform and sodium hydroxide solution. The chloroform extract was dried over sodium sulfate and concentrated. The residue was crystallized from isopropyl ether. Yield of title compound was 19 g, m.p. 61°-62° C.; $[\alpha]_D^{25} = (+) 22.4$ (methanol).

Analysis: Calculated for $C_{11}H_{13}N_2O_2Cl$: C, 54.89; H, 5.44; N, 11.64. Found: C, 54.93; H, 5.51; N, 11.67.

INTERMEDIATE 69

(S)-2-(2-Chloroethyl)-2,3-dihydro-4-methylpyrido[3,2-f][1,4]oxazepine-5(4H)-thione To a stirred suspension of 7.8 g (0.0176 mole) of phosphorus pentasulfide in 65 ml of acetonitrile was added 15.6 g (0.065 mole) of (S)-2-(2-chloroethyl)-2,3-dihydro-4-methylpyrido[3,2-f]-1,4-oxazepine-5(4H)-one and the mixture was stirred at reflux for 3 hr. About 50 ml of toluene was added and the mixture was cooled to 25° C. and the liquid was decanted. The liquid was washed with aqueous potassium bicarbonate, treated with magnesium sulfate and charcoal, and filtered. The filtrate was concentrated, leaving 4.5 g of solid. The pot residue was stirred with a mixture of aqueous potassium bicarbonate, chloroform, and acetonitrile. The organic layer was collected, dried over magnesium sulfate and concentrated. The solid residue (10.5 g) was combined with the above solid, giving a total of 15 g which was recrystallized from a mixture of isopropyl and ethyl alcohols. Yield of title compound was 12.2 g (73%). A one gram sample was recrystallized from isopropyl alcohol-chloroform, m.p. 168°-170° C.; $[\alpha]_D^{25} = (+) 48.2°$ (chloroform).

Analysis: Calculated for $C_{11}H_{13}N_2OSCl$: C, 51.46; H, 5.10; N, 10.91. Found: C, 51.24; H, 5.10; N, 10.85.

INTERMEDIATE 70

(R)-2-(2-Chloroethyl)-2,3-dihydro-4-methylpyrido[3,2-f][1,4]-oxazepine-5(4H)-thione To a suspension of 9 g (0.02 mole) of phosphorus pentasulfide in 75 ml of acetonitrile was added 18 g (0.075 mole) of (R)-2-(2-chloroethyl)-2,3-dihydro-4-methylpyrido[3,2-f]-1,4-oxazepine-5(4H)-one and the mixture was stirred at reflux for 2.5 hr, cooled and treated with 60 ml of toluene. The mixture was filtered and the solid washed twice with 30 ml of 25% acetonitrile-75% toluene. The volume was made to about 400 ml with 50% toluene-50% acetonitrile and extracted with saturated aqueous potassium bicarbonate. The organic layer was separated, treated with magnesium sulfate and charcoal, and filtered. The filtrate was concentrated and the residue was recrystallized from isopropyl alcohol-chloroform. Yield of title compound was 13 g (68%), m.p. 168°-170° C.; $[\alpha]_D^{25} = (-) 47.4$ (chloroform).

Analysis: Calculated for $C_{11}H_{13}N_2OSCl$: C, 51.46; H, 5.10; N, 10.91. Found: C, 51.23; H, 5.12; N, 10.80.

INTERMEDIATE 71

7-Bromo-2-(2-chloroethyl)-2,3-dihydro-4-methyl-pyrido[3,2-f][1,4]oxazepin-5(4H)-one To a suspension of 51.2 g of 60% sodium hydride in oil (1.28 mole) in 1 liter of tetrahydrofuran heated to reflux, and under nitrogen atmosphere was added a solution of 144 g (0.61 mole) of 5-bromo-2-chloropyridine-3-carboxylic acid and 61.6 g (0.61 mole) of N-methyl-3-pyrrolidinol in 1 liter of tetrahydrofuran dropwise at reflux (~1 hr). Heating was continued at reflux with vigorous agitation for 1.5 hr. After cooling, approximately 5 ml of water was added and the mixture soon solidified. Additional tetrahydrofuran was added to aid in stirring. The mixture was filtered, washed with several portions of tetrahydrofuran, and dried at 50° C., 0.05 mm Hg, overnight to give 190 g of crude sodium salt.

The entire amount of crude sodium salt (190 g) was added slowly to 1000 g of thionyl chloride cooled in an ice bath. The reaction mixture was stirred for 10 minutes at ~10° C. and 10 minutes at room temperature. Excess thionyl chloride was removed by rotary evaporation at 65° C., 30 mm Hg and the residue azetroped twice with toluene. The residue was taken up in ~1 liter of methylene chloride and diisopropylethyl amine and was added slowly until the solution just turned basic. The mixture was stirred for 1 hr at room temperature and washed successively with 2×200 ml of 1N hydrochloride acid, 2×200 ml of dilute sodium hydroxide and 100 ml of water. The organic phase was dried over sodium sulfate, filtered, and concentrated by rotary evaporation. The black residue was triturated 5 times with 5% toluene in diisopropyl ether to give 60 g (31%) of light brown crystals. A sample was recrystallized from diisopropyl ether, m.p. 71°-75° C.

Analysis: Calculated for $C_{11}H_{12}N_2O_2BrCl$: C, 41.34; H, 3.79; N, 8.77. Found: C, 41.35; H, 3.81; N, 8.89.

INTERMEDIATE 72

7-Bromo-2-(2-chloroethyl)-2,3-dihydro-4-methyl-pyrido[3,2-f][1,4]oxazepine-5(4H)-thione To a solution of 5.9 g (0.016 mole) of 7-bromo-2-(2-chloroethyl)-2,3-dihydro-4-methylpyrido[3,2-f]-1,4-oxazepin-5(4H)-one in 25 ml of acetonitrile was added 2.07 g (0.005 mole) of phosporous pentasulfide. The mixture was heated to reflux for 3 hr. The reaction mixture was diluted with 100 ml of toluene and filtered. The filtrate was washed with 3×50 ml of saturated sodium bicarbonate and 50 ml of water, dried over sodium sulfate, filtered, and concentrated by rotary evaporation to ~5-10 ml. Crystallization ensued and 3.0 g of crystals were collected. The mother liquor was concentrated giving 1.0 g additional crystals. The two crops were combined and recrystallized from diisopropylether/toluene to give ~3 g (56%) of yellow crystals, m.p. 138°-141° C.

Analysis: Calculated for $C_{11}H_{12}N_2OSBrCl$: C, 39.36; H, 3.60; N, 8.35. Found: C, 39.54; H, 3.63; N, 8.43.

INTERMEDIATE 73

2-(2-Chloroethyl)-2,3-dihydro-4,8-dimethylpyrido[3,2-f][1,4]oxazepin-5(4H)-one hydrate [1:1]

To a solution of 22 g of sodium hydride (60% in oil, 0.55 mole) in 600 ml of tetrahydrofuran at reflux and under nitrogen atmosphere was added a solution of 85 g (0.5 mole) of 2-chloro-6-methyl-3-pyridinecarboxylic acid and 50 g (0.5 mole) of N-methyl-3-pyrrolidinol in 1 liter of tetrahydrofuran at a rate to maintain good reflux. Heating was continued for 6 hr and a suspension of 2.5 g (0.025 mole) of N-methyl-3-pyrrolidinol and 1.0 g of sodium hydride (60% in oil, 0.025 mole) in 25 mole of tetrahydrofuran was added. After heating for another 45 minutes, 1 ml of water was added and the reaction allowed to stand overnight at room temperature. The solvent was then removed by rotary evaporation. Hexane was added to the viscous, semi-crystalline material. The precipitate was filtered to give 78 g of material. The mother liquor was concentrated by rotary evaporation and allowed to stand at room temperature for 2 days to give another 50 g of material.

To a suspension of 130 g of the above material in 1200 ml of chloroform was added hydrogen chloride gas to pH 6 followed by 262 g (1.0 mole) of triphenylphosphine and 262 g of carbon tetrachloride. The mixture was heated to reflux for 2.5 hr and an additional 80 g (0.3 mole) of triphenylphosphine and 80 g of carbon tetrachloride was added. After 30 min at reflux, the reaction flask was cooled in a water bath and ~40 ml of diisopropylethylamine was added. The entire reaction mixture was extracted with 3×500 ml of 1N hydrochloric acid. The acid extracts were combined and washed with 3×300 ml of chloroform. The aqueous layer was made basic with concentrated sodium hydroxide and extracted with 3×400 ml of methylene chloride. The organic layer was dried over sodium sulfate, filtered, concentrated by rotary evaporation, treated twice with activated charcoal in toluene and concentrated by rotary evaporation. The residue was taken up in 600 ml of chloroform and extracted into 1N hydrochloric acid. The aqueous layer was made basic with concentrated sodium hydroxide and extracted with 3×300 ml of chloroform. The organic organic extracts were dried over sodium sulfate, filtered, and concentrated by rotary evaporation. The residue was crystallized from isopropyl ether and water to give 40 g (29%) of title compound, m.p. 73°-74° C.

Analysis: Calculated for $C_{12}H_{17}N_2O_3Cl$: C, 52.85; H, 6.28; N, 10.27. Found: C, 52.58; H, 6.02; N, 10.26.

INTERMEDIATE 74

2-(2-Chloroethyl)-2,3-dihydro-4,8-dimethylpyrido[3,2-f][1,4]-oxazepine-5(4H)-thione hydrate [1:1]

To a suspension of 17.4 g (0.043 mole) of 2,4-bis(4-methoxyphenyl)-1,3-dithia-2,4-diposphetane-2,4-disulfide in ~300 ml of toluene was added 20 g (0.078 mole) of 2-(2-chloroethyl)-2,3-dihydro-4,8-dimethylpyrido[3,2-f][1,4]-oxazepin-5(4H)-one hydrate [1:1]. The mixture was heated to reflux for 3 hr and 4.0 g (0.01 mole) of 2,4-bis(4-methoxyphenyl)-1,3-dithia-2,4-diphosphetane-2,4-disulfide was added and heating was continued for 1 hr. After cooling, toluene was decanted off and washed with 3×100 ml 1N sodium hydroxide and 100 ml water. The organic layer was then extracted with 2×100 ml of 2N hydrochloric acid. The aqueous layer was made just basic to litmus with conc. sodium hydroxide causing the product to precipitate out. Of the 25 g of crude collected, 2 g were recrystallized from diisopropyl ether to give pale yellow crystals, m.p. 80°-86° C.

Analysis: Calculated for $C_{12}H_{17}N_2O_2ClS$: C, 49.91; H, 5.93; N, 9.70. Found: C, 49.76; H, 5.72; N, 9.60.

INTERMEDIATE 75

2-(2-chloroethyl)-2,3-dihydro-4-methyl-7-nitro-1,4-benzoxazepin-5(4H)-one

To a suspension of 109 g (60% in oil, 2.73 mole) of sodium hydride in 800 ml of tetrahydrofuran under nitrogen atmosphere and at reflux was added a solution of 250 g (1.24 mole) of 2-chloro-5-nitro benzoic acid and 125 g (1.24 mole) of N-methyl-3-pyrrolidine in 1 liter of tetrahydrofuran at such a rate as to maintain good reflux. The reaction mixture was heated at reflux for 3 hr. After cooling, concentrated hydrochloric acid was added until the reaction mixture was neutral. Approximately 500 ml of isopropyl alcohol was added and the reaction mixture was filtered to remove sodium chloride. The filtrate was concentrated by rotary evaporation to give approximately 350 g of residue. To 30 g (0.11 mole) of this residue was added 100 ml of thionyl chloride. After 10 min of stirring at room temperature, the thionyl chloride was removed by rotary evaporation at 70° C., 30 mm Hg. Another 30 ml of thionyl chloride was added and the thionyl chloride was again removed by rotary evaporation. The residue was azeotroped once with toluene and taken up in 200 ml of methylene chloride. To the reaction mixture was added diisopropyl ethyl amine until the mixture was just basic. The reaction mixture was washed with 3×100 ml of 1N hydrochloric acid, 100 ml of water, and 3×200 ml of 1N sodium hydroxide, dried over sodium sulfate, filtered, concentrated by rotary evaporation, decolorized twice with activated charcoal in toluene, and concentrated again by rotary evaporation. The crude residue yielded 5 g (16% based on starting 2-chloro-5-nitrobenzoic acid) of light yellow crystals from isopropyl ether/ethyl/acetate, m.p. 91°-92° C.

Analysis: Calculated for $C_{12}H_{13}N_2O_4Cl$: C, 50.03; H, 4.60; N, 9.84. Found: C, 50.51; H, 4.57; N, 9.75.

INTERMEDIATE 76

2-(2-chloroethyl)-2,3-dihydro-4-methyl-7-nitro-1,4-benzoxazepine-5(4H)-thione

To 2.0 g (0.007 mole) of 2-(2-chloroethyl)-2,3-dihydro-4-methyl-7-nitro-1,4-benzoxazepin-5(4H)-one in 35 ml of acetonitrile was added 1.0 g (0.0023 mole) of phosphorus pentasulfide and the mixture heated to reflux for 2 hr. Another 0.4 g (0.001 mole) of phosphorus pentasulfide was added and heating continued for 2 hr. After cooling, the reaction mixture was diluted with 100 ml of toluene and filtered. The filtrate was washed with 3×50 ml of saturated sodium bicarbonate and 100 ml of water, dried over sodium sulfate, filtered, charcoaled, filtered, and concentrated by rotary evaporation. The crude oil was crystallized from isopropyl ether/toluene to give 1.2 g (57%) of yellow crystals, m.p. 153°-155° C.

Analysis: Calculated for $C_{12}H_{13}N_2O_3SCl$: C, 47.92; H, 4.36; N, 9.31. Found: C, 48.03; H, 4.39; N, 9.15.

INTERMEDIATE 77

2-(2-Chloroethyl)-2,3-dihydro-7-fluoro-4-methyl-1,4-benzoxazepine-5(4H)-one

Into a suspension of 22.7 g (0.095 mole) of 5-fluoro-2-(1-methyl-3-pyrrolidinyloxy)benzamide in 350 ml of acetic acid cooled to 10° C. in an ice bath was bubbled hydrogen chloride for 10 minutes. To this mixture was added 76.8 g (0.76 mole) of n-butylnitrite through a dropping funnel equipped to deliver the liquid below the surface of the reaction mixture at 10°-15° C. The reaction mixture was stirred for 1 hr at 10°-15° C. and 18 hr at room temperature. The reaction mixture was heated to reflux for 2 hr. The solvent (acetic acid) was removed at 70° C., 0.5 mm Hg for 5 hrs by rotary evaporation affording 23 g of crude material. The crude material was further purified by dissolving in 1N hydrochloric acid, washing the aqueous with methylene chloride and removing the water.

To 5 g (0.021 mole) of this crude material was added 20 ml of thionyl chloride and the reaction stirred at room temperature for 10 minutes. The thionyl chloride was removed by rotary evaporation (70° C., 30 mm) and the residue azeotroped once with toluene. The residue was taken up in 50 ml of methylene chloride and made basic by the careful addition of diisopropyl ethyl amine. The reaction mixture was washed with 2×50 ml of 1H hydrochloric acid and 2×50 ml of 1N sodium hydroxide, dried over sodium sulfate and concentrated by rotary evaporation. The residue was triturated with hot diisopropyl ether to give 1.1 g (18.5%) of analytically pure crystals, m.p. 113°–116° C.

Analysis: Calculated for $C_{12}H_{13}NO_2ClF$: C, 55.93; H, 5.09; N, 5.44. Found: C, 55.91; H, 5.09; N, 5.52.

INTERMEDIATE 78

2-(2-Chloroethyl)-2,3-dihydro-7-fluoro-4-methyl-1,4-benzoxazepine-5(4H)-thione

To 1.0 g (0.0039 mole) of 2-(2-chloroethyl)-2,3-dihydro-7-fluoro-4-methyl-1,4-benzoxazepin-5(4H)-one in 30 ml of acetonitrile was added 0.7 g (0.0016 mole) of phosphorus pentasulfide and the reaction mixture heated to reflux. After 2 hr, another 0.4 g (0.009 mole) of phosphorus pentasulfide was added and heating continued for 2 hr. The reaction mixture was diluted with 70 ml of toluene and filtered. The filtrate was washed carefully with 3×50 ml of saturated sodium bicarbonate and 50 ml of water, dried over sodium sulfate, filtered, charcoaled, filtered and concentrated by rotary evaporation. The crude material was recrystallized from diisopropyl ether to give 0.55 g (52%) of yellow crystals, m.p. 135°–137° C.

Analysis: Calculated for $C_{12}H_{13}NOSClF$: C, 52.65; H, 4.79; N, 5.12. Found: C, 52.60; H, 4.81; N, 5.08.

TABLE 1

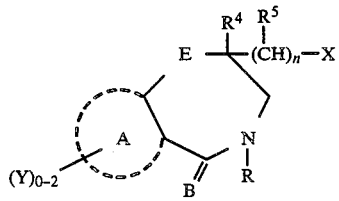

| Intermediate No. | A(Y)$_{0-2}$ | B | R | R$^4$ | E | X | R$^5$<br>$-(CH)_n-$ | Salt | Optical Isomer[a] |
|---|---|---|---|---|---|---|---|---|---|
| 1 | benz | O | $-CH_3$ | H | O | Cl | $-(CH_2)_2-$ | — | Rac. |
| 2 | benz | O | $-CH_2-C_6H_5$ | H | O | Cl | $-(CH_2)_2-$ | — | " |
| 3 | naphth[2,3-f] | O | $-CH_3$ | H | O | Cl | $-(CH_2)_2-$ | — | " |
| 4 | pyrido[3,2-f] | O | $-CH_3$ | H | O | Cl | $-(CH_2)_2-$ | HCl | " |
| 5 | 8-Cl—benz | O | $-CH_3$ | H | O | Cl | $-(CH_2)_2-$ | — | " |
| 6 | 7-Br—benz | O | $-CH_3$ | H | O | Cl | $-(CH_2)_2-$ | — | " |
| 7 | 7-Cl—benz | O | $-CH_3$ | H | O | Cl | $-(CH_2)_2-$ | — | " |
| 8 | naphth[2,1-f] | O | $-CH_3$ | H | O | Cl | $-(CH_2)_2-$ | — | " |
| 9 | 7-OCH$_3$—benz | O | $-CH_3$ | H | O | Cl | $-(CH_2)_2-$ | — | " |
| 10 | benz | S | $-CH_3$ | H | O | Cl | $-(CH_2)_2-$ | — | " |
| 11 | pyrido[3,2-f] | S | $-CH_3$ | H | O | Cl | $-(CH_2)_2-$ | — | " |
| 12 | naphth[2,3-f] | S | $-CH_3$ | H | O | Cl | $-(CH_2)_2-$ | — | " |
| 13 | 8-Cl—benz | S | $-CH_3$ | H | O | Cl | $-(CH_2)_2-$ | — | " |
| 14 | 7-Br—benz | S | $-CH_3$ | H | O | Cl | $-(CH_2)_2-$ | — | " |
| 15 | naphth[2,1-f] | S | $-CH_3$ | H | O | Cl | $-(CH_2)_2-$ | — | " |
| 16 | pyrido[4,3-f] | O | $-CH_3$ | H | O | Cl | $-(CH_2)_2-$ | HCl | " |
| 17 | pyrido[3,4-f] | O | $-CH_3$ | H | O | Cl | $-(CH_2)_2-$ | HCl | " |
| 18 | pyrido[2,3-f] | O | $-CH_3$ | H | O | Cl | $-(CH_2)_2-$ | HCl | " |
| 19 | 7-Cl—benz | S | $-CH_3$ | H | O | Cl | $-(CH_2)_2-$ | — | " |
| 20 | 7,9-diiodo-benz | O | $-CH_3$ | H | O | Cl | $-(CH_2)_2-$ | — | " |
| 21 | pyrido[3,2-f] | S | $-CH_3$ | H | O | Cl | $-CH_2-$ | HCl | " |
| 22 | pyrido[4,3-f] | S | $-CH_3$ | H | O | Cl | $-(CH_2)_2-$ | — | " |
| 23 | 7-OCH$_3$—benz | S | $-CH_3$ | H | O | Cl | $-(CH_2)_2-$ | — | " |
| 24(a) | benz | O | $-C_6H_{11}$ | H | O | Cl | $-(CH_2)_2-$ | — | " |
| 24(b) | benz | O | $-C_2H_5$ | H | O | Cl | $-(CH_2)_2-$ | — | " |
| 24(c) | benz | O | $-CH(CH_3)_2$ | H | O | Cl | $-(CH_2)_2-$ | — | " |
| 24(d) | benz | O | 4-Cl—$C_6H_4$—$CH_2-$ | H | O | Cl | $-(CH_2)_2-$ | — | " |
| 24(e) | benz | O | 4-CH$_3$—$C_6H_4$—$CH_2-$ | H | O | Cl | $-(CH_2)_2-$ | — | " |
| 24(f) | benz | O | 3,5-(OCH$_3$)$_2$—$C_6H$—$CH_2-$ | H | O | Cl | $-(CH_2)_2-$ | — | " |
| 24(g) | benz | O | 3-CF$_3$—$C_6H_4$—$CH_2-$ | H | O | Cl | $-(CH_2)_2-$ | — | " |
| 24(h) | benz | O | 4-NO$_2$—$C_6H_4$—$CH_2-$ | H | O | Cl | $-(CH_2)_2-$ | — | " |
| 25(a) | pyrido[3,2-f] | O | $-C_6H_{11}$ | H | O | Cl | $-(CH_2)_2-$ | HCl | " |
| 25(b) | pyrido[3,2-f] | O | $-C_2H_5$ | H | O | Cl | $-(CH_2)_2-$ | HCl | " |
| 25(c) | pyrido[3,2-f] | O | $-CH(CH_3)_2$ | H | O | Cl | $-(CH_2)_2-$ | HCl | " |
| 25(d) | pyrido[3,2-f] | O | 4-Cl—$C_6H_4$—$CH_2-$ | H | O | Cl | $-(CH_2)_2-$ | HCl | " |
| 25(e) | pyrido[3,2-f] | O | 4-CH$_3$—$C_6H_4$—$CH_2-$ | H | O | Cl | $-(CH_2)_2-$ | HCl | " |
| 25(f) | pyrido[3,2-f] | O | 3,5-(OCH$_3$)$_2$—$C_6H$—$CH_2-$ | H | O | Cl | $-(CH_2)_2-$ | HCl | " |
| 25(g) | pyrido[3,2-f] | O | 3-CF$_3$—$C_6H_4$—$CH_2-$ | H | O | Cl | $-(CH_2)_2-$ | HCl | " |
| 25(h) | pyrido[3,2-f] | O | 4-NO$_2$—$C_6H_4$—$CH_2-$ | H | O | Cl | $-(CH_2)_2-$ | HCl | " |
| 26 | pyrido[3,2-f] | O | $-CH_3$ | H | S | Cl | $-(CH_2)_2-$ | — | " |
| 27 | pyrido[3,2-f] | S | $-CH_3$ | H | S | Cl | $-(CH_2)_2-$ | — | " |
| 28 | pyrido[3,4-f] | O | $-CH_3$ | H | O | Cl | $-(CH_2)_2$ | — | " |
| 29 | pyrido[3,4-f] | S | $-CH_3$ | H | O | Cl | $-(CH_2)_2-$ | HCl | " |
| 30 | pyrido[3,2-f] | O | $-CH_3$ | H | O | $-CN$ | $-(CH_2)_2-$ | — | " |
| 31 | pyrido[3,2-f] | O | $-C_2H_5$ | H | O | Cl | $-(CH_2)_2-$ | HCl | " |
| 32 | pyrido[3,2-f] | S | $-C_2H_5$ | H | O | Cl | $-(CH_2)_2-$ | HCl | " |
| 33 | 7-Cl—pyrido[3,2-f] | O | $-CH_3$ | H | O | Cl | $-(CH_2)_2-$ | — | " |
| 34 | 7-Cl—pyrido[3,2-f] | S | $-CH_3$ | H | O | Cl | $-(CH_2)_2-$ | 13 | " |

TABLE 1-continued

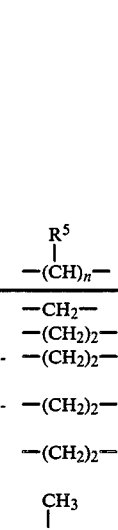

| Intermediate No. | A(Y)$_{0-2}$ | B | R | R$^4$ | E | X | R$^5$<br>—(CH)$_n$— | Salt | Optical Isomer[a] |
|---|---|---|---|---|---|---|---|---|---|
| 35 | pyrido[3,2-f] | O | —C$_6$H$_{11}$ | H | O | Cl | —CH$_2$— | — | " |
| 36 | pyrido[3,2-f] | O | —CH$_2$C$_6$H$_5$ | H | O | Cl | —(CH$_2$)$_2$— | — | " |
| 37 | pyrido[3,2-f] | O | —CH$_3$ | H | O | 1-phthal-imido | —(CH$_2$)$_2$— | — | " |
| 38 | pyrido[3,2-f] | S | —CH$_3$ | H | O | 1-phthal-imido | —(CH$_2$)$_2$— | — | " |
| 39 | pyrido[3,2-f] | S | —CH$_3$ | H | O | CN | —(CH$_2$)$_2$— | — | — |
| 40 | pyrido[3,2-f] | O | —CH$_3$ | H | O | Cl | $-\underset{\underset{\text{CH}_3}{\|}}{\text{C}}-\text{CH}_2-$ | HCl | " |
| 41 | pyrido[3,2-f] | O | —CH$_3$ | —CH$_3$ | O | Cl | —(CH$_2$)$_2$— | HCl | " |
| 42 | pyrido[3,2-f] | O | —CH$_3$ | —CH$_3$ | O | Cl | —(CH$_2$)$_2$— | — | " |
| 43 | pyrido[3,2-f] | O | —CH$_3$ | H | O | Cl | —CH$_2$—C(CH$_3$)(H)—Cl | HCl | " |
| 44 | pyrido[3,2-f] | S | —CH$_3$ | H | O | Cl | —CH$_2$—C(CH$_3$)(H)—Cl | HCl | " |
| 45 | pyrido[3,2-f] | S | —CH$_3$ | H | O | Cl | $-\underset{\underset{\text{CH}_3}{\|}}{\text{C}}-\text{CH}_2-$ | HCl | " |
| 46 | 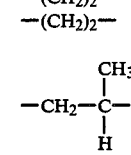 | O | —CH$_3$ | H | O | Cl | —(CH$_2$)$_2$— | — | " |
| 47 | 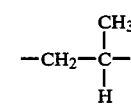 | S | —CH$_3$ | H | O | Cl | —(CH$_2$)$_2$— | — | " |
| 48 | 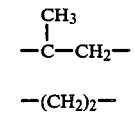 | O | —CH$_3$ | H | O | Cl | —(CH$_2$)$_2$— | HCl | " |
| 49 | 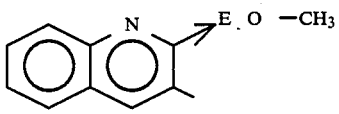 | S | —CH$_3$ | H | O | Cl | —(CH$_2$)$_2$— | — | " |
| 50 | benz | O | —CH(CH$_3$)$_2$ | H | CH$_3$-N(CH$_3$)- | Cl | —CH$_2$— | — | " |

TABLE 1-continued $$\underset{(Y)_{0-2}}{\text{A}} \underset{B}{\overset{E-\overset{R^4}{\underset{|}{C}}\overset{R^5}{\underset{|}{H}}-(CH)_n-X}{\parallel}} \underset{R}{\overset{}{N}}$$

| Intermediate No. | A(Y)$_{0-2}$ | B | R | R$^4$ | E | X | $\overset{R^5}{\underset{|}{-(CH)_n-}}$ | Salt | Optical Isomer[a] |
|---|---|---|---|---|---|---|---|---|---|
| 51 | benz | O | —C$_2$H$_5$ | H | CH$_3$—N— | Cl | —(CH$_2$)$_2$— | — | " |
| 52 | 6-Cl—pyrido[4,3-f] | O | —CH$_3$ | H | O | Cl | —(CH$_2$)$_2$— | — | " |
| 53 | isoquinoline (E at 5, attach at 6) | O | —CH$_3$ | H | O | Cl | —(CH$_2$)$_2$— | — | " |
| 54 | isoquinoline (E at 5, attach at 6) | S | —CH$_3$ | H | O | Cl | —(CH$_2$)$_2$— | — | " |
| 55 | isoquinoline (E at 6) | O | —CH$_3$ | H | O | Cl | —(CH$_2$)$_2$— | — | " |
| 56 | isoquinoline (E at 6) | S | —CH$_3$ | H | O | Cl | —(CH$_2$)$_2$— | — | " |
| 57 | 4-CH$_3$-quinoline (E at 8) | O | —CH$_3$ | H | O | Cl | —(CH$_2$)$_2$ | — | " |
| 58 | 4-CH$_3$-quinoline (E at 8) | S | —CH$_3$ | H | O | Cl | —(CH$_2$)$_2$— | — | " |
| 59 | 2-CH$_3$-quinoline (E at 8) | O | —CH$_3$ | H | O | Cl | —(CH$_2$)$_2$— | — | " |

TABLE 1-continued

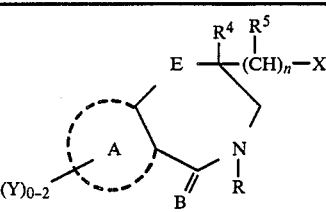

| Intermediate No. | A(Y)₀₋₂ | B | R | R⁴ | E | X | R⁵ —(CH)ₙ— | Salt | Optical Isomer[a] |
|---|---|---|---|---|---|---|---|---|---|
| 60 | (structure: CH₃-substituted quinoline with E) | S | —CH₃ | H | O | Cl | —(CH₂)₂— | — | " |
| 61 | (quinoline structure with E) | O | —CH₃ | H | O | Cl | —(CH₂)₂— | — | " |
| 62 | (quinoline structure with E) | S | —CH₃ | H | O | Cl | —(CH₂)₂— | — | " |
| 63 | (quinoline structure with E) | O | —CH₃ | H | O | Cl | —(CH₂)₂— | — | " |
| 64 | (quinoline structure with E) | S | —CH₃ | H | O | Cl | —(CH₂)₂— | — | " |
| 65 | pyrido[3,2-f] | O | —CH₃ | H | O | Cl | —(CH₂)₂— | HCl | S(—) |
| 66 | pyrido[3,2-f] | O | —CH₃ | H | O | Cl | —(CH₂)₂— | — | S(—) |
| 67 | pyrido[3,2-f] | O | —CH₃ | H | O | Cl | —(CH₂)₂— | HCl | R(+) |
| 68 | pyrido[3,2-f] | O | —CH₃ | H | O | Cl | —(CH₂)₂— | — | R(+) |
| 69 | pyrido[3,2-f] | S | —CH₃ | H | O | Cl | —(CH₂)₂— | — | S(+) |
| 70 | pyrido[3,2-f] | S | —CH₃ | H | O | Cl | —(CH₂)₂— | — | R(—) |
| 71 | 7-Br—pyrido[3,2-f] | O | —CH₃ | H | O | Cl | —(CH₂)₂— | — | Rac. |
| 72 | 7-Br—pyrido[3,2-f] | S | —CH₃ | H | O | Cl | —(CH₂)₂— | — | " |
| 73 | 8-CH₃—pyrido[3,2-f] | O | —CH₃ | H | O | Cl | —(CH₂)₂— | H₂O | " |
| 74 | 8-CH₃—pyrido[3,2-f] | S | —CH₃ | H | O | Cl | —(CH₂)₂— | H₂O | " |
| 75 | 7-NO₂—benz- | O | —CH₃— | H | O | Cl | —(CH₂)₂— | — | " |
| 76 | 7-NO₂—benz- | S | —CH₃ | H | O | Cl | —(CH₂)₂ | — | " |
| 77 | 7-F—benz- | O | —CH₃ | H | O | Cl | —(CH₂)₂— | — | " |
| 78 | 7-F—benz- | S | —CH₃ | H | O | Cl | —(CH₂)₂— | — | " |

[a]Rac = racemic mixture

EXAMPLE 1

2-[2-(Dimethylamino)ethyl]-2,3-dihydro-4-methyl-1,4-benzoxazepin-5(4H)-one hydrochloride A solution of 9 g (0.2 mole) of dimethylamine in 250 ml of ethanol was added to 24 g (0.1 mole) of 2-(2-chloroethyl)-2,3-dihydro-4-methyl-1,4-benzoxazepin-5(4H)one in a steel bomb. The mixture was heated at 100° C. for 18 hrs. The solution was concentrated in vacuo and the residue partitioned between ethyl acetate and dilute sodium hydroxide. The ethyl acetate layer was concentrated and the residue comprised substantially of the free base of the title compound was dissolved in methyl isobutyl ketone-isopropanol mixture. The solution was acidified with hydrogen chloride gas to give the title compound, m.p. 188°–198° C.

EXAMPLE 2

2-[2-(Dimethylamine)ethyl]-2,3-dihydro-4-methyl-1,4-benzoxazepine-5(4H)-one

All of the hydrochloride salt obtained in Example 1 was partitioned between chloroform and dilute sodium hydroxide and the chloroform layer concentrated. The residue was crystallized several times from isopropyl ether to give 6 g (21%) of the free base, m.p. 56°-76° C.

Analysis: Calculated for $C_{14}H_{20}N_2O_2$: C, 67.72; H, 8.12; N, 11.28. Found: C, 67.35; H, 8.16; N, 11.09.

EXAMPLE 3

2,3-Dihydro-4-methyl-2-[2-(4-morpholino)ethyl]-1,4-benzoxazepin-5(4H)-one fumarate [1:1]

To 50 ml of morpholine was added 20 g (0.084 mole) of 2-(2-chloroethyl)-2,3-dihydro-4-methyl-1,4-benzoxazepine-5(4H)-one. The solution was refluxed for 5 hrs and then concentrated in vacuo. The residue was dissolved in chloroform, and the solution was washed with dilute sodium hydroxide, dried over sodium sulfate and concentrated in vacuo. The residue comprised substantially of the free base of the title compound was reacted with 10.5 g (0.09 mole) of fumaric acid in isopropanol-water. The resulting solid was recrystallized from isopropanol-water to give 21.5 g (64%), m.p. 199°-201° C.

Analysis: Calculated for $C_{20}H_{26}N_2O_7$: C, 59.10; H, 6.45; N, 6.89. Found: C, 58.95; H, 6.52; N, 6.88.

EXAMPLE 4

4-Benzyl-2,3-dihydro-2-[2-(4-morpholino)ethyl]-1,4-benzoxazepin-5(4H)-one

To 200 ml of morpholine was added 30 g (0.095 mole) of 4-benzyl-2-(2-chloroethyl)-2,3-dihydro-1,4-benzoxazepin-5-(4H)-one. The solution was refluxed for 3 hrs and then concentrated in vacuo. The residue was partitioned between dilute sodium hydroxide and chloroform. The chloroform layer was dried over sodium sulfate and concentrated in vacuo. The solid obtained was recrystallized from isopropyl ether-ethyl acetate three times to give 15.2 g of solid (43%), m.p. 97°-99° C.

Analysis: Calculated for $C_{22}H_{26}N_2O_3$: C, 72.10; H, 7.15; N, 7.64. Found: C, 72.25; H, 7.22; N, 7.64.

EXAMPLE 5

4-Benzyl-2,3-dihydro-2-[2-(methylamino)-3-ethyl]-1,4-benzoxazepin-5(4H)-one fumarate [1:1]

A solution of 5.95 g (0.19 mole) of monomethylamine in 200 ml of ethanol was added to 30 g (0.095 mole) of 4-benzyl-2-(2-chloroethyl)-2,3-dihydro-1,4-benzoxazepin-5(4H)-one in a steel bomb. The mixture was heated at 100° C. for 16 hr. The solution was concentrated in vacuo and the residue partitioned between chloroform and dilute sodium hydroxide. The chloroform layer was concentrated and the residue comprised substantially of the free base of the title compound was dissolved in isopropanol and reacted with fumaric acid to give the fumarate. The salt was dried under vacuum at 100° C. until entrapped isopropyl alcohol was removed, m.p. 178°-81° C.

Analysis: Calculated for $C_{23}H_{26}N_2O_6$: C, 64.77; H, 6.15; N, 6.57. Found: C, 64.87; H, 6.20; N, 6.62.

EXAMPLE 6

2-[2-(Dimethylamino)ethyl]-2,3-dihydro-4-methyl-1,4-benzoxazepine-5(4H)thione hydrochloride [1:1]

To a solution of 7.2 g (0.16 mole) of dimethylamine in 350 ml of absolute ethanol was added 20.4 g (0.08 mole) of 2-(2-chloroethyl)-2,3-dihydro-4-methyl-1,4-benzoxazepine-5(4H)thione. The solution was heated in a steel bomb for 18 hr at 100° C. and then concentrated. The residue was partitioned between chloroform and dilute sodium hydroxide. The chloroform layer was dried over sodium sulfate and concentrated. The solid comprised substantially of the free base of the title compound was reacted with hydrogen chloride gas in ethanol to give the hydrochloride salt. The salt was recrystallized from ethanol and dimethylformamide followed by three recrystallizations from ethanol to give 7.5 g (28%), m.p. 233°-236° C.

Analysis: Calculated for $C_{14}H_{21}N_2SOCl$: C, 55.90; H, 7.04; N, 9.32. Found: C, 55.72; H, 7.26; N, 8.94.

EXAMPLE 7

4-Benzyl-2-[2-(dimethylamino)ethyl]-2,3-dihydro-1,4-benzoxazepin-5(4H)-one monohydrate Following the procedure of Example 1, 4-benzyl-2-(2-chloroethyl)-2,3-dihydro-1,4-benzoxazepin-5(4H)-one and dimethylamine were reacted and the free base of the title compound was obtained in the concentrated residue. Recrystallization from ethanol-water gave the product, m.p. 75°-77° C.

Analysis: Calculated for $C_{20}H_{26}N_2O_3$: C, 70.13; H, 7.65; N, 8.21. Found: C, 70.02; H, 7.53; N, 8.25.

EXAMPLE 8

2,3-Dihydro-4-methyl-2-[2-(4-morpholino)ethyl]-1,4-benzoxazepine-5(4H)-thione hydrochloride [1.1]

A solution of 20.4 g (0.08 mole) of 2,3-dihydro-4-methyl-2-(2-chloroethyl)-1,4-benzoxazepin-5(4H)-thione in 60 ml of morpholine was refluxed for 5 hr. then concentrated. The residue was partitioned between dilute sodium hydroxide and chloroform. The chloroform layer was dried over sodium sulfate and concentrated to give a residue comprised substantially of the free base of the title compound. The hydrochloride salt was prepared in methyl isobutyl ketone-dimethylformamide solution with hydrogen chloride gas. The salt was recrystallized from ethanol-dimethylformamide to give 14 g solid (51%), m.p. 253°-256° C.

Analysis: Calculated for $C_{16}H_{23}N_2SO_2Cl$: C, 56.04; H, 6.76; N, 8.17. Found: C, 55.73; H, 6.63; N, 7.97.

EXAMPLE 9

2-[2-(Dimethylamino)ethyl]-2,3-dihydro-4-methyl-naphth[2,3-f][1,4]-oxazepin-5(4H)-one oxalate [1:1]

A steel bomb was charged with 5.0 g (0.017 mole) of 2-(2-chloroethyl)-2,3-dihydro-4-methylnaphth[2,3-f][1,4]oxazepin-5(4H)-one, 50ml of absolute ethanol and 3.78 g (0.034 mole) of dimethylamine as 40% aqueous solution. The bomb was heated at 100° C. for 16 hr. Volatiles were removed under reduced pressure and the residue partitioned between chloroform and 15% aqueous sodium hydroxide. The chloroform layer was washed twice with water, dried over magnesium sulfate and concentrated under reduced pressure to give 2.7 g (54%) of viscous yellow oil comprised substantially of the free base of the title compound. The oil was dissolved in isopropyl alcohol and reacted with oxalic acid. The oxalate salt was recrystallized from ethanol-water, m.p. 192°–194° C.

Analysis: Calculated for $C_{20}H_{24}N_2O_6$: C, 61.84; H, 6.23; N, 7.21. Found: C, 61.41; H, 6.27; N, 7.09.

EXAMPLE 10

2-[2-(Dimethylamino)ethyl]-2,3-dihydro-4-methyl-pyrido[3,2-f][1,4]-oxazepin-5(4H)-one fumarate [2:3]

To 90 g (0.8 mole) of 40% aqueous dimethylamine in a steel bomb was added 25 g (0.09 mole) of 2-(2-chloroethyl)-2,3-dihydro-4-methylpyrido[3,2-f][1,4]-oxazepin-5(4H)-one hydrochloride. The mixture was heated to 100° C. for 15 hr under mild agitation. The mixture was partitioned using dilute sodium hydroxide and two chloroform extractions. The chloroform layers were combined and concentrated. The residue comprised substantially of the free base of the title compound was dissolved in 200 ml of isopropyl alcohol and 9 g of oxalic acid added. The oxalate salt was recrystallized from 95% ethanol to give 18 g. The oxalate salt was then converted to the free base by partitioning between chloroform and dilute sodium hydroxide and evaporating the chloroform layer. The residue, the free base of the title compound, was dissolved in isopropyl alcohol and reacted with fumaric acid to give 13 g of white solid (34%), m.p. 146°–148° C.

Analysis Calculated for $C_{19}H_{25}N_3O_8$: C, 53.90; H, 5.90; N, 9.92. Found: C, 53.76; H, 6.02; N, 9.96.

EXAMPLE 11

2-[2-(Dimethylamino)ethyl]-2,3-dihydro-4-methyl-pyrido[3,2-f][1,4]-oxazepine-5(4H)-thione fumarate Compound with ethanol [1:1:0.5]

To a solution of 32.8 g (0.29 mole) of 40% aqueous dimethylamine and 100 ml of ethanol in steel bomb was added 15 g (0.058 mole) of 2-(2-chloroethyl)-2,3-dihydro-4-methylpyrido[3,2-f][1,4]-oxazepine-5(4H)-thione. The mixture was heated to 100° C. for 18 hr under mild agitation. The solution was cooled and partitioned between chloroform and dilute sodium hydroxide. The chloroform layer was dried over sodium sulfate and concentrated. The residue comprised substantially of the free base of the title compound was dissolved in isopropyl alcohol and reacted with 7 g of fumaric acid. The fumarate salt was recrystallized from isopropyl alcohol to give 19 g (86%), m.p. 105°–129° C. A 14 g sample of the salt was recrystallized from ethanol to give 10.5 g yellow solid, m.p. 103°–118° C. The NMR spectra indicates the crystals contain ½ mole ethanol.

Analysis: Calculated for $C_{36}H_{52}N_6O_{11}S_2$: C, 53.45; H, 6.48; N, 10.39. Found: C, 53.07; H, 6.53; N, 10.23.

EXAMPLE 12

2-[2-(Dimethylamino)ethyl]-2,3-dihydro-4-methyl-pyrido[3,2-f][1,4]-oxazepine-5(4H)-thione fumarate [1:1]

To a solution of 113 ml (1.0 mole) of 40% aqueous dimethylamine and 326 ml of ethanol in a steel bomb was added 48.4 g (0.189 mole) of 2-(2-chloroethyl)-2,3-dihydro-4-methylpyrido[3,2-f][1,4]-oxazepine-5(4H)-thione. The mixture was heated at 100° C. for 14 hr. The ethanol was removed in a rotary evaporator leaving some water in the residue. The residue was dissolved in 200 ml of methylene chloride and washed with three 100 ml portions of 20% aqueous potassium carbonate solution. The combined aqueous layers were extracted with three 150 ml portions of methylene chloride. Methylene chloride solutions were combined and treated with charcoal. Charcoal was filtered off and the filtrate was evaporated to give an oil. The oil was dissolved in 215 ml isopropyl alcohol and the solution was heated to a slow boil. A solution of 21.9 g (0.19 mole) of fumaric acid in 150 ml of boiling methanol was added to the isopropyl alcohol solution. Crystalline solid was obtained weighing 63.4 g (88%). The solid was recrystallized from hot 200 proof ethyl alcohol. The crystals were filtered off and triturated in isopropyl ether at room temperature and again separated by filtering. After drying in a vacuum oven overnight at 85° C., crystals in the amount of 72.45 g (79%), m.p. 130°–133° C., were obtained.

Analysis: Calculated for $C_{17}H_{23}N_3O_5S$: C, 53.53; H, 6.08; N, 11.02. Found: C, 53.23; H, 6.11; N, 10.64.

EXAMPLE 13

4-Benzyl-2,3-dihydro-2-[2-(4-morpholino)ethyl]-1,4-benzoxazepine-5(4H)-thione

To a suspension of a finely ground mixture of 2.9 g (0.013 mole) of phosphorus pentasulfide and 2.9 g of potassium sulfide in 75 ml of dry toluene was added 12 g (0.033 mole) of 4-benzyl-2,3-dihydro-2-[2-(4-morpholino)ethyl]-1,4-benzoxazepine-5(4H)-one. The mixture was stirred at reflux for 10 hr. and filtered. The filtrate was concentrated and the residue crystallized from isopropyl ether-toluene to give 2.54 g (20%), m.p. 236°–238° C.

Analysis: Calculated for $C_{22}H_{26}N_2O_2S$: C, 69.08; H, 6.85; N, 7.32. Found: C, 69.60; H, 6.96; N, 7.15.

EXAMPLE 14

2,3-Dihydro-4-methyl-2-[2-(methylamino)ethyl]-1,4-benzoxazepin-5(4H)-one fumarate [1:1]

Following the procedure of Example 5, 50 g (0.21 mole) of 2-(2-chloroethyl)-2,3-dihydro-4-methyl-1,4-benzoxazepin-5(4H)-one and 13.0 g (0.42 mole) of monomethylamine (in 400 ml ethanol) were reacted to give the free base of the title compound which was reacted with fumaric acid to give, after isolation and recrystallization from ethyl alcohol, 17 g (23%) of the title compound, m.p. 154°–156° C.

Analysis: Calculated for $C_{17}H_{22}N_2O_6$: C, 58.27; H, 6.33; N, 8.00. Found: C, 58.34; H, 6.52; N, 7.82.

EXAMPLE 15

2,3-Dihydro-4-methyl-2-[2-(methylamino)ethyl]-1,4-benzoxazepin-5(4H)-one 2,3-Dihydro-4-methyl-2-[2-(methylamino)ethyl]-1,4-benzoxazepin-5(4H)-one fumarate was converted back to the free base by partitioning in dilute sodium hydroxide and chloroform. Evaporation of the chloroform layer and distilling, b.p. 182°/0.2 mm, gave 4.3 g of the product.

Analysis: Calculated for $C_{13}H_{18}N_2O_2$: C, 66.64; H, 7.74; N, 11.96. Found: C, 66.48; H, 7.69; N, 11.88.

EXAMPLE 16

2,3-Dihydro-2-[2-(4-hydroxy-4-phenyl)-piperidinylethyl]-4-methyl-1,4-benzoxazepine-5(4H)-thione (and hydrochloride salt)

A suspension of 10.7 g (0.078 mole) of potassium carbonate, 13.7 g (0.078 mole) of 4-hydroxy-4-phenyl-piperidine and 19.8 g (0.078 mole) of 2-(2-chloroethyl)-2,3-dihydro-4-methyl-1,4-benzoxazepine-5(4H)-thione in 200 ml of n-butanol was refluxed overnight. The mixture was filtered and the filtrate concentrated in vacuo. The residue was dissolved in ethanol-ligroin and reacted with hydrogen chloride gas to give the hydrochloride salt which was recrystallized from ethanol-dimethylformamide. The hydrochloride salt was converted back to the free base by partitioning in chloroform and dilute sodium hydroxide and evaporating the chloroform. Recrystallization twice from isopropyl alcohol gave 9.27 g (30%) product free base, m.p. 142°–148° C.

Analysis: Calculated for $C_{23}N_{28}N_2O_2S$: C, 69.66; H, 7.12; N, 7.07. Found: C, 69.78; H, 7.18; N, 7.00.

EXAMPLE 17

2,3-Dihydro-4-methyl-2-[2-[1-(4-phenyl-1,2,3,6-tetrahydro)pyridinyl]ethyl]-1,4-benzoxazepine-5(4H)thione A suspension of 24.3 g (0.176 mole) of potassium carbonate, 11.5 g (0.059 mole) of 4-phenyl-3,4-tetrahydropyridine and 15 g (0.059 mole) of 2-(2-chloroethyl)-2,3-dihydro-4-methyl-1,4-benzoxazepine-5(4H)-thione and enough n-butanol to form a slurry were refluxed for 72 hr. The reaction mixture was filtered hot and the filtrate cooled to room temperature and refiltered. The last filtrate was concentrated and the residue dissolved in ethyl acetate. The crystals obtained on cooling were recrystallized from ethyl acetate to give 7 g of product (31%), m.p. 153°–155° C.

Analysis: Calculated for $C_{23}H_{26}N_2OS$: C, 72.98; H, 6.92; N, 7.40. Found: C, 73.36; H, 7.01; N, 7.47.

EXAMPLE 18

8-Chloro-2-[2-(dimethylamino)ethyl]-2,3-dihydro-4-methyl-1,4-benzoxazepine-5(4H)-thione hydrochloride [1:1]

A solution of 9.8 g (0.04 mole) of 8-chloro-2-(2-chloroethyl)-2,3-dihydro-4-methyl-1,4-benzoxazepine-5(4H)-thione in 50 ml of absolute ethanol and 10 ml of a 40% aqueous solution of dimethylamine were mixed and heated in a steel bomb at 100° C. for 16 hr. The ethanol was evaporated under reduced pressure and the residue dissolved in chloroform and partitioned with 10% sodium hydroxide solution. The chloroform layer was evaporated under reduced pressure to give an amorphous solid. The solid was dissolved in 6N hydrochloric acid and the solution washed with ethyl acetate. The aqueous layer was basified with 50% sodium hydroxide and extracted with ethyl acetate. The ethyl acetate layer was evaporated under reduced pressure to give a viscous oil comprised substantially of the free base of the title compound which was dissolved in absolute ethanol and reacted with ethereal hydrogen chloride. The hydrochloride salt was recrystallized from ethanol to give 30 g (25%) product, m.p. 196°–199° C.

Analysis: Calculated for $C_{14}H_{20}N_2Cl_2OS$: C, 50.15; H, 6.01; N, 8.35. Found: C, 50.15; H, 6.18; N, 8.07.

EXAMPLE 19

8-Chloro-2-[2-(dimethylamino)ethyl]-2,3-dihydro-4-methyl-1,4-benzoxazepin-5(4H)-one oxalate [1:1]

A solution of 10 g (0.037 mole) of 8-chloro-2-(2-chloroethyl)-2,3-dihydro-4-methyl-1,4-benzoxazepin-5(4H)-one in 50 ml of absolute ethanol and 10 ml of 40% aqueous solution of dimethylamine were mixed and heated in a steel bomb at 100° C. for 16 hr. The solution was concentrated under reduced pressure and the residue dissolved in chloroform and partitioned with 15% sodium hydroxide (2 washes). The chloroform layer was dried over magnesium sulfate and evaporated under reduced pressure to give an oil, comprised substantially of the free base of the title compound. The oil was dissolved in absolute ethanol and reacted with oxalic acid. The oxalate salt was recrystallized from ethanol in the amount of 4 g (38%), m.p. 198°–201° C.

Analysis: Calculated for $C_{16}H_{21}N_2ClO_6$: C, 51.55; H, 5.68; N, 7.51. Found: C, 51.07; H, 5.69; N, 7.43.

EXAMPLE 20

7-Bromo-2-[2-(dimethylamino)ethyl]-2,3-dihydro-4-methyl-1,4-benzoxazepin-5(4H)-one oxalate [1:1]

To a solution of 3.0 g (0.01 mole) of 7-bromo-2-(2-chloroethyl)-2,3-dihydro-4-methyl-1,4-benzoxazepin-5(4H)-one in 50 ml of absolute ethanol was added 2.2 ml of a 40% aqueous solution of dimethylamine. The reaction mixture was heated in a stainless steel bomb at 100° C. for 16 hr and concentrated under reduced pressure. The residue was partitioned between chloroform and 15% sodium hydroxide solution. The chloroform layer was separated and extracted with 3N aqueous hydrochloric acid. The acid layer was basified with 50% aqueous sodium hydroxide and extracted with chloroform. The chloroform was evaporated under reduced pressure to give 2.4 g (73%) viscous brown oil, the free base of the title compound. The oil was dissolved in isopropyl alcohol and reacted with oxalic acid. The oxalate salt was recrystallized from isopropyl alcohol/water to give the title salt, m.p. 192°–194° C.

Analysis: Calculated for $C_{16}H_{21}O_6BrN_2$: C, 46.06; H, 5.07; N, 6.71. Found: C, 46.00; H, 5.10; N, 6.68.

EXAMPLE 21

2-[2-(Dimethylamino)ethyl]-2,3-dihydro-4-methylnaphth[2,1-f][1,4]oxazepin-5(4H)-one oxalate [1:1]

A solution of 8 g (0.028 mole) of 2-(2-chloroethyl)-2,3-dihydro-4-methylnaphth[2,1-f][1,4]oxazepin-5(4H)-one and 6.2 g of 40% dimethylamine (0.055 mole) in 100 ml of ethanol was heated in a steel bomb to 100° C. for 18 hr. The resulting solution was partitioned between methylene chloride and dilute sodium hydroxide solution. The methylene chloride layer was dried over sodium sulfate and concentrated. The residue comprised substantially of the free base of the title compound was dissolved in isopropyl alcohol and reacted with 2.6 g oxalic acid. The oxalate salt obtained was recrystallized from isopropyl alcohol in water, m.p. 206°–209° C.

Analysis: Calculated for $C_{20}H_{24}N_2O_6$: C, 61.85; H, 6.23; N, 7.21. Found: C, 61.61; H, 6.26; N, 7.13.

EXAMPLE 22

When in the procedure of Example 10 equal molar amounts of the following are substituted for 2-(2-chloroethyl)-2,3-dihydro-4-methylpyrido[3,2-f][1,4]-oxazepin-5(4H)-one hydrochloride:

2-(2-chloroethyl)-2,3-dihydro-4-methylpyrido[4,3-f][1,4]-oxazepin-5(4H)-one hydrochloride,
2-(2-chloroethyl)-2,3-dihydro-4-methylpyrido[3,4-f][1,4]-oxazepin-5(4H)-one hydrochloride, and
2-(2-chloroethyl)-2,3-dihydro-4-methylpyrido[2,3-f][1,4]-oxazepin-5(4H)-one hydrochloride, there are obtained:

2-[2-(dimethylamino)ethyl]-2,3-dihydro-4-methylpyrido[4,3-f][1,4]-oxazepin-5(4H)-one fumarate, 2-[2-(dimethylamino)ethyl]-2,3-dihydro-4-methyl-pyrido[3,4-f][1,4]-oxazepin-5(4H)-one fumarate, and
2-[2-(dimethylamino)ethyl]-2,3-dihydro-4-methyl-pyrido[2,3-f][1,4]-oxazepin-5(4H)-one fumarate.

EXAMPLE 23

2-[2-(Dimethylamino)ethyl]-2,3-dihydro-4-methyl-pyrido[4,3-f][1,4]-oxazepine-5(4H)-thione hydrochloride [2:3]

To a solution of 0.5 g (0.002 mole) of 2-(2-chloroethyl)-2,3-dihydro-4-methylpyrido[4,3-f][1,4]-oxazepine-5(4H)-thione in 20 ml of ethyl alcohol was added 2 ml of 40% aqueous dimethylamine. The mixture was heated in a steel bomb to 100° C. for 14 hr. The resulting solution was filtered and concentrated. The residue was dissolved in isopropyl alcohol and a few drops of ethereal hydrogen chloride were added. The hydrochloride salt crystals were recrystallized by dissolving in ethyl alcohol and boiling while replacing the ethyl alcohol with isopropyl alcohol. The yield of product was 0.3 g (47%), m.p.: decomp. above 200° C.

Analysis: Calculated for $C_{26}H_{41}N_6O_2S_2Cl_3$: C, 48.78; H, 6.46; N, 13.13. Found: C, 49.34; H, 6.47; N, 13.03.

EXAMPLE 24

2-[2-(Diethylamino)ethyl]-2,3-dihydro-4-methyl-pyrido[3,2-f][1,4]oxazepine-5(4H)-thione 2-(2-Chloroethyl)-2,3-dihydro-4-methylpyrido[3,2-f][1,4]-oxazepine-5(4H)-thione and diethylamine in ethanol are heated together to obtain the title compound.

EXAMPLE 25

2-[2-(Dimethylamino)ethyl]-2,3-dihydro-4methyl-naphth[2,3-f][1,4]-oxazepine-5(4H)thione oxalate [1:1]hemihydrate To a solution of 15 g (0.05 mole) of 2-(2-chloroethyl)-2,3-dihydro-4-methylnaphth[2,3-f][1,4]-oxazepine-5(4H)-thione in 50 ml of absolute ethanol was added 10 ml of a 45% aqueous solution of dimethylamine. The solution was heated in a steel bomb for 16 hr. The ethanol was evaporated under reduced pressure and the residue partitioned between chloroform and 15% aqueous sodium hydroxide. The chloroform layer was separated and extracted with 3N aqueous hydrochloric acid. The acid layer was basified with 50% aqueous sodium hydroxide and extracted with chloroform. The chloroform solution was concentrated under reduced pressure and the residue was dissolved in isopropyl alcohol and reacted with oxalic acid. The salt was recrystallized from isopropyl alcohol and water to give the title compound, m.p. 115°–118° C.

Analysis: Calculated for $C_{40}H_{50}N_4O_{11}S_2$: C, 58.09; H, 6.09; N, 6.77. Found: C, 58.42; H, 5.85; N, 6.70.

EXAMPLE 26

2-[2-(Dimethylamino)ethyl]-2,3-dihydro-7,9-diiodo-4-methyl-1,4-benzoxazepin-5(4H)-one Utilizing the procedures of Example 1 and 2 and substituting 2-(2-chloroethyl)-7,9-diiodo-4-methyl-2,3-dihydro-4-methyl-1,4-benzoxazepin-5(4H)-one for 2-(chloroethyl)-4-methyl-2,3-dihydro-1,4-benzoxazepin-5(4H)-one, the title compound is obtained.

EXAMPLE 27

7-Chloro-2-[2-(dimethylamino)ethyl]-2,3-dihydro-4-methyl-1,4-benzoxazepin-5(4H)-one oxalate [1:1]

To a solution of 9.0 g (0.033 mole) of 7-chloro-2-(2-chloroethyl)-2,3-dihydro-4-methyl-1,4-benzoxazepin-5(4H)-one in 50 ml absolute ethanol was added 7 g (0.066 mole) of a 45% aqueous solution of dimethylamine. The solution was heated in a stainless steel bomb at 100° C. for 14 hr. The reaction mixture was concentrated under reduced pressure and the residue was partitioned between chloroform and 15% aqueous sodium hydroxide. The chloroform layer was separated and evaporated under reduced pressure to give a viscous brown oil. The oil was dissolved in isopropyl alcohol and oxalic acid added. Recrystallization from isopropyl alcohol/water gave 7.0 g (57%) oxalate salt, m.p. 199°–200° C.

Analysis: Calculated for $C_{16}H_{21}N_2O_6Cl$: C, 51.55; H, 5.68; N, 7.51. Found: C, 51.52; H, 5.72; N, 7.44.

EXAMPLE 28

2-(Dimethylamino)methyl-2,3-dihydro-4-methyl-pyrido[3,2-f][1,4]-oxazepin-5(4H)-one When in the procedure of Example 10, 2-chloromethyl-2,3-dihydro-4-methylpyrido[3,2-f][1,4]-oxazepin-5(4H)-one is substituted for 2-(2-chloroethyl)-2,3-dihydro-4-methylpyrido[3,2-f][1,4]-oxazepin-5(4H)-one, the title compound is prepared and is isolated if desired as a pharmaceutically acceptable salt.

EXAMPLE 29

2-[2-(Dimethylamino)ethyl]-2,3-dihydro-4-methyl-pyrido[3,2-f][1,4]-oxazepine-5(4H)-thione methiodide 2-[2-(Dimethylamino)ethyl]-2,3-dihydro-4-methyl-pyrido[3,2-f][1,4]-oxazepine-5(4H)-thione fumarate [1:1], ethanol [2:1], 3.8 g (0.01 mole) was partitioned between chloroform and dilute sodium hydroxide. The chloroform extract was dried over sodium sulfate and concentrated. The residue was dissolved in 15 ml of methyl isobutyl ketone and added to a solution of 1.4 g (0.01 mole) of methyl iodide in 15 ml of isobutyl ketone. Recrystallization from 50% ethanol—50% methyl isobutyl ketone gave 2.5 g (78%) of the product, m.p. 221°–225° C.

Analysis: Calculated for $C_{14}H_{22}N_3OSI$: C, 41.28; H, 5.44; N, 10.31. Found: C, 41.29; H, 5.51; N, 10.30.

EXAMPLE 30

7-Chloro-2-[2-(dimethylamino)ethyl]-2,3-dihydro-4-methyl-1,4-benzoxazepine-5(4H)-thione oxalate [1:1]hemihydrate To a solution of 8.0 g (0.027 mole) of 7-chloro-2-(2-chloroethyl)-2,3-dihydro-4-methyl-1,4-benzoxazepine-5(4H)-thione in 50 ml of absolute ethanol was added 6 ml (0.054 mole) of 40% aqueous solution of dimethylamine. The solution was heated in a steel bomb at 90° C. for 14 hr. The ethanol was removed under reduced pressure and the residue was partitioned between chloroform and aqueous sodium hydroxide. The chloroform layer was concentrated to give a viscous yellow oil. The oil was dissolved in isopropyl alcohol and reacted with oxalic acid. The oxalate salt immediately precipitated. The mixture was heated and a small amount of water was added to dissolve the salt. A white crystalline powder was obtained, m.p. 150°–151° C.

Analysis: Calculated for $C_{32}H_{44}N_4Cl_2O_{11}S_2$: C, 48.30; H, 5,57; N, 7.04. Found: C, 48.74; H, 5.34; N, 6.95.

EXAMPLE 31

2-[2-(Dimethylamino)ethyl]-2,3-dihydro-4-methylnaphth[2,1-f][1,4]-oxazepine-5(4H)-thione hydrochloride [1:1]

To a solution of 15.0 g (0.05 mole) of 2-(2-chloroethyl)-2,3-dihydro-4-methylnaphth[2,1-f][1,4]-oxazepine-5(4H)-thione in 50 ml of absolute ethanol was added 10 g of a 40% aqueous solution of dimethylamine. The resulting solution was heated in a steel bomb at 100° C. for 40 hr and concentrated under reduced pressure. The residue was partitioned between 15% aqueous sodium hydroxide and chloroform. The chloroform layer was evaporated and the residue partitioned between 3N hydrochloric acid and chloroform. The aqueous layer was made alkaline with 50% sodium hydroxide and extracted with chloroform. The chloroform extract was concentrated and the residue dissolved in isopropyl alcohol. Ethereal hydrogen chloride was added. Recrystallization of the precipitate from isopropyl alcohol/water gave 3.0 g (20%) of the product, m.p. 238°-240° C.

Analysis: Calculated for $C_{18}H_{23}N_2ClOS$: C, 61.61; H, 6.61; N, 7.98. Found: C, 61.80; H, 6.61; N, 7.91.

EXAMPLE 32

When in the procedure of Example 11 equal molar amounts of the following are substituted for 2-(2-chloroethyl)-2,3-dihydro-4-methylpyrido[3,2-f][1,4]-oxazepine-5(4H)-thione:

2-(2-chloroethyl)-2,3-dihydro-4-methylpyrido[3,4-f][1,4]-oxazepine-5(4H)-thione, and 2-(2-chloroethyl)-2,3-dihydro-4-methylpyrido[2,3-f][1,4]-oxazepine-5(4H)-thione, there are obtained:
(a) 2-[2-(dimethylamino)ethyl]-2,3-dihydro-4-methylpyrido[3,4-f][1,4]-oxazepine-5(4H)-thione fumarate, and
(b) 2-[2-(dimethylamino)ethyl]-2,3-dihydro-4-methylpyrido[2,3-f][1,4]-oxazepine-5(4H)-thione fumarate.

EXAMPLE 33

2-[2-(Dimethylamino)ethyl]-2,3-dihydro-7-methoxy-4-methyl-1,4-benzoxazepin-5(4H)-one oxalate [1:1]hemihydrate To a solution of 3.0 g (0.011 mole) of 2-(2-chloroethyl)-2,3-dihydro-7-methoxy-4-methyl-1,4-benzoxazepin-(5(4H)-one in 50 ml of absolute ethanol was added 3.0 g of a 40% aqueous solution of dimethylamine. The reaction mixture was heated in a stainless steel bomb at 100° C. for 16 hr, cooled and evaporated under reduced pressure. The residue was partitioned between chloroform and 15% sodium hydroxide solution. The chloroform layer was concentrated and the residue, the free base, was dissolved in isopropyl alcohol and reacted with oxalic acid. The resulting oxalate salt was recrystallized from isopropyl alcohol/H$_2$O to give 1.9 g (45%) of the title salt, m.p. 176°-178° C.

Analysis: Calculated for $C_{34}H_{50}N_4O_{15}$: C, 54.10; H, 6.67; N, 7.42. Found: C, 54.29; H, 6.59; N, 7.53.

EXAMPLE 34

7-Bromo-2-[2-(dimethylamino)ethyl]-2,3-dihydro-4-methyl-1,4-benzoxazepine-5(4H)-thione oxalate [1:1]monohydrate To a solution of 13 g (0.04 mole) of 7-bromo-2-(2-chloroethyl)-2,3-dihydro-4-methyl-1,4-benzoxazepine-5(4H)-thione in 50 ml of absolute ethanol was added 8 ml of a 45% aqueous solution of dimethylamine. The solution was heated at 100° C. in a steel bomb for 16 hr. The ethanol was evaporated under reduced pressure and the residue partitioned between ethyl acetate and 3N aqueous hydrochloric acid. The aqueous extract was basified with 50% aqueous sodium hydroxide and extracted with chloroform. The chloroform was concentrated under reduced pressure. The residue, the free base of the title compound, was dissolved in isopropyl alcohol and reacted with oxalic acid. The oxalate salt was recrystallized from 95% ethanol to give the title salt, m.p. 155°-157° C.

Analysis: Calculated for $C_{32}H_{46}N_4Br_2O_{12}S_2$: C, 42.58; H, 5.14; N, 6.12. Found: C, 42.93; H, 4.79; N, 6.19.

EXAMPLE 35a to h

When in the process of Example 27, equal molar amounts of the following are substituted for 7-chloro-2-(2-chloroethyl)-2,3-dihydro-4-methyl-1,4-benzoxazepin-5(4H)-one, 2-(2-chloroethyl)-4-cyclohexyl-2,3-dihydro-1,4-benzoxazepin-5(4H)-one, 2-(2-chloroethyl)-2,3-dihydro-4-ethyl-1,4-benzoxazepin-5(4H)-one, 2-(2-chloroethyl)-2,3-dihydro-4-isopropyl-1,4-benzoxazepin-5(4H)-one, 2-(2-chloroethyl)-4-(4-chlorobenzyl)-2,3-dihydro-1,4-benzoxazepin-5(4H)-one, 2-(2-chloroethyl)-2,3-dihydro-4-(4-methylbenzyl)-1,4-benzoxazepin-5(4H)-one, 2-(3-chloroethyl)-2,3-dihydro-4-(3,5-dimethoxybenzyl)-1,4-benzoxazepin-5(4H)-one, 2-(2-chloroethyl)-2,3-dihydro-4-(3-trifluoromethylbenzyl)-1,4-benzoxazepin-5(4H)-one, and 2-(2-chloroethyl)-2,3-dihydro-4-(4-nitrobenzyl)-1,4-benzoxazepin-5(4H)-one, there are obtained:
(a) 4-cyclohexyl-2-[2-(dimethylamino)ethyl]-2,3-dihydro-1,4-benzoxazepin-5(4H)-one oxalate,
(b) 2-[2-(dimethylamino)ethyl]-2,3-dihydro-4-ethyl-1,4-benzoxazepin-5(4H)-one oxalate,
(c) 2-[2-(dimethylamino)ethyl]-2,3-dihydro-4-isopropyl-1,4-benzoxazepin-5(4H)-one oxalate,
(d) 4-(4-chlorobenzyl)-2-[2-(dimethylamino)ethyl]-2,3-dihydro-1,4-benzoxazepin-5(4H)-one oxalate,
(e) 2-[2-(dimethylamino)ethyl]-2,3-dihydro-4-(4-methylbenzyl)-1,4-benzoxazepin-5(4H)-one oxalate,
(f) 2-[2-(dimethylamino)ethyl]-2,3-dihydro-4-(3,5-dimethoxybenzyl)-1,4-benzoxazepin-5(4H)-one oxalate,
(g) 2-[2-(dimethylamino)ethyl]-2,3-dihydro-4-[(3-(trifluoromethyl)benzyl]-1,4-benzoxazepin-5(4H)-one oxalate, and
(h) 2-[2-(dimethylamino)ethyl]-2,3-dihydro-4-(4-nitrobenzyl)-1,4-benzoxazepin-5(4H)-one oxalate.

EXAMPLE 36a to h

When in the procedure of Example 10, equal molar amounts of the following are substituted for 2-(2- chloroethyl)-2,3-dihydro-4-methylpyrido[3,2-f][1,4]-oxazepin-5(4H)-one hydrochloride, 2-(2-chloroethyl)-4-cyclohexyl-2,3-dihydropyrido[3,2-f][1,4]oxazepin-5(4H)-one hydrochloride, 2-(2-chloroethyl)-2,3-dihydro-4-ethylpyrido[3,2f][1,4]-oxazepin-5(4H)-one hydrochloride, 2-(2-chloroethyl)-2,3-dihydro-4-isopropylpyrido[3,2-f][1,4]-oxazepin-5(4H)-one hydrochloride, 2-(2-chloroethyl)-4-(4-chlorobenzoyl)-2,3-dihydropyrido[3,2-f][1,4]oxazepin-5(4H)-one hydrochloride, 2-(2-chloroethyl)-4-(4-chlorobenzoyl)-4-(4-methylbenzyl)pyrido[3,2-f][1,4]-oxazepin-5(4H)-one hydrochloride, 2-(2-chloroethyl)-2,3-dihydro-4-(4-methoxybenzyl)-pyrido[3,2-f][1,4]-oxazepin-5(4H)-one hydrochloride, 2-(2-chloroethyl)-2,3-dihydro-4-(3-trifluoromethylbenzyl)pyrido[3,2-f][1,4]-oxazepin-5(4H)-one hydrochloride, and 2-(2-chloroethyl)-2,3-dihydro-4-(4-nitrobenzyl)-pyrido[3,2-f][1,4]-oxazepin-5(4H)-one hydrochloride, there are obtained:

(a) 4-cyclohexyl-2-[2-(dimethylamino)ethyl]-2,3-dihydropyrido[3,2-f][1,4]-oxazepin-5(4H)-one fumarate, (b) 2-[2-(dimethylamino)ethyl]-2,3-dihydro-4-ethyl-pyrido[3,2-f][1,4]-oxazepin-5(4H)-one fumarate, (c) 2-[2-(dimethylamino)ethyl]-2,3-dihydro-4-isopropyl-pyrido[3,2-f][1,4]-oxazepin-5(4H)-one fumarate, (d) 4-(4-chlorophenyl)-2-[2-(dimethylamino)ethyl]2,3-dihydro-pyrido[3,2-f][1,4]-oxazepin-5(4H)-one fumarate, (e) 2-[2-(dimethylamino)ethyl]-2,3-dihydro-4-(4-methylbenzyl)-pyrido[3,2-f][1,4]-oxazepin-5(4H)-one fumarate, (f) 2-[2-(dimethylamino)ethyl]-2,3-dihydro-4-(4-methoxybenzyl)-pyrido[3,2-f][1,4]-oxazepin-5(4H)-one fumarate, (g) 2-[2-(dimethylamino)ethyl]-2,3-dihydro-4-(3-trifluoromethylbenzyl)-pyrido[3,2-f][1,4]-oxazepin5(4H)-one fumarate, and (h) 2-[2-(dimethylamino)ethyl]-2,3-dihydro-4-(4-nitrobenzyl)-pyrido[3,2-f][1,4]-oxazepin-5(4H)-one fumarate.

EXAMPLE 37a to d

When in the procedure of Example 3, equal molar amounts of the following are substituted for morpholine:

pyrrolidine,
piperidine,
piperazine, and
4-methyl-piperazine, there are obtained:

(a) 2,3-dihydro-4-methyl-2-[2-(1-pyrrolidino)ethyl]-1,4-benzoxazepin-5(4H)-one fumarate, (b) 2,3-dihydro-4-methyl-2-[2-(1-piperidino)ethyl]-1,4-benzoxazepin-5(4H)-one fumarate, (c) 2,3-dihydro-4-methyl-2-[2-(1-piperazino)ethyl]-1,4-benzoxazepin-4(4H)-one fumarate, and (d) 2,3-dihydro-4-methyl-2-[2-(4-methylpiperazin-1-yl)ethyl]-1,4-benzoxazepin-5(4H)-one fumarate.

EXAMPLE 38

2-[2-(Dimethylamino)ethyl]-2,3-dihydro-4-methylpyrido[3,2-f][1,4]-thiazepin-5(4H)-one dihydrochloride A solution of 1.5 g (0.0058 mole) of 2-(2-chloroethyl)-2,3-dihydro-4-methylpyrido[3,2-f][1,4]-thiazepin-5(4H)-one in 20 ml of dimethylamine was stirred at 25° C. in a sealed container for 72 hr. The excess dimethylamine was allowed to evaporate and the residue was partitioned between chloroform and dilute sodium hydroxide. The chloroform layer was concentrated and the residue, the free base of the title compound, was dissolved in isopropyl alcohol and reacted with hydrogen chloride. The resulting hydrochloride salt weighed 1.5 g (77%), m.p. >250° C.

Analysis: Calculated for $C_{13}H_{21}N_3OSCl_2$: C, 46.16; H, 6.27; N, 12.42. Found: C, 45.68; H, 6.18; N, 12.35.

EXAMPLE 39

2-[2-(Dimethylamino)ethyl]-2,3-dihydro-4-methylpyrido[3,2-f][1,4]-thiazepine-5(4H)-thione oxalate A solution of 1.5 g (0.005 mole) of 2-(2-chloroethyl)-2,3-dihydro-4-methylpyrido[3,2-f][1,4]-thiazepine-5(4H)-thione in 40 ml of dimethylamine was stirred at 25° C. in a sealed container for 96 hr. The dimethylamine was allowed to evaporate and the residue was partitioned between methylene chloride and dilute sodium hydroxide. The chloroform layer was concentrated and the residue, the free base of the title compound, was reacted with 0.4 g oxalic acid in a solution of 30 ml of 90–100 isopropyl alcohol water. The resulting crystals were recrystallized from the same solvent to give 1 g of the product, m.p. 191°–193° C.

Analysis: Calculated for $C_{15}H_{21}N_3S_2O_4$: C, 48.50; H, 5.70; N, 11.33. Found: C, 48.49; H, 5.84; N, 10.99.

EXAMPLE 40

2-[2-(Dimethylamino)ethyl]-2,3-dihydro-4-methylpyrido[3,4-f][1,4]-oxazepin-5(4H)-one oxalate (1:2) hemihydrate A solution of 5 g (0.02 mole) of 2-(2-chloroethyl)-2,3-dihydro-4-methylpyrido[3,4-f][1,4]oxazepin-5(4H)-one, in 25 ml of dimethylamine was placed in a sealed vessel and stirred for 72 hr. The vessel was opened and the excess dimethylamine allowed to evaporate. The residue was dissolved in chloroform and the solvent was stripped off in vacuo to remove excess dimethylamine. The residue was partitioned between dilute sodium hydroxide and ethyl acetate. The ethyl acetate solution was concentrated and the residue was treated with 3 g (0.033 mole) of oxalic acid in 50 ml of isopropyl alcohol and enough water to dissolve the salt while boiling. The resulting crystals were recrystallized from the same solvent. Yield of product was 5.3 g (60%), m.p. 179°–181° C.

Analysis: Calculated for $C_{34}H_{48}N_6O_{21}$: C, 46.48; H, 5.52; N, 9.58. Found: C, 46.58; H, 5.70 N, 9.61.

EXAMPLE 41

2-[2-(Dimethylamino)ethyl]-2,3-dihydro-4-methylpyrido[3,4-f][1,4]oxazepine-5(4H)-thione oxalate (1:2)

A 4 g (0.009 mole) sample of 2-[2-(dimethylamino)ethyl]-2,3-dihydro-4-methylpyrido[3,4-f][1,4]oxazepin-5(4H)-one oxalate (1:2) hemihydrate was partitioned between dilute sodium hydroxide and chloroform. The aqueous layer was extracted three times and the combined chloroform extracts were dried over sodium sulfate and concentrated. The residue was dissolved in 200 ml of dry toluene and again concentrated in vacuo to effect drying. The residue was dissolved in dry pyridine (10 ml) and treated with 2.8 g (0.01 mole) of phosporus pentasulfide. The mixture was stirred at reflux for 20 hr. The cooled mixture was partitioned between dilute sodium hydroxide and chloroform. The aqueous layer was extracted three times with chloroform. The combined chloroform extracts were dried over sodium sulfate and concentrated. One gram of the residue was treated with 0.6 g of oxalic acid in isopropyl alcohol/10% water. The resulting crystals were collected by filtration. Yield of oxalate salt was 0.37 g., m.p. 111°–114° C.

Analysis: Calculated for $C_{17}H_{23}N_3SO_9$: C, 45.84; H, 5.20; N, 9.43. Found: C, 45.46; H, 5.38; N, 9.28.

EXAMPLE 42

2-(3-Aminopropyl)-2,3-dihydro-4-methyl-pyrido[3,2-f][1,4]-oxazepin-5(4H)-one, oxalate [1:1]

2,3-Dihydro-4-methyl-5(4H)-oxopyrido[3,2-f][1,4]oxazepine-2-propanenitrile, 5 g (0.22 mole, in 150 ml of ethanol was treated with about 1.5 g of wet Raney nickel. The mixture was hydrogenated in a Parr apparatus at 60° C. and 40 psi. The mixture was cooled and filtered and the filtrate concentrated. The residue was treated with 3.9 g of oxalic acid in 130 ml of boiling isopropyl alcohol containing 2 ml of water. The hot solution was filtered and allowed to cool. The resulting solid was recrystallized from ethanol. Yield of oxalate hemihydrate was 3 g (43%), m.p. 126°–134° C.

Analysis: Calculated for $C_{28}H_{40}N_6O_7$: ,50.30; H,6.03; N,12.57. Found: C,50.46; H,5.71; N,12.21.

EXAMPLE 43

2,3-Dihydro-4-methyl-2-[2-(4-morpholinyl)ethyl]-pyrido[3,2-f][1,4oxazepin-5(4H)-one maleate [1:1]

2-(2-Chloroethyl)-2,3-dihydro-4-methylpyrido[3,2-f][1,4]oxazepin-5(4H)-one hydrochloride, 16 g (058 mole) was dissolved in morpholine (30 ml) and stirred overnight at room temperature. To the solution was added dilute sodium hydroxide solution (50 ml) and the resulting mixture extracted with chloroform (3×30 ml). The chloroform was removed on the rotary evaporator with aspiration. The residual morpholine was removed in vacuo at 50° C. (rotary evaporator). To the residual free base (15.5 g, 0.053 mole) was added isopropyl alcohol (1 liter) and maleic acid (9.24 g g, 0.080 mole). The mixture was heated to boiling and the clear solution cooled at 20° C. for several hours. The resulting crystals, 16 g (68.1%), were recrystallized from isopropyl alcohol, m.p. 163°–165° C.

Analysis: Calculated for $C_{19}H_{25}N_3O_7$: C,56.01; H,6.18; N,10.31. Found: C,55.71; H,6.21; N,10.18.

EXAMPLE 44

2,3-Dihydro-4-methyl-2-[2-(1-pyrrolidinyl)ethyl]-pyrido[3,2-f][1,4]-oxazepin-5(4H)-one fumarate [1:1]

A sample of 2-(2-chloroethyl)-2,3-dihydro-4-methyl-pyrido[3,2-f][1,4]-oxazepine-5(4H)-one hydrochloride, 16 g (0.058 mole), was dissolved in 65 ml of pyrrolidine. The stirred solution was heated to 80° C. for 3 hr. The solution was cooled to room temperature and dilute sodium hydroxide solution (50 ml) was added. The resulting solution was extracted with chloroform (3×30 ml) and concentrated in vacuo. The residue was taken up in boiling isopropyl alcohol (500 ml/and fumaric acid (9.2 g, 0.079 mole) was added. The solution was filtered hot and the filtrate cooled to 20° C. for several hours. The resulting crystals, 14 g (47.8%) were collected and recrystallized from isopropyl alcohol, m.p. 147°–149° C.

Analysis: Calculated for $C_{23}O_{10}N_3H_{29}$: C,54.43; H,5.76; N,8.28. Found: C,54.38; H,5.83; N,8.27.

EXAMPLE 45

2-[2-(Dibutylamino)ethyl]-2,3-dihydro-4-methyl-pyrido[3,2-f][1,4]oxazepin-5(4H)-one maleate [1:1]

2-(2-Chloroethyl)-2,3-dihydro-4-methylpyrido[3,2-f][1,4]oxazepine-5(4H)-one hydrochloride, 16 g (0.058 mole) was dissolved in dimethylformamide (30 ml) and di-n-butylamine (30 ml). The solution was stirred at 90° C. for 3 hr at 100° C. for 2.5 hr. The solution was cooled and to it was added 50 ml of dilute sodium hydroxide solution. The resulting mixture was extracted with chloroform (3×50 ml). The chloroform was removed on the rotary evaporator with water aspiration at 50° C. Residual dimethylformamide and di-n-butylamine were removed at low vacuum and 50° C. (rotary evaporator). To the residual free base, 13.8 g (0.041 mole) was added isopropyl alcohol (900 ml) and oxalic acid, 5.6 g (0.062 mole) and the solution heated to boiling. The clear solution was cooled overnight at 20° C. and filtered to give 13.6 g (56.5%) of crystals which were recrystallized from isopropyl alcohol, m.p. 195°–196° C.

Analysis: Calculated for $C_{21}H_{33}N_3O_6$: C,59.59; H,7.85; N,9.72. Found: C,59.37; H,7.91; N,9.86.

EXAMPLE 46

2-[2-(Diethylamino)ethyl]-2,3-dihydro-4-methyl-pyrido[3,2-f][1,4]oxazepin-5(4H)-one oxalate [1:1]

2-(2-Chloroethyl)-2,3-dihydro-4-methylpyrido[3,2-f][1,4]oxazepin-5(4H)-one hydrochloride, 16 g (0.058 mole) was suspended in diethylamine (30 ml). The suspension was stirred for 72 hr at room temperature. The mass spectrum indicated that the reaction had progressed 33% at this point. The mixture was then heated to reflux for 6 hr. Diethylamine was removed by rotary evaporation (70° C. water aspirator). The residue was taken up in chloroform (100 ml) and washed with dilute aqueous sodium hydroxide (2×30 ml). The organic layer was concentrated by rotary evaporation (70° C., water aspirator). The residue was dissolved in boiling isopropyl alcohol and treated with oxalic acid. Upon cooling, 18.6 g (87.7%) of light brown crystals were collected (m.p. 150°–155° C.). A sample was recrystallized three more times from isopropyl alcohol, m.p. 156°–157° C.

Analysis: Calculated for $C_{17}H_{25}N_3O_6$: C,55.57; H,6.86; N,11.43. Found: C,55.28; H,6.85; N,11.27.

EXAMPLE 47

2,3-Dihydro-4-methyl-2-[2-(1-piperidinyl)ethyl]-pyrido[3,2-f][1,4]oxazepin-5(4H)-one oxalate [1:1]

2-(2-Chloroethyl)-2,3-dihydro-4-methylpyrido[3,2-f][1,4]oxazepin-5(4H)-one hydrochloride, 4 g (0.015 mole) was dissolved in piperidine (30 ml) and heated to 80° C. with stirring for 20 minutes. The piperidine was removed by rotary evaporation (85° C., vacuum pump) and the residue taken up in chloroform (50 ml). The organic layer was washed with dilute aqueous sodium hydroxide (2×20 ml) and concentrated by rotary evaporation (80° C., water aspirator). The resulting oil was taken up in hot isopropyl alcohol and treated with oxalic acid. Upon cooling, crystals of the oxalate salt were collected and recrystallized from isopropyl alcohol, to give 3.4 g (62%) of pale brown crystals, m.p. 133°–136° C.

Analysis: Calculated for $C_{18}H_{25}N_3O_6$: C,56.98; H,6.64; N,11.07. Found: C,56.95; H,6.87; N,10.79.

EXAMPLE 48

2,3-Dihydro-4-methyl-2-[2-[methyl(phenylmethyl)amino]ethyl]pyrido[3,2-f][1,4]oxazepin-5(4H)-one maleate [1:1]

2-(2-Chloroethyl)-2,3-dihydro-4-methylpyrido[3,2-f][1,4]oxazepin-5(4H)-one hydrochloride, 4 g (0.015 mole) was dissolved in methyl benzyl amine (30 ml) and heated to 80° C. with stirring. After three hours, the excess amine was removed by rotary evaporation (90° C., vacuum pump). The residual oil was taken up in chloroform (40 ml) and washed with dilute aqueous sodium hydroxide (30 ml). The chloroform layer was concentrated by rotary evaporation (90° C., water aspirator). The residual oil was dissolved in hot isopropyl alcohol and treated with maleic acid. Upon cooling, 4.23 g (66%) of pale brown crystals were collected, m.p. 167°–169° C.

Analysis: Calculated for $C_{23}H_{27}N_3O_6$: C,62.57; H,6.16; N,9.52. Found: C,62.28; H,6.16; N,9.24.

EXAMPLE 49

2,3-Dihydro-4-methyl-2-[2-(methylphenylamino)ethyl]pyrido[3,2-f][1,4]oxazepin-5(4H)-one 2-(2-Chloroethyl)-2,3-dihydro-4-methylpyrido[3,2-f][1,4]oxazepin-5(4H)-one hydrochloride, 4.00 g (0.015 mole) was dissolved in N-methylaniline (30 ml) and heated to 95° C. with stirring for 2 days. Excess N-methylaniline was removed by rotary evaporation (95° C., vacuum pump). The residue was taken up in chloroform (80 ml) and washed with dilute aqueous sodium hydroxide (30 ml) The chloroform layer was decolorized with activated carbon and dried over sodium sulfate, filtered and concentrated by rotary evaporation. The remaining residue was dissolved in ethyl acetate (50 ml) and purified by high pressure liquid chromatography using a silica gel column and ethyl acetate as the eluent. After purification, crystals formed from ethyl acetate. These crystals were recrystallized from ethyl acetate, giving 1.40 g (31%) of pale brown crystals.

Analysis: Calculated for $C_{18}H_{21}N_3O_2$: C,69.43; H,6.79; N,13.49. Found: C,69.31; H,6.77; N,13.54.

EXAMPLE 50

2-[2-(2,5-Dimethyl-1-pyrrolidinyl)ethyl]-2,3-dihydro-4-methylpyrido[3,2-f][1,4]oxazepin-5(4H)-one fumarate [1:1]

2-(2-Chloroethyl)-2,3-dihydro-4-methylpyrido[3,2-f][1,4]oxazepin-5(4H)-one, 5.0 g (0.021 mole), was dissolved in 25 ml of absolute ethanol and 3 g (0.03 mole) of 2,5-dimethylpyrrolidine was added. The solution was heated to 75° C. for 48 hrs with stirring. Because the reaction was incomplete at this time, an additional amount of 2,5-dimethylpyrrolidine (1.00 g, 0.01 mole) was added and the reaction continued. After 5 days, the reaction was still incomplete and more 2,5-dimethylpyrrolidine (1.00 g, 0.01 mole) was added. The reaction appeared complete 2 days later. Solvent was removed by rotary evaporation (80° C., water aspirator). Excess 2,5-dimethylpyrrolidine was removed by rotary evaporation (80° C., vacuum pump). The residue was taken up in chloroform (200 ml) and washed with dilute aqueous sodium hydroxide (2×75 ml). The organic layer was dried over sodium sulfate, filtered, and concentrated by rotary evaporation (70° C., water aspirator). The resulting oil was dissolved in hot isopropyl alcohol and treated with fumaric acid. Upon cooling, 2.38 g (27.4%) of pale brown crystals was collected, m.p. 161°–162° C.

Analysis: Calculated for $C_{21}H_{29}N_3O_6$: C,60.13; H,6.96; N,10.02. Found: C,59.79; H,6.93; N,9.76.

EXAMPLE 51

2,3-Dihydro-4-methyl-2-[2-(2-methyl-1-pyrrolidinyl)ethyl]pyrido[3,2-f][1,4]oxazepin-5(4H)-one To a solution of 3.5 g (0.0145 mole) of 2-(2-chloroethyl)-2,3-dihydro-4-methylpyrido[3,2-f][1,4]oxazepine-5(4H)-one in ethanol (15 ml) was added 2-methyl pyrrolidine (5.0 g, 0.063 mole). The solution was heated to reflux for 3 hours with stirring. The ethanol was removed by rotary evaporation (water aspirator, 80° C.). The residual oil was partitioned between dilute aqueous sodium hydroxide (50 ml) and chloroform (50 ml). The organic layer was saved and the aqueous layer extracted with chloroform (2×30 ml). All the chloroform layers were combined, dried over anhydrous sodium sulfate and concentrated by rotary evaporation (water aspirator, 70° C.). The residual oil was then distilled at 200° C. and low vacuum (vacuum pump) giving 1.5 g (35.7%) of a clear oil.

Analysis: Calculated for $C_{16}H_{23}N_3O_2$: C,66.41; H,8.01; N,14.52. Found: C,65.83; H,8.06; N,14.39.

EXAMPLE 52

2,3-Dihydro-4-methyl-2-[2-(1H-pyrazol-1-yl)ethyl]pyrido[3,2-f][1,4]oxazepin-5(4H)-one To a suspension of sodium hydride (1.2 g active, 0.05 mole) in dimethylformamide (15 ml) was added dropwise a solution of pyrazole (3.10 g, 0.045 mole) in dimethylformamide (15 ml). The resulting solution was then added to a solution of 2-(2-chloroethyl)-2,3-dihydro-4-methylpyrido[3,2-f][1,4]oxazepine-5(4H)-one (9.12 g, 0.038 mole) in 30 ml of dimethylformamide. The flask was sealed and stirred overnight. Because the reaction had not yet gone to completion at this point, pyrazole (3.12 g, 0.045 mole) was added to the reaction solution and stirred overnight. The reaction was still not complete and another suspension of sodium hydride (0.5 g active, 0.021 mole) and pyrazole (1.5 g, 0.022 mole) in dimethylformamide (10 ml) was added and the reaction stirred overnight. The reaction appeared to be complete. Dimethylformamide was removed by rotary evaporation (80° C., vacuum pump), and the residue taken up in chloroform (100 ml) which was washed with dilute aqueous sodium hydroxide (1×50 ml), dried over anhydrous sodium sulfate and concentrated by rotary evaporation (70° C., water aspirator). The material was purified by high pressure liquid chromatography, 95:5 by volume ethanol:methanol on a silica gel column. The fractions containing the desired product were concentrated by rotary evaporation (70° C., water aspirator). Crystallization ensued upon cooling. The crystals were collected and recrystallized from ethanol. The yield was 1.5 (14.5%), m.p. 132°–134° C.

Analysis: Calculated for $C_{14}H_{16}N_4O_2$: C, 61.75; H, 5.92; N, 20.58. Found: C, 61.35; H, 5.89; N, 20.67.

EXAMPLE 53

2,3-Dihydro-2-[2-(1H-imidazol-1-yl)ethyl]-4-methylpyrido[3,2-f][1,4]oxazepin-5(4H)-one To a solution of 2-(2-chloroethyl)-2,3-dihydro-4-methylpyrido[3,2-f][1,4]-oxazepine-5(4H)-one, 9.12 g (0.038 mole) in dimethylformamide (30 ml) was added imidazole, 5.66 g (0.083 mole). The solution was heated to 130° C. for 18 hr. Dimethylformamide was removed by rotary evaporation (80° C., vacuum pump) and the residue taken up in chloroform (100 ml). The chloroform was washed with dilute aqueous sodium hydroxide (30 ml), dried over sodium sulfate and concentrated by rotary evaporation (70° C., water aspirator) to an oil. Crystallization was induced with ethanol. White crystals, 1.5 g (14.5%) were collected, m.p. 150°–152° C.

Analysis: Calculated for $C_{14}H_{16}N_4O_2$: C, 61.75; H, 5.92; N, 20.58. Found: C, 61.36; H, 5.92; N, 20.60.

EXAMPLE 54

2-[2-(Dimethylamino)ethyl]-4-ethyl-2,3-dihydropyrido[3,2-f][1,4]oxazepin-5(4H)-one oxalate [1:1]

To 30 ml of dimethylamine collected at 0° C. was added 6 g (0.021 mole) 2-(2-chloroethyl)-4-ethyl-2,3-dihydropyrido[3,2-f][1,4]oxazepin-5(4H)-one, hydrochloride. The flask was sealed tightly and stirred 70 hr at room temperature. The solution was then cooled to 0° C. and the stopper of the flask removed. Dimethylamine was allowed to evaporate. The residue was taken up in chloroform (1×150 ml) and washed with dilute aqueous sodium hydroxide (1×50 ml). The organic layer was dried over sodium sulfate, filtered and concentrated by rotary evaporation (70° C., water aspirator). The residue was dissolved in hot isopropyl alcohol and treated with oxalic acid. Upon cooling, 4.5 (61.5%) was collected, m.p. 208° C.

Analysis: Calculated for $C_{16}H_{23}N_3O_6$: C, 54.38; H, 6.56; N, 11.89. Found: C, 54.26; H, 6.61; N, 11.81.

EXAMPLE 55

2,3-Dihydro-4-ethyl-2-[2-(1-pyrrolidinyl)ethyl]-pyrido[3,2-f][1,4]oxazepin-5(4H)-one oxalate [1:1]

2-(2-Chloroethyl)-4-ethyl-2,3-dihydropyrido[3,2-f][1,4]oxazepin-5(4H)-one hydrochloride, 3 g (0.01 mole) was dissolved in pyrrolidine (30 ml) and heated to 70° C. for 30 minutes with stirring. After cooling, the contents of the reaction flask were diluted with dilute aqueous sodium hydroxide (40 ml) and extracted with chloroform (2×30 ml). The chloroform layer was dried over sodium sulfate, filtered and concentrated to a viscous brown oil by rotary evaporation (70° C., water aspirator). The oil was taken up in hot isopropyl alcohol and treated with oxalic acid. Upon cooling, the resulting solid was recrystallized from isopropyl alcohol, giving pale brown crystals, 1.80 g (45.4%), m.p. 185°–188° C.

Analysis: Calculated for $C_{18}H_{25}N_3O_6$: C, 56.98; H, 6.64; N, 11.07. Found: C, 56.90; H, 6.67; N, 10.90.

EXAMPLE 56

2,3-Dihydro-4-methyl-2-[2-(4-morpholinyl)ethyl]-pyrido[3,2-f][1,4]oxazepin-5(4H)-thione 2-(2-Chloroethyl)-2,3-dihydro-4-methylpyrido[3,2-f][1,4]oxazepine-5(4H)-thione, 4.5 g (0.018 mole) was dissolved in morpholine (30 ml). The solution was heated with stirring to 50°–60° C. for 6 hr. The morpholine was then removed by rotary evaporation (90° C., vacuum pump). The residue was taken up in chloroform (100 ml) and washed with dilute aqueous sodium hydroxide (2×30 ml). The organic layer was concentrated by rotary evaporation (60° C., water aspirator). The residue was recrystallized from ethanol giving 3.26 g (60%) of light yellow crystals, m.p. 152°–153° C.

Analysis: Calculated for $C_{15}H_{21}N_3O_2S$: C, 58.61; H, 6.89; N, 13.66. Found: C, 58.48; H, 6.92; N, 13.62.

EXAMPLE 57

2-[2-(Dibutylamino)ethyl]-2,3-dihydro-4-methyl-pyrido[3,2-f][1,4]oxazepine-5(4H)-thione oxalate [1:1]

2-(2-Chloroethyl)-2,3-dihydro-4-methylpyrido[3,2-f][1,4-oxazepine-5(4H)-thione, 4 g (0.016 mole) was suspended in di-n-butylamine (30 ml). Dimethylformamide (ca. 10 ml) was added to the stirred mixture until dissolution occurred. The solution was heated to 140° C. for 3.5 hr with stirring. Di-n-butylamine and dimethylformamide were removed by rotary evaporation (80° C. vacuum pump). The residue was then diluted with dilute aqueous sodium hydroxide (50 ml) and extracted with chloroform (3×40 ml). Chloroform was removed by rotary evaporation (70° C., water aspirator). The residue was dissolved in boiling isopropyl alcohol and treated with oxalic acid. Upon cooling, the resulting oxalate salt was filtered and recrystallized from isopropyl alcohol to give 3.2 g (47%) of yellow crystals, m.p. 208° C.

Analysis: Calculated for $C_{21}H_{33}N_3O_5S$: C, 57.38; H, 7.57; N, 9.56. Found: C, 57.04; H, 7.63; N, 9.31.

EXAMPLE 58

2-[2-(Diethylamino)ethyl]-2,3-dihydro-4-methyl-pyrido[3,2-f][1,4]oxazepine-5(4H)-thione oxalate [1:1]

2-(2-Chloroethyl)-2,3-dihydro-4-methyl[3,2-f][1,4]oxazepine-5(4H)-thione, 4 g (0.016 mole) was suspended in diethylamine (30 ml). Dimethylformamide was added to the stirred suspension until dissolution occurred (10 ml). The stirred solution was heated to 65° C. for 8 hr. Diethylamine was removed by rotary evaporation (70° C., water aspirator); the remaining dimethylformamide was removed at low pressure (vacuum pump) and 90° C. The residue was taken up in chloroform (100 ml) and washed with dilute aqueous sodium hydroxide (2×30 ml). The organic layer was concentrated by rotary evaporation (70° C., water aspirator). The residue was dissolved in boiling isopropyl alcohol and treated with oxalic acid. Upon cooling, the oxalate salt, 1.7 g (28.5%) was obtained, m.p. 142°–144° C.

Analysis: Calculated for $C_{17}H_{25}N_3O_5S$: C, 53.25; H, 6.57; N, 10.95. Found: C, 53.14; H, 6.60; N, 10.72.

EXAMPLE 59

2,3-Dihydro-4-methyl-2-[2-(1-pyrrolidinyl)ethyl]-pyrido[3,2-f][1,4]oxazepine-5(4H)-thione oxalate [1:1]

2-(2-Chloroethyl)-2,3-dihydro-4-methylpyrido[3,2-f][1,4]oxazepine-5(4H)-thione, 5 g (0.02 mole) was dissolved in 30 ml of pyrrolidine. The solution was heated to 60°–80° C. for 35 minutes with stirring. After cooling to room temperature, the reaction mixture was diluted with dilute aqueous sodium hydroxide (50 ml) and extracted with chloroform (2×50 ml). The organic layer was concentrated by rotary evaporation (70° C., water aspirator). Residual pyrrolidine was removed at 90° C. and vacuum pump. The residue was dissolved in hot ethanol and treated with oxalic acid. Upon cooling, the oxalate salt was collected and recrystallized twice from ethanol to give 3.35 g, (45%) of product, m.p. 141° C.

Analysis: Calculated for $C_{17}H_{23}N_2O_5S$: C, 53.53; H, 6.08; N, 11.02. Found: C, 53.39; H, 6.11; N, 10.91.

EXAMPLE 60

2,3-Dihydro-2-[2-(1H-imidazol-1-yl)ethyl]-4-methyl-pyrido-[3,2-f][1,4]oxazepine-5(4H)-thione oxalate [2:3]

To a solution of 2-(2-chloroethyl)-2,3-dihydro-4-methylpyrido[3,2-f][1,4]oxazepine-5(4H)-thione, 4.5 g (0.018 mole) in dimethylformamide (35 ml) was added imidazole (2.20 g, 0.038 mole). The resulting solution was heated to 130° C. for 15 hrs. Dimethylformamide was removed by rotary evaporation (80° C., vacuum pump), and the residue diluted with dilute aqueous sodium hydroxide (50 ml). The aqueous solution was extracted with chloroform (1×50 ml), dried over anhydrous sodium sulfate and concentrated by rotary evaporation (water aspirator, 70° C.). The resulting oil was treated with oxalic acid in ethanol. Four grams (54%) of pale yellow crystals were collected and recrystallized again with ethanol, m.p. 163°–167° C.

Analysis: Calculated for $C_{17}H_{19}O_7N_4S$: C, 48.22; H, 4.52; N, 13.23. Found: C, 48.04; H, 4.62; N, 13.18.

EXAMPLE 61

2-[2-(Dimethylamino)ethyl]-4-ethyl-2,3-dihydropyrido[3,2-f][1,4]oxazepin-5(4H)-thione 2-(2-Chloroethyl)-4-ethyl-2,3-dihydropyrido[3,2-f][1,4]oxazepin-5(4H)-thione hydrochloride, 5.00 g (0.016 mole) was added to 20 ml of anhydrous dimethylamine. The reaction flask was sealed tightly and stirred at room temperature for 6 days. The flask was opened after cooling to 0° C. and dimethylamine allowed to evaporate at room temperature. The residue was taken up in chloroform (100 ml) and washed with dilute aqueous sodium hydroxide (1×30 ml). The chloroform layer was dried over sodium sulfate, filtered and concentrated by rotary evaporation. The residual oil was dissolved in hot cyclohexane. Upon cooling, 1.76 g (39.4%) of light yellow crystals were collected, m.p. 73° C.

Analysis: Calculated for $C_{14}H_{21}N_3OS$: C, 60.18; H, 7.58; N, 15.03. Found: C, 60.32; H, 7.70; N, 15.13.

EXAMPLE 62

2,3-Dihydro-4-methyl-2-[2-[methyl(phenylmethyl)amino]ethyl]pyrido[3,2-f][1,4]oxazepine-5(4H)-thione oxalate [1:1]

To a solution of 4 g (0.0155 mole) of 2-(2-chloroethyl)-2,3-dihydro-4-methylpyrido[3,2-f][1,4]oxazepine-5(4H)-thione in 70 ml of chloroform was added 10.0 g (0.086 mole) of benzylmethylamine. The solution was stirred at reflux for 24 hr. The reaction solution was washed with water (2×50 ml) and concentrated by rotary evaporation (~70° C., water aspirator). The residue was distilled on a molecular still at 165° C./0.1 mm. The residue was treated with oxalic acid in hot isopropyl alcohol. Upon cooling, two crops of crystals were collected. The purity of each crop was checked. The two crops were combined and recrystallized together in hot isopropyl alcohol. Upon cooling, 3.69 g (55%) of pale yellow crystals, m.p. 163°–166° C. were collected.

Analysis: Calculated for $C_{21}H_{25}N_3O_5S$: C, 58.45; H, 5.84; N, 9.74. Found: C, 58.24; H, 5.92; N, 9.61.

EXAMPLE 63

2,3-Dihydro-2-[2-(methylamino)ethyl]-4-methyl-pyrido[3,2-f][1,4]oxazepine-5(4H)-thione oxalate [1:1.5]

2-(2-Chloroethyl)-2,3-dihydro-4-methylpyrido[3,2-f][1,4]oxazepine-5(4H)-thione, 4.0 g (0.016 mole) was suspended in a 30% solution of methylamine in 70 ml of ethanol and allowed to stir for 56 hr at room temperature. Because of incomplete reaction, the reaction solution was heated slowly over a 2 hr period to 55° C. and stirred at that temperature for 24 hr. Methylamine was removed by water aspiration for 1.5 hr. The resulting solution was concentrated by rotary evaporation (70° C., water aspirator). The residual oil was taken up in chloroform (150 ml) and washed with 2M aqueous potassium hydroxide (2×50 ml). The chloroform layer was dried over sodium sulfate and concentrated by rotary evaporation (70° C., water aspirator). The residue was dissolved in hot ethanol and treated with oxalic acid. Upon cooling, 2.0 g (37.5%) of yellow crystals were collected, m.p. 137°–138° C.

Analysis: Calculated for $C_{15}H_{20}N_3O_7S$: C, 46.43; H, 5.22; N, 10.67. Found: C, 46.47; H, 5.35; N, 10.85.

EXAMPLE 64

7-Chloro-2,3-dihydro-4-methyl-2-[2-(1-pyrrolidino)ethyl]pyrido[3,2-f][1,4]oxazepin-5(4H)-one fumarate[1:2.5]

7-Chloro-2-(2-chloroethyl)-2,3-dihydro-4-methyl-pyrido[3,2-f][1,4]oxazepin-5(4H)-one (2.5 g, 0.009 mole) was dissolved in 50 ml pyrrolidine and the solution was heated to 80° C. for 1 hr. The pyrrolidine was removed by rotary evaporation (80° C., water aspirator) and the residue dissolved in 100 ml of chloroform. The organic layer was washed with water (2×50 ml), dried over sodium sulfate and concentrated by rotary evaporation (~80° C., water aspirator). The residue was treated with fumaric acid and allowed to stand overnight. The resulting crystals were collected, 1.25 g (23.2%), m.p. 164°–166° C.

Analysis: Calculated for $C_{25}H_{30}N_3O_{12}Cl$: C, 50.05; H, 5.04; N, 7.00. Found: C, 50.22; H, 5.14; N, 7.02.

EXAMPLE 65

7-Chloro-2-[2-(dimethylamino)ethyl]-2,3-dihydro-4-methylpyrido[3,2-f][1,4]oxazepin-5(4H)-one oxalate [1:1]

A 2.8 g (0.01 mole) sample of 7-chloro-2-(2-chloroethyl)-2,3-dihydro-4-methylpyrido[3,2-f][1,4]oxazepin-5(4H)-one was added to 25 ml of dimethylamine and stirred for 96 hr in a sealed flask. The excess amine was allowed to evaporate and the residue was partitioned between chloroform and dilute sodium hydroxide. The chloroform was dried over sodium sulfate and concentrated. The residue was treated with 0.7 g of oxalic acid in isopropyl alcohol. The resulting crystals were recrystallized from the same solvent. Yield was 1.5 g of oxalate salt (40%), m.p. 150°–156° C.

Analysis: Calculated for $C_{15}H_{20}N_3O_6Cl$: C, 48.20; H, 5.39; N, 11.24. Found: C, 48.09; H, 5.47. N, 11.12.

EXAMPLE 66

4-Cyclohexyl-2-[(dimethylamino)methyl]-2,3-dihydropyrido[3,2-f][1,4]oxazepin-5(4H)-one oxalate Utilizing the procedure of Example 10, 2-(chloromethyl)-4-cyclohexyl-2,3-dihydropyrido[3,2-f][1,4]oxazepin-5(4H)-one (Intermediate 35) is reacted with 40% aqueous dimethylamine and reacted with oxalic acid in isopropyl alcohol.

EXAMPLE 67

2-[2-(Dimethylamino)ethyl]-2,3-dihydro-4-phenylmethylpyrido[3,2-f][1,4]oxazepin-5(4H)-one oxalate[1:1.5]hemihydrate A solution containing 94.2 g (0.6 mole) of 2 chloronicotinic acid and 100 g (0.54 mole) of 1-benzyl-3-pyrrolidinol in 800 ml of dry tetrahydrofuran was added at a rapid drop to a stirred suspension of 52 g (1.3 mole) of 60% sodium hydride/mineral oil in 500 ml of dry tetrahydrofuran at reflux temperature (addition time was about 1 hr). The mixture was heated to reflux for an additional 1.5 hr and then cooled to room temperature. Approximately 1 liter of ethyl acetate was added and filtration attempted unsuccessfully. The mixture was allowed to stand overnight at room temperature and then was concentrated on the rotary evaporator at 100° C. and 50 mm pressure. The residue was dissolved in 1 liter of chloroform and the pH of the solution was adjusted to 6.15 with hydrogen chloride gas. To the solution was added, with stirring, 383 g (1.0 mole) of triphenylphosphine and 383 g (2.48 mole) of carbon tetrachloride. The mixture was refluxed for 1 hr and 50 ml of ethanol was added. The solution was cooled to room temperature and extracted three times with 400 ml portions of dilute hydrochloric acid. The chloroform layer was extracted with dilute sodium hydroxide, dried over sodium sulfate and concentrated. The mass spectra indicated the presence of 2-(2-chloroethyl)-2,3-dihydro-4-(phenylmethyl)pyrido[3,2-f][1,4]oxazepin-5(4H)-one (mass 316), triphenylphosphine (mass 262) and triphenylphosphine oxide (mass 278). One-third of the residue was chromatographed on a high pressure liquid chromatopraph in an unsuccessful attempt to purify the compound. The other ⅔ of the residue was dissolved in 30 ml of chloroform and added to a solution of 30 g of dimethyl amine in ethanol. The solution was heated to reflux for 4 hr and concentrated on the rotary evaporator. The residue was partitioned between chloroform and 1N hydrochloric acid. The acid layer was made basic with sodium hydroxide and extracted with chloroform. The chloroform layer was dried over sodium sulfate and concentrated. The residue (10 g) was treated with an equivalent amount of oxalic acid in a mixture of isopropyl alcohol-ethanol-isopropyl ether. The resulting crystals in the amount of 9 g (5%) were recrystallized from the same solvent mixture, m.p. 95°-98° C.

Analysis: Calculated for $C_{44}H_{54}N_6O_{17}$: C, 56.28; H, 5.79; N, 8.95. Found: C, 56.61; H, 5.76; N, 8.77.

EXAMPLE 68-a

2-[2-(Dimethylamino)ethyl]-2,3-dihydropyrido[3,2-f][1,4]oxazepin-5(4H)-one

A solution of 3.0 g (0.006 mole) of 2-[2-(dimethylamino ethyl]-2,3-dihydro-4-phenylmethylpyrido[3,2-f][1,4]oxazepin-5(4H)-one oxalate[1:1.5]hemihydrate in about 50 ml of water was made basic with dilute aqueous sodium hydroxide solution and then extracted with three 50 ml portions of benzene. The combined benzene extract was dried over anhydrous sodium sulfate and concentrated on the rotary evaporator (steam bath/50 mm). The residue was dried further by azeotroping 2 times with about 50 ml of dry benzene, evaporating to dryness each time. The final residue was dissolved in 40 ml of liquid ammonia and small spheres of sodium were added with stirring to the solution until a blue color persisted for 20 minutes. (Addition time was about 1 hr). Three grams of ammonium chloride was added slowly and the ammonia was allowed to evaporate. The residue was suspended in chloroform and the mixture was filtered. The filtrate was concentrated and the residue chromatographed on preparative high pressure liquid chromatograph using a silica gel column and eluting with 75% ethyl acetate/25% dimethylformamide. The yield of product was 0.1 g (7%). The chemical ionization mass spectrophotometer gave a peak at 236 corresponding to a molecular weight of 235. The $^1$H NMR spectrum of the subject compound was obtained in CDCl$_3$ containing 1% tetramethylsilane (TMS) and is consistent with the proposed structure and dimethylformamide (DMF) and mineral oil as minor impurities. The chemical shifts, multiplicities, and assignments are given below:

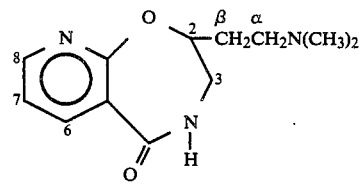

| Chemical Shifts (multiplicities) | Assignments |
|---|---|
| 8.45 (multiplet) | H(8) and H(6) |
| 8.00 (singlet) | C—H(DMF) |
| 7.85 (broad singlet) | N—H |
| 7.20 (doublet of doublets) | H(7) |
| 4.65 (pentet) | H(2) |
| 4.05 (broad singlet) | unknown impurity |
| 3.50 (triplet) | H$_2$(3) |
| 2.95 (singlet) | CH$_3$(DMF) |
| 2.90 (singlet) | CH$_3$(DMF) |
| 2.60 (triplet) | H$_2$—α to amino nitrogen |
| 2.25 (singlet) | N(CH$_3$)$_2$ |
| 2.05 (multiplet) | H$_2$—β to amino nitrogen |
| 0.7–1.7 (multiplet) | mineral oil |

EXAMPLE 68-b (Refer to Chart VIII)

2-[2-(Dimethylamino)ethyl]-2,3-dihydropyrido[3,2-f]-1,4-oxazepin-5(4H)-one fumarate[1:1]

An 8 g (0.026 mole) sample of 2-chloro-N-[4-(dimethylamino)-2-hydroxybutyl]-3-pyridinecarboxamide monohydrochloride was partitioned between chloroform and dilute sodium hydroxide. The chloroform was dried over anhydrous sodium sulfate and concentrated. The residue was dissolved in 80 ml of dry benzene which was removed on the rotary evaporator (100° C./30 min). The residue in 20 ml of dry tetrahydrofuran was added slowly to a stirred suspension of 8.3 g (0.052 mole) of potassium hydride/mineral oil in 80 ml of dry tetrahydrofuran. The mixture was stirred at reflux for 4 hr, cooled and treated with 10 ml of isopropyl alcohol. The solution was partitioned between isopropyl ether and dilute hydrochloric acid. The acid layer was made basic with sodium hydroxide and extracted 4 times with chloroform. The chloroform was concentrated and the residue was chromatographed on HPLC (silica; 90% ethanol-10% triethylamine. The desired fractions were concentrated and the residue (1.3 g) treated with 0.7 g of fumaric acid in 25 ml of isopropyl alcohol. The resulting crystals weighed 1.2 g (13%) and melted at 160°-164° C.

Analysis: Calculated for $C_{16}H_{21}N_3O_6$: C, 54.69; H, 6.02; N, 11.96. Found: C, 54.29; H, 6.02; N, 11.54.

EXAMPLE 69

2-[3-(Dimethylamino)propyl]-2,3-dihydro-4-methyl-pyrido[3,2-f][1,4]oxazepin-5(4H)-one fumarate[1:1.5]hemihydrate To 5.0 g (0.21 mole) of 2-(3-aminopropyl)-2,3-dihydro-4-methylpyrido[3,2-f][1,4]-oxazepin-5(4H)-one was added, while cooling in a water bath, an 88% aqueous solution of formic acid, 20 g (0.38 mole). To the resulting solution was added a solution of 37% aqueous formaldehyde (inhibited with 13% methanol), 10.7 g (0.13 mole). The resulting solution was heated on a steam bath for 5.5 hr. The mixture was cooled and 100 ml of dilute aqueous hydrochloric acid was added. The solution was evaporated to dryness and the residue was dissolved in 50 ml of water. The solution was neutralized with dilute aqueous potassium hydroxide and extracted with four 50 ml portions of chloroform. The combined chloroform extracts was dried over sodium sulfate and concentrated by rotary evaporation. The residue was reacted with fumaric acid in hot isopropyl alcohol. The collected product, 3.0 g (31.8%) was recrystallized twice from isopropyl alcohol, m.p. 108°–110° C.

Analysis: Calculated for $C_{40}H_{56}N_6O_{17}$: C, 53.81; H, 6.32; N, 9.41. Found: C, 53.69; H, 6.33; N, 9.41.

EXAMPLE 70

2-[3-(Dimethylamino)propyl]-2,3-dihydro-4-methyl-pyrido[3,2-f][1,4]oxazepine-5(4H)-thione oxalate[1:2]

To a solution of 11.0 g (0.042 mole) of 2-[3-(dimethylamino)propyl]-2,3-dihydro-4-methylpyrido[3,2-f][1,4]-oxazepin-5(4H)-one in 125 ml of pyridine was added 9.25 g (0.042 mole) of phosphorus pentasulfide. The mixture was heated to reflux for 3.5 hr while stirring. After cooling to room temperature, the reaction solution was added to an equal volume of 2 molar potassium hydroxide. The mixture was extracted with 800 ml of methylene chloride in several portions. The organic phase was washed with three 100 ml portions of dilute potassium hydroxide, dried over sodium sulfate, filtered and concentrated by rotary evaporator (water-aspirator, 70° C.). The residual oil was subjected to reduced pressure of the vacuum pump for 2 hr at 90° C. and then cooled and reacted with oxalic acid in isopropyl alcohol. Two crops, 4.5 and 3.1 g were collected, combined and recrystallized from isopropyl alcohol to give 6.5 g (34%) of yellow crystals, m.p. 136°–138° C.

Analysis: Calculated for $C_{18}H_{25}N_3O_9S$: C, 47.05; H, 5.42; N, 9.16. Found: C, 46.76; H, 5.75; N, 9.04.

EXAMPLE 71

7-Chloro-2-[2-(dimethylamino)ethyl]-2,3-dihydro-4-methylpyrido[3,2-f][1,4]oxazepine-5(4H)-thione fumarate[1:1]hemihydrate, hemiisopropyl alcoholate To 55 ml of a methanolic solution containing 57% by volume dimethylamine was added 2.50 g (0.009 mole) of 7-chloro-2-(2-chloroethyl)-2,3-dihydro-4-methyl-pyrido[3,2-f][1,4]-oxazepine-5(4H)-thione. The reaction vessel was sealed and allowed to stand for 16 hr. Thin-layer chromatography indicated the reaction was about 60% complete. The solution was heated gradually to 45° C. (heating time about 5 hr). Methanol and unreacted dimethylamine were removed by rotary evaporator (water aspirator, 60° C.). The residue was taken up in 100 ml of chloroform and the solution was washed with two 40 ml portions of water. The organic layer was dried over sodium sulfate, filtered and concentrated by rotary evaporator. The residue was reacted with fumaric acid in isopropyl alcohol. The resulting crystals, 1.43 g (36.5%) were recrystallized from isopropyl alcohol and dried thoroughly in a drying pistol, m.p. 98°–104° C.

Analysis: Calculated for $C_{37}H_{54}N_6O_{12}Cl_2S_2$: C, 48.84; H, 5.98; N, 9.23. Found: C, 48.82; H, 5.80; N, 9.37.

EXAMPLE 72

2,3-Dihydro-4-methyl-2-[2-(methylamino)ethyl]-pyrido[3,2-f][1,4]-oxazepin-5(4H)-one oxalate [1:1]

To 90 ml of a solution of 30% monomethylamine in ethanol was added 11.0 g (0.04 mole) of 2-(2-chloroethyl)-2,3-dihydro-4-methylpyrido[3,2-f]-1,4-oxazepin-5(4H)-one hydrochloride. The solution was heated gradually over a period of 2 hr to 55° C. and held at that temperature overnight.

Monomethylamine and ethanol were removed by rotary evaporation (water aspirator, 70° C.) and the residue was taken up in 100 ml of chloroform. The organic layer was washed with dilute aqueous sodium hydroxide (2×30 ml), dried over anhydrous sodium sulfate, filtered, and concentrated by rotary evaporation (70° C., water aspirator). The 9.0 g of crude oil was treated with oxalic acid in isopropyl alcohol. The resulting crystals weighed 8.77 g (67.8%), m.p. 148°–50° C.

Analysis: Calculated for $C_{14}H_{19}N_3O_6$: C, 51.69; H, 5.89; N, 12.92. Found: C, 51.88; H, 5.97; N, 12.96.

EXAMPLE 73

2-(2-Aminoethyl)-2,3-dihydro-4-methylpyrido[3,2-f][1,4]oxazepin-5(4H)-one, fumarate [1:1]

To a suspension of 17.0 g (0.048 mole) of 2,3-dihydro-2-[1,3-dihydro-1,3-dioxo-2H-isoindol-2-yl)ethyl]-4-methylpyrido[3,2-f]oxazepin-5(4H)-one in 100 ml of absolute ethanol was added 3.0 g (0.051 mole) of 85% hydrazine hydrate in water and the mixture heated to reflux with stirring. In 15 minutes the reaction mixture became clear. After 40 min a copious precipitate of presumably phthaly hydrazide had formed. Another 100 ml of absolute ethanol was added to ensure good mixing. After 2 hr at reflux, the cooled mixture was filtered. The filtrate was concentrated on the rotary evaporator (water aspirator, 80° C.) and the residue taken up in 75 ml of chloroform. The organic layer was washed with dilute aqueous sodium hydroxide (2×3 ml), dried over anhydrous sodium sulfate, filtered, and the filtrate concentrated by rotary evaporation (water aspirator, 75° C.). The residue was treated with fumaric acid in isopropyl alcohol and yielded 7.0 g (43%) of pale white crystals, m.p. 196°–197° C.

Analysis: Calculated for $C_{15}H_{19}N_3O_6$: C, 53.41; H, 5.68; N, 12.46. Found: C, 53.63; H, 5.78 N, 12.33.

EXAMPLE 74

2-(2-Aminoethyl)-2,3-dihydro-4-methylpyrido[3,2-f][1,4]oxazepin-5(4H)-thione, fumarate [2:1]

To a suspension of 12.15 (0.033 mole) of 2-[2-(2,3-dihydro-5(4H)-thioxopyrido[3,2-f][1,4]oxazepin-2-yl)ethyl]-1H-isoindole-1,3(2H)dione in 150 ml of absolute ethanol was added 2.08 g (0.035 mole) of an 85% solution of hydrazine hydrate in water. The mixture was heated to reflux for 2 hrs. After cooling, solid phthalylhydrazide was filtered off. Ethanol was removed by rotary evaporation (85° C., water aspirator) and the residue partitioned between 180 ml chloroform and 50 ml dilute aqueous sodium hydroxide. The organic layer was washed further with dilute aqueous sodium hydroxide (3×30 ml), dried over anhydrous sodium sulfate, filtered and concentrated by rotary evaporation (water aspirator, 70° C.). The crude oil was treated with fumaric acid in isopropyl alcohol which yielded 6.70 g (68.7%) of pale yellow crystals, m.p. 208°–09° C.

Analysis: Calculated for $C_{13}H_{17}N_3O_3S$: C,52.87; H,5.80; N,14.23. Found: C,52.72; H,5.81; N,14.16.

EXAMPLE 75

2,3-Dihydro-4-methyl-2[2-[(1-methylethyl)amino]ethyl]pyrido[3,2-f][1,4]oxazepin-5(4H)-one, fumarate [1:2]

To a solution of 2.52 g (0.011 mole) of 2-(2-aminoethyl)-2,3-dihydro-4-methylpyrido[3,2-f][1,4]oxazepin-5(4H)-one in 50 ml dry methanol was added methanolic hydrogen chloride until pH 6 was reached. To this solution was added 3.29 g (0.057 mole) of acetone, 1.79 g (0.029 mole) of sodium cyanoborohydride and 5 g 3A molecular sieves. The pH was checked and readjusted to pH 7–8 with methanolic hydrogen chloride and stirred 24 hr at room temperature. The reaction mixture was filtered, and concentrated by rotary evaporation (70° C., water aspirator). The residue was taken up in 100 ml of chloroform, washed with dilute aqueous sodium hydroxide, dried over anhydrous sodium sulfate, filtered, and concentrated by rotary evaporation (water aspirator, 70° C.). The residue was treated with fumaric acid in isopropyl alcohol which gave 1.58 g (29%) of white crystals, m.p. 152°–153° C.

Analysis: Calculated for $C_{22}H_{29}N_3O_{10}$: C, 53.33; H, 5.89; N, 8.48. Found: C, 53.43; H, 5.94; N, 8.54.

EXAMPLE 76

2-[2-[Bis(phenylmethyl)amino]ethyl]-2,3-dihydro-4-methylpyrido[3,2-f][1,4]oxazepine-5(4H)-thione, fumarate [1:1]

To a solution of 3.16 g (0.013 mole) of 2-(2-aminoethyl)-2,3-dihydro-4-methylpyrido[3,2-e][1,4]oxazepine-5(4H)thione in ~25 ml dry methanol was added methanolic hydrogen chloride to pH 5–6, followed by ~2–3 g 3A molecular sieves, 6.89 g (0.065 mole) benzaldehyde and 2.04 g (0.0325 g) sodium cyanoborohydride. The pH was again adjusted to pH 7 with methanolic hydrogen chloride. After 6 hr of stirring at room temperature, TLC (eluting with 6% triethylamine in methanol) showed what appeared to be exclusively monoalkylated product with very little starting material. To the reaction mixture was then added 1.0 g (0.009 mole) of benzaldehyde and the mixture stirred overnight at room temperature. The reaction mixture was filtered and concentrated by rotary evaporation (70° C., water aspirator). The residue was taken up in 100 ml of chloroform and washed with 2×30 ml dilute aqueous sodium hydroxide. The chloroform was removed by rotary evaporation (70° C., water aspirator). The residue was dissolved in 100 ml dilute hydrochloric acid which was subsequently washed with 2×30 ml ethyl acetate, made basic with dilute aqueous sodium hydroxide, extracted with 4×30 ml chloroform. The chloroform was dried over anhydrous sodium sulfate, filtered and concentrated by rotary evaporation (70° C., water aspirator. The residue showed both the mono- and dialkylated product by TLC (6% triethylamine/94 methanol) and NMR.

To a solution of the 3.0 g crude material dissolved in 30 ml dry methanol was added methanolic hydrogen chloride to pH 4–5, 10.0 g (10.094 mole) of benzaldehyde and 2.00 g (0.0319 mole) of sodium cyanoborohydride. The pH was neutral. To the reaction mixture was added ~1 g of 3A molecular sieves. The reaction mixture was stirred for 6 days at room temperature.

The methanol was removed by rotary evaporation (70° C., water aspirator) after filtration. The residue was dissolved in ~100 ml chloroform and washed with 2×50 ml dilute aqueous sodium hydroxide. The chloroform was removed by rotary evaporation (70°, water aspirator) and the residue dissolved in 100 ml of dilute aqueous hydrochloric acid. The aqueous layer was washed with 2×50 ml of ethyl acetate (the ethyl acetate was extracted with 2×30 ml of dilute hydrochloric acid and all acid layers combined; this was done because the product appeared to be somewhat soluble in ethyl acetate). The hydrochloric acid layer was made basic with concentrated sodium hydroxide solution and extracted with 2×50 ml of chloroform. The chloroform layer was dried over anhydrous sodium sulfate, filtered and concentrated by rotary evaporation (70° C., water aspirator. The 3.0 g of crude product obtained was dissolved in hot isopropyl alcohol) and treated with fumaric acid. The resulting crystals, 1.40 g (20.2%), melted at 123°–126° C. with slight shrinkage occurring at 118° C.

Analysis: Calculated for $C_{29}H_{31}N_3O_5S$: C, 65.27; H, 5.86; N, 7.87. Found: C, 65.11; H, 5.87; N, 8.05.

EXAMPLE 77

2,3-Dihydro-4-methyl-2-[2-(4-methyl-1-piperazinyl)ethyl]pyrido[3,2-f][1,4]oxazepin-5(4H)-one fumarate [1:2]monohydrate To a solution of 10.45 g (0.043 mole) of 2-(2-chloroethyl)-2,3-dihydro-4-methylpyrido[3,2-f]-1,4-oxazepine-5(4H)-one in 80 ml of absolute ethanol was added 10.84 g (0.1084 mole) of N-methyl piperazine and the resulting solution heated to reflux for 4 hr. At that time, because ~25% starting material was present by mass spec, an additional 5.0 g (0.05 mole) of N-methyl piperazine was added and heating to reflux was continued for 2 hr. Ethanol was removed by rotary evaporation (70°, water aspirator) and the residue diluted with 150 ml of water. The water was extracted with 4×50 ml of chloroform and the organic layer was washed with 2×50 ml of water, dried over anhydrous sodium sulfate, filtered and concentrated by rotary evaporation (70° C., water aspirator). The residue was concentrated (vacuum pump/95°–100° C.) for 3.5 hr. Treatment of the residue with fumaric acid in isopropyl alcohol yielded 8.45 g (35.4%) of pale white crystals, m.p. 162°–167° C.

Analysis: Calculated for $C_{24}H_{34}N_4O_{11}$: C, 51.98; H, 6.17; N, 10.10. Found: C, 52.03; H, 6.00; N, 10.17.

EXAMPLE 78

2,3-Dihydro-4-methyl-2-[2-(4-methyl-1-piperazinyl)ethyl]pyrido[3,2-f][1,4]oxazepine-5(4H)-thione fumarate [1:2]hemihydrate To 8.0 g (0.031 mole of 2-(2-chloroethyl)-2,3-dihydro-4-methylpyrido[3,2-f]-1,4-oxazepine-5-(4H)-thione in 80 ml of absolute ethanol was added 9.30 g (0.093 mole) of N-methyl piperazine. The mixture was heated to reflux for 2 hr and an additional 5.0 G (0.05 mole)

N-methyl piperazine was added. Reflux was continued for an additional 5 hr.

Ethanol was removed by rotary evaporation (90° C., water aspirator). Residual N-methyl piperazine was removed at 90° C. with vacuum pump for 2 hr. The residue was taken up in 150 ml of chloroform and washed with 2×50 ml of water. The organic layer was dried over anhydrous sodium sulfate, filtered and concentrated by rotary evaporation (90° C., water aspirator). The residue was concentrated further with a vacuum pump at 90° C. The 10.0 g of crude material was treated with fumaric acid in isopropyl alcohol which yielded 10.0 g (57.4%) of light yellow crystals, m.p. 184°–185° C.

Analysis: Calculated for $C_{24}H_{33}N_4O_{9.5}S$: C, 51.32; H, 5.92; N, 9.98. Found: C, 51.56; H, 5.89; N, 9.86.

EXAMPLE 79

2-[2-[4-Bis(4-fluorophenyl)methyl]-1-piperidinyl]ethyl]-2,3-dihydro-4-methylpyrido[3,2-f][1,4]-oxazepin-5(4H)one dihydrochloride hemihydrate Ten grams (0.036 mole) of 2-(2-chloroethyl)-2,3-dihydro-4-methylpyrido[3,2-f]-1,4-oxazepin-5-(4H)-one hydrochloride were partitioned between dilute sodium hydroxide and chloroform. The chloroform was dried over sodium sulfate and concentrated on the rotary evaporator. The residue was dissolved in 50 ml of ethanol and 10.3 g (0.036 mole) of 4-[bis(4-fluorophenyl)-methyl]piperidine was added. The solution was heated to reflux for 18 hr and concentrated on the rotary evaporator. The residue was partitioned between dilute sodium hydroxide and chloroform. The chloroform was dried over anhydrous sodium sulfate and concentrated. The residue was chromatographed on a Waters 500 HPlC (silica/92% ethyl acetate-8% triethylamine). After concentration of the desired product, the residue was dissolved in isopropyl alcohol and treated with ethereal hydrogen chloride. The resulting crystals weighed 3 g (14%) and melted at 160°–180° C.

Analysis: Calculated for $C_{58}H_{68}H_6O_5Cl_4F_4$: C, 60.73; H, 5.98; N, 7.33. Found: C, 60.60; H, 6.04; N, 7.12.

EXAMPLE 80

2-[2-(4,5-Dihydro-1H-imidazol-2-yl)ethyl]-2,3-dihydro-4-methylpyrido[3,2-f][1,4]oxazepin-5(4H)-one oxalate [1:1]

Into a cooled (water bath) solution of 10 g (0.043 mole) of 2,3,4,5-tetrahydro-4-methyl-5-oxopyrido[3,2-f][1,4]oxazepine-2-propane-nitrile in 50 ml of ethylenediamine was bubbled hydrogen sulfide gas for 10 min. The reaction flask was tightly stoppered and left standing at room temperature for 5 days. The reaction solution (now partially solidified) was diluted with 100 ml of dilute sodium hydroxide and extracted with 5×30 ml of chloroform. The organic extracts were dried over anhydrous sodium sulfate, filtered, and concentrated by rotary evaporation (70° C. water aspirator). The entire residue was dissolved in 50 ml of ethylenediamine and saturated with hydrogen sulfide for 10 minutes while cooling in a water bath. The flask was tightly stoppered and left standing at room temperature for 5 days. The contents of the reaction flask were diluted with 200 ml of 2N aqueous potassium hydroxide and extracted with 3×125 ml of chloroform. The organic extracts were washed with 3×50 ml 2N aqueous potassium hydroxide and extracted into 3×50 ml of dilute aqueous hydrochloric acid. The acid extracts were basified with concentrated sodium hydroxide and extracted into 3×40 ml of chlofoform. The organic extracts were dried over sodium sulfate, filtered and concentrated by rotary evaporation. The syrupy residue was treated with oxalic acid in isopropyl alcohol to give 3.5 g (22%) of white crystals. One recrystallization from isopropyl alcohol afforded an analytical sample, m.p. 198° C. with decomposition.

Analysis: Calculated for $C_{16}H_{21}N_4O_6$: C, 52.74; H, 5.53; N, 15.38. Found: C, 52.76; H, 5.58; N, 15.51.

EXAMPLE 81

2,3-Dihydro-4-methyl-2-[2-(methylphenylamino)ethyl]-pyrido[3,2-f][1,4]oxazepine-5(4H)-thione To a suspension of 2-(2-chloroethyl)-2,3-dihydro-4-methylpyrido[3,2-f][1,4]oxazepine-5(4H)-thione in 100 ml of toluene was added 11.49 g (0.11 mole) N-methylaniline and the mixture heated to reflux with stirring for 2 days (after approx. 6 hr, 23.0 g (0.22 mole) additional N-methylaniline was added). Toluene was removed by rotary evaporation (90° C., water aspirator). The N-methylaniline was removed also by rotary evaporation (90° C., vacuum pump). The residue was taken up in 100 ml of chloroform and washed with 3×30 ml dilute aqueous sodium hydroxide. The organic layer was dried over anhydrous sodium sulfate, filtered and concentrated by rotary evaporation (80° C., water aspirator). More N-methylaniline was removed with the vacuum pump at 90° C. for several hours. To the residue was added 150 ml of ethyl acetate at which point some product crystallized out. However, since much remained in solution, preparative HPLC on a silica gel column eluting with 60% hexane/40% ethyl acetate was effected. After concentrating the flasks containing the product, crystallization was effected induced by seeding. The chromatographed product was recrystallized from ethyl acetate/isopropyl alcohol and amounted to 1.1 g m.p. 164°–5° C. Approximately 2 g additional was collected by recrystallization of crude product, m.p. 163°–4° C. The combined yield was 3.1 g (26%).

Analysis: Calculated for $C_{18}H_{21}N_3OS$: C, 66.03; H, 6.46; N, 12.83. Found: C, 65.72; H, 6.51; N, 13.13.

EXAMPLE 82

2-(3-Aminopropyl)-2,3-dihydro-4-methylpyrido[3,2-f][1,4]oxazepine-5(4H)-thione fumarate [1:1]

A sample of 15.0 g (0.064 mole) of 2-(3-aminopropyl)-2,3-dihydro-4-methylpyrido[3,2-f][1,4]-oxazepin-5(4H)-one was dissolved in 50 ml methylene chloride and to it was added 15.24 g (0.07 mole) of di-tertbutyl dicarbonate. The solution was stirred for 30 minutes at room temperature. The protected amine was purified by HPLC on a silica gel column, eluting with ethyl acetate. Approximately 15 g (0.045 mole 70.3%) of the protected amine was collected as an oil. To a solution of 13.5 g (0.04 mole) of this oil in dry toluene was added 8.16 g (0.02 mole) of 2,4-bis(4-methoxyphenyl)-1,3-dithia-2,4-diphosphetane-2,4-disulfide. The reaction mixture was heated to 80° C. for 2 hr. An additional amount (2.0 g, 0.005 mole) of 2,4-bis(4-methoxyphenyl)-1,3-dithia-2,4-diphosphetane-2,4-disulfide was added and heating continued for 1 hr. Another 4.0 g (0.01 mole) of 2,4-bis(4-methoxyphenyl)-1,3-dithia-2,4-diphosphetane-2,4-disulfide was added and the heating continued for 5 hr. After cooling, the toluene was decanted off, washed with 5×30 ml dilute aqueous sodium hydroxide, dried over sodium sulfate, filtered and concentrated by rotary evaporation. Isopropyl alcohol was added to the residue, resulting in precipitation of an impurity (possibly spent Lawesson's Reagent). Isopropyl alcohol was removed by rotary evaporation and the residue purified by HPLC on a silica gel column, eluting with 1% methanol/99% chloroform. Approximately 6 g (0.017 mole, 42.6%) of material was collected and treated with 100 ml of a solution of trifluoro acetic acid/anisole/methylene chloride, 40/10/50, v/v/v for 30 minutes. The solvent blend was removed by rotary evaporation (70° C., water aspirator) and the residue taken up in 150 ml of methylene chloride. This layer was washed with 3×40 ml dilute aqueous sodium hydroxide, dried over anhydrous sodium sulfate, filtered and concentrated by rotary evaporation. The residue was treated with fumaric acid in isopropyl alcohol, which yielded 4.0 g (0.011 mole, 64%) of the salt. Recrystallization from isopropyl alcohol afforded an analytical sample, m.p. 164°-166° C.

Analysis: Calculated for $C_{16}H_{21}N_2O_5$: C, 52.30; H, 5.76; N, 11.43. Found: C, 52.43; H, 5.83; N, 11.51.

EXAMPLE 83

2-[2-(Dimethylamino)ethyl]-2,3-dihydropyrido[3,2-f][1,4]oxazepine-5(4H)-thione dihydrochloride monohydrate To 5 g (0.021 mole of 2-[2-(dimethylamino)ethyl]-2,3-dihydropyrido[3,2-f]-1,4-oxazepin-5(4H)-one in 50 ml of pyridine was added 5.1 g (0.046 mole) of phosphorus pentasulfide. An exothermic reaction insued, When the temperature dropped, the mixture was heated to 70° C. for 3.5 hr and allowed to cool. The mixture was partitioned between dilute sodium hydroxide and chloroform while cooling by addition of ice. The aqueous layer was extracted 3 more times with chloroform. The combined chloroform extracts were dried over anhydrous sodium sulfate and concentrated. The residue was dissolved in 40 ml of ethanol and made acidic with ethereal hydrogen chloride. The resulting crystals were recrystallized from 95% ethanol. Yield was 1.4 g (19%), m.p. 172°-175° C.

Analysis: Calculated for $C_{12}H_{21}N_3SO_2Cl_2$: C, 42.10; H, 6.18; N, 12.28. Found: C, 42.66; H, 5.74; N, 12.34.

EXAMPLE 84

2-[2-[4-[Bis(4-fluorophenyl)methyl]-1-piperidinyl]ethyl]2,3-dihydro-4-methylpyrido[3,2-f][1,4]oxazepine-5(4H)-thione oxalate hydrate [1:1:1]

A solution of 4 g (0.016 mole) of 2-(2-chloroethyl)-2,3-dihydro-4-methylpyrido[3,2-f][1,4]-oxazepine-5(4H)-thione and 4.5 g (0.016 mole) of 4-[bis(4-fluorophenyl)methyl]piperidine in 100 ml of ethanol was refluxed for 48 hr. One gram of $K_2CO_3$ was added and this mixture stirred at reflux for 144 hr. The mixture was concentrated and the residue partitioned between chloroform and dilute sodium hydroxide. The chloroform was dried over anhydrous sodium sulfate and concentrated. The residue was chromatographed on a Waters ® 500 HPLC using a silica column and eluting with absolute ethanol. The material with mass 507 was collected and concentrated. The residue (6 g) was reacted with 1.2 g of oxalic acid in ethanol. Yield was 5 g, m.p. 125°-138° C.

Analysis: Calculated for $C_{31}H_{35}N_3O_6SF_2$: H, 5.72; N, 6.82. Found: C, 60.62; H, 5.60; N, 6.68.

EXAMPLE 85

2,3-Dihydro-4-methyl-2-[2-(1H-pyrazol-1-yl)ethyl]-pyrido[3,2-f][1,4]oxazepine-5(4H)-thione To a suspension of 2.16 g (0.054 mole) of sodium hydride in 20 ml of dimethylformamide was added dropwise a solution of 2.92 g (0.043 mole) of pyrazole in 10 ml of dimethylformamide. There was a slight exotherm at this point with some evolution of hydrogen gas. The resulting solution was then added dropwise to a solution of 10.0 g (0.039 mole) of 2-(2-chloroethyl)-2,3-dihydro-4-methylpyrido[3,2-f]-1,4-oxazepine-5(4H)-thione in 30 ml of dimethylformamide. The reaction flask was sealed and stirred overnight at room temperature.

The solvent dimethylformamide was removed by rotary evaporation (90° C.; 30 mm). The residue was taken up in 200 ml of chloroform which was subsequent washed with 2×50 ml of water followed by 50 ml dil. aqueous sodium hydroxide. The organic layer was then dried over sodium sulfate, filtered and concentrated by rotary evaporation (70° C.; 30 mm). Isopropyl alcohol was added to the residue and crystallization ensued after cooling. The crude crystals (4.5 g) were recrystallized from isopropyl alcohol giving 3.45 g (31%) of yellow crystals, m.p. 119°-121° C.

Analysis: Calculated for $C_{14}N_{16}N_4OS$: C, 58.31; H, 5.59; N, 19.43. Found: C, 58.01; H, 5.59; N, 19.37.

EXAMPLE 86

2-[2-(Dimethylamino)-1-methylethyl]-2,3-dihydro-4-methylpyrido[3,2-f][1,4]-oxazepin-5(4H)-one oxalate [1:1]

To 4.5 g (0.018 mole of 2-(2-chloro-1-methylethyl)-2,3-dihydro-4-methylpyrido[3,2-f]-1,4-oxazepin-5(4H)-one was added 20 ml of methanol and 40 ml of dimethylamine. The reaction flask was tightly sealed and left standing at room temperature for 72 hr. The flask was opened after cooling and the methanol and dimethylamine evaporated. Another 15 ml of methanol and 40 ml of dimethylamine were added, the flask sealed tightly and left standing at room temperature for 7 days. The methanol and dimethylamine were evaporated and the residue taken up in 100 ml of chloroform. The chloroform layer was washed with 2×50 ml dil sodium hydroxide and 50 ml of water, dried over anhydrous sodium sulfate, filtered and concentrated by rotary evaporation. The crude material which was collected was treated with oxalic acid in isopropyl alcohol which afforded 3.5 g (55%) white crystals, m.p. 204°-05° C.

Analysis: Calculated for $C_{16}H_{23}N_3O_6$: C, 54.38; H, 6.56; N, 11.89. Found: C, 54.32; H, 6.61; N, 11.86.

EXAMPLE 87

2,3-Dihydro-2-[2-(4,5-dihydro-1H-imidazol-2-yl)ethyl]-4-methylpyrido[3,2-f][1,4]-oxazepine-5(4H)-thione oxalate [2:3]

Into a suspension of 2,3,4,5-tetrahydro-4-methyl-5-thioxopyrido[3,2-f][1,4]-oxazepine-2-propanenitrile in 30 ml of ethylene diamine was bubbled hydrogen sulfide gas for 15 min while cooling in a water bath. The flask was then sealed and stirred at room temperature for 5 days. Mass spectra showed much starting material. An additional 15 ml of methylene diamine was added and the mixture saturated again with hydrogen sulfide. The flask was resealed and left standing for 8 days. The reaction mixture was diluted with 100 ml dil aqueous sodium hydroxide and extracted into 3×60 ml of chloroform. The chloroform extracts were combined and washed with 50 ml of water. Some crystallization occurred in the separatory funnel but complete crystallization could not be effected. The organic layer was concentrated by rotary evaporation and the residue treated with oxalic acid in isopropyl alcohol. The crude crystals, 7.0 g, (55%) were recrystallized from methanol/ethanol yielding an analytical sample, m.p. 198°–200° C.

Analysis: Calculated for $C_{17}H_{21}N_4O_7S$: C, 47.99; H, 4.97; N, 13.16. Found: C, 47.63; H, 5.09; N, 13.04.

EXAMPLE 88

2-[2-(Dimethylamino)ethyl]-2,3-dihydro-2,4-dimethylpyrido[3,2-f][1,4]oxazepin-5(4H)-one dihydrochloride To 4.5 g (0.015 mole) of 2-(2-chloroethyl)-2,3-dihydro-2,4-dimethylpyrido[3,2-f]-1,4-oxazepin-5(4H)-one hydrochloride in 15 ml of methanol was added 40 ml of dimethylamine. The flask was sealed tightly and left standing at room temperature for 8 days. The methanol and dimethylamine were removed by rotary evaporation (70° C.; 30 mm). The residue was taken up in 150 ml of chloroform, washed with 2×50 ml dil aqueous sodium hydroxide, dried over anhydrous sodium sulfate, filtered and concentrated by rotary evaporation (70° C.; 30 mm). The syrupy residue was treated with hydrogen chloride in isopropyl alcohol, which afforded 3.5 g (67%) of white crystals, m.p. 188°–90° C.

Analysis: Calculated for $C_{14}H_{23}N_3O_2Cl_2$: C, 50.01; H, 6.89; N, 12.50. Found: C, 50.00; H, 6.98; N, 12.49.

EXAMPLE 89

2-[2-(Dimethylamino)ethyl]-2,3-dihydro-2,4-dimethylpyrido[3,2-f][1,4]oxazepine-5(4H)-thione monohydrochloride To a suspension of 4.5 g (0.017 mole) of 2-(2-chloroethyl)-2,3-dihydro-2,4-dimethylpyrido[3,2-f]-1,4-oxazepine-5(4H)-thione in 20 ml of methanol, cooled in an ice bath, was added 40 ml of dimethylamine. The flask was sealed tightly and left standing at room temperature for 10 days. The dimethylamine and methanol were removed by rotary evaporation (60° C.; 30 mm). The residue was taken up in 150 ml of chloroform, washed with 3×50 ml dil sodium hydroxide, dried over anhydrous sodium sulfate, filtered and concentrated by rotary evaporation (70° C.; 30 mm). The crude oil was dissolved in isopropyl alcohol and treated with ethereal hydrogen chloride, which yielded 4.0 g (76%) of yellow crystals, m.p. 255° C. with decomposition.

Analysis: Calculated for $C_{14}H_{22}N_3OSCl$: C, 53.23; H, 7.02; N, 13.30. Found: C, 53.21; H, 7.15; N, 13.19.

EXAMPLE 90 (Refer to Chart VII)

2-[2-(Dimethylamino)ethyl]-2,3-dihydro-4-methyl[1,4]-oxazepino[6,7-c]quinolin-5(4H)-one oxalate [1:1]

To a suspension of 19.4 g (35% in oil, 0.172 mole) of KH in 150 ml tetrahydrofuran was added at a rapid drop 12.4 g (0.086 mole) of 1-dimethylamino-4-methylamino-2-butanol. After 10 minutes, 20 g (0.086 mole) of 3-carboxyethyl 4-chloroquinoline was added by a powder dropping funnel over a period of 30 min. The mixture was stirred at room temperature overnight.

Approximately 50 ml of water was added to quench the reaction and the mixture partitioned between isopropyl ether and water. The aqueous layer was extracted again with 2×70 ml of isopropyl ether. The aqueous layer was then continuously extracted for 15 hr with chloroform. The chloroform layer was collected, filtered and concentrated by rotary evaporation (80° C., 30 mm). The crude material (18 g) was purified by HPLC using silica gel as the stationary phase and 3% triethylamine/ethanol as the eluent. Approximately 4 g (15.6%) of reasonably pure free base of the title compound was collected. A 1.5 g sample of the free base was reacted with 0.5 g oxalic acid in 10 ml of ethanol. The resulting crystals weighed 2 g and melted at 214°–218° C.

Analysis: Calculated for $C_{19}H_{23}N_3O_6$: C, 58.60; H, 5.95; N, 10.79. Found: C, 58.46; H, 6.10; N, 10.75.

EXAMPLE 91

2-[2-(Dimethylamino)-1-methylethyl]-2,3-dihydro-4-methylpyrido[3,2-f][1,4]-oxazepine-5(4H)-thione oxalate [1:1]

To a suspension of 4.0 g (0.013 mole) of 2-(2-chloro-1-methylethyl)-2,3-dihydro-4-methylpyrido[3,2-f][1,4]oxazepine-5(4H)-thione hydrochloride in 20 ml of methanol cooled in an ice bath was added 35 ml of dimethylamine previously collected at 0° C. The reaction flask was sealed tightly and left standing at room temperature for 10 days. The solvent was removed by rotary evaporation (80° C., water aspirator) and the residue taken up in 150 ml of chloroform. The organic layer was washed with 2×50 ml of dilute aqueous sodium hydroxide, dried over anhydrous sodium sulfate, filtered, and concentrated by rotary evaporation. The crude residue was treated with oxalic acid in isopropyl alcohol and left standing overnight at room temperature, yielding 3.1 g (65%) of yellow crystals, m.p. 211°–213° C.

Analysis: Calculated for $C_{16}H_{23}O_5N_3S$: C, 52.02; H, 6.18; N, 11.37. Found: C, 51.79; H, 6.34; N, 11.24.

EXAMPLE 92

2-[2-(Dimethylamino)propyl]-2,3-dihydro-4-methylpyrido[3,2-f][1,4]oxazepin-5(4H)-one dihydrochloride Into a stainless steel bomb was placed 1.0 g sodium iodide, 5.0 g (0.017 mole) of 2-(2-chloropropyl)-2,3-dihydro-4-methylpyrido[3,2-f][1,4]oxazepin-5(4H)-one and 40 ml of dimethylamine. The bomb was sealed tightly, placed in the oven at 60° C. and rolled continuously for 7 days. The bomb was allowed to stand at room temperature for several days. The residue was combined with that of a previous run of equal size and separated via column chromatography using silica gel and eluting with ethanol and then with 3% triethylamine/ethanol. The fractions containing the desired product were combined and concentrated by rotary evaporation (80° C., 30 mm). The residue was taken up in 150 ml of chloroform and washed with 2×50 ml diluted sodium hydroxide. The chloroform was removed by rotary evaporation (70° C., 30 mm) and the residue treated with ethereal hydrogen chloride and hydrogen chloride in isopropyl alcohol. The white crystals which were collected weighed 3 g (28%), m.p. 173°–76° C.

Analysis: Calculated for $C_{14}H_{23}N_2O_2Cl_2$: C, 50.01; H, 6.89; N, 12.50. Found: C, 50.40; H, 7.04 N, 12.36.

EXAMPLE 93

2,3-Dihydro-4-methyl-2-[2-(2-methyl-1-pyrrolidinyl)ethyl]pyrido[3,2-f][1,4]oxazepine-5(4H)-thione fumarate compound with 2-propanol [1:1:1]

To a suspension of 5.0 g (0.019 mole) of 2-(chloroethyl)-2,3-dihydro-4-methylpyrido[3,2-f]-1,4-oxazepine-5(4H)-thione in 25 ml of absolute ethanol was added 3.5 g (0.04 mole) of 2-methylpyrrolidine. The mixture was heated to reflux for 6.5 hr and left standing at room temperature overnight. Mass spec and TLC showed presence of starting materials. Approximately 5 g of potassium carbonate was added and heating at reflux was continued for 24 hr. Ethanol was removed by rotary evaporation (70° C., 30 mm). The residue was taken up in 100 ml of methylene chloride and washed with 2×50 ml dil. aqueous sodium hydroxide. The organic layer was dried over anhydrous sodium sulfate, filtered, and concentrated by rotary evaporation (70° C., 30 mm). The residual syrup was dissolved in isopropyl aocohol and treated with fumaric acid affording 4.5 g (0.01 mole, 49.2%) of crude crystals. Two recrystallizations from isopropyl afforded 1.5 g (16.4%) of yellow crystals, m.p., 92°–95° C.

Analysis: Calculated for $C_{23}H_{35}N_3O_6S$: C, 57.36; H, 7.33; N, 8.72. Found: C, 57.12; H, 7.30; N, 8.70.

EXAMPLE 94

2-[2-(Dimethylamino)ethyl]-2,3-dihydro-4-methyl-9-(trifluoromethyl)-[1,4]oxazepino[6,7-c]quinolin-5(4H)-one fumarate [1:1]

To 55 ml of dimethylamine collected over an ice/methanol bath was added 2.2 g (0.005 mole) of 2-(2-chloroethyl)-2,3-dihydro-4-methyl-9-(trifluoromethyl)-1,4-oxazepino[6,7-c]quinolin-5(4H)-one hydrochloride. The flask was sealed tightly and left standing at room temperature for 6 days. After cooling to 0° C., the flask as opened and the solvent allowed to evaporate at room temperature overnight. The residue was taken up in 100 ml of chloroform, washed with 3×30 ml of dil sodium hydroxide, dried over anhydrous sodium sulfate and concentrated to rotary evaporation (70° C., 30 mm). The residual oil was treated with fumaric acid in isopropyl alcohol and dried, giving 2.2 g (81%) of white crystals, m.p. 204°–05° C.

Analysis: Calculated for $C_{22}H_{24}N_3O_6F_3$: C, 54.66; H, 5.00; N, 8.69. Found: C, 54.74; H, 5.12; N, 8.55.

EXAMPLE 95

2-[2-(Dimethylamino)ethyl]-2,3-dihydro-4-methyl[1,4]oxazepino[6,7-b]quinolin-5(4H)-one fumarate hydrate [1:1:0.5]

To 40 ml of dimethylamine cooled to ~0° C. in an ice water bath was added 3.85 g (0.013 mole) of 2-(2-chloroethyl)-2,3-dihydro-4-methyl-1,4-oxazepino[6,7-b]-quinoline-5(4H)-one in 25 ml of methanol. The reaction flask was sealed tightly and left standing at room temperature for 5 days. After cooling, the reaction flask was opened and the solvent allowed to evaporate in a stream of air. The residue was taken up in 100 ml of chloroform and washed with 2×50 ml of dilute aqueous sodium hydroxide. The organic layer was dried over anhydrous sodium sulfate, filtered, and concentrated by rotary evaporation (70° C., 30 mm). The residual oil was treated with fumaric acid in isopropyl alcohol which afforded 3.7 g (67%) of white crystals, m.p. 125°–130° C.

Analysis: Calculated for $C_{21}H_{26}N_3O_{6.5}$: C, 59.43; H, 0.17; N, 9.90. Found: C, 59.59; H, 6.36; N, 9.60.

EXAMPLE 96

2-[2-(Dimethylamino)ethyl]-2,3-dihydro-4-methyl[1,-4]oxazepino[6,7-b]quinoline-5(4H)-thione fumarate compound with isopropanol hydrate (1:1:0.5:0.5]

To 45 ml of dimethylamine was added 0.95 g (0.003 mole) of 2-(2-chloroethyl)-2,3-dihydro-4-methyl-1,4-oxazepino[6,7-b]quinoline-5(4H)-thione. The reaction flask was sealed tightly and left standing at room temperature for 6 days. After cooling to 0° C., the flask was opened and the solvent allowed to evaporate at room temperature. The residue was taken up in 50 ml of chloroform and washed with 3×30 ml of dilute aqueous sodium hydroxide. The organic layer was dried over anhydrous sodium sulfate, filtered, and concentrated by rotary evaporation, yielding 0.94 g of syrup (99%). This was combined with 1.0 g of the same product from a previous run* and treated with fumaric acid in isopropyl alcohol affording 1.5 g of yellow crystals, m.p. 123°–26° C.

*The previous run was made in the same manner as above except that hydrochloride salt was collected. However, the hydrochloride salt partially decomposed upon drying in a drying pistol at 82.5° C. Caution should be exercised not to heat the product above the boiling point of acetone (56°–57° C.) while drying.

Analysis: Calculated for $C_{22.5}H_{30}N_3O_6S$: C, 57.43; H, 6.43; N, 8.92. Found: C, 57.60; H, 6.21; N, 9.02.

EXAMPLE 97

4-Ethyl-1,2,3,4-tetrahydro-2-[2-(4-hydroxy-4-phenyl-1-piperidinyl)-ethyl]-1-methyl-5H-1,4-benzodiazepin-5-one fumarate compound with 2-propanol [1:1:1]

A mixture of 13.4 g (0.05 mole) of 2-(2-chloroethyl)-4-ethyl-1-methyl-1,2,3,4-tetrahydro-5H-1,4-benzodiazepin-5-one, 8.85 g (0.05 mole) of 4-hydroxy-4-phenyl-piperidine, and 14 g (0.1 mole) of potassium carbonate in 100 ml of n-butanol was refluxed for 18 hr and filtered. The filtrate was concentrated and the residue partitioned between chloroform and dilute sodium hydroxide. The organic layer was dried over anhydrous sodium sulfate and concentrated. The residue was chromatographed on a 4.5×45 cm Florisil ® column eluting with chloroform-methanol mixture with a gradation from 100% to 84% chloroform. The fractions containing the pure product (as seen on tlc using 95% chloroform-5% methanol on Florisil ®) were combined and concentrated. The residue was molecularly distilled at 250° C. and 0.02 mm Hg. The fumarate salt was prepared in isopropyl alcohol and recrystallized from isopropyl alcohol-water. Yield 5.8 g. (20%) m.p. 128°–139° C.

Analysis: Calculated for $C_{32}H_{45}N_3O_7$: C, 65.85; H, 7.77; N, 7.20. Found: C, 64.85; H, 7.49; N, 7.06.

EXAMPLE 98

4-Ethyl-1-methyl-2-(2-morpholinoethyl)-1,2,3,4-tetrahydro-5H-1,4-benzodiazepin-5-one A solution of 30 g (0.112 mole) of 2-(2-chloroethyl)-4-ethyl-1-methyl-1,2,3,4-tetrahydro-5H-1,4-benzodiazepin-5-one in 70 ml of morpholine was refluxed for 3 hrs, concentrated on the rotary evaporator and the residue partitioned between chloroform and dilute sodium hydroxide. The chloroform was dried over anhydrous sodium sulfate and concentrated on the rotary evaporator. The residue was crystallized twice from isopropyl ether containing a small amount of ethanol, m.p. 128°–148° C. Recrystallization from toluene gave 19.5 g (61%) of product, m.p. 128°–148° C.

Analysis: Calculated for $C_{16}H_{27}N_3O_2$: C, 68.11; H, 8.57; N, 13.24. Found: C, 68.29; H 8.57; N, 13.26.

EXAMPLE 99

1,2,3,4-Tetrahydro-1-methyl-2-[(dimethylamino)methyl]-4-(1-methylethyl)-5H-1,4-benzodiazepin-5-one A mixture of 5.0 g (0.02 mole) of 2-chloromethyl-1,2,3,4-tetrahydro-1-methyl-4-(1-methylethyl)-5H-1,4-benzodiazepin-5-one, and 15.0 g (0.45 mole) of dimethylamine, and 200 ml of methanol were placed in a steel bomb and heated and stirred at 100° C. for 15 hr. After concentrating in vacuo, the residue partitioned between dilute sodium hydroxide solution and chloroform. The chloroform layer was dried over anhydrous sodium sulfate, filtered and concentrated in vacuo. The residue crystallized in isopropyl ether and was recrystallized twice from the same. It weighed 29.0 g (68%), m.p. 93°–95° C.

Analysis: Calculated for $C_{16}H_{25}N_3O$: C, 69.78; H, 9.15; N, 15.26. Found: C, 69.81; H, 9.01; N, 15.33.

EXAMPLE 100

2-(2-Dimethylaminoethyl)-4-ethyl-1-methyl-1,2,3,4-tetrahydro-5H-1,4-benzodiazepin-5-one A solution of 30 g (0.112 mole) of 2-(2-chloroethyl)-4-ethyl-1-methyl-1,2,3,4-tetrahydro-5H-1,4-benzodiazepin-5-one and 10 g (0.224 mole) of dimethylamine in 300 ml of ethanol was heated at 125° C. for 8 hrs and concentrated. The residue was partitioned between chloroform and dilute sodium hydroxide. The chloroform was dried over anhydrous sodium sulfate, concentrated and distilled. Yield of product was 20.5 g (66.5%), b.p. 175°–178°/0.1 mm.

Analysis: Calculated for $C_{16}H_{25}N_3O$: C, 69.78; H, 9.15; N, 15.25. Found: C, 69.60; H, 9.17; N, 15.20.

EXAMPLE 101

2,3-Dihydro-4-methyl-2-[2-(1-piperidinyl)ethyl]pyrido[3,2-f][1,4]oxazepine-5(4H)-thione fumarate, hydrate compound with isopropyl alcohol [1:1:0.5:0.5]

To a suspension of 5.0 g (0.019 mole) of 2-(2-chloroethyl)-2,3-dihydro-4-methylpyrido[3,2-f]-1,4-oxazepine-5(4H)-thione in 75 ml of absolute ethanol was added 10 ml of pyridine and the mixture heated to 50° C. for 4 days. Ethanol was removed by rotary evaporation (70° C., 30 mm Hg). Piperidine was removed by rotary evaporation (80° C., 5 mm Hg) followed by azeotroping with 2×100 ml of toluene. The syrupy residue was taken up in 200 ml of isopropyl alcohol and heated with fumaric acid which afforded 5.2 g (57%) yellow crystals, m.p. 133°–40° C.

Analysis: Calculated for $C_{21.5}H_{32}N_3O_6S$: C, 56.07; H, 7.00; N, 9.12. Found: C, 55.90; H, 6.86; N, 9.17.

EXAMPLE 102

6-Chloro-2,3-dihydro-4-methyl-2-[2-(dimethylamino)ethyl]-4-methylpyrido[4,3-f][1,4]-oxazepin-5(4H)-one fumarate [1:0.5]

To 40 ml of freshly collected dimethylamine at −10° C. was added 4.0 g (0.015 mole) of 6-chloro-2-(2-chloroethyl)-2,3-dihydro-4-methylpyrido[4,3-f]-1,4-oxazepin-5(4H)-one. The reaction flask was sealed tightly and left standing at room temperature for 5 days. After cooling to −10° C., the flask was opened and the dimethylamine allowed to evaporate overnight. The residue was taken up in 100 ml of chloroform, washed with 2×30 ml of dilute sodium hydroxide, dried over anhydrous sodium sulfate, filtered and concentrated by rotary evaporation (70° C., 30 mm Hg). The residue was treated with fumaric acid in isopropyl alcohol which upon crystallization afforded 3.8 g (76.7%) of yellow crystals.

Analysis: Calculated for $C_{15}H_{20}N_3O_4Cl$: C, 52.70; H, 5.90; N, 12.29. Found: C, 52.67; H, 5.96; N, 12.01.

EXAMPLE 103

2,3-Dihydro-4-methyl-6-dimethylamino-2-[2-(dimethylamino)ethyl]-4-methylpyrido[4,3-f][1,4]-oxazepin-5(4H)-one fumarate [1:1.5]

To 100 ml of freshly collected dimethylamine in a stainless steel bomb was added 4.5 g (0.016 mole) of 6-chloro-2-(2-chloroethyl)-2,3-dihydro-4-methylpyrido[4,3-f]-1,4-oxazepin-5(4H)-one. The bomb was sealed tightly and placed in an oven at 100° C. for 18 hr. After cooling, the bomb was opened and the dimethylamine allowed to evaporate at room temperature. The residue was taken up in 150 ml of chloroform, washed with 2×40 ml of dilute aqueous sodium hydroxide, dried over anhydrous sodium sulfate, filtered and concentrated by rotary evaporation (70° C., 30 mm Hg). The residue was treated with fumaric acid in isopropyl alcohol. The resulting crystals were collected, dried overnight at room temperature, 0.5 mm Hg. The white crystals were collected and afforded 4.2 g (56.3%) of the title compound, m.p. 172°–75° C.

Analysis: Calculated for $C_{21}H_{30}N_4O_8$: C, 54.07; H, 6.48; N, 12.01. Found: C, 54.01; H, 6.58; N, 12.00.

EXAMPLE 104

2,3-Dihydro-2-[2-(2,5-dihydro-1H-pyrrol-1-yl)ethyl]-4-methylpyrido[3,2-f]-1,4-oxazepin-5(4H)-one fumarate [1:2]

To a solution of 10.0 g (0.041 mole) of 2-(2-chloroethyl)-2,3-dihydro-4-methylpyrido[3,2-f]-1,4-oxazepin-5(4H)-one in 50 ml of dimethylformamide was added 9.0 g (0.14 mole) of a mixture of 3-pyrroline:pyrrolidine*, 3:1, v/v. The solution was heated to 65° C. under an N$_2$ blanket overnight. The solvent was removed by rotary evaporation (70° C., 0.5 mm Hg). The syrupy residue was taken up in 100 ml of chloroform, washed with 2×30 ml of dil. aqueous sodium hydroxide, dried over anhydrous sodium sulfate, filtered and concentrated by rotary evaporation (60° C., 30 mm). The residue was azetroped with 3×100 ml of toluene. The residue was purified by HPLC to separate out the pyrrolidine derivative, eluting with 2% triethylamine in methylene chloride (v/v). Fractions with similar TLC's were combined and concentrated by rotary evaporation. To the residue was added ~100 ml of toluene and the mixture heated to 70° C. and filtered hot. Approximately 0.2–0.3 g of hygroscopic crystals were collected. The toluene was removed by rotary evaporation (70° C., 30 mm Hg). The residual syrup was treated with fumaric acid in isopropyl alcohol. Two crops of crystals were collected, combined and recrystallized together giving 4.6 g (22.1%) of white crystals, m.p. 158°–159° C.

*Pyrroline contains pyrrolidine as impurity.

Analysis: Calculated for $C_{23}H_{27}N_3O_{10}$: C, 54.65; H, 5.38; N, 8.31. Found: C, 54.58; H, 5.49; N, 8.30.

EXAMPLE 105

2,3-Dihydro-2-(2,5-dihydro-1H-pyrrol-1-yl)ethyl-4-methylpyrido[3,2-f]-1,4-oxazepine-5(4H)-thione fumarate [1:1]

To a solution of 9.0 g (0.035 mole) of 2-(2-chloroethyl)-2,3-dihydro-4-methylpyrido[3,2-f]-1,4-oxazepine-5(4H)-thione in 50 ml of dry dimethylformamide was added 10.0 g (0.141 mole) of pyrroline/pyrrolidine*, 3:1, v/v, and the mixture heated to 60° C. for 18 hr. The solvent was removed by rotary evaporation (70° C., 0.5 mm Hg) and the syrupy residue purified by HPLC separating out the pyrrolidine derivative eluting with 2% triethylamine in methylene chloride (v/v) over silica gel. Fractions having similar TLC's were combined and concentrated by rotary evaporation. The syrupy residue was treated with fumaric acid in isopropyl alcohol which afforded 4.0 g (28.1%) of crystals. One recrystallization from isopropyl alcohol afforded an analytical sample, m.p. 143°–45° C.
*Pyrroline contains pyrrolidine as impurity.

Analysis: Calculated for $C_{19}H_{23}N_3O_5S$: C, 56.28; H, 5.72; N, 10.36 Found: C, 56.03; H, 5.23; N, 10.22

EXAMPLE 106

2-[2-(1-Azetidinyl)ethyl]-2,3-dihydro-4-methylpyrido[3,2-f][1,4]oxazepin-5(4H)-one oxalate hydrate[1:1:0.5]

To a solution of 4.1 g (0.017 mole) of 2-(2-chloroethyl)-2,3-dihydro-4-methylpyrido[3,2-f]-1,4-oxazepin-5(4H)-one in 50 ml of dimethylformamide under nitrogen was added a solution/suspension of 0.7 g (60% in oil, 0.017 mole) of sodium hydride in 0.10 ml of dimethylformamide to which 1.0 g (0.017 mole) of azetidine in 20 ml of dimethylformamide had been added and allowed to stir under nitrogen atmosphere until hydrogen evolution ceased (15 min). The reaction mixture was stirred for 18 hr under nitrogen at room temperature. The solvent was removed by rotary evaporation (70° C., 0.5 mm Hg) and the residue taken up in 100 ml of chloroform, washed with 3×30 ml dil. aqueous sodium hydroxide, dried over anhydrous sodium sulfate, filtered and concentrated by rotary evaporation. The residue was treated with oxalic acid in isopropyl alcohol which afforded 1.3 g (21.2%) of white crystals, m.p. 172°–174° C. with slight decomposition.

Analysis: Calculated for $C_{16}H_{22}N_3O_{6.5}$: C,53.33; H,6.15; N,11.66. Found: C, 53.73; H,6.11; N,11.67.

EXAMPLE 107 (Refer to Chart VIII)

2-[(Dimethylamino)methyl]-2,3-dihydro-4-methylpyrido[3,2-f][1,4]oxazepin-5(4H)-one fumarate[1:1]

Dimethylamine 22.6 g 40% solution (0.2 mole) was added dropwise to a solution of 16 ml of epichlorohydrin (0.2 mole) in 100 ml of methanol at 5° C. stirring in an ice bath. After two hours at 5° C. a chilled solution of 86 ml methylamine of 40% solution (1 mole) was poured into the reaction mixture. Stirring was continued in ice bath for one hour and then room temperature overnight. The solvents were evaporated and the clear oil was pumped under vacuum at 75° C. for 1.5 hr to give 28.23 g (~84% yield) of 1-dimethylamino-3-methylamino-2-propanol hydrochloride (I) as the main product.

Compound I, 21.4 g (0.143 mole) and 22.6 g of 2-chloronicotinic acid (0.143 mole) were stirred in 150 ml acetonitrile and 60 ml water as a two-layer system. Dicyclohexylcarbodiimide, 33 g (0.16 mole) dissolved in 90 ml of acetonitrile was added in four portions. After the addition of the second portion, an ice bath was necessary for controlling the temperature at around 25° C. Two and a half hours later, 10 g of 2-chloronicotinic acid was added to the reaction mixture and 15 g of dicyclohexylcarbodiimide in 200 ml of acetonitrile was added in another hour. The reaction was stirred at room temperature overnight. Concentrated hydrochloric acid was added to the reaction mixture to pH 2 in order to convert the excess carbodiimide to urea. The white solid was removed by filtration and rinsed with aqueous acetonitrile. The filtrate and washings were evaporated to a paste which was partitioned between methylene chloride and potassium carbonate solution. The aqueous layer was extracted two more times with methylene chloride. The methylene chloride solutions were back washed with sodium chloride solution, dried over anhydrous sodium sulfate and evaporated to give 56 g of oil. This oil was chromatographed on 250 g of silica gel eluting with methanol to give 26.97 g of light brown oil containing mainly the 2-chloronicotinamide of compound I.

The 26.97 g of compound obtained from chromatography was dissolved in 200 ml of toluene and heated to distill out about 40 ml solvent and then refluxed under a Dean-Stark trap for one half hour. Sodium hydride, 15 g (50% suspension in mineral oil, 0.3 mole) was added portionwise to the toluene solution at room temperature. The mixture was then heated to reflux for 20 min. The cooled mixture was treated with isopropanol and celite and then filtered. The filtrate was acidified with hydrogen chloride solution in isopropanol. The white solid thus formed was collected by filtration, rinsed with isopropyl alcohol-isopropyl ether and dried under nitrogen. This material weighed 11 g and absorbed moisture from air readily. Some second and third crop materials were obtained from the mother liquor and washings. All three crops were combined and dissolved in water, the solution was made basic with excess amount of potassium carbonate and then extracted three times with methylene chloride; the methylene chloride solutions were back washed with saturated sodium chloride solution, dried over magnesium sulfate and treated with activated charcoal, filtered and evaporated to give 8.8 g of brown oil, the free base of the title compound.

A 1.9 g sample of the brown oil was dissolved in methanol and kept warm on steam bath. Fumaric acid was added and the solution was concentrated to a small volume. Excess amount of acetone was added to crystallize out the fumarate salt. The salt was recrystallized once to 1.4 g of white solid, m.p. 150°–151° C.

Analysis: Calculated for $C_{16}H_{21}N_3O_6$: C,54.70; H,6.02; N,11.96. Found: C,54.69; H,6.07; N,11.88.

EXAMPLE 108

2-[(Dimethylamino)methyl]-2,3-dihydro-4-methylpyrido[3,2-f][1,4]oxazepine-5(4H)-thione fumarate[2:1]

2-[(Dimethylamino)methyl]-2,3-dihydro-4-methylpyrido[3,2-f][1,4]oxazepine-5(4H)-one, 4.8 g, was dried azotropically in about 50 ml of toluene. To the warm solution was added Lawesson reagent (Aldrich #22, 743-9, 4.9 g) and the reduction mixture was kept at reflux for two hours. On contact with concentrated potassium carbonate solution, the reaction mixture became a three-layer system; both the aqueous layer and the toluene layer contained product but not the third gummy layer. The layers were separated and the aqueous layer was extracted three times with methylene chloride which was back washed with saturated sodium chloride solution, combined with the toluene layer, dried over sodium sulfate and evaporated to 5.25 g oil. This oil was dissolved in methanol and 2.45 g fumaric acid was added. With heating and stirring, isopropanol was added to the point of cloudiness and then left stirring overnight. The mixture first deposited out a layer of brown gummy material and then crystallized to a yellow powder. The yellow powder, 2.85 g, was collected and recrystallized from methanol, m.p. 178°–179° C.

Analysis: Calculated for $C_{14}H_{19}N_3O_3S$: C,54.35; H,6.19; N,13.58. Found: C,54.21; H,6.20; N,13.53.

EXAMPLE 109 (Refer to Chart VIII)

2-[2-(Dimethylamino)ethyl]-2,3-dihydro-4-methyl-pyrido[3,2-f][1,4]oxazepin-5(4H)-one To a cold (ice bath) solution of 3.2 g (0.02 mole) of 2-chloronicotinic acid and 3 g (0.02 mole) of 1-dimethylamino-4-methylamino-2-butanol in 25 ml of methylene chloride was added 4.55 g (0.022 mole) of dicyclohexyl carbodiimide. Methanesulfonic acid, 1.8 ml, was added to bring the pH to 6. White solid appeared in the reaction mixture. The ice bath was removed after 1 hr and the mixture was allowed to stand at room temperature overnight. The white solid was removed by filtration and the filter cake rinsed with methylene chloride. The combined filtrate and wash was extracted twice with 0.6N hydrochloric acid (15 ml and 10 ml). To the combined acidic aqueous extracts was added 6 g of potassium bicarbonate and methylene chloride with stirring. The layers were separated and the aqueous basic layer was extracted with methylene chloride. The methylene chloride layers were combined, dried over anhydrous sodium sulfate and evaporated to give 4.5 g brown oil which was predominantly 2-chloro-N-[4-(dimethylamino)-2-hydroxybutyl]-N-methyl-3-pyridinecarboxamide.

The 4.26 g (0.0149 mole) of the foregoing prepared 3-pyridinecarboxamide was mixed with 50 ml of toluene and the mixture was heated to distill off about 20 ml of solvent and then kept at reflux using a Dean-Stark trap to collect moisture. The temperature of the solution was lowered somewhat and 0.864 g (0.018 mole) of sodium hydride in mineral oil was added to produce gentle reflux. After a total of 45 min, the mixture was cooled and to it was added 0.5 ml of isopropyl alcohol and 0.5 ml of water. Carbon dioxide was bubbled in to convert the sodium hydroxide produced to sodium bicarbonate. The mixture was then azeotroped to dryness using a Dean-Stark trap. Some acetonitrile was added to the hot mixture. After cooling, the mixture was filtered through celite rinsing with acetonitrile. The filtrate was evaporated to give a mixture of the title product and a trace of mineral oil. The amount of title product obtained was 3.45 g (93% yield). The NMR and Mass Spec agreed with that of the free base of the compound prepared in Example 10.

EXAMPLE 110

2-[2-(Dimethylamino)ethyl]-2,3-dihydro-4-methyl-1,4-oxazepino[7,6-f]isoquinolin-5(4H)-one oxalate Following the procedure of Example 21, 2-(2-chloroethyl)-2,3-dihydro-4-methyl-1,4-oxazepino[7,6-f]isoquinolin-5(4H)-one is reacted with dimethylamine to give the title compound.

EXAMPLE 111

2-[2-(Dimethylamino)ethyl]-2,3-dihydro-4-methyl-1,4-oxazepino[7,6-f]isoquinoline-5(4H)-thione hydrochloride Following the procedure of Example 31, 2-(2-chloroethyl)-2,3-dihydro-4-methyl-1,4-oxazepino[7,6-f]isoquinoline-5(4H)-thione is reacted with dimethylamine to give the title compound.

EXAMPLE 112

2-[2-(Dimethylamino)ethyl]-2,3-dihydro-4-methyl-1,4-oxazepino[6,7-g]isoquinolin-5(4H)-one oxalate Following the procedure of Example 21, 2-(2-chloroethyl)-2,3-dihydro-4-methyl-1,4-oxazepino[6,7-g]isoquinolin-5(4H)-one is reacted with dimethylamine to give the title compound.

EXAMPLE 113

2-[2-(Dimethylamino)ethyl]-2,3-dihydro-4-methyl-1,4-oxazepine[6,7-g]isoquinoline-5(4H)-thione hydrochloride Following the procedure of Example 31, 2-(2-chloroethyl)-2,3-dihydro-4-methyl-1,4-oxazepino[6,7-g]isoquinoline-5(4H)-thione is reacted with dimethylamine to give the title compound.

EXAMPLE 114

2-[2-(Dimethylamino)ethyl]-2,3-dihydro-4,7-dimethyl-1,4-oxazepino[6,7-b]quinolin-5(4H)-one oxalate Following the procedure of Example 21, 2-(2-chloroethyl)-2,3-dihydro-4,7-dimethyl-1,4-oxazepino[6,7-h]quinolin-5(4H)-one is reacted with dimethylamine to give the title compound.

EXAMPLE 115

2-[2-(Dimethylamino)ethyl]-2,3-dihydro-4,7-dimethyl-1,4-oxazepino[6,7-h]quinoline-5(4H)-thione hydrochloride Following the procedure of Example 31, 2-(2-chloroethyl)-2,3-dihydro-4,7-dimethyl-1,4-oxazepino[6,7-h]quinoline-5(4H)-thione is reacted with dimethylamine to give the title compound.

EXAMPLE 116

2-[2-(Dimethylamino)ethyl]-2,3-dihydro-4,10-dimethyl-1,4-oxazepino[6,7-h]qiinolin-5(4H)-one oxalate Following the procedure of Example 21, 2-(2-chloroethyl)-2,3-dihydro-4,10-dimethyl-1,4-oxazepino[6,7-h]quinolin-5(4H)-one is reacted with dimethylamine to give the title compound.

EXAMPLE 117

2-[2-(Dimethylamino)ethyl]-2,3-dihydro-4,10-dimethyl-1,4-oxazepino[6,7-h]quinoline-5(4H)-thione hydrochloride Following the procedure of Example 31, 2-(2-chloroethyl)-2,3-dihydro-4,10-dimethyl-1,4-oxazepino[6,7-h]quinoline-5(4H)-thione is reacted with dimethylamine to give the title compound.

EXAMPLE 118

4-[2-(Dimethylamino)ethyl]-3,4-dihydro-2-methyl-[1,4]-oxazepino[6,7-f]quinolin-1(2H)-one oxalate Following the procedure of Example 21, 2-(2-chloroethyl)-3,4-dihydro-2-methyl[1,4]-oxazepino[6,7-f]quinolin-1(2H)-one is reacted with dimethylamine to give the title compound.

EXAMPLE 119

4-[2-(Dimethylamino)ethyl]-3,4-dihydro-2-methyl[1,4]-oxazepino[6,7-f]quinoline-1(2H)-thione hydrochloride Following the procedure of Example 31, 4-(2-chloroethyl)-3,4-dihydro-2-methyl-[1,4]-oxazepino[6,7-f]quinoline-1(2H)-thione is reacted with dimethylamine to give the title compound.

EXAMPLE 120

2-[2-(Dimethylamino)ethyl]-2,3-dihydro-4-methyl-1,4-oxazepino[6,7-h]quinolin-5(4H)-one oxalate Following the procedure of Example 21, 2-(2-chloroethyl)-2,3-dihydro-4-methyl-1,4-oxazepino[6,7-h]quinolin-5(4H)-one is reacted with dimethylamine to give the title compound.

EXAMPLE 121

2-[2-(Dimethylamino)ethyl]-2,3-dihydro-4-methyl-1,4-oxazepino[6,7-h]quinoline-5(4H)-thione hydrochloride Following the procedure of Example 31, 2-(2-chloroethyl)-2,3-dihydro-4-methyl-1,4-oxazepino[6,7-h]quinoline-5(4H)-thione is reacted with dimethylamine to give the title compound.

EXAMPLE 122

2-[2-(1-Azetidinyl)ethyl]-2,3-dihydro-4-methyl-pyrido[3,2-f][1,4]oxazepin-5(4H)-one oxalate hydrate[1:1:0.5]

To a solution of 5.0 g (0.021 mole) of 2-(2-chloroethyl)-2,3-dihydro-4-methylpyrido[3,2-f]-1,4-oxazepin-5(4H)-one dissolved in 40 ml of dimethylsulfoxide was added 8.7 g (0.063 mole) of potassium carbonate followed by 1.40 g (0.025 mole) of azetidine. The mixture was stirred for 4 days at room temperature*. Another 0.5 g (0.009 mole) of azetidine was added and stirring continued for 24 hr. Another 0.7 g (0.012 mole) of azetidine was added and the mixture was stirred for 24 hr. The potassium carbonate was filtered off and the dimethyl sulfoxide was removed from the filtrate by rotary evaporation at 90° C., 0.5 mm Hg. The residue was taken up in 100 ml of methylene chloride and the solution was washed with two 30 ml portions of water followed by 30 ml of dilute aqueous sodium hydroxide. The organic layer was dried over magnesium sulfate, filtered and concentrated by rotary evaporation. The residual syrup was reacted with oxalic acid in isopropyl alcohol giving 3.3 g (44%) of white crystals, m.p. 170°-172° C. $^1$HNMR analysis was essentially the same as for the same compound obtained in Example 106.
*Stirrer had malfunctioned causing need for a longer stirring period than an estimated 1-2 days that should be required.

EXAMPLE 123

2-[2-(1-Azetidinyl)ethyl]-2,3-dihydro-4-methyl-pyrido[3,2-f][1,4]oxazepine-5(4H)-thione fumarate To 5.0 g (0.0914 mole) of 2-(2-chloroethyl)-2,5-dihydro-4-methylpyrido[3,2-f]-1,4-oxazepine-5(4H)-thione dissolved in 50 ml of dimethylsulfoxide was added 8.04 g (0.058 mole) of potassium carbonate and 1.21 g (0.021 mole) of azetidine. The reaction mixture was stirred at room temperature for 8 hr after which was added 0.5 g (0.009 mole) of azetidine and the mixture was stirred overnight at room temperature. An additional 0.3 g (0.005 mole of azetidine was added and stirring was continued for 24 hr. The mixture was filtered and solvent removed by rotary evaporator at 80° C., 0.5 mm Hg. The residue was taken up in 100 ml of chloroform and the solution was washed with two 30 ml portions of dilute aqueous sodium hydroxide. The organic layer was dried over magnesium sulfate, filtered and concentrated by rotary evaporator. The residue was reacted with fumaric acid in isopropyl alcohol to give 2.5 g (31%) of pale yellow crystals, m.p. 122°-126° C.

EXAMPLE 124

2-[2-(1-Azetidinyl)ethyl]-7-chloro-2,3-dihydro-4-methyl-1,4-benzoxazepine-5(4H)-thione oxalate[1:1:0.5]

To 5.0 g (0.017 mole) of 7-chloro-2-(2-chloroethyl)-2,3-dihydro-4-methyl-1,4-benzoxazepine-5(4H)-thione dissolved in 50 ml of dimethyl sulfoxide was added 7 g of crushed potassium carbonate and 1.47 g (0.025 mole of azetidine. The mixture was stirred for 3 days at room temperature. Because of incomplete reaction, 0.5 g (0.009 mole) of azetidine was added and the reaction stirred an additional 24 hrs at room temperature. The potassium carbonate was filtered off and dimethylsulfoxide removed by rotary evaporation at 90° C. and 0.5 mm Hg. The residue was taken up in 100 ml of chloroform and washed with 2×30 ml of dil. sodium hydroxide and 2×30 ml of water. The organic layer was dried over magnesium sulfate, filtered, and concentrated by rotary evaporation. Treatment of the residual syrup in isopropyl alcohol with oxalic acid gave 3.3 g (47%) of yellow crystals, m.p. 121°-126° C.

Analysis: Calculated for $C_{17}H_{22}N_2O_{5.5}SCl$: C,49.81; H,5.41; N,6.83. Found: C,49.64; H,5.20; N,6.72.

EXAMPLE 125

(S)-2-[2-(Dimethylamino)ethyl]-2,3-dihydro-4-methyl-pyrido[3,2-f][1,4]oxazepine-5(4H)-thione hydrochloride[1:2]

Procedure: A 10 g (0.042 mole) sample of (S)-2-(2-chloroethyl)-2,3-dihydro-4-methylpyrido[3,2-f][1,4]oxazepine-5(4H)-thione was treated with 50 ml of methylamine and sealed in a flask. The resulting solution was stirred at 25° C. for 48 hr. The excess amine was allowed to evaporate and the residue was partitioned between chloroform and dilute sodium hydroxide. The chloroform was dried over sodium sulfate and concentrated. The residue was dissolved in acetonitrile and treated with ethereal hydrogen chloride. The resulting crystals were recrystallized from isopropyl alcohol-ethyl alcohol. Yield of title compound was 5 g (36%), m.p. 170°-179° C. $[\alpha]_D^{25} = +20.8$ (water).

Analysis: Calculated for $C_{13}H_{21}N_3OSCl_2$: C,46.16; H,6.26; N,12.42. Found: C,46.03; H,6.35; N,12.38.

EXAMPLE 126

(R)-2-[2-(Dimethylamino)ethyl]-2,3-dihydro-4-methyl-pyrido[3,2-f][1,4]-oxazepine-5(4H)-thione hydrochloride[1:2]

Procedure: A 10 g (0.042 mole) sample of (R)-2-(2-chloroethyl-2,3-dihydro-4-methylpyrido[3,2-f][1,4]oxazepine-5(4H)-thione was treated with 50 ml of methylamine and sealed in a flask. The resulting solution was stirred at 25° C. for 48 hr. The excess amine was allowed to evaporate and the residue was partitioned between chloroform and dilute sodium hydroxide. The chloroform was dried over sodium sulfate and and concentrated. The residue was dissolved in acetonitrile and treated in an acetonitrile solution of hydrogen chloride. The resulting crystals were recrystallized from ethanol. Yield of title compound was 7 g (50%); m.p. 170°–176° C.; $[\alpha]_D^{25} = -21.6$ (water).

Analysis: Calculated for $C_{13}H_{21}N_3OSCl_2$: C,46.16; H,6.26; N,12.42. Found: C,46.02; H,6.36; N,12.36.

EXAMPLE 127

2-[2-(1-Azetidinyl)ethyl]-2,3-dihydro-4-methyl-pyrido[3,2-f][1,4]oxazepine-5(4H)-thione fumarate, 2-propanol[1:1:0.33]

To a solution of 5.0 g (0.0195 mole) of 2-(2-chloroethyl)-2,3-dihydro-4-methylpyrido[3,2-f][1,4]oxazepine-5(4H)-thione in 40 ml of dimethylsulfoxide was added 8.0 g of crushed potassium carbonate followed by 1.40 g (0.023 mole) of azetidine. The reaction flask was stoppered and stirred at room temperature for 24 hr and 0.8 g (0.014 mole) of azetidine was added. After 24 hr, another 0.4 g (0.007 mole) of azetidine was added and stirring at room temperature continued. After 24 hr, the reaction mixture was diluted with 100 ml of water and extracted with 3×100 ml of benzene. The benzene extracts were combined, washed with 3×50 ml of water and 50 ml of saturated sodium chloride, dried over sodium sulfate, filtered, and concentrated by rotary evaporation. The residue was treated with fumaric acid in isopropyl alcohol which yielded 4.2 g (49.5%) of yellow crystals, m.p. 106°–22° C. with decomposition.

Analysis: Calculated for $C_{18}H_{23}N_3O_5S^*$: C,54.95; H,5.89; N,10.68. Found: C,53.73; H,6.11; N,9.75.

*calculated analysis does not include the isopropyl alcohol.

EXAMPLE 128

7-Chloro-2-[2-(diethylamino)ethyl]-2,3-dihydro-4-methylpyrido[3,2-f][1,4]-oxazepin-5(4H)-one oxalate [1:1]

To a suspension of 7-chloro-2-(2-chloroethyl)-2,3-dihydro-4-methylpyrido[3,2-f][1,4]oxazepine-5(4H)-one in 50 ml of absolute ethanol was added 2.26 ml (0.022 mole) of diethylamine and the mixture heated to reflux. (Complete dissolution occurred). After 1 hr, another 2.26 ml (0.022 mole) of diethylamine was added followed by 5.0 ml (0.049 mole) and heating continued for 2 more hours. TLC (ethylacetate/methanol/conc. ammonium hydroxide, 7:2:1, v/v/v) still showed presence of starting material; another 2.26 ml (0.022 mole) of diethylamine was added and heating continued for 15 hr at reflux. Solvent was removed by rotary evaporation (60° C., 30 mm Hg) and the residue taken up in methylene chloride, washed twice with dilute aqueous sodium hydroxide and once with water. The organic layer was dried over sodium sulfate, filtered and concentrated by rotary evaporation, and azeotroped once with toluene. The oil was treated with oxalic acid in isopropyl alcohol which yielded 6.7 g (76%) of white crystals, m.p. 163°–164° C.

Analysis: Calculated for $C_{17}H_{24}N_3O_6Cl$: C,50.81; H,6.02; N,10.40. Found: C,50.83; H,6.13; N,10.50.

EXAMPLE 129

2-[2-(1-Azetidinyl)ethyl]-7-chloro-2,3-dihydro-4-methylpyrido[3,2-f][1,4]-oxazepin-5(4H)-one oxalate [1:1]

To a solution of 6 g (0.022 mole) of 7-chloro-2-(2-chloroethyl)-2,3-dihydro-4-methylpyrido[3,2-f][1,4]-oxazepine-5(4H)-one in 40 ml of dimethyl sulfoxide was added 8.0 g of crushed potassium carbonate and 1.5 g (0.026 mole) of azetidine. The reaction was stirred at room temperature for 24 hr. After checking ty TLC 7:2:1 by volume ethyl acetate:methanol:conc. ammonium hydroxide, another 0.4 g (0.007 mole) of azetidine was added. Two days later, another 0.5 g (0.0087 mole) of azetidine was added and the mixture stirred for 24 hr more. The reaction mixture was diluted with 100 ml of water and extracted with 4×100 ml of benzene. The organic extracts were combined, washed with 3×100 ml of water, dried over sodium sulfate, filtered, and concentrated by rotary evaporation. The syrupy residue was treated with oxalic acid in isopropyl alcohol. This yielded 4.2 g (56.5%) of white material, m.p. 169°–174° C. with decomposition.

Analysis: Calculated for $C_{16}H_{20}N_3O_6Cl$: C,49.81; H,5.23; N,10.89. Found: C,49.70; H,5.33; N,10.79.

EXAMPLE 130

7-Choloro-2,3-dihydro-4-methyl-2-[2-methyl(phenylmethyl)amino]pyrido[3,2-f][1,4]oxazepin-5(4H)-one oxalate [1:1]

To a solution of 6.0 g (0.022 mole) of 7-chloro-2-(2-chloroethyl)-2,3-dihydro-4-methylpyrido[3,2-f][1,4]-oxazepine-5(4H)-one in 50 ml of absolute ethanol was added 5.3 g (0.044 mole) of benzylmethylamine and the mixture heated to reflux for three days. The solvent was removed by rotary evaporation, and the residue was taken up in 100 ml of methylene chloride, which was subsequently washed with 2×50 ml of dilute sodium hydroxide and 50 ml water, dried over sodium sulfate, filtered, and concentrated by rotary evaporation. Residual benzylmethylamine was removed at 95° C., 0.5 mm Hg. However, the mass spectrum now showed starting material; therefore, the residue was taken up in 50 ml of absolute ethanol. To the resulting solution was added 2.7 g (0.022 mole) of benzylmethylamine and the mixture heated to reflux for 24 hrs. The reaction mixture was subjected to the same work-up as mentioned before. The syrup was treated with oxalic acid in isopropyl alcohol. The resulting crystals were recrystallized from ethanol/isopropyl alcohol to give 4.7 g (47.9%) of white crystals, m.p. 176°–179° C.

Analysis: Calculated for $C_{21}H_{24}N_3O_6Cl$: C,56.07; H,5.38; N,9.34. Found: C,56.07; H,5.46; N,9.28.

EXAMPLE 131

7-Chloro-2,3-dihydro-4-methyl-2-[2-(methylamino)ethyl]pyrido[3,2-f][1,4]-oxazepin-5(4H)-one oxalate [1:1]

To 6 g (0.022 mole) of 7-chloro-2-(2-chloroethyl)-2,3-dihydro-4-methylpyrido[3,2-f][1,4]-oxazepine-5(4H)-one was added 80 ml of 30% monomethylamine (by weight) in absolute ethanol. The reaction flask was sealed and left standing at room temperature for ~4 days. The solvent was evaporated in a stream of air. The residue was taken up in 200 ml of methylene chloride, washed with 2×50 ml diluted aqueous sodium hydroxide and 50 ml of water, dried over sodium sulfate, filtered, and concentrated by rotary evaporation (60° C., 20 mm Hg). The residue was treated with oxalic acid in isopropyl alcohol which yielded 4.5 g (67%) of white crystals, m.p. 109°–113° C. with decomposition.

Analysis: Calculated for $C_{14}H_{18}N_3O_6Cl$: C,46.74; H,5.04; N,11.68. Found: C,46.73; H,5.27; N,11.31.

EXAMPLE 132

7-Bromo-2-[2-(dimethylamino)ethyl]-2,3-dihydro-4-methylpyrido[3,2-f][1,4]-oxazepin-5(4H)-one oxalate [1:1]

To 60 ml of freshly collected dimethylamine was added 6.0 g (0.019 mole) of 7-bromo-2-(2-chloroethyl)-2,3-dihydro-4-methylpyrido[3,2-f][1,4]-oxazepin-5(4H)-one. The flask was sealed and left standing at room temperature for three days. The dimethylamine was evaporated in a stream of air. The residue was taken up in 200 ml of methylene chloride, washed with 2×50 ml diluted aqueous sodium hydroxide and 50 ml of water, dried over sodium sulfate, filtered and concentrated by rotary evaporation at 60° C., 30 mm Hg. The residue was treated with oxalic acid in isopropyl alcohol which afforded 4.6 g (59%) of white crystals, m.p. 165°–167° C.

Analysis: Calculated for $C_{15}H_{20}O_6N_3Br$: C,43.08; H,4.82; N,10.05. Found: C,43.10; H,4.87; N,10.04.

EXAMPLE 133

2-[2-(1-Azetidinyl)ethyl]-7-bromo-2,3-dihydro-4-methylpyrido[2,3-f][1,4]-oxazepin-5(4H)-one oxalate [1:1]

To 40 ml of dimethylsulfoxide was added 6.0 g (0.019 mole) of 7-bromo-2-(2-chloroethyl)-2,3-dihydro-4-methylpyrido[3,2-f][1,4]-oxazepin-5(4H)-one, 8.0 g of crushed potassium carbonate, and 1.28 g (0.023 mole) of azetidine. The reaction mixture was sealed and stirred at room temperature for two days, after which 0.5 g (0.009 mole) more azetidine was added. Stirring was continued for 24 hr and still another 0.5 g (0.009 mole) of azetidine was added. After 24 hr, the reaction mixture was diluted with 200 ml of water, dried over sodium sulfate, filtered, and concentrated by rotary evaporation (60° C., 30 mm Hg). The residual syrup was treated with oxalic acid in isopropyl alcohol to give 4.9 g (61%) of white crystals, m.p. 163°–169° C. with decomposition.

Analysis: Calculated for $C_{16}H_{20}N_3O_6Br$: C,44.67; H,4.69; N,9.77. Found: C,44.59; H,4.77; N,9.70.

EXAMPLE 134

7-Bromo-2,3-dihydro-4-methyl-2-[2-[methyl(phenylmethyl)amino]ethyl]pyrido[3,2-f][1,4]-oxazepin-5(4H)-one oxalate [1:1]

To 6.0 g (0.019 mole) of 7-bromo-2-(2-chloroethyl)-2,3-dihydro-4-methylpyrido[3,2-f]-1,4-oxazepin-5(4H)-one in 40 ml of absolute ethanol was added 4.54 g (0.038 mole) of benzylmethylamine and the solution heated to reflux. After 2 days, another 2.75 g (0.023 mole) of benzylmethylamine was added and heating continued for 24 hr. Solvent was removed by rotary evaporation at 70° C., 30 mm Hg, the residual syrup taken up in 200 ml of methylene chloride, washed with 2×50 ml dilute aqueous sodium hydroxide and 50 ml of water, dried over sodium sulfate, filtered, and concentrated by rotary evaporation (60° C., 30 mm Hg). Most of the remaining benzylmethylamine was removed at 100° C., 0.5 mm over 2.5 hr periods. The residual syrup was treated with oxalic acid in isopropyl alcohol. Recrystallization from ethanol/isopropyl alcohol gave 5.3 g (57%) of white crystals, m.p. 180°–183° C.

Analysis: Calculated for $C_{21}H_2N_3O_6Br$: C,51.02; H,4.89; N,8.50. Found: C,50.87; H,5.00; N,8.49.

EXAMPLE 135

7-Bromo-2-[2-(dimethylamino)ethyl]-2,3-dihydro-4-methylpyrido[3,2-f][1,4]-oxazepine-5(4H)-thione oxalate [1:1]

To 50 ml of freshly collected dimethylamine was added 5.5 g (0.0164 mole) of 7-bromo-2-(2-chloroethyl)-2,3-dihydro-4-methylpyrido[3,2-f]-1,4-oxazepine-5(4H)-thione. The reaction flask was sealed tightly and left standing at room temperature for three days. The dimethylamine was evaporated in a stream of air and the residue taken up in 200 ml of methylene chloride which was washed with 2×50 ml of dilute aqueous sodium hydroxide and 50 ml of water, dried over sodium sulfate, filtered and concentrated by rotary evaporation. The residual syrup was treated with oxalic acid in isopropyl alcohol which gave 5.1 g (72%) of yellow crystals, m.p. 145°–151° C.

Analysis: Calculated for $C_{15}N_{20}N_3O_5SBr$: C,41.48; H,4.54; N,9.68. Found: C,41.38; H,4.66; N,9.71.

EXAMPLE 136

2-[2-(1-Azetidinyl)ethyl]-7-bromo-2,3-dihydro-4-methylpyrido[3,2-f][1,4]-oxazepine-5(4H)-thione oxalate [1:1]

Into 40 ml of dimethylsulfoxide was dissolved 5.5 g (0.0164 mole) of 7-bromo-2-(2-chloroethyl)-2,3-dihydro-4-methylpyrido[3,2-f]-1,4-oxazepine-5(4H)-thione followed by addition of 8.0 g of potassium carbonate and 1.40 g (0.0246 mole) of azetidine. The mixture was stirred 24 hr and 0.5 g (0.009 mole) of azetidine was added. After 24 hr, still another 0.5 g (0.009 mole) of azetidine was added. After 24 hr, the reaction mixture was diluted with 200 ml of water and extracted with 3×75 ml benzene. The organic extracts were combined and washed with 3×50 ml of water, dried over sodium sulfate, filtered and concentrated by rotary evaporation. Treatment of the residual syrup with oxalic acid in isopropyl alcohol afforded 5.85 g (80%) of yellow crystals, m.p. 161°–170° C. with decomposition.

Analysis: Calculated for $C_{16}H_{20}N_3O_5SBr$: C,43.06; H,4.52; N,7.42. Found: C,43.15; H,4.62; N,9.50.

EXAMPLE 137

7-Chloro-2,3-dihydro-4-methyl-2-[2-(1-pyrrolidinyl)ethyl]pyrido[3,2-f][1,4]-oxazepine-5(4H)-thione fumarate [1:1]

To a suspension of 4.75 g (90.0164 mole) of 7-chloro-2-(2-chloroethyl)-2,3-dihydro-4-methylpyrido[3,2-f]-1,4-oxazepine-5(4H)-thione in absolute ethanol was added 3.4 ml (0.04 mole) of pyrrolidine. The suspension was heated to reflux (complete solution occurred) for 3 hr and another 1.7 ml (0.2 mole) of pyrrolidine was added. After 5 hr more at reflux, solvent was removed by rotary evaporation and azeotroped twice with toluene. The residue was taken up in 100 ml of methylene chloride, washed with 2×50 ml of dilute aqueous sodium hydroxide and 50 ml of water, dried over sodium sulfate, filtered, and concentrated by rotary evaporation (60° C., 30 mm Hg) and stripped further at 85° C., 0.5 mm Hg for 2 hr. The residue was treated with fumaric acid in isopropyl alcohol. The resulting crystals were recrystallized from ethanol/isopropyl alcohol to give 5.1 g (70%) of yellow crystals, m.p. 172°–173° C.

Analysis: Calculated for $C_{19}H_{24}N_3O_5SCl$: C,51.64; H,5.47; N,9.51. Found: C,51.49; H,5.58; N,9.53.

EXAMPLE 138

7-Chloro-2,3-dihydro-4-methyl-2-[2-(methylamino)ethyl]pyrido[3,2-f][1,4]-oxazepine-5(4H)-thione oxalate [1:1]

To 60 ml of 30% monomethylamine in ethanol was added 4.75 g (0.016 mole) of 7-chloro-2-(2-chloroethyl)-2,3-dihydro-4-methylpyrido[3,2-f]-1,4-oxazepine-5(4H)-thione. The reaction flask was sealed tightly and left standing at room temperature. After 8 days, the solvent was removed by rotary evaporation. Another 40 ml of 30% monomethylamine in ethanol was added since some starting material remained. After 2 days, the solvent was evaporated in a stream of air and the residue taken up in 100 ml of methylene chloride. The organic layer was washed twice with dilute sodium hydroxide and once with water, dried over sodium sulfate, filtered, and concentrated by rotary evaporation. The residue was treated with oxalic acid in isopropyl alcohol. The resulting crystals were recrystallized from isopropyl alcohol/ethanol to give 0.85 g (13.8%) of yellow crystals, m.p. 112°–129° C. with decomposition.

Analysis: Calculated for $C_{14}H_{18}N_3O_5SCl$: C,44.74; H,4.83; N,11.18. Found: C,44.69; H,5.20; N,11.01.

EXAMPLE 139

2-[2-(1-Azetidinyl)]ethyl-7-chloro-2,3-dihydro-4-methylpyrido[3,2-f][1,4]-oxazepine-5(4H)-thione oxalate [1:1]

To a solution of 4.75 g (0.0164 mole) of 7-chloro-2-(2-chloroethyl)-2,3-dihydro-4-methylpyrido[3,2-f]-1,4-oxazepine-5(4H)-thione in 40 ml of dimethyl sulfoxide was added 8.0 g of crushed potassium carbonate and 1.4 g (0.0246 mole) of azetidine. The flask was sealed and stirred at room temperature for 24 hr after which an additional 0.6 g (0.011 mole) of azetidine was added. After 24 hr, another 0.5 (0.009 mole) of azetidine was added and stirring continued at room temperature. After 48 hr, the entire reaction mixture was diluted with 200 ml of water and extracted with 2×100 ml of benzene. The organic extracts were combined, washed with 3×100 ml of water and 1×100 ml saturated sodium chloride, dried over sodium sulfate, filtered, and concentrated by rotary evaporation (65° C., 30 mm Hg). The residue was treated with oxalic acid in isopropyl alcohol to give 5.4 g (82%) of yellow crystals, m.p. 146°–150° C.

Analysis: Calculated for $C_{16}H_{20}N_3O_5SCl$: C,47.82; H,5.02; N,10.46. Found: C,47.66; H,5.12; N,10.30.

EXAMPLE 140

7-Bromo-2,3-dihydro-4-methyl-2-[2-[methyl(phenylmethyl)amino]ethyl]pyrido[3,2-f][1,4]-oxazepine-5(4H)-thione oxalate [1:1]

To a suspension of 5.00 g (0.015 mole) of 7-bromo-2-(2-chloroethyl)-2,3-dihydro-4-methylpyrido[3,2-f]-1,4-oxazepine-5(4H)-thione in 40 ml of absolute ethanol was added 3.63 g (0.030 mole) of benzylmethylamine. The reaction mixture was heated to reflux. After 3 hr, an additional 1.8 g (0.015 mole) of benzylmethylamine was added and heating continued for 24 hr. The solvent was removed by rotary evaporation at 60° C., 30 mm Hg) followed by 75° C., 0.5 mm Hg for 1 hr. The residue was taken up in 100 ml of methylene chloride, washed with 2×50 ml dilute sodium hydroxide and 50 ml water, dried over sodium sulfate, filtered, concentrated by rotary evaporation, and subjected 0.5 mm Hg vac at 75° C. for 2 hr. The residue was treated with oxalic acid in isopropyl alcohol. The resulting crystals were recrystallized from isopropyl alcohol/ethanol to give 5.9 g (77%) of yellow crystals, m.p. 192°–203° C. with decomposition.

Analysis: Calculated for $C_{21}H_{24}N_3O_5SBr$: C,49.42; H,4.74; N,8.23. Found: C,49.40; H,4.77; N,8.22.

EXAMPLE 141

7-Chloro-2-[2-(diethylamino)ethyl]-2,3-dihydro-4-methylpyrido[3,2-f][1,4]-oxazepine-5(4H)-thione fumarate [1:1]

To a suspension of 4.75 g (0.0164 mole) of 7-chloro-2-(2-chloroethyl)-2,3-dihydro-4-methylpyrido[3,2-f][1,4]-oxazepine-5(4H)-thione in 40 ml of absolute ethanol was added 10 ml of diethylamine and the reaction mixture was heated to reflux. After 3 hr, another 5 ml of diethylamine was added and heating continued for 24 hr. Another 2 ml of diethylamine was added and heating was continued for 2 hr. The solvent was then removed by rotary evaporation and the residue azeotroped once with toluene and subjected to 0.5 mm Hg vacuum at 70° C. for 20 min. The syrupy residue was taken up in 100 ml of methylene chloride, washed with 2×50 ml of dilute sodium hydroxide, dried over sodium sulfate, filtered and concentrated by rotary evaporation. The residue syrup was treated with fumaric acid in isopropyl alcohol giving 3.86 g (53%) of yellow crystals, m.p. 141°–143° C.

Analysis: Calculated for $C_{19}H_{26}N_3O_5SCl$: C,51.40; H,5.90; N,9.47. Found: C,51.20; H,5.96; N,9.42.

EXAMPLE 142

7-Chloro-2,3-dihydro-4-methyl-2-[2-[methyl(phenylmethyl)amino]ethyl]pyrido[3,2-f][1,4]-oxazepine-5(4H)-thione oxalate [1:1]

To a suspension of 4.75 g (0.016 mole) of 7-chloro-2-(2-chloroethyl)-2,3-dihydro-4-methylpyrido[3,2-f]-1,4-oxazepine-5(4H)-thione in 50 ml of absolute ethanol was added 4.00 g (0.033 mole) of benzylmethylamine and the mixture heated to reflux. After 24 hr, an additional 2.00 g (0.017 mole) of benzylmethylamine was added and heat continued. Still another 2.00 (0.017 mole) of benzylmethylamine was added and heating continued for 24 hr. The solvent was removed by rotary evaporation at 70° C., 30 mm Hg, and the residue taken up in 100 ml of methylene chloride, washed with 1N sodium hydroxide, dried over sodium sulfate, filtered, concentrated by rotary evaporation (70° C., 30 mm Hg). The syrupy residue was then subjected to 100° C., 0.5 mm Hg, and subsequently treated with oxalic acid in isopropyl alcohol. The resulting crystals were recrystallized from ethanol and isopropyl alcohol to give 4.9 g (64%) of yellow crystals.

Analysis: Calculated for $C_{21}H_{24}N_3O_5SCl$: C,54.13; H,5.19; N,9.02. Found: C,53.99; H,5.25; N,8.93.

EXAMPLE 143

2-[2-(Ethylmethylamino)ethyl]-2,3-dihydro-4-methylpyrido[3,2-f][1,4]-oxazepin-5(4H)-one oxalate [1:1]

To a solution of 5.00 g (0.021 mole) of 2-(2-chloroethyl)-2,3-dihydro-4-methylpyrido[3,2-f]-1,4-oxazepin- 5(4H)-one in 40 ml of absolute ethanol was added 10 ml of ethylmethylamine. The reaction flask was sealed and stirred at room temperature for 7 days. The reaction mixture was then heated on low heat for 14 hr after which was added 2.5 ml of ethylmethylamine and heating continued for 15 hr. The solvent was then removed by rotary evaporation and syrupy residue taken up in methylene chloride which was washed twice with dilute aqueous sodium hydroxide dried over sodium sulfate, filtered, and concentrated by rotary evaporation. The residue was treated with oxalic acid in isopropyl alcohol which afforded 5.0 g (74.5%) of white crystals, m.p. 133° C.

Analysis: Calculated for $C_{16}H_{23}N_3O_6$: C,54.38; H,6.56; N,11.89. Found: C,54.19; H,6.68; N,11.83.

EXAMPLE 144

2-[(Ethylmethylamino)ethyl]-2,3-dihydro-4-methylpyrido[3,2-f][1,4]-oxazepine-5(4H)-thione oxalate [1:1]

To a suspension of 5 g (0.019 mole) of 2-(2-chloroethyl-2,3-dihydro-4-methylpyrido[3,2-f]-1,4-oxazepine-5(4H)-thione in 40 ml of absolute ethanol was added 10 ml of methylethylamine and the mixture stirred at room temperature for 14 days. An additional 7.5 ml of methylethylamine was added and the reaction mixture heated for 18 hr very gently and stirred at room temperature for 12 days. The solvent was removed by rotary evaporation. The residue was taken up in 100 ml of methylene chloride, washed with 2×30 ml 1N sodium hydroxide and 30 ml of water, dried over sodium sulfate, filtered, concentrated by rotary evaporation and azeotroped once with toluene. The residue was reacted with oxalic acid in isopropyl alcohol to give 2.2 g (31.3%) of crystals, m.p. 127°–131° C.

Analysis: Calculated for $C_{16}H_{23}N_3O_5S$: C,52.0; H,6.28; N,11.37. Found: C,51.62; H,6.27; N,11.22.

EXAMPLE 145

2-[2-(Dimethylamino)ethyl]-2,3-dihydro-4,8-dimethylpyrido[3,2-f][1,4]-oxazepin-5(4H)-one fumarate [1:2]

To 50 ml of freshly collected dimethylamine was added 5.0 g (0.020 mole) of 2-(2-chloroethyl)-2,3-dihydro-4,8-dimethylpyrido[3,2-f]-1,4-oxazepin-5(4H)-one hydrate [1:1]. The reaction flask was sealed tightly and left standing at room temperature for 3 days. The dimethylamine was evaporated in a stream of air. The residue was taken up in methylene chloride, washed twice with 1N sodium hydroxide and once with water, dried over sodium sulfate, filtered and concentrated by rotary evaporation. The syrupy residue was treated with 2 equivalents of fumaric acid in isopropyl alcohol which yield 5.2 g (52%) of white crystals, m.p. 164°–165° C.

Analysis: Calculated for $C_{22}H_{29}N_3O_{10}$: C,53.33; H,5.90; N,8.48. Found: C,53.33; H,5.94; N,8.44.

EXAMPLE 146

2-[2-(Dimethylamino)ethyl]-3,4-dihydro-4,8-dimethylpyrido[3,2-f][1,4]-oxazepine-5(4H)-thione oxalate [1:1]

To 40 ml of freshly collected dimethylamine was added a solution of 4.9 g (0.018 mole) of 2-(2-chloroethyl)-2,3-dihydro-4,8-dimethylpyrido[3,2-f]-1,4-oxazepine-5(4H)-thione in 15 ml of methanol. The flask was sealed and left standing at room temperature for 3 days. The solvent was evaporated in a stream of air and the syrupy residue taken up in methylene chloride which was washed twice with 1N sodium hydroxide and once with water, dried over sodium sulfate, filtered, and concentrated by rotary evaporation. The residual syrup was treated with oxalic acid in isopropyl alcohol to give 5.5 g of yellow crystals, m.p. 216° C.

Analysis: Calculated for $C_{16}H_{23}N_3O_5S$: C,52.02; H,56.28; N,11.37. Found: C,51.96; H,6.37; N,11.30.

EXAMPLE 147

2-[2-(Dimethylamino)ethyl]-2,3-dihydro-4-methyl-7-nitro-1,4-benzoxazepin-5(4H)-one fumarate [2:3]

To 60 ml of freshly collected dimethylamine was added 5.0 g (0.018 mole) of 2-(2-chloroethyl)-2,3-dihydro-4-methyl-7-nitro-1,4-benzoxazepin-5(4H)-one. The reaction flask was sealed tightly and allowed to stand 72 hr at room temperature The solvent was removed by rotary evaporation and the residue taken up in 200 ml of methylene chloride washed with 3×50 ml of 1N sodium hydroxide and 100 ml of water, dried over sodium sulfate, filtered and concentrated by rotary evaporation. The residue was treated with fumaric acid in isopropyl alcohol to give 6.4 g (76%) of yellow crystals, m.p. 167°–169° C.

Analysis: Calculated for $C_{20}H_{25}N_3O_{10}$: C,51.39; H,5.39; N,8.99. Found: C,51.47; H,5.43; N,8.94.

EXAMPLE 148

2-[2-(Dimethylamino)ethyl]-2,3-dihydro-4-methyl-7-nitro-1,4-benzoxazepine-5(4H)-thione To 50 ml of freshly collected dimethylamine was added 4.25 g (0.014 mole) of 2-(2-chloroethyl)-2,3-dihydro-4-methyl-7-nitro-1,4-benzoxazepine-5(4H)-thione. The reaction flask was sealed tightly and allowed to stand at room temperature for 6 days. The dimethylamine was evaporated at room temperature. The solid residue was taken up in methylene chloride, washed twice with 1N hydroxide and once with water, dried over sodium sulfate, filtered and concentrated by rotary evaporation. Approximately 0.8 g of the crude solid residue was triturated with isopropyl/ether to give the crystalline free base, m.p. 104°–109° C.

Analysis: Calculated for $C_{14}H_{19}N_3O_3S$: C,54.35; H,6.19; N,13.58. Found: C,54.20; H,6.21; N,13.54.

EXAMPLE 149

2-[2-(Dimethylamino)ethyl]-2,3-dihydro-4-methyl-7-nitro-1,4-benzoxazepine-5(4H)-thione fumarate [4:3]

A sample of crude solid residue obtained in Example 148 was treated with fumaric acid in isopropyl alcohol to give the title fumarate salt. One recrystallization from methanol gave 2.8 g of yellow crystals, m.p. 192°–194° C.

Analysis: Calculated for $C_{17}H_{22}N_3O_6S$: C,51.50; H,5.59; N,10.60. Found: C,51.54; H,5.59; N,10.47.

EXAMPLE 150

2-[2-(Cyclopropylamino)ethyl]-2,3-dihydro-4-methylpyrido[3,2-f][1,4]-oxazepine-5(4)-thione fumarate [1:0.5]

To a solution of 10 g (0.039 mole) of 2-(2-chloroethyl)-2,3-dihydro-4-methylpyrido[3,2-f]-1,4-oxazepine-5(4H)-thione in 50 ml of dimethyl sulfoxide was added 8 g of crushed potassium carbonate and 5.56 g (0.098 mole) of cyclopropylamine and the mixture stirred at room temperature for 72 hr. Another 2.6 g (0.035 mole) of cyclopropylamine was added and stirring at room temperature continued for 3 hr. The reaction mixture was poured into 200 ml of water and extracted with 2×100 ml of benzene. The combined organic extracts were washed with 2×100 ml of water, dried over sodium sulfate, filtered and concentrated by rotary evaporation. The residue was taken up in 250 ml of 1N hydrochloric acid and washed with 3×100 ml of methylene chloride. The aqueous layer was made just basic with concentrated aqueous sodium hydroxide and extracted with 3×100 ml of methylene chloride. The combined organic extracts were dried over sodium sulfate, filtered, and concentrated by rotary evaporation. The residue was further purified by preparative HPLS using 1% triethylamine in methylene chloride. Like fractions were combined and concentrated to give ~5 g of oil which was treated with fumaric acid in isopropyl alcohol to give 2.8 g (21%) of yellow crystals, m.p. 152°–154° C.

Analysis: Calculated for $C_{16}H_{21}N_3O_3S$: C,57.29; H,6.31; N,12.53. Found: C,57.27; H,6.38; N,12.42.

EXAMPLE 151

2-[2-(Dimethylamino)ethyl]-2,3-dihydro-7-fluoro-4-methyl-1,4-benzoxazepin-5(4H)-one oxalate [1:1]

To 60 ml of freshly collected dimethylamine was added 5.0 g (0.0195 mole) of 2-(2-chloroethyl)-2,3-dihydro-7-fluoro-4-methyl-1,4-benzoxazepin-5(4H)-one. The reaction flask was sealed tightly and allowed to stand at room temperature for 72 hr. After cooling, the flask was opened and the excess dimethylamine allowed to evaporate at room temperature. The residue was taken up in methylene chloride and washed twice with 1N sodium hydroxide and once with water. The organic layer was dried over sodium sulfate, filtered, and concentrated by rotary evaporation. The residue was treated with oxalic acid in isopropyl alcohol to give 5.35 g (77%) of white crystals, m.p. 201°–203° C.

Analysis: Calculated for $C_{16}H_{21}N_2O_6F_1$: C,53.93; H,5.94; N,7.86. Found: C,53.93; H,5.98; N,7.89.

EXAMPLE 152

2-[2-(Dimethylamino)ethyl]-2,3-dihydro-7-fluoro-4-methyl-1,4-benzoxazepine-5(4H)-thione oxalate hydrate [1:1:0.5]

To 60 ml of freshly collected dimethylamine was added 5.0 g (0.018 mole) of 2-(2-chloroethyl)-2,3-dihydro-7-fluoro-4-methyl-1,4-benzoxazepine-5(4H)-thione. The reaction flask was sealed tightly and allowed to stand at room temperature for 72 hr. After cooling, the flask was opened and the excess dimethylamine allowed to evaporate at room temperature. The residue was taken up in methylene chloride, washed twice with 1N sodium hydroxide and once with water, dried over sodium sulfate, filtered and concentrated by rotary evaporation. The residue was treated with oxalic acid in isopropyl alcohol to give 6 g (87%) of pale yellow crystals, m.p. 180°–182° C.

Analysis: Calculated for $C_{16}H_{22}N_2O_{5.5}S_1F_1$: C,50.38; H,5.81 N,7.30. Found: C,50.10; H,5.65; N,7.28.

TABLE 2

[Structure: A ring with (Y)0-2 substituent, fused to a ring containing E, with R4, R5, (CH)n-Z groups and N-R, B= group]

| Ex. No. | (Y)0-2 | B | R | R4 | E | Z | R5-(CH)n- | Salt | Optical Isomer(b) |
|---|---|---|---|---|---|---|---|---|---|
| 1 | benz | O | —CH3 | H | O | —N(CH3)2 | —(CH2)2— | HCl | Rac. |
| 2 | benz | O | —CH3 | H | O | —N(CH3)2 | " | — | " |
| 3 | benz | O | —CH3 | H | O | [morpholino] | " | fumarate | " |
| 4 | benz | O | —CH2φ | H | O | [morpholino] | " | — | " |
| 5 | benz | O | —CH2φ | H | O | —NHCH3 | " | fumarate | " |
| 6 | benz | S | —CH3 | H | O | —N(CH3)2 | " | HCl H2O | " |
| 7 | benz | O | —CH2φ | H | O | —N(CH3)2 | " | — | " |
| 8 | benz | S | —CH3 | H | O | [morpholino] | " | HCl | " |
| 9 | naphth[2,3-f] | O | —CH3 | H | O | —N(CH3)2 | " | oxalate | " |
| 10 | pyrido[3,2-f] | O | —CH3 | H | O | —N(CH3)2 | " | 1.5 fumarate | " |
| 11 | pyrido[3,2-f] | S | —CH2φ | H | O | —N(CH3)2 | " | fumarate, 0.5 ethanol | " |
| 12 | pyrido[3,2-f] | S | —CH3 | H | O | —N(CH3)2 | " | fumarate | " |
| 13 | benz | S | —CH2φ | H | O | [morpholino] | " | — | " |
| 14 | benz | O | —CH3 | H | O | —NHCH3 | " | fumarate | " |
| 15 | benz | O | —CH3 | H | O | —NHCH3 | " | — | " |

TABLE 2-continued

| Ex. No. | (Y)₀₋₂ | B | R | $R^4$ | E | Z | $-(CH)_n-$ $R^5$ | Salt | Optical Isomer[b] |
|---|---|---|---|---|---|---|---|---|---|
| 16 | benz | S | —CH₃ | H | O | 1-methyl-4-hydroxy-4-phenylpiperidine | | — | |
| 17 | benz | S | —CH₃ | H | O | 1-methyl-4-phenyl-tetrahydropyridine | | — | " |
| 18 | 8-Cl—benz | S | —CH₃ | H | O | —N(CH₃)₂ | " | HCl | " |
| 19 | 8-Cl—benz | O | —CH₃ | H | O | —N(CH₃)₂ | " | oxalate | " |
| 20 | 7-Br—benz | O | —CH₃ | H | O | —N(CH₃)₂ | " | oxalate | " |
| 21 | naph[2,1-f] | O | —CH₃ | H | O | —N(CH₃)₂ | " | oxalate | " |
| 22[a] | pyrido[4,3-f] | O | —CH₃ | H | O | —N(CH₃)₂ | " | fumarate | " |
| b | pyrido[3,4-f] | O | —CH₃ | H | O | —N(CH₃)₂ | " | fumarate | " |
| c | pyrido[2,3-f] | O | —CH₃ | H | O | —N(CH₃)₂ | " | fumarate | " |
| 23 | pyrido[4,3-f] | S | —CH₃ | H | O | —N(CH₃)₂ | " | 1.5 HCl | " |
| 24 | pyrido[3,2-f] | S | —CH₃ | H | O | —N(C₂H₅)₂ | " | oxalate, ½H₂O | " |
| 25 | naphth[2,3-f] | S | —CH₃ | H | O | —N(CH₃)₂ | " | — | |
| 26 | 7,9 diiodobenz | O | —CH₃ | H | O | —N(CH₃)₂ | " | oxalate | " |
| 27 | 7-Cl—benz | O | —CH₃ | H | O | —N(CH₃)₂ | —CH₂— | — | |
| 28 | pyrido[3,2-f] | O | —CH₃ | H | O | —N(CH₃)₂ | —(CH₂)— | methiodide | " |
| 29 | pyrido[3,2-f] | S | —CH₃ | H | O | —N(CH₃)₂ | " | oxalate.½ | " |
| 30 | 7-Cl—benz | S | —CH₃ | H | O | —N(CH₃)₂ | " | HCl H₂O | " |
| 31 | naphth[2,1-f] | S | —CH₃ | H | O | —N(CH₃)₂ | " | fumarate H₂O | " |
| 32[a] | pyrido[3,4-f] | S | —CH₃ | H | O | —N(CH₃)₂ | " | fumarate H₂O | " |
| b | pyrido[2,3-f] | S | —CH₃ | H | O | —N(CH₃)₂ | " | oxalate.H₂O | " |
| 33 | 7-OCH₃—benz | O | —CH₃ | H | O | —N(CH₃)₂ | " | ½H₂O | " |
| 34 | 7-Br—benz | S | —CH₃ | H | O | —N(CH₃)₂ | " | oxalate.H₂O | " |
| 35[a] | benz | O | —C₆H₁₁ | H | O | —N(CH₃)₂ | " | oxalate | " |
| b | benz | O | —C₂H₅ | H | O | —N(CH₃)₂ | " | oxalate | " |
| c | benz | O | —CH(CH₃)₂ | H | O | —N(CH₃)₂ | " | oxalate | " |
| d | benz | O | 4-Cl—C₆H₄CH₂— | H | O | —N(CH₃)₂ | " | oxalate | " |
| e | benz | O | 4-CH₃—C₆H₄CH₃— | H | O | —N(CH₃)₂ | " | oxalate | " |

TABLE 2-continued

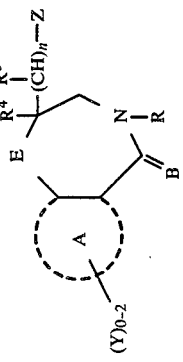

| Ex. No. | (Y)$_{0-2}$ | B | R | R$^4$ | E | Z | R$^5$ —(CH)$_n$— | Salt | Optical Isomer[b] |
|---|---|---|---|---|---|---|---|---|---|
| f | benz | O | 3,5-(OCH$_3$)$_2$—C$_6$H$_3$CH$_2$— | H | O | —N(CH$_3$)$_2$ | " | oxalate | " |
| g | benz | O | 3-CF$_3$—C$_6$H$_4$CH$_3$— | H | O | —N(CH$_3$)$_2$ | " | oxalate | " |
| h | benz | O | 4-NO$_2$—C$_6$H$_4$CH$_3$— | H | O | —N(CH$_3$)$_2$ | " | oxalate | " |
| 36[a] | pyrido[3,2-f] | O | —C$_6$H$_{11}$ | H | O | —N(CH$_3$)$_2$ | " | fumarate | " |
| b | pyrido[3,2-f] | O | —C$_2$H$_5$ | H | O | —N(CH$_3$)$_2$ | " | fumarate | " |
| c | pyrido[3,2-f] | O | —CH(CH$_3$)$_2$ | H | O | —N(CH$_3$)$_2$ | " | fumarate | " |
| d | pyrido[3,2-f] | O | 4-Cl—C$_6$H$_4$CH$_3$— | H | O | —N(CH$_3$)$_2$ | " | fumarate | " |
| e | pyrido[3,2-f] | O | 4-CH$_3$—C$_6$H$_4$CH$_3$— | H | O | —N(CH$_3$)$_2$ | " | fumarate | " |
| f | pyrido[3,2-f] | O | 4-OCH$_3$—C$_6$H$_4$CH$_3$— | H | O | —N(CH$_3$)$_2$ | " | fumarate | " |
| g | pyrido[3,2-f] | O | 3-CF$_3$—C$_6$H$_4$CH$_2$— | H | O | —N(CH$_3$)$_2$ | " | fumarate | " |
| h | pyrido[3,2-f] | O | 4-NO$_2$—C$_6$H$_4$CH$_2$— | H | O | —N(CH$_3$)$_2$ | " | fumarate | " |
| 37[a] | benz | O | —CH$_3$ | H | O | 1-pyrrolidinyl | " | fumarate | " |
| b | benz | O | —CH$_3$ | H | O | 1-piperidinyl | " | fumarate | " |
| c | benz | O | —CH$_3$ | H | O | 1-piperazinyl | " | fumarate | " |
| d | benz | O | —CH$_3$ | H | O | 4-CH$_3$—piperizinyl | " | fumarate | " |
| 38 | pyrido[3,2-f] | O | —CH$_3$ | H | S | —N(CH$_3$)$_2$ | " | 2.HCl | " |
| 39 | pyrido[3,2-f] | S | —CH$_3$ | H | S | —N(CH$_3$)$_2$ | " | oxalate ½H$_2$O | " |
| 40 | pyrido[3,4-f] | O | —CH$_3$ | H | O | —N(CH$_3$)$_2$ | " | 2 oxalate | " |
| 41 | pyrido[3,4-f] | S | —CH$_3$ | H | O | —N(CH$_3$)$_2$ | —(CH$_2$)$_3$— | 2 oxalate ½H$_2$O | |
| 42 | pyrido[3,2-f] | O | —CH$_3$ | H | O | —NH$_2$ | | oxalate | |
| 43 | pyrido[3,2-f] | O | —CH$_3$ | H | O | morpholino | —(CH$_2$)$_3$— | maleate | |
| 44 | pyrido[3,2-f] | O | —CH$_3$ | H | O | 1-pyrrolidinyl | " | 2 fumarate | " |
| 45 | pyrido[3,2-f] | O | —CH$_3$ | H | O | —N(n-butyl)$_2$ | " | maleate | " |
| 46 | pyrido[3,2-f] | O | —CH$_3$ | H | O | —N(C$_2$H$_5$)$_2$ | " | oxalate | " |
| 47 | pyrido[3,2-f] | O | —CH$_3$ | H | O | 1-piperidinyl | " | oxalate | " |
| 48 | pyrido[3,2-f] | O | —CH$_3$ | H | O | —N(CH$_3$)(benzyl) | " | maleate | " |
| 49 | pyrido[3,2-f] | O | —CH$_3$ | H | O | —N(CH$_3$)—C$_6$H$_5$ | " | — | " |

TABLE 2-continued

| Ex. No. | (Y)₀₋₂ | B | R | R⁴ | E | Z | $-(CH)_n-\overset{R^5}{|}$ | Salt | Optical Isomer[b] |
|---|---|---|---|---|---|---|---|---|---|
| 50 | pyrido[3,2-f] | O | —CH₃ | H | O | ![pyrrolidine with 2,5-diCH₃, N] | | fumarate | " |
| 51 | pyrido[3,2-f] | O | —CH₃ | H | O | ![pyrrolidine with CH₃, N] | " | — | " |
| 52 | pyrido[3,2-f] | O | —CH₃ | H | O | ![pyrazole N–N] | " | — | " |
| 53 | pyrido[3,2-f] | O | —CH₃ | H | O | ![imidazole N] | " | — | " |
| 54 | pyrido[3,2-f] | O | —C₂H₅ | H | O | —N(CH₃)₂ | " | oxalate | " |
| 55 | pyrido[3,2-f] | O | —C₂H₅ | H | O | 1-pyrrolidinyl | " | oxalate | " |
| 56 | pyrido[3,2-f] | S | —CH₃ | H | O | ![morpholine] | " | — | " |
| 57 | pyrido[3,2-f] | S | —CH₃ | H | O | —N(n-butyl)₂ | " | oxalate | " |
| 58 | pyrido[3,2-f] | S | —CH₃ | H | O | —N(C₂H₅)₂ | " | oxalate | " |
| 59 | pyrido[3,2-f] | S | —CH₃ | H | O | 1-pyrrolidinyl | " | oxalate | " |

TABLE 2-continued

| Ex. No. | (Y)$_{0-2}$ | B | R | R$^4$ | E | Z | R$^5$ —(CH)$_n$— | Salt | Optical Isomer[b] |
|---|---|---|---|---|---|---|---|---|---|
| 60 | pyrido[3,2-f] | S | —CH$_3$ | H | O | [imidazole ring] | " | 1.5 oxalate | |
| 61 | pyrido[3,2-f] | S | —C$_2$H$_5$ | H | O | —N(CH$_3$)$_2$ | —(CH$_3$)$_2$— | — | " |
| 62 | pyrido[3,2-f] | S | —CH$_3$ | H | O | —N(CH$_3$)(benzyl) | " | oxalate | " |
| 63 | pyrido[3,2-f] | S | —CH$_3$ | H | O | —NHCH$_3$ | " | 1.5 oxalate | " |
| 65 | 7-Cl—pyrido[3,2-f] | O | —CH$_3$ | H | O | 1-pyrrolidinyl | " | 2.5 fumarate | " |
|  |  | O | —CH$_3$ | H | O | —N(CH$_3$)$_2$ | " | oxalate | " |
| 66 | pyrido[3,2-f] | O | —C$_6$H$_{11}$ | H | O | —N(CH$_3$)$_2$ | —CH$_2$— | oxalate | " |
| 67 | pyrido[3,2-f] | O | —CH$_2$C$_6$H$_5$ | H | O | —N(CH$_3$)$_2$ | —(CH$_2$)$_2$— | 1.5 oxalate, ¼H$_2$O | " |
| 68[a] | pyrido[3,2-f] | O | H | H | O | —N(CH$_3$)$_2$ | " | — | " |
| 68[b] | pyrido[3,2-f] | O | H | H | O | —N(CH$_3$)$_2$ | —(CH$_2$)$_2$— | fumarate | " |
| 69 | pyrido[3,2-f] | O | —CH$_3$ | H | O | —N(CH$_2$)$_2$ | —(CH$_2$)$_3$— | 1.5 fumarate, 0.5 H$_2$O | " |
| 70 | pyrido[3,2-f] | S | —CH$_3$ | H | O | —N(CH$_3$)$_2$ | —(CH$_2$)$_2$— | 2 oxalate | " |
| 71 | 7-Cl—pyrido[3,2-f] | S | —CH$_3$ | H | O | —N(CH$_3$)$_2$ | " | ½H$_2$O, ½(CH$_3$)$_2$HOH | " |
| 72 | pyrido[3,2-f] | O | —CH$_3$ | H | O | —NHCH$_3$ | " | oxalate | " |
| 73 | pyrido[3,2-f] | O | —CH$_3$ | H | O | —NH$_2$ | " | fumarate | " |
| 74 | pyrido[3,2-f] | S | —CH$_3$ | H | O | —NH$_2$ | " | 0.5 fumarate | " |
| 75 | pyrido[3,2-f] | O | —CH$_3$ | H | O | H | " | 2.0 fumarate | " |
| 76 | pyrido[3,2-f] | S | —CH$_3$ | H | O | —N—CH(CH$_3$)$_2$ | " | fumarate | " |
| 77 | pyrido[3,2-f] | O | —CH$_3$ | H | O | —N(CH$_2$C$_6$H$_5$)$_2$ | " | 2.0 fumarate, hydrate | " |
| 78 | pyrido[3,2-f] | S | —CH$_3$ | H | O | 4-methyl-piperazin-1-yl | " | 2.0 fumarate, ½H$_2$O | " |
| 79 | pyrido[3,2-f] | O | —CH$_3$ | H | O | 4-methyl-piperazin-1-yl[a] | " | 2.0 fumarate, ½H$_2$O | " |
| 80 | pyrido[3,2-f] | O | —CH$_3$ | H | O | [imidazoline ring with NH] | " | oxalate | " |
| 81 | pyrido[3,2-f] | S | —CH$_3$ | H | O | —N(CH$_3$)(C$_6$H$_5$) | " | — | " |

TABLE 2-continued

| Ex. No. | (Y)$_{0-2}$ | B | R | R$^4$ | E | Z | $-\overset{R^4}{\underset{(CH_2)_n}{C}}-R^5$ | Salt | Optical Isomer[b] |
|---|---|---|---|---|---|---|---|---|---|
| 82 | pyrido[3,2-f] | S | —CH$_3$ | H | O | —NH$_2$ | —(CH$_2$)$_3$— | fumarate | " |
| 83 | pyrido[3,2-f] | S | H | H | O | —N(CH$_3$)$_2$ | —(CH$_2$)$_2$— | 2HCl, H$_2$O | " |
| 84 | pyrido[3,2-f] | S | —CH$_3$ | H | O | a | " | oxalate, H$_2$O | " |
| 85 | pyrido[3,2-f] | S | —CH$_3$ | H | O | pyrazolyl | " | — | " |
| 86 | pyrido[3,2-f] | O | —CH$_3$ | H | O | —N(CH$_3$)$_2$ | —CH(CH$_3$)—CH$_3$ | oxalate | " |
| 87 | pyrido[3,2-f] | S | —CH$_3$ | H | O | imidazolinyl | —(CH$_2$)$_2$— | 1.5 oxalate | " |
| 88 | pyrido[3,2-f] | O | —CH$_3$ | —CH$_3$ | O | —N(CH$_3$)$_2$ | " | 2HCl | " |
| 89 | pyrido[3,2-f] | S | —CH$_3$ | —CH$_3$ | O | —N(CH$_3$)$_2$ | " | HCl | " |
| 90 | pyrido[3,2-f] | O | —CH$_3$ | H | O | —N(CH$_3$)$_2$ | " | oxalate | |
| 91 | pyrido[3,2-f] | S | —CH$_3$ | H | O | —N(CH$_3$)$_2$ | —CH(CH$_3$)—CH$_2$— | oxalate | " |
| 92 | pyrido[3,2-f] | O | —CH$_3$ | H | O | —N(CH$_3$)$_2$ | —CH$_2$—C(CH$_3$)— | HCl | " |

TABLE 2-continued

| Ex. No. | (Y)$_{0-2}$ | B | R | R$^4$ | E | Z | R$^5$ —(CH)$_n$— | Salt | Optical Isomer[b] |
|---|---|---|---|---|---|---|---|---|---|
| 93 | pyrido[3,2-f] | S | —CH$_3$ | H | O | 3-CH$_3$-pyrrolidin-1-yl | —(CH$_2$)$_2$— | fumarate, isopropyl alcohol | " |
| 94 | 3-E, 6-CF$_3$ quinolinyl | O | —CH$_3$ | H | O | —N(CH$_3$)$_2$ | —(CH$_2$)$_2$— | fumarate | " |
| 95 | 3-E quinolinyl | O | —CH$_3$ | H | O | —N(CH$_3$)$_2$ | —(CH$_2$)$_2$— | fumarate, 0.5 H$_2$O | " |
| 96 | 3-E quinolinyl | S | —CH$_3$ | H | O | —N(CH$_3$)$_2$ | —(CH$_2$)$_2$— | fumarate, isopropyl alcohol, H$_2$O | " |
| 97 | benz | O | —C$_2$H$_5$ | H | N-CH$_3$ | 4-hydroxy-4-phenyl-piperidin-1-yl | —(CH$_3$)$_2$— | fumarate, isopropyl alcohol | " |
| 98 | benz | O | —C$_2$H$_5$ | H | N-CH$_3$ | 4-(dimethylamino)morpholino | —(CH$_2$)$_2$ | — | " |

TABLE 2-continued

| Ex. No. | (Y)$_{0-2}$ | B | R | R$^4$ | E | Z | $-(CH_2)_n-$ R$^5$ | Salt | Optical Isomer[b] |
|---|---|---|---|---|---|---|---|---|---|
| 99 | benz | O | —CH(CH$_3$)$_2$ | H | CH$_3$ N | —N(CH$_3$)$_2$ | —CH$_2$— | — | " |
| 100 | benz | O | —C$_2$H$_5$ | H | CH$_3$ N | —N(CH$_3$)$_2$ | —(CH$_2$)$_2$— | — | " |
| 101 | pyrido[3,2-f] | S | —CH$_3$ | H | O | piperidino | —(CH$_2$)$_2$— | fumarate, 0.5 H$_2$O, 0.5 isopropyl alcohol | " |
| 102 | 6-Cl—pyrido[4,3-f] | O | —CH$_3$ | H | O | —N(CH$_3$)$_2$ | —(CH$_2$)$_2$— | 0.5 fumarate | " |
| 103 | 6-[N(CH$_3$)$_2$]—pyrido[4,3-f] | O | —CH$_3$ | H | O | —N(CH$_3$)$_2$ | —(CH$_2$)$_2$— | 1.5 fumarate | " |
| 104 | pyrido[3,2-f] | O | —CH$_3$ | H | O | pyrrolidino | —(CH$_2$)$_2$— | 2.0 fumarate | " |
| 105 | pyrido[3,2-f] | S | —CH$_3$ | H | O | pyrrolidino | —(CH$_2$)$_2$— | fumarate | " |
| 106 | pyrido[3,2-f] | O | —CH$_3$ | H | O | azetidino | —(CH$_2$)$_2$— | oxalate, 0.5 H$_2$O | " |

TABLE 2-continued
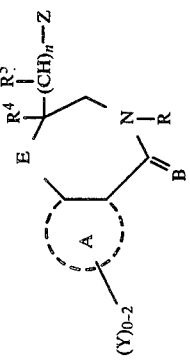
| Ex. No. | (Y)₀₋₂ | B | R | R⁴ | E | Z | R⁵ —(CH₂)ₙ— | Salt | Optical Isomer[b] |
|---|---|---|---|---|---|---|---|---|---|
| 107 | pyrido[3,2-f] | O | —CH₃ | H | O | —N(CH₃)₂ | —CH₂— | fumarate | " |
| 108 | pyrido[3,2-f] | S | —CH₃ | H | O | —N(CH₃)₂ | —CH₂— | 0.5 fumarate | " |
| 109 | pyrido[3,2-f] | O | —CH₃ | H | O | —N(CH₃)₂ | —(CH₂)₂— | — | " |
| 110 | (structure) | O | —CH₃ | H | O | —N(CH₃)₂ | —(CH₂)₂— | oxalate | " |
| 111 | (structure) | S | —CH₃ | H | O | —N(CH₃)₂ | —(CH₂)₂— | HCl | " |
| 112 | (structure) | O | —CH₃ | H | O | —N(CH₃)₂ | —(CH₂)₂— | oxalate | " |
| 113 | (structure) | S | —CH₃ | H | O | —N(CH₃)₂ | —(CH₂)₂— | HCl | " |
| 114 | (structure) | O | —CH₃ | H | O | —N(CH₃)₂ | —(CH₂)₂— | oxalate | " |

TABLE 2-continued

| Ex. No. | (Y)$_{0-2}$ | B | R | E | Z | R$^4$ | $-\overset{R^5}{(CH_2)_n}-$ | Salt | Optical Isomer[b] |
|---|---|---|---|---|---|---|---|---|---|
| 115 | (quinoline with E and CH$_3$) | S | —CH$_3$ | O | —N(CH$_3$)$_2$ | H | —(CH$_2$)$_2$— | HCl | " |
| 116 | (quinoline with E and CH$_3$) | O | —CH$_3$ | O | —N(CH$_3$)$_2$ | H | —(CH$_2$)$_2$— | oxalate | " |
| 117 | (quinoline with E and CH$_3$) | S | —CH$_3$ | O | —N(CH$_3$)$_2$ | H | —(CH$_2$)$_2$— | HCl | " |
| 118 | (naphthalene with E) | O | —CH$_3$ | O | —N(CH$_3$)$_2$ | H | —(CH$_2$)$_2$— | oxalate | " |
| 119 | (naphthalene with E) | S | —CH$_3$ | O | —N(CH$_3$)$_2$ | H | —(CH$_2$)$_2$— | HCl | " |

TABLE 2-continued

Structure:
(Y)$_{0-2}$ substituted ring A with E, connected to C(=B)-N(R)-CH$_2$-C(R$^4$)(R$^5$)-(CH)$_n$-Z

| Ex. No. | (Y)$_{0-2}$ | B | R | R$^4$ | E | Z | R$^5$–(CH)$_n$– | Salt | Optical Isomer[b] |
|---|---|---|---|---|---|---|---|---|---|
| 120 | (quinoline with E) | O | —CH$_3$ | H | O | —N(CH$_3$)$_2$ | —(CH$_2$)$_2$— | oxalate | " |
| 121 | (quinoline with E) | S | —CH$_3$ | H | O | —N(CH$_3$)$_2$ | —(CH$_2$)$_2$— | HCl | " |
| 122 | pyrido[3,2-f] | O | —CH$_3$ | H | O | —N(azetidinyl) | —(CH$_2$)$_2$— | oxalate, 0.5 H$_2$O | " |
| 123 | pyrido[3,2-f] | S | —CH$_3$ | H | O | —N(azetidinyl) | —(CH$_2$)$_2$— | fumarate | " |
| 124 | 7-Cl—benz- | S | —CH$_3$ | H | O | —N(azetidinyl) | —(CH$_2$)$_2$— | oxalate 0.5 H$_2$O | " |
| 125 | pyrido[3,2-f]- | S | —CH$_3$ | H | O | —N(CH$_3$)$_2$ | —(CH$_2$)$_2$— | 2HCl | S(+) |
| 126 | pyrido[3,2-f]- | S | —CH$_3$ | H | O | —N(CH$_3$)$_2$ | —(CH$_2$)$_2$— | 2HCl | R(−) |
| 127 | pyrido[3,2-f] | S | —CH$_3$ | H | O | —N(azetidinyl) | —(CH$_2$)$_2$— | fumarate 0.33 H$_2$O | Rac. |

TABLE 2-continued

| Ex. No. | (Y)₀₋₂ | B | R | R⁴ | E | Z | $-\overset{R^5}{(CH)_n}-$ | Salt | Optical Isomer[b] |
|---|---|---|---|---|---|---|---|---|---|
| 128 | 7-Cl—pyrido-[3,2-f]- | O | —CH₃ | H | O | —N(CH₂H₅)₂ | —(CH₂)₂— | oxalate | " |
| 129 | 7-Cl—pyrido-[3,2-f]- | O | —CH₃ | H | O | ![azetidine] | —(CH₂)₂— | oxalate | " |
| 130 | 7-Cl—pyrido-[3,2-f]- | O | —CH₃ | H | O | —N(CH₃)CH₂C₆H₅ | —(CH₂)— | oxalate | " |
| 131 | 7-Cl—pyrido-[3,2-f] | O | —CH₃ | H | O | —NHCH₃ | —(CH₂)₂— | oxalate | " |
| 132 | 7-Br—pyrido-[3,2-f]- | O | —CH₃ | H | O | —N(CH₃)₂ | —(CH₂)₂— | oxalate | " |
| 133 | 7-Br—pyrido-[3,2-f] | O | —CH₃ | H | O | ![azetidine] | —(CH₂)₂— | oxalate | " |
| 134 | 7-Br—pyrido [3,2-f]- | O | —CH₃ | H | O | —N(CH₃)CH₂C₆H₅ | —(CH₂)₂— | oxalate | " |
| 135 | 7-Br—pyrido-[3,2-f]- | S | —CH₃ | H | O | —N(CH₃)₂ | —(CH₂)₂— | oxalate | " |
| 136 | 7-Br—pyrido [3,2-f]- | S | —CH₃ | H | O | ![azetidine] | —(CH₂)₂— | " | |
| 137 | 7-Cl—pyrido [3,2-f]- | S | —CH₃ | H | O | ![pyrrolidine] | —(CH₂)₂— | fumarate | " |

TABLE 2-continued

| Ex. No. | (Y)₀₋₂ | B | R | R⁴ | E | Z | R⁵ —(CH)ₙ— | Salt | Optical Isomer[b] |
|---|---|---|---|---|---|---|---|---|---|
| 138 | 7-Cl—pyrido [3,2-f]- | S | —CH₃ | H | O | —NHCH₃ | —(CH₂)₂— | oxalate | " |
| 139 | 7-Cl—pyrido [3,2-f]- | S | —CH₃ | H | O |  | —(CH₂)₂— | oxalate | " |
| 140 | 7-Br—pyrido [3,2-f]- | S | —CH₃ | H | O | —N(CH₃)CH₂C₆H₅ | —(CH₂)₂— | oxalate | " |
| 141 | 7-Cl—pyrido [3,2-f]- | S | —CH₃ | H | O | —N(C₂H₅)₂ | —(CH₂)₂— | " | " |
| 142 | 7-Cl—pyrido [3,2-f]- | S | —CH₃ | H | O | —N(CH₃)CH₂C₆H₅ | —(CH₂)₂— | oxalate | " |
| 143 | pyrido[3,2-f]- | O | —CH₃ | H | O | —N(CH₃)C₂H₅ | —(CH₂)₂— | oxalate | " |
| 144 | pyrido[3,2-f]- | S | —CH₃ | H | O | —N(CH₃)C₂H₅ | —(CH₂)₂— | oxalate | " |
| 145 | 8-CH₃—pyrido [3,2-f]- | O | —CH₃ | H | O | —N(CH₃)₂ | —(CH₂)₂— | 2 fumarate | " |
| 146 | 8-CH₃—pyrido [3,2-f]- | S | —CH₃ | H | O | —N(CH₃)₂ | —(CH₂)₂— | oxalate | " |
| 147 | 7-NO₂—pyrido [3,2-f]- | O | —CH₃ | H | O | —N(CH₃)₂ | —(CH₂)₂— | 1.5 fumarate | " |
| 148 | 7-NO₂—pyrido [3,2-f]- | S | —CH₃ | H | O | —N(CH₃)₂ | —(CH₂)₂— | — | " |
| 149 | 7-NO₂—pyrido [3,2-f]- | S | —CH₃ | H | O | —N(CH₃)₂ | —(CH₂)₂— | ½ fumarate | " |
| 150 | pyrido[3,2-f]- | S | —CH₃ | H | O | —NH— 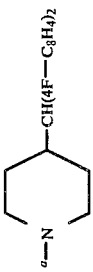 | —(CH₂)₂— | 0.5 fumarate | " |
| 151 | 7-F—benz- | O | —CH₃ | H | O | —N(CH₃)₂ | —(CH₂)₂— | oxalate | " |
| 152 | 7-F—benz- | S | —CH₃ | H | O | —N(CH₃)₂ | —(CH₂)₂— | oxalate 0.5 H₂O | " |

Footnote:

[a] —N⟩—CH(4F—C₆H₄)₂

[b] Rac = racemic mixture.

ADDITIONAL PHARMACOLOGY

Experiments were conducted to determine whether sedation was present as a result of administration of the compounds of the invention as antihistaminics and the results on compounds tested suggests they are non-sedative antihistaminics. The comparative antihistaminic agent used was diphenhydramine which does cause sedation. See Douglas, W. C. (1980), "Histamine and 5-hydroxytryptamine (serotonin) and their antagonists" in *The Pharmacological Basis of Therapeutics* (ed: A. G. Gilman, L. S. Goodman, A. Gilman, 6th edition, Macmillan, New York, pp 609–641. In the present tests, sedation is defined as a change in the electroencephalograms (EEGs) from the normal pattern of low voltage, fast ($\beta$) cerebral cortical waves (12–25 Hz, <50 mV amplitude) to synchronized high voltage, slow ($\alpha$, $\Delta$) cerebral cortical waves (1–3, 4–7 Hz, >50 mV amplitude) with frequent periods of sleep spindles predominating.

EXPERIMENTAL METHOD FOR SEDATIVE ACTIVITY

Ten cats of both sexes were anesthetized with halothane and cannulae placed in the trachea, the left cephalic vein, and the right femoral artery for artificial ventilation, drug administration, and blood pressure recording, respectively. The head was fixed in a Kopf stereotaxic unit and the calvarium was widely exposed. Stainless steel screw electrodes ($\frac{1}{4}''$) were placed through the calvarium so that the tips rested on the dura over the frontal, parietal, and occipital areas, bilaterally. An electrode of the same type was placed in the right frontal sinus and served as the reference electrode for monopolar EEG recordings. After completion of the surgery, the animal was given gallamine triethiodide (20 mg, IV; supplemented as necessary) and the halothane withdrawn. Artificial respiration was instituted (10 ml room air/kg/3 sec).

EEGs were made on a Grass, Model 5, electroencephalograph along with (lead II) EKG. Typically, EEGs were recorded for 2–3 min every 10 min. Arterial blood pressure was continuously monitored on a Grass, Model 79, polygraph.

In most experiments, histamine (0.5 µg/kg, IV) was given to produce a transient (<30 sec) hypotensive effect. It was normally given 10, 20 and 30 min prior to the first dose of the test drug and then 5, 10 and 20 min after each dose of the test drug. In this way an indication of the antihistaminic activity of test drug could be quantified.

Concomitant with the antihistaminic quantification was the effect of test drug on EEG. Test drugs was usually given in increasing doses of 0.1, 0.3, 0.5, 1, 3, 5, 10 and 20 mg/kg, IV.

EXPERIMENTAL RESULTS ON SEDATIVE POTENTIAL

Illustratively of the compounds tested (Examples 12, 65 and 71) the compound of Example 12 produced a 50% reduction of the histamine-induced depressor effect on blood pressure at 0.3 mg/kg, IV and a 100% suppression at 1–3 mg/kg, IV. There were no signs of sedation in these animals at any dose up to 20 mg/kg, IV.

On the other hand, the comparative drug, diphenhydramine, known to produce sedation (tested here in 6 cats) produced a 50% suppression of the histamine-induced depressor effect on blood pressure at 0.5 mg/kg, IV and a 100% suppression at 3–5 mg/kg, IV. Signs of sedation with diphenhydramine occurred in the EEG tracings as low as 0.5 mg/kg, IV with marked slowing, synchronized waves, and sleep spindles at 1–3 mg/kg, IV. In summary, diphenhydramine produced an antihistaminic effect in doses which also produced a sedative effect. This is similar to what is seen in man with diphenhydramine.

In contrast to the effects of diphenhydramine, compounds such as that of Example 12 do not produce sedation at any dose up to 20 mg/kg, even though the antihistaminic effects occurred at much lower doses. These data, therefore, suggest the nonsedative nature of compounds of the invention.

PHARMACEUTICAL COMPOSITIONS

The invention further provides pharmaceutical compositions for administration to a living animal body comprising, as active ingredients, at least one of the compounds of Formula I according to the invention in association with a pharmaceutical carrier or excipient. The compounds are thus presented in a therapeutic composition suitable for oral, rectal, parenteral, subcutaneous, intramuscular, intraperitoneal, intravenous, or intranasal administration. Thus, for example, compositions for oral administration can take the form of elixirs, capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be comprised of a sterile parenterally acceptable liquid; e.g. water or arachis oil contained in ampoules.

In compositions for rectal administration, the carrier can be comprised of a suppository base; e.g., cocoa butter or a glyceride.

Application to the nose, throat or bronchial region can be in the form of gargle or an aerosol spray containing small particles of the agent of Formula I in a spray or dry powder form.

Advantageously, the compositions are formulated as dosage units, each unit being adapted to supply a fixed dose of active ingredients. Tablets, coated tablets, capsules, ampoules and suppositories are examples of preferred dosage forms according to the invention, It is only necessary that the active ingredient constitute an effective amount; i.e., such that a suitable effective dosage will be consistent with the dosage form employed. The exact individual dosages, as well as daily dosages, will of course be determined according to standard medical principles under the direction of a physician or veterinarian. Generally, the pharmacology tests on guinea pigs in comparison to certain other antihistaminic drugs and limited testing in humans suggests an effective dose for an adult will be in the range of 1 to 50 mg for the more active compounds.

Based on the animal data and limited human testing, unit dosages containing an amount of compound equivalent to about 0.01 to about 1.0 mg of active drug per kilogram of body weight are contemplated. Daily dosages of about 0.04 to 4.0 mg/kg body weight are contemplated for humans and obviously several small unit dosage forms may be administered at one time. However, the scope of the invention is not to be limited by these contemplations due to uncertainty in transposing from animal data to humans and preliminary human testing.

Examples of unit dosage compositions are as follows:

| Ingredients | |
| --- | --- |
| Capsules: | Per Capsule |
| 1. Active ingredient | 4 mg. |
| 2. Lactose | 150 mg. |
| 3. Magnesium stearate | 4 mg. |
| Tablets: | |
| 1. Active ingredient | 4 mg. |
| 2. Corn starch | 20 mg. |
| 3. Kelacid | 20 mg. |
| 4. Keltose | 20 mg. |
| 5. Magnesium stearate | 1.3 mg. |

PROCEDURE FOR TABLETS

1. Blend 1, 2, 3, and 4 in larger amounts.
2. Add sufficient water portionwise to blend to the blend from step 1 with careful stirring after each addition. Such additions of water and stirring continue until the mass is of a constituency to permit its conversion to wet granules.
3. The wet mass is converted to granules by passing it through the oscillating granulator using 8 mesh screen.
4. The wet granules are then dried in an oven at 140° F.
5. The dry granules are lubricated with the magnesium stearate.
6. The lubricated granules are compressed on a suitable tablet press.

| Intramuscular Injection | |
| --- | --- |
| | Per ml. |
| 1. Active ingredients | 10.0 mg. |
| 2. Isotonic buffer solution 4.0 q.s to | 1.0 ml. |

Procedure

1. Dissolve the active ingredient in the buffer solution.
2. Aseptically filter the solution from step 1.
3. The sterile solution is now aseptically filled into sterile ampuls.
4. The ampuls are sealed under aseptic condition.

Suppositories

| Ingredients | Per Supp. |
| --- | --- |
| 1. Active ingredient | 10.0 mg. |
| 2. Polyethylene Glycol 1000 | 1350.0 mg. |
| 3. Polyethylene Glycol 4000 | 450.0 mg. |

Procedure

1. Melt 2 and 3 together and stir until uniform.
2. Dissolve No. 1 in the molten mass from step 1 and stirr until uniform.
3. Pour the molten mass from step 2 into suppository molds and chill.
4. Remove the suppositories from molds and wrap.

Therapeutic compositions for combatting histamine in unit dosage form, comprising a pharmaceutical carrier and an effective amount of a compound of Formula I or a pharmaceutically acceptable acid addition salt thereof are therefore an embodiment of this invention.

Various modifications and equivalents will be apparent to one skilled in the art and may be made in the compounds, methods, processes and pharmaceutical compositions of the present invention without departing from the spirit and scope thereof, and it is therefore to be understood that the invention is to be limited only by the scope of the appended claims.

What is claimed is:

1. A method of counteracting histamine in a living animal body which comprises administering to said animal body an effective amount of a compound selected from the group having the formula:

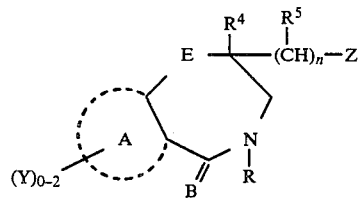

wherein;

A represents an aromatic ring having two of its carbon atoms held mutually with the oxazepine, thiazepine, or diazepine moiety selected from the group consisting of benzene, naphthalene, a quinoline, or a pyridine in any of its four positions, any of the rings optionally substituted by one or two Y radicals selected from the group consisting of halo, loweralkyl, loweralkoxy, diloweralkylamino, nitro or trifluoromethyl;

E is selected from oxygen, sulfur or

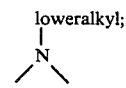

B is selected from oxygen or sulfur;

R is selected from the group consisting of hydrogen, loweralkyl, cycloalkyl or phenyl-loweralkyl of which phenyl may be optionally substituted by one or two radicals selected from halo, loweralkyl, loweralkoxy, nitro, or trifluoromethyl;

n is 1, 2 or 3;

$R^4$ and $R^5$ are selected from hydrogen or loweralkyl (1–5 C);

Z is selected from the group consisting of —$NR^1R^2$, 1H-pyrazol-1-yl, 1H-imidazol-1-yl, 1H-imidazol-2-yl or 4,5-dihydro-1H-imidazol-2-yl;

$R^1$ and $R^2$ are selected from the group consisting of hydrogen, loweralkyl, cycloalkyl and phenyl-loweralkyl of which phenyl may be optionally substituted by 1 or 2 radicals selected from halo, loweralkyl, loweralkoxy, nitro, trifluoromethyl or cyano, or $R^1$ and $R^2$ taken together with the adjacent nitrogen atom may form a heterocyclic residue selected from the group consisting of 1-azetidinyl, 1-pyrrolidinyl, 2,5-dimethylpyrrolidin-1-yl, 2-methylpyrrolidin-1-yl, 1-piperidinyl, 4-substituted piperidin-1-yl, 4-[bis(4-fluorophenyl)methyl]piperidin-1-yl, 4-morpholinyl, 1-piperazinyl, 4-substituted piperazin-1-yl, 1,2,3,6-tetrahydropyridin-1-yl, 1H-pyrrol-1-yl or 2,5-dihydro-1H-pyrrol-1-yl;

the optical isomers thereof and the pharmaceutically acceptable salts thereof with the proviso that when R=H, Z is never a primary or secondary amine and a further proviso that when n=4, Z is not pyrazolyl or imidazolyl.

2. The method of claim 1 wherein the compound is 2-[2-(dimethylamino)ethyl]-4-methyl-2,3-dihydro-1,4-benzoxazepin-5(4H)-one or a pharmaceutically acceptable salt thereof.

3. The method of claim 1 wherein the compound is 2,3-dihydro-4-methyl-2-[2-(4-morpholino)ethyl]-1,4-benzoxazepin-5(4H)-one or a pharmaceutically acceptable salt thereof.

4. The method of claim 1 wherein the compound is 4-benzyl-2,3-dihydro-2-[2-(4-morpholino)ethyl]-1,4-benzoxazepin-5(4H)-one or a pharmaceutically acceptable salt thereof.

5. The method of claim 1 wherein the compound is 4-benzyl-2,3-dihydro-2-[2-(methylamino)ethyl]-1,4-benzoxazepin-5(4H)-one or a pharmaceutically acceptable salt thereof.

6. The method of claim 1 wherein the compound is 2-[2-(dimethylamino)ethyl]-2,3-dihydro-4-methyl-1,4-benzoxazepine-5(4H)-thione or a pharmaceutically acceptable salt thereof.

7. The method of claim 1 wherein the compound is 4-benzyl-2-[2-(dimethylamino)ethyl]-2,3-dihydro-1,4-benzoxazepin-5(4H)-one or a pharmaceutically acceptable salt thereof.

8. The method of claim 1 wherein the compound is 2,3-dihydro-4-methyl-2-[2-(4-morpholino)ethyl]-1,4-benzoxazepine-5(4H)-thione or a pharmaceutically acceptable salt thereof.

9. The method of claim 1 wherein the compound is 2-[2-(dimethylamino)ethyl]-2,3-dihydro-4-methyl-naphth[2,3-f][1,4]-oxazepin-5(4H)-one or a pharmaceutically acceptable salt thereof.

10. The method of claim 1 wherein the compound is 2-[2-(dimethylamino)ethyl]-2,3-dihydro-1-methyl-pyrido[3,2-f][1,4]oxazepin-5(4H)-one or a pharmaceutically acceptable salt thereof.

11. The method of claim 1 wherein the compound is 2-[2-(dimethylamino)ethyl]-2,3-dihydro-4-methyl-pyrido[3,2-f][1,4]-oxazepine-5(4H)-thione or a pharmaceutically acceptable salt thereof.

12. The method of claim 1 wherein the compound is 4-benzyl-2,3-dihydro-2-[2-(4-morpholino)ethyl]-1,4-benzoxazepine-5(4H)-thione or a pharmaceutically acceptable salt thereof.

13. The method of claim 1 wherein the compound is 2,3-dihydro-4-methyl-2-[2-(methylamino)ethyl]-1,4-benzoxazepin-5(4H)-one or a pharmaceutically acceptable salt thereof.

14. The method of claim 1 wherein the compound is 2,3-dihydro-4-methyl-2-[2-(methylamino)ethyl]-1,4-benzoxazepin-5(4H)-one fumarate.

15. The method of claim 1 wherein the compound is 2,3-dihydro-2-[2-(4-hydroxy-4-phenyl)piperidinylethyl]-4-methyl-1,4-benzoxazepine-5(4H)-thione or a pharmaceutically acceptable salt thereof.

16. The method of claim 1 wherein the compound is 2,3-dihydro-4-methyl-2-[2-[1-(4-phenyl-1,2,3,6-tetrahydro)pyridinyl]ethyl-1,4-benzoxazepine-5(4H)-thione or a pharmaceutically acceptable salt thereof.

17. The method of claim 1 wherein the compound is 8-chloro-2-[2-(dimethylamino)ethyl]-2,3-dihydro-4-methyl-1,4-benzoxazepine-5(4H)-thione or a pharmaceutically acceptable salt thereof.

18. The method of claim 1 wherein the compound is 8-chloro-2-[2-(dimethylamino)ethyl]-2,3-dihydro-4-methyl-1,4-benzoxazepin-5(4H)-one or a pharmaceutically acceptable salt thereof.

19. The method of claim 1 wherein the compound is 7-bromo-2-[2-(dimethylamino)ethyl]-2,3-dihydro-4-methyl-1,4-benzoxazepine-5(4H)-thione or a pharmaceutically acceptable salt thereof.

20. The method of claim 1 wherein the compound is 2-[2-(dimethylamino)ethyl]-2,3-dihydro-4-methyl-naphth[2,1-f][1,4]oxazepin-5(4H)-one or a pharmaceutically acceptable salt thereof.

21. The method of claim 1 wherein the compound is 2-[2-(dimethylamino)ethyl]-2,3-dihydro-4-methyl-pyrido[4,3-f][1,4]oxazepine-5(4H)-thione or a pharmaceutically acceptable salt thereof.

22. The method of claim 1 wherein the compound is 2-[2-(diethylamino)ethyl]-2,3-dihydro-4-methyl-pyrido[3,2-f][1,4]-oxazepine-5(4H)-thione or a pharmaceutically acceptable salt thereof.

23. The method of claim 1 wherein the compound is 2-[2-(dimethylamino)ethyl]-2,3-dihydro-4-methyl-naphth[2,3-f][1,4]oxazepine-5(4H)-thione or a pharmaceutically acceptable salt thereof.

24. The method of claim 1 wherein the compound is 7-chloro-2-[2-(dimethylamino)ethyl]-2,3-dihydro-4-methyl-1,4-benzoxazepin-5(4H)-one or a pharmaceutically acceptable salt thereof.

25. The method of claim 1 wherein the compound is 2-[2-(dimethylamino)ethyl]-2,3-dihydro-4-methyl-pyrido[3,2-f][1,4]oxazepin-5(4H)-thione methiodide.

26. The method of claim 1 wherein the compound is 7-chloro-2-[2-(dimethylamino)ethyl]-2,3-dihydro-4-methyl-1,4-benzoxazepine-5(4H)-thione or a pharmaceutically acceptable salt thereof.

27. The method of claim 1 wherein the compound is 2-[2-(dimethylamino)ethyl]-2,3-dihydro-4-methyl-naphth[2,1-f][1,4]oxazepine-5(4H)-thione or a pharmaceutically acceptable salt thereof.

28. The method of claim 1 wherein the compound is 2-[2-(dimethylamino)ethyl]-2,3-dihydro-7-methoxy-4-methyl-1,4-benzoxazepin-5(4H)-one or a pharmaceutically acceptable salt thereof.

29. The method of claim 1 wherein the compound is 7-bromo-2-[2-(dimethylamino)ethyl]-2,3-dihydro-4-methyl-1,4-benzoxazepine-5(4H)-thione or a pharmaceutically acceptable salt thereof.

30. The method of claim 1 wherein the compound is 2-[2-(dimethylamino)ethyl]-2,3-dihydro-4-methyl-pyrido[3,2-f][1,4]-thiazepin-5(4H)-one or a pharmaceutically acceptable salt thereof.

31. The method of claim 1 wherein the compound is 2-[2-(dimethylamino)ethyl]-2,3-dihydro-4-methyl-pyrido[3,2-f][1,4]-thiazepine-5(4H)-thione or a pharmaceutically acceptable salt thereof.

32. The method of claim 1 wherein the compound is 2-[2-(dimethylamino)ethyl]-2,3-dihydro-4-methyl-pyrido-[3,4-f][1,4]-oxazepin-5(4H)-one or a pharmaceutically acceptable salt thereof.

33. The method of claim 1 wherein the compound is 2-[2-(dimethylamino)ethyl]-2,3-dihydro-4-methyl-pyrido-[3,4-f][1,4]oxazepine-5(4H)-thione or a pharmaceutically acceptable salt thereof.

34. The method of claim 1 wherein the compound is 2-(3-aminopropyl)-2,3-dihydro-4-methylpyrido[3,2-f][1,4]-oxazepin-5(4H)-one or a pharmaceutically acceptable salt thereof.

35. The method of claim 1 wherein the compound is 2,3-dihydro-4-methyl-2-[2-(4-morpholinyl)ethyl]-pyrido-[3,2-f][1,4]-oxazepin-5(4H)-one or a pharmaceutically acceptable salt thereof.

36. The method of claim 1 wherein the compound is 2,3-dihydro-4-methyl-2-[2-(1-pyrrolidinyl)ethyl]pyrido-[3,2-f][1,4]-oxazepin-5(4H)-one or a pharmaceutically acceptable salt thereof.

37. The method of claim 1 wherein the compound is 2-[2-(dibutylamino)ethyl]-2,3-dihydro-4-methyl-pyrido[3,2-f][1,4]-oxazepin-5(4H)-one or a pharmaceutically acceptable salt thereof.

38. The method of claim 1 wherein the compound is 2-[2-(diethylamino)ethyl]-2,3-dihydro-4-methylpyrido-[3,2-f][1,4]-oxazepin-5(4H)-one or a pharmaceutically acceptable salt thereof.

39. The method of claim 1 wherein the compound is 2,3-dihydro-4-methyl-2-[2-(1-piperidinyl)ethyl]pyrido-[3,2-f][1,4]-oxazepin-5(4H)-one or a pharmaceutically acceptable salt thereof.

40. The method of claim 1 wherein the compound is 2,3-dihydro-4-methyl-2-[2-[methyl(phenylmethyl)amino]ethyl]pyrido[3,2-f][1,4]-oxazepin-5(4H)-one or a pharmaceutically acceptable salt thereof.

41. The method of claim 1 wherein the compound is 2,3-dihydro-4-methyl-2-[2-(methylphenylamino)ethyl]-pyrido[3,2-f][1,4]-oxazepin-5(4H)-one or a pharmaceutically acceptable salt thereof.

42. The method of claim 1 wherein the compound is 2-[2-(2,5-dimethyl-1-pyrrolidinyl)ethyl]-2,3-dihydro-4-methylpyrido[3,2-f][1,4]-oxazepin-5(4H)-one or a pharmaceutically acceptable salt thereof.

43. The method of claim 1 wherein the compound is 2,3-dihydro-4-methyl-2-[2-(2-methyl-1-pyrrolidinyl)ethyl]pyrido[3,2-f][1,4]oxazepin-5(4H)-one or a pharmaceutically acceptable salt thereof.

44. The method of claim 1 wherein the compound is 2,3-dihydro-4-methyl-2-[2-(1H-pyrazol-1-yl)ethyl]-pyrido[3,2-f][1,4]-oxazepin-5(4H)-one or a pharmaceutically acceptable salt thereof.

45. The method of claim 1 wherein the compound is 2,3-dihydro-2-[2-(1H-imidazol-1-yl)ethyl]-4-methyl-pyrido[3,2-f][1,4]oxazepin-5(4H)-one or a pharmaceutically acceptable salt thereof.

46. The method of claim 1 wherein the compound is 2-[2-(dimethylamino)ethyl]-4-ethyl-2,3-dihydropyrido[3,2-f][1,4]-oxazepin-5(4H)-one or a pharmaceutically acceptable salt thereof.

47. The method of claim 1 wherein the compound is 2,3-dihydro-4-ethyl-2-[2-(1-pyrrolidinyl)ethyl]-pyrido[3,2-f][1,4]-oxazepin-5(4H)-one or a pharmaceutically acceptable salt thereof.

48. The method of claim 1 wherein the compound is 2,3-dihydro-4-methyl-2-[2-(4-morpholinyl)ethyl]-pyrido[3,2-f[1,4-]-oxazepin-5(4H)-thione or a pharmaceutically acceptable salt thereof.

49. The method of claim 1 wherein the compound is 2-[2-(dibutylamino)ethyl]-2,3-dihydro-4-methyl-pyrido[3,2-f][1,4]-oxazepine-5(4H)-thione or a pharmaceutically acceptable salt thereof.

50. The method of claim 1 wherein the compound is 2-[2-(diethylamino)ethyl]-2,3-dihydro-4-methyl-pyrido[3,2-f][1,4]-oxazepine-5-(4H)-thione or a pharmaceutically acceptable salt thereof.

51. The method of claim 1 wherein the compound is 2,3-dihydro-4-methyl-2-[2-(1-pyrrolidinyl)ethyl]-pyrido[3,2-f][1,4]oxazepine-5(4H)-thione or a pharmaceutically acceptable salt thereof.

52. The method of claim 1 wherein the compound is 2,3-dihydro-2-[2-(1H-imidazol-1-yl)ethyl]-4-methyl-pyrido[3,2-f][1,4]-oxazepin-5(4H)-thione or a pharmaceutically acceptable salt thereof.

53. The method of claim 1 wherein the compound is 2-[2-(dimethylamino)ethyl]-4-ethyl-2,3-dihydropyrido[3,2-f][1,4]-oxazepine-5(4H)-thione or a pharmaceutically acceptable salt thereof.

54. The method of claim 1 wherein the compound is 2,3-dihydro-4-methyl-2-[2-[methyl(phenylmethyl)amino]ethyl]pyrido-[3,2-f][1,4]-oxazepine-5(4H)-thione or a pharmaceutically acceptable salt thereof.

55. The method of claim 1 wherein the compound is 2,3-dihydro-2-[2-(methylamino)ethyl]-4-methylpyrido-[3,2-f][1,4]-oxazepine-5(4H)-thione or a pharmaceutically acceptable salt thereof.

56. The method of claim 1 wherein the compound is 7-chloro-2,3-dihydro-4-methyl-2-[2-(1-pyrrolidino)ethyl]pyrido[3,2-f][1,4]-oxazepin-5(4H)-one or a pharmaceutically acceptable salt thereof.

57. The method of claim 1 wherein the compound is 7-chloro-2-[2-(dimethylamino)ethyl]-2,3-dihydro-4-methylpyrido[3,2-f][1,4]-oxazepin-5(4H)-one or a pharmaceutically acceptable salt thereof.

58. The method of claim 1 wherein the compound is 2-[2-(dimethylamino)ethyl]-2,3-dihydro-4-phenylmethylpyrido[3,2-f][1,4]-oxazepine-5(4H)-one or a pharmaceutically acceptable salt thereof.

59. The method of claim 1 wherein the compound is 2-[2-(dimethylamino)ethyl]-2,3-dihydropyrido[3,2-f][1,4]-oxazepin-5(4H)-one or a pharmaceutically acceptable salt thereof.

60. The method of claim 1 wherein the compound is 2-[3-(dimethylamino)propyl]-2,3-dihydro-4-methyl-pyrido[3,2-f][1,4]-oxazepin-5(4H)-one or a pharmaceutically acceptable salt thereof.

61. The method of claim 1 wherein the compound is 2-[3-(dimethylamino)propyl]-2,3-dihydro-4-methyl-pyrido[3,2-f][1,4]-oxazepine-5(4H)-thione or a pharmaceutically acceptable salt thereof.

62. The method of claim 1 wherein the compound is 7-chloro-2-[2-(dimethylamino)ethyl]-2,3-dihydro-4-methylpyrido-[3,2-f][1,4]-oxazepine-5(4H)-thione or a pharmaceutically acceptable salt thereof.

63. The method of claim 1 wherein the compound is 2,3-dihydro-4-methyl-2-[2-(methylamino)ethyl]-pyrido[3,2-f][1,4]-oxazepin-6(4H)-one or a pharmaceutically acceptable salt thereof.

64. The method of claim 1 wherein the compound is 2-(-2-aminoethyl)-2,3-dihydro-4-methylpyrido[3,2-f][1,4]-oxazepin-5(4H)-one or a pharmaceutically acceptable salt thereof.

65. The method of claim 1 wherein the compound is 2-(-2-aminoethyl)-2,3-dihydro-4-methylpyrido[3,2-f][1,4]-oxazepine-5(4H)-thione or a pharmaceutically acceptable salt thereof.

66. The method of claim 1 wherein the compound is 2,3-dihydro-4-methyl-2-[2-[1-(methylethyl)amino]ethyl]-pyrido[3,2-f][1,4]-oxazepin-5(4H)-one or a pharmaceutically acceptable salt thereof.

67. The method of claim 1 wherein the compound is 2-[2-[bis-(phenylmethyl)amino]ethyl]-2,3-dihydro-4-methylpyrido[3,2-f][1,4]oxazepine-5(4H)-thione or a pharmaceutically acceptable salt thereof.

68. The method of claim 1 wherein the compound is 2,3-dihydro-4-methyl-2-[2,4-methyl-1-piperizinyl)ethyl]-pyrido[3,2-f]-[1,4]-oxazepin-5(4H)-one or a pharmaceutically acceptable salt thereof.

69. The method of claim 1 wherein the compound is 2,3-dihydro-4-methyl-2-[2-(4-methyl-1-piperazinyl)ethyl]-pyrido[3,2-f]-[1,4]-oxazepine-5(4H)-thione or a pharmaceutically acceptable salt thereof.

70. The method of claim 1 wherein the compound is 2-[2-[4-bis(4-fluorophenyl)methyl]-1-piperidinyl]ethyl]-2,3-dihydro-4-methylpyrido[3,2-f][1,4]-oxazepin-5(4H)-one or a pharmaceutically acceptable salt thereof.

71. The method of claim 1 wherein the compound is 2-[2-(4,5-dihydro-1H-imidazol-2-yl)ethyl]-2,3-dihydro-4-methylpyrido-[3,2-f]-[1,4]-oxazepin-5(4H)-one or a pharmaceutically acceptable salt thereof.

72. The method of claim 1 wherein the compound is 2,3-dihydro-4-methyl-2-[2-(methylphenylamino)ethyl]-pyrido[3,2-f][1,4]-oxazepine-5(4H)-thione or a pharmaceutically acceptable salt thereof.

73. The method of claim 1 wherein the compound is 2-(3-aminopropyl)-2,3-dihydro-4-methylpyrido[3,2-f][1,4]-oxazepine-5(4H)-thione or a pharmaceutically acceptable salt thereof.

74. The method of claim 1 wherein the compound is 2-[2-(dimethylamino)ethyl]-2,3-dihydropyrido[3,2-f][1,4]-oxazepine-5(4H)-thione or a pharmaceutically acceptable salt thereof.

75. The method of claim 1 wherein the compound is 2-[2-[4-[bis(4-fluorophenyl)methyl]-1-piperidinyl]ethyl]-2,3-dihydro-4-methylpyrido[3,2-f][1,4]-oxazepine-5(4H)-thione or a pharmaceutically acceptable salt thereof.

76. The method of claim 1 wherein the compound is 2,3-dihydro-4-methyl-2-[2-(1H-pyazol-1-yl)ethyl]-pyrido[3,2-f][1,4]-oxazepine-5(4H)-thione or a pharmaceutically acceptable salt thereof.

77. The method of claim 1 wherein the compound is 2-[2-(dimethylamino)-1-methylethyl]-2,3-dihydro-4-methylpyrido[3,2-f][1,4]-oxazepin-5(4H)-one or a pharmaceutically acceptable salt thereof.

78. The method of claim 1 wherein the compound is 2,3-dihydro-2-[2-(4,5-dihydro-1H-imidazol-2-yl)ethyl]-4-methylpyrido-[3,2-f][1,4]-oxazepine-5(4H)-thione or a pharmaceutically acceptable salt thereof.

79. The method of claim 1 wherein the compound is 2-[2-(dimethylamino)ethyl]-2,3-dihydro-2,4-dimethylpyrido-[3,2-f][1,4]-oxazepin-5(4H)-one or a pharmaceutically acceptable salt thereof.

80. The method of claim 1 wherein the compound is 2-[2-(dimethylamino)ethyl]-2,3-dihydro-2,4-dimethylpyrido-[3,2-f][1,4]-oxazepine-5(4H)-thione or a pharmaceutically acceptable salt thereof.

81. The method of claim 1 wherein the compound is 2-[2-(dimethylamino)ethyl]-2,3-dihydro-4-methyl[1,4]-oxazepino[6,7-c]-quinolin-5(4H)-one or a pharmaceutically acceptable salt thereof.

82. The method of claim 1 wherein the compound is 2-[2-(dimethylamino)-1-methylethyl]-2,3-dihydro-4-methylpyrido[3,2-f][1,4]-oxazepine-5(4H)-thione or a pharmaceutically acceptable salt thereof.

83. The method of claim 1 wherein the compound is 2-[2-(dimethylamino)propyl]-2,3-dihydro-4-methylpyrido[3,2-f][1,4]-oxazepin-5(4H)-one or a pharmaceutically acceptable salt thereof.

84. The method of claim 1 wherein the compound is 2,3-dihydro-4-methyl-2-[2-methyl-1-pyrrolidinyl)ethyl]pyrido-[3,2-f]-[1,4]-oxazepine-5(4H)-thione or a pharmaceutically acceptable salt thereof.

85. The method of claim 1 wherein the compound is 2-[2-dimethylamino)ethyl]-2,3-dihydro-4-methyl-9-(trifluoromethyl)[1,4]-oxazepino-[6,7-c]-quinolin-5(4H)-one or a pharmaceutically acceptable salt thereof.

86. The method of claim 1 wherein the compound is 2-[2-dimethylamino)ethyl]-2,3-dihydro-4-methyl[1,4]-oxazepino[6,7-b]-quinolin-5(4H)-one or a pharmaceutically acceptable salt thereof.

87. The method of claim 1 wherein the compound is 2-[2-(dimethylamino)ethyl]-2,3-dihydro-4-methyl-[1,4]-oxazepino-[6,7b]-quinoline-5(4H)-thione or a pharmaceutically acceptable salt thereof.

88. The method of claim 1 wherein the compound is 4-ethyl-1,2,3,4-tetrahydro-2-[2-(4-hydroxy-4-phenyl-1-piperidinyl)ethyl]-1-methyl-5H-1,4-benzodiazepin-5-one or a pharmaceutically acceptable salt thereof.

89. The method of claim 1 wherein the compound is 4-ethyl-1-methyl-2-(2-morpholinoethyl)-1,2,3,4-tetrahydro-5H-1,4-benzodiazepin-5-one or a pharmaceutically acceptable salt thereof.

90. The method of claim 1 wherein the compound is 1,2,3,4-tetrahydro-1-methyl-2-[(dimethylamino)methyl]-4-(1-methylethyl)-5H-1,4-benzodiazepin-5-one or a pharmaceutically acceptable salt thereof.

91. The method of claim 1 wherein the compound is 2-(2-dimethylaminoethyl)-4-ethyl-1-methyl-1,2,3,4-tetrahydro-5H-1,4-benzodiazepin-5-one or a pharmaceutically acceptable salt thereof.

92. The method of claim 1 wherein the compound is 2,3-dihydro-4-methyl-2[2-(1-piperidinyl)ethyl]-pyrido[3,2-f][1,4]-oxazepine-5(4H)-thione or a pharmaceutically acceptable salt thereof.

93. The method of claim 1 wherein the compound is 6-chloro-2,3-dihydro-4-methyl-2-[2-(dimethylamino)ethyl]-4-methylpyrido[4,3-f][1,4]-oxazepine-5(4H)-thione or a pharmaceutically acceptable salt thereof.

94. The method of claim 1 wherein the compound is 2,3-dihydro-4-methyl-6-dimethylamino-2[2-(dimethylamino)ethyl]-4-methylpyrido[4,3-f][1,4]-oxazepin-5(4H)-one or a pharmaceutically acceptable salt thereof.

95. The method of claim 1 wherein the compound is 2,3-dihydro-2-[2-(2,5-dihydro-1H-pyrrol-1-yl)ethyl]-4-methylpyrido[3,2-f]-1,4-oxazepin-5(4H)-one or a pharmaceutically acceptable salt thereof.

96. The method of claim 1 wherein the compound is 2,3-dihydro-2-[2-(2,5-dihydro-1H-pyrrol-1-yl)ethyl]-4-methylpyrido[3,2-f]-1,4-oxazepin-5(4H)-thione or a pharmaceutically acceptable salt thereof.

97. The method of claim 1 wherein the compound is 2-[2-(1-azetidinyl)ethyl]-2,3-dihydro-4-methylpyrido-[3,2-f]-[1,4]-oxazepin-5(4H)-one or a pharmaceutically acceptable salt thereof.

98. The method of claim 1 wherein the compound is 2-[(dimethylamino)methyl]-2,3-dihydro-4-methylpyrido[3,2-f][1,4]-oxazepin-5(4H)-one or a pharmaceutically acceptable salt thereof.

99. The method of claim 1 wherein the compound is 2-[(dimethylamino)methyl]-2,3-dihydro-4-methylpyrido[3,2-f][1,4]-oxazepine-5(4H)-thione or a pharmaceutically acceptable salt thereof.

100. The method of claim 1 wherein the compound is 2-[2-(dimethylamino)ethyl]-2,3-dihydro-4-methylpyrido[3,2-f][1,4]-oxazepine-5(4H)-thione fumarate[1:1].

101. The method of claim 1 wherein the compound is 2-[2-(1-azetidinyl)ethyl]-2,3-dihydro-4-methylpyrido[3,2-f][1,4]oxazepine-5(4H)-thione or a pharmaceutically acceptable salt thereof.

102. A pharmaceutical composition suitable for counteracting histamine comprising:
(a) an effective amount of a compound selected from the group having the formula:

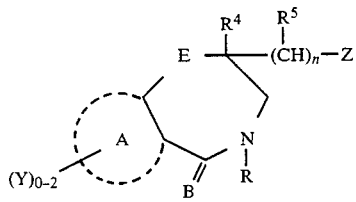

wherein;
A represents an aromatic ring having two of its carbon atoms held mutually with the oxazepine, thiazepine, or diazepine moiety selected from the group consisting of benzene, naphthalene, a quinoline, or a pyridine in any of its four positions, any of the rings optionally substituted by one or two Y radicals selected from the group consisting of halo, loweralkyl, loweralkoxy, diloweralkylamino, nitro or trifluoromethyl;
E is selected from oxygen, sulfur or

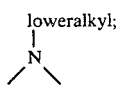

B is selected from oxygen or sulfur;
R is selected from the group consisting of hydrogen, loweralkyl, cycloalkyl or phenyl-loweralkyl of which phenyl may be optionally substituted by one or two radicals selected from halo, loweralkyl, loweralkoxy, nitro, or trifluoromethyl;
n is 1, 2 or 3;
$R^4$ and $R^5$ are selected from hydrogen or loweralkyl (1–5 C);
Z is selected from the group consisting of —$NR^1R^2$, 1H-pyrazol-1-yl, 1H-imidazol-1-yl, 1H-imidazol-2-yl or 4,5-dihydro-1H-imidazol-2-yl;
$R^1$ and $R^2$ are selected from the group consisting of hydrogen, loweralkyl, cycloalkyl and phenyl-loweralkyl of which phenyl may be optionally substituted by 1 or 2 radicals selected from halo, loweralkyl, loweralkoxy, nitro, trifluoromethyl or cyano, or $R^1$ and $R^2$ taken together with the adjacent nitrogen atom may form a heterocyclic residue selected from the group consisting of 1-azetidinyl, 1-pyrrolidinyl, 2,5-dimethylpyrrolidin-1-yl, 2-methylpyrrolidin-1-yl, 1-piperidinyl, 4-substituted piperidin-1-yl, 4-[bis(4-fluorophenyl)methyl]-piperidin-1-yl, 4-morpholinyl, 1-piperazinyl, 4-substituted piperazin-1-yl, 1,2,3,6-tetrahydropyridin-1-yl, 1H-pyrrol-1-yl or 2,5-dihydro-1H-pyrrol-1-yl; the optical isomers thereof and the pharmaceutically acceptable salts thereof with the proviso that when R=H, Z is never a primary or secondary amine and a further proviso that when N=3, Z is not pyrazolyl or imidazolyl, and
(b) a pharmaceutical carrier therefor.

103. The pharmaceutical composition of claim 102 wherein the compound is 2-[2-(dimethylamino)ethyl]-4-methyl-2,3-dihydro-1,4-benzoxazepin-5(4H)-one or a pharmaceutically acceptable salt thereof.

104. The pharmaceutical composition of claim 102 wherein the compound is 2,3-dihydro-4-methyl-2-[2-(4-morpholino)ethyl]-1,4-benzoxazepin-5(4H)-one or a pharmaceutically acceptable salt thereof.

105. The pharmaceutical composition of claim 102 wherein the compound is 4-benzyl-2,3-dihydro-2-[2-(4-morpholino)ethyl]-1,4-benzoxazepin-5(4H)-one or a pharmaceutically acceptable salt therof.

106. The pharmaceutical composition of claim 102 wherein the compound is 4-benzyl-2,3-dihydro-2-[2-methylamino)ethyl]-1,4-benzoxazepin-5(4H)-one or a pharmaceutically acceptable salt thereof.

107. The pharmaceutical composition of claim 102 wherein the compound is 2-[2-(dimethylamino)ethyl]2,3-dihydro-4-methyl-1,4-benzoxazepine-5(4H)-thione or a pharmaceutically acceptable salt thereof.

108. The pharmaceutical composition of claim 102 wherein the compound is 4-benzyl-2-[2-(dimethylamino)-ethyl]-2,3-dihydro-1,4-benzoxazepin-5(4H)-one or a pharmaceutically acceptable salt thereof.

109. The pharmaceutical composition of claim 102 wherein the compound is 2,3-dihydro-4-methyl-2-[2-(4-morpholino)ethyl]-1,4-benzoxazepine-5(4H)-thione or a pharmaceutically acceptable salt thereof.

110. The pharmaceutical composition of claim 102 wherein the compound is 2-[2-(dimethylamino)ethyl]-2,3-dihydro-4-methylnaphth[2,3-f][1,4]oxazepin-5(4H)-one or a pharmaceutically acceptable salt thereof.

111. The pharmaceutical composition of claim 102 wherein the compound is 2-[2-(dimethylamino)ethyl]-2,3-dihydro-4-methylpyrido[3,2-f][1,4]oxazepin-5(4H)-one or a pharmaceutically acceptable salt thereof.

112. The pharmaceutical composition of claim 102 wherein the compound is 2-[2-(dimethylamino)ethyl]-2,3-dihydro-4-methylpyrido[3,2-f]-1,4-oxazepine-5(4H)-thione or a pharmaceutically acceptable salt thereof.

113. The pharmaceutical composition of claim 102 wherein the compound is 4-benzyl-1,3-dihydro-2-[2-(4-morpholino)ethyl]-1,4-benzoxazepine-5(4H)-thione or a pharmaceutically acceptable salt thereof.

114. The pharmaceutical composition of claim 102 wherein the compound is 2,3-dihydro-4-methyl-2-[2-(methylamino)ethyl]-1,4-benzoxazepin-5(4H)-one or a pharmaceutically acceptable salt thereof.

115. The pharmaceutical composition of claim 102 wherein the compound is 2,3-dihydro-4-methyl-2-[2-(methylamino)ethyl]-1,4-benzoxazepin-5(4H)-one or a pharmaceutically acceptable salt thereof.

116. The pharmaceutical composition of claim 102 wherein the compound is 2,3-dihydro-2-[2-(4-hydroxy-4-phenyl)piperidinylethyl]-4-methyl-1,4-benzoxazepine-5(4H)-thione or a pharmaceutically acceptable salt thereof.

117. The pharmaceutical composition of claim 102 wherein the compound is 2,3-dihydro-4-methyl-2-[1-[4-phenyl-1,2,3,6-tetrahydro)pyridyl]ethyl-1,4-benzoxazepine-5(4H)-thione or a pharmaceutically acceptable salt thereof.

118. The pharmaceutical composition of claim 102 wherein the compound is 8-chloro-2-[2-(dimethylamino)-ethyl]-2,3-dihydro-4-methyl-1,4-benzoxazepine-5(4H)-thione or a pharmaceutically acceptable salt thereof.

119. The pharmaceutical composition of claim 102 wherein the compound is 8-chloro-2-[2-(dimethylamino)-ethyl]-2,3-dihydro-4-methyl-1,4-benzoxazepin-5(4H)-one or a pharmaceutically acceptable salt thereof.

120. The pharmaceutical composition of claim 102 wherein the compound is 7-bromo-2-[2-(dimethylamino)-ethyl]-2,3-dihydro-4-methyl-1,4-benzoxazepine-5(4H)-thione or a pharmaceutically acceptable salt thereof.

121. The pharmaceutical composition of claim 102 wherein the compound is 2-[2-(dimethylamino)ethyl]-2,3-dihydro-4-methylnaphth[2,1-f][1,4]oxazepin-5(4H)-one or a pharmaceutically acceptable salt thereof.

122. The pharmaceutical composition of claim 102 wherein the compound is 2-[2-(dimethylamino)ethyl]-2,3-dihydro-4-methylpyrido[4,3-f][1,4]oxazepine-5(4H)-thione or a pharmaceutically acceptable salt thereof.

123. The pharmaceutical composition of claim 102 wherein the compound is 2-[2-(diethylamino)ethyl]-2,3-dihydro-4-methylpyrido[3,2-f]-1,4-oxazepine-5(4H)-thione or a pharmaceutically acceptable salt thereof.

124. The pharmaceutical composition of claim 102 wherein the compound is 2-[2-(dimethylamino)ethyl]-2,3-dihydro-4-methylnaphth[2,3-f][1,4]oxazepine-t(4H)-thione or a pharmaceutically acceptable salt thereof.

125. The pharmaceutical composition of claim 102 wherein the compound is 7-chloro-2-[2-(dimethylamino)-ethyl]-2,3-dihydro-4-methyl-1,4-benzoxazepin-5(4H)-one or a pharmaceutically acceptable salt thereof.

126. The pharmaceutical composition of claim 102 wherein the compound is 2-[2-(dimethylamino)ethyl]-2,3-dihydro-4-methylpyrido[3,2][1,4]oxazepin-5(4H)-thione methiodide.

127. The pharmaceutical composition of claim 102 wherein the compound is 7-chloro-2-[2-(dimethylamino)-ethyl]-2,3-dihydro-4-methyl-1,4-benzoxazepine-5(4H)-thione or a pharmaceutically acceptable salt thereof.

128. The pharmaceutical composition of claim 102 wherein the compound is 2-[2-(dimethylamino)ethyl]-2,3-dihydro-4-methylnephth[2,1-f][1,4]oxazepine-5(4H)-thione or a pharmaceutically acceptable salt thereof.

129. The pharmaceutical composition of claim 102 wherein the compound is 2-[2-(dimethylamino)ethyl]-2,3-dihydro-7-methoxy-4-methyl-1,4-benzoxazepine-5(4H)-one or a pharmaceutically acceptable salt thereof.

130. The pharmaceutical composition of claim 102 wherein the compound is 7-bromo-2-[2-(dimethylamino)-ethyl]-2,3-dihydro-4-methyl-1,4-benzoxazepine-5(4H)-thione or a pharmaceutically acceptable salt thereof.

131. The pharmaceutical composition of claim 102 wherein the compound is 2-[2-(dimethylamino)ethyl]-2,3-dihydro-4-methylpyrido[3,2-f][1,4]-one or a pharmaceutically acceptable salt thereof.

132. The pharmaceutical composition of claim 102 wherein the comnpound is 2-[2-(dimethylamino)ethyl]-2,3-dihydro-4-methylpyrido[3,2-f][1,4]-thiazepine-5(4H)-thione or a pharmaceutically acceptable salt thereof.

133. The pharmaceutical composition of claim 102 wherein the compound is 2-[2-(dimethylamino)ethyl]-2,3-dihydro-4-methylpyrido-[3,4-f][1,4]-oxazepin-5(4H)-one or a pharmaceutically acceptable salt thereof.

134. The pharmaceutical composition of claim 102 wherein the compound is 2-[2-(dimethylamino)ethyl]-2,3-dihydro-4-methylpyrido[3,4-f][1,4]oxazepine-5(4H)-thione or a pharmaceutically acceptable salt thereof.

135. The pharmaceutical composition of claim 102 wherein the compound is 2-(3-aminopropyl)-2,3-dihydro-4-methyl-pyrido[3,2-f][1,4]-oxazepin-5(4H)-one or a pharmaceutically acceptable salt thereof.

136. The pharmaceutical composition of claim 102 wherein the compound is 2,3-dihydro-4-methyl-2-[2-(4-morpholinyl)ethyl]-pyrido[3,2-f][1,4]-oxazepin-5(4H)-one or a pharmaceutically acceptable salt thereof.

137. The pharmaceutical composition of claim 102 wherein the compound is 2,3-dihydro-4-methyl-2-[2-(1-pyrrolidinyl)ethyl]-pyrido-[3,2-f][1,4]-oxazepin-5(4H)-one or a pharmaceutically acceptable salt thereof.

138. The pharmaceutical composition of claim 102 wherein the compound is 2-[2-(dibutylamino)ethyl]-2,3-dihydro-4-methyl-pyrido-[3,2-f][1,4]-oxazepin-5(4H)-one or a pharmaceutically acceptable salt thereof.

139. The pharmaceutical composition of claim 102 wherein the compound is 2-[2-(diethylamino)ethyl]-2,3-dihydro-4-methylpyrido-[3,2-f][1,4]-oxazepin-5(4H)-one or a pharmaceutically acceptable salt thereof.

140. The pharmaceutical composition of claim 102 wherein the compound is 2,3-dihydro-4-methyl-2-[2-(1-piperidinyl)ethyl]pyrido[3,2-f][1,4]-oxazepin-5(4H)-one or a pharmaceutically acceptable salt thereof.

141. The pharmaceutical composition of claim 102 wherein the compound is 2,3-dihydro-4-methyl-2-[2-[methyl-(phenylmethyl)amino]ethyl]pyrido-[3,2-f][1,4]-oxazepin-5(4H)-one or a pharmaceutically acceptable salt thereof.

142. The pharmaceutical composition of claim 102 wherein the compound is 2,3-dihydro-4-methyl-2-[2-(methylphenylamino)ethyl]pyrido[3,2-f][1,4-oxazepin-5(4H)-one or a pharmaceutically acceptable salt thereof.

143. The pharmaceutical composition of claim 102 wherein the compound is 2-[2-(2,5-dimethyl-1-pyrrolidinyl)-ethyl]-2,3-dihydro-4-methyl-pyrido[3,2-f][1,4]-oxazepin-5(4H)-one or a pharmaceutically acceptable salt thereof.

144. The pharmaceutical composition of claim 102 wherein the compound is 2,3-dihydro-4-methyl-2-[2-(2-methyl-1-pyrrolidinyl)ethyl]pyrido-[3,2-f][1,4]-oxazepin-5(4H)-one or a pharmaceutically acceptable salt thereof.

145. The pharmaceutical composition of claim 102 wherein the compound is 2,3-dihydro-4-methyl-2-[2-(1H-pyrazol-1-yl)ethyl]-pyrido[3,2-f][1,4]-oxazepin-5(4H)-one or a pharmaceutically acceptable salt thereof.

146. The pharmaceutical composition of claim 102 wherein the compound is 2,3-dihydro-2-[2-(1H-imidazol-1-yl)ethyl]-4-methylpyrido[3,2-f][1,4]oxazepin-5(4H)-one or a pharmaceutically acceptable salt thereof.

147. The pharmaceutical composition of claim 102 wherein the compound is 2-[2-(dimethylamino)ethyl]-4-ethyl-2,3-dihydro-pyrido[3,2-f][1,4]-oxazepin-5(4H)-one or a pharmaceutically acceptable salt thereof.

148. The pharmaceutical composition of claim 102 wherein the compound is 2,3-dihydro-4-ethyl-2-[2-(1-pyrrolidinyl)ethyl]pyrido[3,2-f][1,4]oxazepin-5(4H)-one or a pharmaceutically acceptable salt thereof.

149. The pharmaceutical composition of claim 102 wherein the compound is 2,3-dihydro-4-methyl-2-[2-(4-morpholinyl)ethyl]pyrido[3,2-f][1,4]oxazepine-5(4H)-thione or a pharmaceutically acceptable salt thereof.

150. The pharmaceutical composition of claim 102 wherein the compound is 2-[2-(dibutylamino)ethyl]-2,3-dihydro-4-methylpyrido[3,2-f][1,4]oxazepine-5(4H)-thione or a pharmaceutically acceptable salt thereof.

151. The pharmaceutical composition of claim 102 wherein the compound is 2-[2-(diethylamino)ethyl]-2,3-dihydro-4-methylpyrido[3,2-f][1,4]-oxazepine-5(4H)-thione or a pharmaceutically acceptable salt thereof.

152. The pharmaceutical composition of claim 102 wherein the compound is 2,3-dihydro-4-methyl-2-[2-(1-pyrrolidinyl)ethyl]pyrido-[3,2-f][1,4]oxazepine-5(4H)-thione or a pharmaceutically acceptable salt thereof.

153. The pharmaceutical composition of claim 102 wherein the compound is 2,3-dihydro-2-[2-(1H-imidazol-1-yl)ethyl]-4-methylpyrido[3,2-f][1,4]-oxazepine-5(4H)-thione or a pharmaceutically acceptable salt thereof.

154. The pharmaceutical composition of claim 102 wherein the compound is 2-[2-(dimethylamino)ethyl]-4-ethyl-2,3-dihydropyrido[3,2-f][1,4]-oxazepine-5(4H)-thione or a pharmaceutically acceptable salt thereof.

155. The pharmaceutical composition of claim 102 wherein the compound is 2,3-dihydro-4-methyl-2-[2-[methyl-(phenylmethyl)amino]ethyl]pyrido-[3,2-f][1,4]-oxazepine-5(4H)-thione or a pharmaceutically acceptable salt thereof.

156. The pharmaceutical composition of claim 102 wherein the compound is 2,3-dihydro-2-[2-(methylamino)ethyl)-4-methylpyrido-[3,2-f][1,4]-oxazepine-5(4H)-thione or a pharmaceutically acceptable salt thereof.

157. The pharmaceutical composition of claim 102 wherein the compound is 7-chloro-2,3-dihydro-4-methyl-2-[2-(2-pyrrolidino)ethyl]pyrido[3,2-f][1,4]-oxazepin-5(4H)-one or a pharmaceutically acceptable salt thereof.

158. The pharmaceutical composition of claim 102 wherein the compound is 7-chloro-2[2-(dimethylamino)ethyl]-2,3-dihydro-4-methylpyrido[3,2-f][1,4]-oxazepin-5(4H)-one or a pharmaceutically acceptable salt thereof.

159. The pharmaceutical composition of claim 102 wherein the compound is 2-[2-(dimethylamino)ethyl]-2,3-dihydro-4-phenylmethylpyrido[3,2-f][1,4]-oxazepin-5(4H)-one or a pharmaceutically acceptable salt thereof.

160. The pharmaceutical composition of claim 102 wherein the compound is 2-[2-(dimethylamino)ethyl]-2,3-dihydropyrido[3,2-f][1,4]-oxazepin-5(4H)-one or a pharmaceutically acceptable salt thereof.

161. The pharmaceutical composition of claim 102 wherein the compound is 2-[3-(dimethylamino)propyl]-2,3-dihydro-4-methylpyrido[3,2-f][1,4]-oxazepin-5(4H)-one or a pharmaceutically acceptable salt thereof.

162. The pharmaceutical composition of claim 102 wherein the compound is 2-[3-(dimethylamino)propyl]-2,3-dihydro-4-methylpyrido[3,2-f][1,4]-oxazepine-5(4H)-thione or a pharmaceutically acceptable salt thereof.

163. The pharmaceutical composition of claim 102 wherein the compound is 7-chloro-2-[2-(dimethylamino)ethyl]-2,3-dihydro-4-methylpyrido-[3,2-f][1,4]-oxazepine-5(4H)-thione or a pharmaceutically acceptable salt thereof.

164. The pharmaceutical composition of claim 102 which is 2,3-dihydro-4-methyl-2-[2(methylamino)ethyl]-pyrido[3,2-f][1,4]-oxazepin-5(4H)-one or a pharmaceutically acceptable salt thereof.

165. The pharmaceutical composition of claim 102 which is 2-(-2-aminoethyl)-2,3-dihydro-4-methylpyrido[3,2-f][1,4]-oxazepin-5(4H)-one or a pharmaceutically acceptable salt thereof.

166. The pharmaceutical composition of claim 102 which is 2-(-2-aminoethyl)-2,3-dihydro-4-methylpyrido[3,2-f][1,4]-oxazepine-5(4H)-thione or a pharmaceutically acceptable salt thereof.

167. The pharmaceutical composition of claim 102 which is 2,3-dihydro-4-methyl-2-[2-(1-(methylethyl)amino]ethyl]-pyrido-[3,2-f][1,4]-oxazepin-5(4H)-one or a pharmaceutically acceptable salt thereof.

168. The pharmaceutical composition of claim 102 which is 2-[2-[bis-(phenylmethyl)amino]ethyl]-2,3-dihydro-4-methylpyrido-[3,2-f][1,4]oxazepine-5(4H)-thione or a pharmaceutically acceptable salt thereof.

169. The pharmaceutical composition of claim 102 which is 2,3-dihydro-4-methyl-2-[2,4-methyl-1-piperizinyl)ethyl]-pyrido[3,2-f]-[1,4]-oxazepin-5(4H)-one or a pharmaceutically acceptable salt thereof.

170. The pharmaceutical composition of claim 102 which is 2,3-dihydro-4-methyl-2-[2-(4-methyl-1-piperazinyl)ethyl]pyrido[3,2-f]-[1,4]-oxazepine-5(4H)-thione or a pharmaceutically acceptable salt thereof.

171. The pharmaceutical composition of claim 102 which is 2-[2-[4-bis(4-fluorophenyl)methyl]-1-piperidinyl]ethyl]-2,3-dihydro-4-methylpyrido[3,2-f][1,4]-oxazepin-5(4H)-one or a pharmaceutically acceptable salt thereof.

172. The pharmaceutical composition of claim 102 which is 2-[2-(4,5-dihydro-1H-imidazol-2-yl)ethyl]-2,3-dihydro-4-methylpyrido-[3,2-f]-[1,4]-oxazepin-5(4H)-one or a pharmaceutically acceptable salt thereof.

173. The pharmaceutical composition of claim 102 which is 2,3-dihydro-4-methyl-2-[2-(methylphenylamino)ethyl]pyrido[3,2-f][1,4]-oxazepine-5(4H)-thione or a pharmaceutically acceptable salt thereof.

174. The pharmaceutical composition of claim 102 which is 2-(3-aminopropyl)-2,3-dihydro-4-methylpyrido[3,2-f][1,4]oxazepine-5(4H)-thione or a pharmaceutically acceptable salt thereof.

175. The pharmaceutical composition of claim 102 which is 2-[2-(dimethylamino(ethyl)-2,3-dihydro[3,2-f][1,4]-oxazepine-5(4H)-thione or a pharmaceutically acceptable salt thereof.

176. The pharmaceutical composition of claim 102 which is 2-[2-[4-[bis(4-fluorophenyl)methyl]-1-piperidinyl]ethyl]-2,3-dihydro-4-methylpyrido[3,2-f][1,4]-oxazepine-5(4H)-thione or a pharmaceutically acceptable salt thereof.

177. The pharmaceutical composition of claim 102 which is 2,3-dihydro-4-methyl-2-[2-(1H-pyazol-1-yl)ethyl]pyrido[3,2-f]-[1,4]-oxazepine-5(4H)-thione or a pharmaceutically acceptable salt thereof.

178. The pharmaceutical composition of claim 102 which is 2-[2-(dimethylamino)-1-methylethyl]-2,3-dihydro-4-methylpyrido-[3,2-f][1,4]-oxazepin-5(4H)-one or a pharmaceutically acceptable salt thereof.

179. The pharmaceutical composition of claim 102 which is 2,3-dihydro-2-[2-(4,5-dihydro-1H-imidazol-2-yl)ethyl]-4-methylpyrido-[3,2-f][1,4]-oxazepine-5(4H)-thione or a pharmaceutically acceptable salt thereof.

180. The pharmaceutical composition of claim 102 which is 2-[2-(dimethylamino)ethyl]-2,3-dihydro-2,4-dimethylpyrido[3,2-f]-[1,4]-oxazepin-5(4H)-one or a pharmaceutically acceptable salt thereof.

181. The pharmaceutical composition of claim 102 which is 2-[2-(dimethylamino)ethyl]-2,3-dihydro-2,4-dimethylpyrido[3,2-f][1,4]-oxazepine-5(4H)-thione or a pharmaceutically acceptable salt thereof.

182. The pharmaceutical composition of claim 102 which is 2-[2-(dimethylamino)ethyl]-2,3-dihydro-4-methyl[1,4]-oxazepino-[6,7-c]-quinolin-5(4H)-one or a pharmaceutically acceptable salt thereof.

183. The pharmaceutical composition of claim 102 which is 2-[2-(dimethylamino)-1-methylethyl]-2,3-dihydro-4-methylpyrido-[3,2-f][1,4]-oxazepine-5(4H)-thione or a pharmaceutically acceptable salt thereof.

184. The pharmaceutical composition of claim 102 which is 2-[2-(dimethylamino)propyl]-2,3-dihydro-4-methylpyrido[3,2-f]-[1,4]-oxazepin-5(4H)-one or a pharmaceutically acceptable salt thereof.

185. The pharmaceutical composition of claim 102 which is 2,3-dihydro-4-methyl-2-[2-methyl-1-pyrrolidinyl)ethyl]pyrido[3,2-f][1,4]-oxazepine-5(4H)-thione or a pharmaceutically acceptable salt thereof.

186. The pharmaceutical composition of claim 102 which is 2-[2-dimethylamino)ethyl]-2,3-dihydro-4-methyl-9-(trifluoromethyl)[1,4]-oxazepino-[6,7-c]-quinolin-5(4H)-one or a pharmaceutically acceptable salt thereof.

187. The pharmaceutical composition of claim 102 which is 2-[2-dimethylamino)ethyl]-2,3-dihydro-4-methyl[1,4]-oxazepino-[6,7-b]-quinolin-5(4H)-one or a pharmaceutically acceptable salt thereof.

188. The pharmaceutical composition of claim 102 which is 2-[2-(dimethylamino)ethyl]-2,3-dihydro-4-methyl-[1,4]-oxazepino[6,7b]-quinoline-5(4H)-thione or a pharmaceutically acceptable salt thereof.

189. The pharmaceutical composition of claim 102 which is 4-ethyl-1,2,3,4-tetrahydro-2-[2-(4-hydroxy-4-phenyl-1-piperidinyl)ethyl]-1-methyl-5H-1,4-benzodiazepin-5-one or a pharmaceutically acceptable salt thereof.

190. The pharmaceutical composition of claim 102 which is 4-ethyl-1-methyl-2-(2-morpholinoethyl)-1,2,3,4-tetrahydro-5H-1,4-benzodiazepin-5-one or a pharmaceutically acceptable salt thereof.

191. The pharmaceutical composition of claim 102 which is 1,2,3,4-tetrahydro-1-methyl-2-[(dimethylamino)methyl]-4-(1-methylethyl)-5H-1,4-benzodiazepin-5-one or a pharmaceutically acceptable salt thereof.

192. The pharmaceutical composition of claim 102 which is 2-(2-dimethylaminoethyl)-4-ethyl-1-methyl-1,2,3,4-tetrahydro-5H-1,4-benzodiazepin-5-one or a pharmaceutically acceptable salt thereof.

193. The pharmaceutical composition of claim 102 which is 2,3-dihydro-4-methyl-2[2-(1-piperidinyl)ethyl]pyrido[3,2-f]-[1,4]-oxazepine-5(4H)-thione or a pharmaceutically acceptable salt thereof.

194. The pharmaceutical composition of claim 102 which is 6-chloro-2,3-dihydro-4-methyl-2-[2-(dimethylamino)ethyl]-4-methylpyrido[4,3-f][1,4]-oxazepine-5(4H)-thione or a pharmaceutically acceptable salt thereof.

195. The pharmaceutical composition of claim 102 which is 2,3-dihydro-4-methyl-6-dimethylamino-2[2-(dimethylamino)ethyl]-4-methyl-pyrido[4,3-f][1,4]-oxazepin-5(4H)-one or a pharmaceutically acceptable salt thereof.

196. The pharmaceutical composition of claim 102 which is 2,3-dihydro-2-[2-(2,5-dihydro-1H-pyrrol-1-yl)ethyl]-4-methylpyrido[3,2-f]-1,4-oxazepin-5(4H)-one or a pharmaceutically acceptable salt thereof.

197. The pharmaceutical composition of claim 102 which is 2,3-dihydro-2-[2-(2,5-dihydro-1H-pyrrol-1-yl)ethyl]-4-methylpyrido[3,2-f]-1,4-oxazepin-5(4H)-thione or a pharmaceutically acceptable salt thereof.

198. The pharmaceutical composition of claim 102 which is 2-[2-(1-azetidinyl)ethyl]-2,3-dihydro-4-methyl-pyrido-[3,2-f][1,4]-oxazepin-5(4H)-one or a pharmaceutically acceptable salt thereof.

199. The pharmaceutical composition of claim 102 which is 2-[(dimethylamino)methyl]-2,3-dihydro-4-methylpyrido[3,2-f]-[1,4]-oxazepin-5(4H)-one or a pharmaceutically acceptable salt thereof.

200. The pharmaceutical composition of claim 102 which is 2-[(dimethylamino)methyl]-2,3-dihydro-4-methylpyrido[3,2-f]-[1,4]-oxazepine-5(4H)-thione or a pharmaceutically acceptable salt thereof.

201. The pharmaceutical composition of claim 102 which is 2-[2-(dimethylamino)ethyl]-2,3-dihydro-4-methylpyrido[3,2-f]-[1,4]-oxazepine-5(4H)-thione fumarate[1:1].

202. The pharmaceutical composition of claim 102 which is 2-[2-(dimethylamino)ethyl]-2,3-dihydro-4-methylpyrido[3,2-f]-[1,4]-oxazepine-5(4H)-thione fumarate [1:1] compound with ethanol [1:1:0.5].

203. The method of claim 1 wherein the compound is 2-[2-(1-azetidinyl)ethyl]-7-chloro-2,3-dihydro-4-methyl-1,4-benzoxazepine-5(4H)-thione or a pharmaceutically acceptable salt thereof.

204. The method of claim 1 wherein the compound is (S)-2-[2-(dimethylamino)ethyl]-2,3-dihydro-4-methyl-pyrido-[3,2-f]-1,4-oxazepine-5(4H)-thione or a pharmaceutically acceptable salt thereof.

205. The method of claim 1 wherein the compound is (R)-2-[2-(dimethylamino)ethyl]-2,3-dihydro-4-methyl-pyrido-[3,2-f]-1,4-oxazepine-5(4H)-thione or a pharmaceutically acceptable salt thereof.

206. The method of claim 1 wherein the compound is 7-chloro-2-[2-(diethylamino)ethyl]-2,3-dihydro-4-methylpyrido-[3,2-f]-1,4-oxazepin-5(4H)-one or a pharmaceutically acceptable salt thereof.

207. The method of claim 1 wherein the compound is 2-[2-(1-azetidinyl)ethyl]-7-chloro-2,3-dihydro-4-methylpyrido[3,2-f]-1,4-oxazepin-5(4H)-one or a pharmaceutically acceptable salt thereof.

208. The method of claim 1 wherein the compound is 7-chloro-2,3-dihydro-4-methyl-2-[2-methyl(phenylmethyl)-amino]pyrido[3,2-f]-1,4-oxazepin-5(4H)-one or a pharmaceutically acceptable salt thereof.

209. The method of claim 1 wherein the compound is 7-chloro-2,3-dihydro-4-methyl-2-[2-(methylamino)ethyl]-pyrido[3,2-f]-1,4-oxazepin-5(4H)-one or a pharmaceutically acceptable salt thereof.

210. The method of claim 1 wherein the compound is 7-bromo-2-[2-(dimethylamino)ethyl]-2,3-dihydro-4-methylpyrido-[3,2-f]-1,4-oxazepin-5(4H)-one or a pharmaceutically acceptable salt thereof.

211. The method of claim 1 wherein the compound is 2-[2-(1-azetidinyl)ethyl]-7-bromo-2,3-dihydro-4-methylpyrido-[2,3-f][1,4]-oxazepin-5(4H)-one or a pharmaceutically acceptable salt thereof.

212. The method of claim 1 wherein the compound is 7-bromo-2,3-dihydro-4-methyl-2-[2-[methyl(phenylmethyl)-amino]ethyl]pyrido-[3,2-f][1,4]-oxazepin-5(4H)-one or a pharmaceutically acceptable salt thereof.

213. The method of claim 1 wherein the compound is 7-bromo-2-[2-(dimethylamino)ethyl]-2,3-dihydro-4-methylpyrido-[3,2-f][1,4]-oxazepine-5(4H)-thione or a pharmaceutically acceptable salt thereof.

214. The method of claim 1 wherein the compound is 2-[2-(1-azetidinyl)ethyl]-7-bromo-2,3-dihydro-4-methylpyrido-[3,2-f][1,4]-oxazepine-5(4H)-thione or a pharmaceutically acceptable salt thereof.

215. The method of claim 1 wherein the compound is 7-chloro-2,3-dihydro-4-methyl-2-[2-(1-pyrrolidinyl)ethyl]-pyrido-[3,2-f][1,4]-oxazepine-5(4H)-thione or a pharmaceutically acceptable salt thereof.

216. The method of claim 1 wherein the compound is 7-chloro-2,3-dihydro-4-methyl-2-[2-(methylamino)ethyl]-pyrido-[3,2-f]-[1,4]-oxazepine-5(4H)-thione or a pharmaceutically acceptable salt thereof.

217. The method of claim 1 wherein the compound is 2-[2-(1-azetidinyl)ethyl]-7-chloro-2,3-dihydro-4-methylpyrido-[3,2-f][1,4]-oxazepine-5(4H)-thione or a pharmaceutically acceptable salt thereof.

218. The method of claim 1 wherein the compound is 7-bromo-2,3-dihydro-4-methyl-2-[2-[methyl(phenylmethyl)-amino]-ethyl]pyrido[3,2-f][1,4]-oxazepine-5(4H)-thione or a pharmaceutically acceptable salt thereof.

219. The method of claim 1 wherein the compound is 7-chloro-2-[2-(diethylamino)ethyl]-2,3-dihydro-4-methylpyrido-[3,2-f][1,4]-oxazepine-5(4H)-thione or a pharmaceutically acceptable salt thereof.

220. The method of claim 1 wherein the compound is 7-chloro-2,3-dihydro-4-methyl-2-[2-[methyl(phenylmethyl)-amino]ethyl]-pyrido[3,2-f][1,4]-oxazepine-5(4H)-thione or a pharmaceutically acceptable salt thereof.

221. The method of claim 1 wherein the compound is 2-[2-(ethyl-methylamino)ethyl]-2,3-dihydro-4-methylpyrido-[3,2-f]-[1,4]-oxazepin-5(4H)-one or a pharmaceutically acceptable salt thereof.

222. The method of claim 1 wherein the compound is 2-[2-(ethylmethylamino)ethyl]-2,3-dihydro-4-methylpyrido-[3,2-f][1,4]-oxazepine-5(4H)-thione or a pharmaceutically acceptable salt thereof.

223. The method of claim 1 wherein the compound is 2-[2-dimethylamino)ethyl]-2,3-dihydro-4,8-dimethylpyrido[3,2-f][1,4]-oxazepin-5(4H)-one or a pharmaceutically acceptable salt thereof.

224. The method of claim 1 wherein the compound is 2-[2-(dimethylamino)ethyl]-3,4-dihydro-4,8-dimethylpyrido-[3,2-f][1,4]-oxazepine-5(4H)-thione or a pharmaceutically acceptable salt thereof.

225. The method of claim 1 wherein the compound is 2-[2-dimethylamino)ethyl]-3,4-dihydro-4-methyl-7-nitro-1,4-benzoxazepin-5(4H)-one or a pharmaceutically acceptable salt thereof.

226. The method of claim 1 wherein the compound is 2-[2-(dimethylamino)ethyl]-2,3-dihydro-4-methyl-7-nitro-1,4-benzoxazepine-5(4H)-thione or a pharmaceutically acceptable salt thereof.

227. The method of claim 1 wherein the compound is 2-[2-(dimethylamino)ethyl]-2,3-dihydro-4-methyl-7-nitro-1,4-benzoxaze-pine-5(4H)-thione or a pharmaceutically acceptable salt thereof.

228. The method of claim 1 wherein the compound is 2-[2-(cyclopropylamino)ethyl]-2,3-dihydro-4-methyl-pyrido[3,2-f]-[1,4]-oxazepine-5(4H)-thione or a pharmaceutically acceptable salt thereof.

229. The method of claim 1 wherein the compound is 2-[2-(dimethylamino)ethyl]-2,3-dihydro-7-fluoro-4-methyl-1,4-benzoxazepin-5(4H)-one or a pharmaceutically acceptable salt thereof.

230. The method of claim 1 wherein the compound is 2-[2-(dimethylamino)ethyl]-2,3-dihydro-7-fluoro-4-methyl-1,4-benzoxazepine-5(4H)-thione or a pharmaceutically acceptable salt thereof.

231. The pharmaceutical composition of claim 102 wherein the compound is 2-[2-(1-azetidinyl)ethyl]-7-chloro-2,3-dihydro-4-methyl-1,4-benzoxazepine-5(4H)-thione or a pharmaceutically acceptable salt thereof.

232. The pharmaceutical composition of claim 102 wherein the compound is (S)-2-[2-(dimethylamino)ethyl]-2,3-dihydro-4-methylpyrido-[3,2-f]-1,4-oxazepine-5(4H)-thione or a pharmaceutically acceptable salt thereof.

233. The pharmaceutical composition of claim 102 wherein the compound is (R)-2-[2-(dimethylamino)ethyl]-2,3-dihydro-4-methylpyrido[3,2-f]-1,4-oxazepine-5(4H)-thione or a pharmaceutically acceptable salt thereof.

234. The pharmaceutical composition of claim 102 wherein the compound is 7-chloro-2-[2-(diethylamino)ethyl]-2,3-dihydro-4-methylpyrido-[3,2-f]-1,4-oxazepin-5(4)-one or a pharmaceutically acceptable salt thereof.

235. The pharmaceutical composition of claim 102 wherein the compound is 2-[2-(1-azetidinyl)ethyl]-7-chloro-2,3-dihydro-4-methylpyrido[3,2-f]-1,4-oxazepin-5(4H)-one or a pharmaceutically acceptable salt thereof.

236. The pharmaceutical composition of claim 102 wherein the compound is 7-chloro-2,3-dihydro-4-methyl-2-[2-methyl(phenylmethyl)amino]pyrido[3,2-f]-1,4-oxazepin-5(4H)-one or a pharmaceutically acceptable salt thereof.

237. The pharmaceutical composition of claim 102 wherein the compound is 7-chloro-2,3-dihydro-4-methyl-2-[2-(methylamino)ethyl]pyrido[3,2-f]-1,4-oxazepin-5(4H)-one or a pharmaceutically acceptable salt thereof.

238. The pharmaceutical composition of claim 102 wherein the compound is 7-bromo-2-[2-(dimethylamino)ethyl]-2,3-dihydro-4-methylpyrido-[3,2-f]-1,4-oxazepin-5(4H)-one or a pharmaceutically acceptable salt thereof.

239. The pharmaceutical composition of claim 102 wherein the compound is 2-[2-(1-azetidinyl)ethyl]-7-bromo-2,3-dihydro-4-methyl-pyrido-[2,3-f][1,4]-oxazepin-5(4H)-one or a pharmaceutically acceptable salt thereof.

240. The pharmaceutical composition of claim 102 wherein the compound is 7-bromo-2,3-dihydro-4-methyl-2-[2-[methyl(phenylmethyl)amino]ethyl]pyrido-[3,2-f][1,4]-oxazepin-5(4H)-one or a pharmaceutically acceptable salt thereof.

241. The pharmaceutical composition of claim 102 wherein the compound is 7-bromo-2-[2-(dimethylamino)-ethyl]-2,3-dihydro-4-methylpyrido-[3,2-f][1,4]-oxazepine-5(4H)-thione or a pharmaceutically acceptable salt thereof.

242. The pharmaceutical composition of claim 102 wherein the compound is 2-[2-(1-azetidinyl)ethyl]-7-bromo-2,3-dihydro-4-methylpyrido-[3,2-f][1,4]-oxazepine-5(4H)-thione or a pharmaceutically acceptable salt thereof.

243. The pharmaceutical composition of claim 102 wherein the compound is 7-chloro-2,3-dihydro-4-methyl-2-[2-(1-pyrrolidinyl)ethyl]pyrido-[3,2-f][1,4]-oxazepine-5(4H)-thione or a pharmaceutically acceptable salt thereof.

244. The pharmaceutically composition of claim 102 wherein the compound is 7-chloro-2,3-dihydro-4-methyl-2-[2-(methylamino)ethyl]pyrido-[3,2-f]-[1,4]-oxazepine-5(4H)-thione or a pharmaceutically acceptable salt thereof.

245. The pharmaceutical composition of claim 102 wherein the compound is 2-[2-(1-azetidinyl)ethyl]-7-chloro-2,3-dihydro-4-methylpyrido-[3,2-f][1,4]-oxazepine-5(4H)-thione or a pharmaceutically acceptable salt thereof.

246. The pharmaceutical composition of claim 102 wherein the compound is 7-bromo-2,3-dihydro-4-methyl-2-[2-[methyl(phenylmethyl)amino]-ethyl]pyrido[3,2-f][1,4]-oxazepine-5(4H)-thione or a pharmaceutically acceptable salt thereof.

247. The pharmaceutical composition of claim 102 wherein the compound is 7-chloro-2-[2-(diethylamino)ethyl]-2,3-dihydro-4-methylpyrido-[3,2-f][1,4]-oxazepine-5(4H)-thione or a pharmaceutically acceptable salt thereof.

248. The pharmaceutical composition of claim 102 wherein the compound is 7-chloro-2,3-dihydro-4-methyl-2-[2-[methyl(phenylmethyl)amino]ethyl]-pyrido[3,2-f][1,4]-oxazepine-5(4H)-thione or a pharmaceutically acceptable salt thereof.

249. The pharmaceutical composition of claim 102 wherein the compound is 2-[2-(ethylmethylamino)ethyl]-2,3-dihydro-4-methylpyrido[3,2-f]-[1,4]-oxazepin-5(4H)-one or a pharmaceutically acceptable salt thereof.

250. The pharmaceutical composition of claim 102 wherein the compound is 2-[2-(ethylmethylamino)ethyl]-2,3-dihydro-4-methylpyrido[3,2-f][1,4]-oxazepine-5(4H)-thione or a pharmaceutically acceptable salt thereof.

251. The pharmaceutical composition of claim 102 wherein the compound is 2-[2-dimethylamino)ethyl]-2,3-dihydro-4,8-dimethylpyrido[3,2-f][1,4]-oxazepin-5(4H)-one or a pharmaceutically acceptable salt thereof.

252. The pharmaceutical composition of claim 102 wherein the compound is 2-[2-(dimethylamino)ethyl]-3,4-dihydro-4,8-dimethylpyrido[3,2-f][1,4]-oxazepine-5(4H)-thione or a pharmaceutically acceptable salt thereof.

253. The pharmaceutical composition of claim 102 wherein the compound is 2-[2-dimethylamino)ethyl]-3,4-dihydro-4-methyl-7-nitro-1,4-benzoxazepin-5(4H)-one or a pharmaceutically acceptable salt thereof.

254. The pharmaceutical composition of claim 102 wherein the compound is 2-[2-(dimethylamino)ethyl]-2,3-dihydro-4-methyl-7-nitro-1,4-benzoxazepine-5(4H)-thione or a pharmaceutically acceptable salt thereof.

255. The pharmaceutical composition of claim 102 wherein the compound is 2-[2-(dimethylamino)ethyl]-2,3-dihydro-4-methyl-7-nitro-1,4-benzoxazepine-5(4H)-thione or a pharmaceutically acceptable salt thereof.

256. The pharmaceutical composition of claim 102 wherein the compound is 2-[2-(cyclopropylamino)ethyl]-2,3-dihydro-4-methylpyrido[3,2-f]-[1,4]-oxazepine-5(4H)-thione or a pharmaceutically acceptable salt thereof.

257. The pharmaceutical composition of claim 102 wherein the compound is 2-[2-(dimethylamino)ethyl]-2,3-dihydro-7-fluoro-4-methyl-1,4-benzoxazepin-5(4H)-one or a pharmaceutically acceptable salt thereof.

258. The pharmaceutical composition of claim 102 wherein the compound is 2-[2-(dimethylamino)ethyl]-2,3-dihydro-7-fluoro-4-methyl-1,4-benzoxazepine-5(4H)-thione or a pharmaceutically acceptable salt thereof.

* * * * *